United States Patent
García Collazo et al.

(10) Patent No.: US 11,739,072 B2
(45) Date of Patent: Aug. 29, 2023

(54) HETEROARYL COMPOUNDS AND THEIR USE

(71) Applicant: Minoryx Therapeutics S.L., Barcelona (ES)

(72) Inventors: Ana Maria García Collazo, Barcelona (ES); Xavier Barril Alonso, Montferri (ES); Elena Cubero Jordà, Barcelona (ES); Marc Revés Vilaplana, Barcelona (ES); Richard Spurring Roberts, Barcelona (ES)

(73) Assignee: Minoryx Therapeutics S.L., Mataró (ES)

( * ) Notice: Subject to any disclaimer, the term of this patent is extended or adjusted under 35 U.S.C. 154(b) by 0 days.

(21) Appl. No.: 17/495,542

(22) Filed: Oct. 6, 2021

(65) Prior Publication Data
US 2022/0135535 A1 May 5, 2022

Related U.S. Application Data

(62) Division of application No. 16/474,461, filed as application No. PCT/IB2017/058477 on Dec. 28, 2017, now Pat. No. 11,174,242.

(30) Foreign Application Priority Data

Dec. 29, 2016 (EP) .................................... 16382672

(51) Int. Cl.
| | | |
|---|---|---|
| C07D 403/06 | (2006.01) | |
| C07D 401/06 | (2006.01) | |
| C07D 401/12 | (2006.01) | |
| C07D 239/49 | (2006.01) | |
| C07D 251/18 | (2006.01) | |
| C07D 405/12 | (2006.01) | |
| A61P 43/00 | (2006.01) | |

(52) U.S. Cl.
CPC ............ *C07D 401/06* (2013.01); *A61P 43/00* (2018.01); *C07D 239/49* (2013.01); *C07D 251/18* (2013.01); *C07D 401/12* (2013.01); *C07D 403/06* (2013.01); *C07D 405/12* (2013.01)

(58) Field of Classification Search
CPC ..... A61P 43/00; C07D 405/12; C07D 251/18; C07D 239/49; C07D 401/06; C07D 401/12; C07D 403/06
See application file for complete search history.

(56) References Cited

U.S. PATENT DOCUMENTS

| | | | |
|---|---|---|---|
| 7,737,153 B2 | 6/2010 | Feurer et al. | |
| 7,973,044 B2 | 7/2011 | Konradi et al. | |
| 2009/0226422 A1 | 9/2009 | Jaideep et al. | |
| 2016/0207933 A1 | 7/2016 | Bourque et al. | |

FOREIGN PATENT DOCUMENTS

| | | |
|---|---|---|
| CN | 1346350 A | 4/2002 |
| CN | 1351592 A | 5/2002 |
| CN | 1499970 A | 5/2004 |
| CN | 105412114 A | 3/2016 |
| JP | 2011522894 A | 8/2011 |
| WO | WO-2002046172 A2 | 6/2002 |
| WO | WO-02060392 A2 | 8/2002 |
| WO | WO-2003062225 A1 | 7/2003 |
| WO | WO-2004039796 A1 | 5/2004 |
| WO | WO-2004039797 A1 | 5/2004 |
| WO | WO-2006110763 A1 | 10/2006 |
| WO | WO-2007031529 A1 | 3/2007 |
| WO | WO-2009038695 A1 | 3/2009 |
| WO | WO-2009086303 A2 | 7/2009 |
| WO | WO-2009152083 A1 | 12/2009 |
| WO | WO-2011049737 A1 | 4/2011 |
| WO | WO-2012035055 A1 | 3/2012 |
| WO | WO-2012177997 A1 | 12/2012 |
| WO | WO-2013019469 A1 | 2/2013 |
| WO | WO-2013059119 A1 | 4/2013 |
| WO | WO-2013148103 A1 | 10/2013 |
| WO | WO-2014064118 A1 | 5/2014 |
| WO | WO-2015014900 A1 | 2/2015 |
| WO | WO-2015123398 A1 | 8/2015 |
| WO | WO-2016073895 A1 | 5/2016 |
| WO | WO-2016120808 A1 | 8/2016 |
| WO | WO-2016133446 A1 | 8/2016 |

(Continued)

OTHER PUBLICATIONS

Beutler E., et al., "Glucocerebrosidase Mutations in Gaucher Disease," Molecular Medicine 1(1):82-92, BioMed Central, England, (1994).
Boyd R.E., et al., "Pharmacological Chaperones as Therapeutics for Lysosomal Storage Diseases," Journal of Medicinal Chemistry 56(7):2705-2725, American Chemical Society, United States (2013).
Carrasco, M. P., et al., "Exploring the Molecular Basis of $Q_0$ $bc_1$ Complex Inhibitors Activity to Find Novel Antimalarial Hits," Mol. Inf. 0000: 1-12, DOI: 10.1002/minf.201300024, Wiley Online Library, Germany (2013).

(Continued)

*Primary Examiner* — Rebecca L Anderson
(74) *Attorney, Agent, or Firm* — Sterne, Kessler, Goldstein & Fox P.L.L.C.

(57) ABSTRACT

The application is directed to compounds of formula (I): and their salts and solvates, wherein $R^1$, $R^2$, $R^3$, $A^1$, $A^2$, $A^3$, and n are as set forth in the specification, as well as to a method for their preparation, pharmaceutical compositions comprising the same, and use thereof for the treatment and/or prevention of a lysosomal storage disease, such as Gaucher's, and other diseases or disorders that are synucleinopathies.

(I)

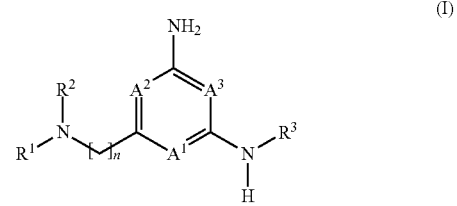

30 Claims, No Drawings

(56) References Cited

FOREIGN PATENT DOCUMENTS

| WO | WO-2016168420 A1 | 10/2016 |
|---|---|---|
| WO | WO-2017031116 A1 | 2/2017 |
| WO | WO-2018122775 A1 | 7/2018 |

OTHER PUBLICATIONS

Cavasotto, C.N., et al., "Discovery of Novel Chemotypes to a G-Protein-Coupled Receptor through Ligand-Steered Homology Modeling and Structure-Based Virtual Screening," J. Med. Chem 51:581-588, American Chemistry Society, United States (2008).

Coutinho, M.F., et al., "Less is More: Substrate Reduction Therapy for Lysosomal Storage Disorders," International Journal of Molecular Sciences 17(7):1065, MDPI, Switzerland (Jul. 2016) (22 pages).

Ekonomiuk, D., et al., "Discovery of a Non-Peptidic Inhibitor of West Nile Virus NS3 Protease by High-Throughput Docking," PLOS 3(1):E356, Public Library of Science, United States (2009) (9 pages).

Gabrielsen, M., et al., "Molecular mechanism of serotonin transporter inhibition elucidated by a new flexible docking protocol," European Journal of Medicinal Chemistry 47:24-37, Elsevier, Netherlands (2012).

Glass, L.S., et al., "Semi-automated high-throughput fluorescent intercalator displacement-based discovery of cytotoxic DNA binding agents from a large compound library," Bioorganic & Medicinal Chemistry Letters 20:1685-1688, Elsevier Ltd., United Kingdom (2010).

Huang, W., et al., "$N^4$-Phenyl Modifications of $N^2$-(2-hydroxyl)ethyl-6-(pyrrolidin-1-yl)1-1,3,5-triazine-2,4-diamines enhance glucocerebrosidase inhibition by small molecules with potential as chemical chaperones for Gaucher disease," Bioorg. Med. Chem. Letters 17:5783-5789, Elsevier Ltd., United Kingdom (2007).

International Preliminary Report on Patentability for Application No. PCT/IB2017/058477, dated Dec. 5, 2018, 68 pages.

International Search Report and Written Opinion for Application No. PCT/IB2017/058477, dated May 3, 2018, 9 pages.

Kagawa, C.M., et al., "Diuretic Effects of Formoguanamine and Other S-Triazines," J. Pharmacol Exp. Ther. 124(4):318-323, Highwire, United States (1958).

Katritch V., et al., "Structure-Based Discovery of Novel Chemotypes for Adenosine A2A Receptor Antagonists," J. Med. Chem. 53:1799-1809, Journal of Medicinal Chemistry Article, American Chemical Society, United States (2010).

Kim, S-Y., et al., "Predicted Ligands for the Humand Urotensin-II G Protein-Coupled Receptor with Some Experimental Validation," ChemMedChem 9:1732-1743, Wiley-VCH Verlag & Co., Germany (2014).

Lu, P., et al., "Discovery of a novel NEDD8 Activating Enzyme Inhibitor with Piperidin-4-amine Scaffold by Structure-Based Virtual Screening," ACS Chemical Biology 11: 1901-1907, American Chemical Society, United States (May 2016).

Marugan, J.J., et al., "Evaluation of Quinazoline Analogues as Glucocerebrosidase Inhibitors with Chaperone Activity," J. Med. Chem. 54:1033-1058, American Chemical Society, United States (2011).

Morshed, M.N., et al., "Computational approach to the identification of novel Aurora—A inhibitors," Bioorganic & Medicinal Chemistry 19:907-916, Elsevier Ltd., United Kingdom (2011).

Muwa, C., et al., "Structure-based virtual screening of novel, high-affinity BRD4 inhibitors," Mol. BioSyst 10:2384-2397, Royal Society of Chemistry, United Kingdom (2014).

Patnaik S., et al., "Discovery, SAR, and Biological Evaluation of Noninhibitory Small Molecule Chaperones of Glucocerebrosidase," Journal of Medicinal Chemistry 55(12):5734-5748, American Chemical Society, United States (2012) (42 pages).v.

Pop, M. S., et al., "A Small Molecule That Binds and Inhibits the ETV1 Transcription Factor Oncoprotein," Molecular Cancer Therapeutics 13(6):1492-1502, American Association for Cancer Research, United States (2014).

Shapiro, S. L., et al., "Guanamines. II. Oxyalkyguanamine Anticonvulsants," J. Am. Chem. Soc. 81 (1):3996-4000, American Chemistry Society, United States (1959).

Shapiro, S. L., et al., "Guanamines. V. Chloromethylguanamines," J. Am Chem. Soc. 26(1):68-74, American Chemistry Society, United States (1961).

Shapiro, S. L., et al., "Guanamines. VI. Aminomethylguanamines," J. Am. Chem. Soc. 26(1):74-76, American Chemistry Society, United States (1961).

Shen, M., et al., "Discovery and optimization of triazine derivatives as ROCK1 inhibitors: molecular docking, molecular dynamics simulations and free energy calculations," Molecular Biosystems 9:361-374, Royal Society of Chemistry, Great Britain (2013).

Siebert, M., et al., "Glucocerebrosidase is shaking up the synucleinopathies," Brain 137(Pt 5):1304-1322, Oxford University Press, England (2014).

Solankee, A., et al., "Synthesis of some new S-triazine based chalcones and their derivatives as potent antimicrobial agents," European Journal of Medicinal Chemistry 42:510-518, Elsevier, Netherlands (2010).

Svajger, U., et al., "Novel toll-like receptor 4 (TLR4) antagonists identified by structure- and ligand-based virtual screening," European Journal of Medicinal Chemistry 70:393-399, Elsevier, Netherlands (2013).

Trapero, A., et al., "Potent Aminocyclitol Glucocerebrosidase Inhibitors are Subnanomolar Pharmacological Chaperones for Treating Gaucher Disease," J. Med. Chem 55(9):44 79-4488, American Chemistry Society, United States (2012) (33 pages).

Viira, B., et al., "Design, discovery, modelling, synthesis, and biological evaluation of novel and small, low toxicity s-triazine derivatives as HIV-1 non-nucleoside reverse transcriptase inhibitors," Bioorganic & Medicinal Chemistry 24:2519-2529, Elsevier Ltd., United Kingdom (Apr. 2016).

Written Opinion for Application No. PCT/IB2017/058477, dated Jul. 5, 2018, 5 pages.

Yang, L-L., et al., "Discovery of N6-phenyl-1 H-pyrazolo[3,4-d]pyrimidine-3,6-diamine derivatives as novel CK1 inhibitors using common-feature pharmacophore model based virtual screening and hit-to-lead optimization," European Journal of Medicinal Chemistry 56:30-38, Elsevier, Netherlands (2012).

Zheng, W., et al., "Three classes of glucocerebrosidase inhibitors identified by quantitative high-throughput screening are chaperone leads for Gaucher disease," PNAS 104(32):13192-13197, United States National Academy of Sciences, United States (2007).

Registry No. 1556118-00-3, pp. 1-5, Feb. 26, 2014, File Registry on STN.

Registry No. 1330938-07-2, STN Entry Date Sep. 11, 2011, N2-(2-Methoxyphenyl)-6-[[methyl(phenylmethyl)amino]methyl]-1,3,5-triazine-2,4-diamine), 1 page.

Non-Final Office Action issued in U.S. Appl. No. 16/474,461, having a 371(c) dated Jun. 27, 2019, dated Jan. 4, 2021, 7 pages.

HETEROARYL COMPOUNDS AND THEIR USE

CROSS-REFERENCE TO RELATED APPLICATION

This application claims priority to European Application No. EP16382672.0, filed on Dec. 29, 2016, the entirety of which is incorporated by reference herein.

FIELD OF THE DISCLOSURE

The present disclosure is related to heteroaryl compounds, and especially pyridyl, pyrimidinyl, and triazinyl compounds, new processes for their preparation, and the use of the heteroaryl compounds in the treatment and/or prevention of lysosomal storage disorders in a patient, such as Gaucher's disease. The present disclosure is also related to the use of the heteroaryl compounds described herein in the treatment and/or prevention of other medical disorders in a patient, such as, for example, Parkinson's disease, Lewy body disease, dementia, multiple system atrophy, epilepsy, bipolar disorder, schizophrenia, an anxiety disorder, major depression, polycyctic kidney disease, type 2 diabetes, open angle glaucoma, multiple sclerosis, or multiple myeloma.

BACKGROUND OF THE DISCLOSURE

Gaucher's disease, suggested to arise from β-glucocerebrosidase enzyme deficiency, is very rare lysosomal storage disease. Said condition associated with β-glucocerebrosidase is known to be caused by a deficiency of the enzyme β-glucocerebrosidase due to mutations in the gene.

β-Glucocerebrosidase cleaves β-glucocerebroside from different substrates, and deficiencies in its activity cause said substrates (i.e., gangliosides, and oligosaccharides carrying terminal β-linked glucocerebroside) to accumulate in patients suffering from conditions associated with β-glucocerebrosidase activity, such as Gaucher's disease. Beutler et al. (*Mol Med.* 1(1):82-92 (1994)) reported that deficiency of glucocerebrosidase leads to accumulation of insoluble glucocerebrosides in the tissues, resulting in the clinical manifestations of Gaucher's disease.

In many lysosomal disorders, like Gaucher's disease, the mutant enzymes often retain catalytic activity but fold improperly in the endoplasmic reticulum ("ER"). This triggers ER accumulation of the mutant protein, which is eventually tagged for proteasome degradation by ubiquitination, avoiding the transport of the enzyme to the lysosome. See, e.g., Patniak et al., *Journal of Medicinal Chemistry* 55(12):5734-5748 (2012).

Gaucher's (or Gaucher) disease is a heterogenous disorder having three subtypes. The majority of patients, those without neurologic manifestations of the disease, are classified as type 1. In type I, clinical manifestations include enlarged spleen and liver, platelet deficiency, anemia, and bone disease. Types II and III are neuronopathic forms, classified with respect to severity and to the time of onset of neurologic disease. Type 11 is most severe with symptoms at or near the time of birth. Patients with type II have a median life span of 9 months. Type III has a later onset. See, e.g., Patniak et al., *Journal of Medicinal Chemistry* 55(12):5734-5748 (2012). Patients with Gaucher's disease exhibit hematological manifestations, such as anemia and thrombocytopenia, as well as hepatosplenomegaly, skeletal deformities, and in some cases, neurological impairment. See, e.g., Boyd et al., *Journal of Medicinal Chemistry* 56 (7):2705-2725 (2013).

Enzyme replacement therapy ("ERT") and substrate inhibition therapy ("SRT") are two current therapies for type I Gaucher's disease. ERT involves long term treatment via injection of a recombinant enzyme (imiglucerase) into patients. While ERT may be effective in reducing and reversing the clinical symptoms of the disease, it is very costly. SRT is generally indicated for the treatment of adult patients with mild to moderate type I Gaucher's disease for whom ERT is not a therapeutic option. The prescribed drug, an iminosugar miglustat, inhibits glucosylceramide synthetase, reducing the production of glucocerebrosides in the lysosome. While SRT may be effective for some patients, it is associated with side effects, including weight loss, diarrhea, tremors, and peripheral nerve damage. Neither ERT nor SRT are effective against the neuronopathic types II and III of Gaucher's disease. See, e.g., Patniak et al., *Journal of Medicinal Chemistry* 55(12):5734-5748 (2012).

Mutations in the gene encoding glucocerebrosidase are also a risk factor for synucleinopathies, such as Parkinson's disease and diffuse Lewy Body disease. Parkinson's disease is a degenerative disorder of the central nervous system associated with death of dopamine-containing cells in a region of the midbrain. Diffuse Lewy Body disease is a dementia that is sometimes confused with Alzheimer's disease.

Small molecules capable of binding allosterically or competitively to mutated β-glucocerebrosidase enzyme, thereby stabilizing the enzyme against degradation (chaperones), constitute an important therapeutic target in conditions associated with the alteration of the activity of 0-glucocerebrosidase. By binding and stabilizing mutant proteins, these chemical chaperones facilitate protein folding and eventually increase their transport to the lysosome. Improved trafficking of the mutant protein from the ER to the lysosome results in the reduction of lysosome size and correction of the storage. These chaperones may also increase the stability of mutant enzymes toward degradation in the lysosome. See, e.g., Patniak et al., *Journal of Medicinal Chemistry* 55(12): 5734-5748 (2012).

It has been surprisingly found that compounds of formula (I) are capable of binding to β-glucocerebrosidase thereby stabilizing the enzyme against denaturation.

BRIEF SUMMARY OF THE DISCLOSURE

The present disclosure is related to the discovery that heteroaryl compounds represented by formula (I) are capable of binding to mutated β-glucocerebrosidase and are thus useful in the treatment or prevention of a lysosomal storage disease, such as Gaucher's disease.

The present disclosure provides a method of treating or preventing a lysosomal storage disease, such as Gaucher's disease, in a patient in need thereof by administering an effective amount of a compound of formula (I), or a salt or solvate thereof, as described herein. Compounds represented by formula (I) and the salts and solvates thereof, are herein collectively referred to as "Compounds of the Disclosure" (each individually referred to as a "Compound of the Disclosure").

In another aspect, the present method of treating a lysosomal storage disease, such as Gaucher's disease, further comprises administering to the patient at least one other therapeutic agent. In one embodiment, the therapeutic agent is an effective amount of an enzyme for enzyme replacement therapy. In another embodiment, the enzyme is β-glucocerebrosidase or an analog thereof. In another embodiment, the enzyme is imiglucerase.

In another aspect, the method further comprises administering to the patient an effective amount of a small molecule chaperone. In another embodiment, the small molecule chaperone binds competitively to an enzyme. In another embodiment, the small molecule chaperone is selected from the group consisting of iminoalditols, iminosugars, aminosugars, thiophenylglycosides, glycosidase, sulfatase, glycosyl transferase, phosphatase, and peptidase inhibitors. In another embodiment, the small molecule chaperone is selected from the group consisting of isofagomine, N-nonyl-1-deoxynojirimycin (NN-DNJ), ambroxol, and miglustat. In another embodiment, the small molecule chaperone is selected from the group consisting of isofagomine, N-nonyl-1-deoxynojirimycin (NN-DNJ), and ambroxol. In another embodiment, the small molecule chaperone is miglustat.

In another embodiment, the therapeutic agent is an effective amount of substrate reduction agent for substrate reduction therapy. In another embodiment, the substrate reduction agent is miglustat.

The present disclosure is also directed to the use of a compound of formula (I), or a salt or solvate thereof, as described herein, for the treatment or prevention of a lysosomal storage disease, such as Gaucher's disease.

A number of compounds useful in the treatment or prevention of the present disclosure have not been heretofor reported. Thus, one aspect of the present disclosure is directed to the novel compounds of formula (I), and the salts and solvates thereof. Another aspect of the present disclosure is directed to pharmaceutical compositions comprising these novel compounds of formula (I), and the salts and solvates thereof, and at least one pharmaceutically acceptable excipient.

In one aspect, the present disclosure provides compounds of formula (I), and the salts and solvates thereof, with the proviso that no more than two of $A^1$, $A^2$, or $A^3$ is N.

In another aspect, the present disclosure provides a pharmaceutical composition comprising a compound of formula (I), or a pharmaceutically acceptable salt or solvate thereof, as defined herein, and at least one pharmaceutically acceptable excipient.

In another aspect, the present disclosure provides compounds of formula (I) as defined herein, and the pharmaceutically acceptable salts and solvates thereof, for use as a medicament.

In another aspect, the present disclosure provides compounds of formula (I) as defined herein, and the pharmaceutically acceptable salts and solvates thereof, for use in the prevention or treatment of a lysosomal storage disease, such as Gaucher's disease.

In another aspect, the present disclosure provides use of a compound of formula (I), and the pharmaceutically acceptable salts and solvates thereof, as defined herein, in the preparation of a medicament for the prevention or treatment of a lysosomal storage disease, such as Gaucher's disease.

In another aspect, the present disclosure provides a pharmaceutical composition comprising a compound of formula (I), or a pharmaceutically acceptable salt or solvate thereof, as defined herein, and at least one pharmaceutically acceptable excipient, for use in the treatment or prevention of a lysosomal storage disease, such as Gaucher's disease.

In another aspect, the present disclosure is directed to method of treating or preventing a disease or disorder selected from the group consisting of Parkinson's disease, Lewy body disease, dementia, multiple system atrophy, epilepsy, bipolar disorder, schizophrenia, an anxiety disorder, major depression, polycyctic kidney disease, type 2 diabetes, open angle glaucoma, multiple sclerosis, and multiple myeloma, comprising administering to a patient in need thereof an effective amount of a compound of formula (I), or a pharmaceutically acceptable salt or solvate thereof. In one embodiment, the method further comprises administering to the patient at least one other therapeutic agent. In another embodiment, the therapeutic agent is an effective amount of an enzyme for enzyme replacement therapy. In another embodiment, the enzyme is β-glucocerebrosidase or an analog thereof. In another embodiment, the enzyme is imiglucerase. In another embodiment, the therapeutic agent is an effective amount of a small molecule chaperone. In another embodiment, the small molecule chaperone hinds competitively to an enzyme. In another embodiment, the small molecule chaperone is selected from the group consisting of iminoalditols, iminosugars, aminosugars, thiophenylglycosides, glycosidase, sulfatase, glycosyl transferase, phosphatase, and peptidase inhibitors. In another embodiment, the small molecule chaperone is selected from the group consisting of isofagomine, N-nonyl-1-deoxynojirimycin (NN-DNJ), ambroxol, and miglustat. In another embodiment, the small molecule chaperone is selected from the group consisting of isofagomine, N-nonyl-1-deoxynojirimycin (NN-DNJ), and ambroxol. In another embodiment, the small molecule chaperone is miglustat.

In another aspect, the present disclosure is directed to a compound of formula (I), or a pharmaceutically acceptable salt or solvate thereof, for use in treating or preventing a disease or disorder selected from the group consisting of Parkinson's disease, Lewy body disease, dementia, multiple system atrophy, epilepsy, bipolar disorder, schizophrenia, an anxiety disorder, major depression, polycyctic kidney disease, type 2 diabetes, open angle glaucoma, multiple sclerosis, and multiple myeloma, in a patient. In one embodiment, the compound of formula (I), or a pharmaceutically acceptable salt or solvate thereof, is administered to the patient in combination with at least one other therapeutic agent. In another embodiment, the therapeutic agent is an effective amount of an enzyme for enzyme replacement therapy. In another embodiment, the enzyme is β-glucocerebrosidase or an analog thereof. In another embodiment, the enzyme is imiglucerase. In another embodiment, the therapeutic agent is an effective amount of a small molecule chaperone. In another embodiment, the small molecule chaperone binds competitively to an enzyme. In another embodiment, the small molecule chaperone is selected from the group consisting of iminoalditols, iminosugars, aminosugars, thiophenylglycosides, glycosidase, sulfatase, glycosyl transferase, phosphatase, and peptidase inhibitors. In another embodiment, the small molecule chaperone is selected from the group consisting of isofagomine, N-nonyl-1-deoxynojirimycin (NN-DNJ), ambroxol, and miglustat. In another embodiment, the small molecule chaperone is selected from the group consisting of isofagomine, N-nonyl-1-deoxynojirimycin (NN-DNJ), and ambroxol. In another embodiment, the small molecule chaperone is miglustat.

In another aspect, the present disclosure is directed to a compound of formula (I), or a pharmaceutically acceptable salt or solvate thereof, for use in the treatment or prevention of a disease or disorder selected from the group consisting of Parkinson's disease, Lewy body disease, dementia, multiple system atrophy, epilepsy, bipolar disorder, schizophrenia, an anxiety disorder, major depression, polycyctic kidney disease, type 2 diabetes, open angle glaucoma, multiple sclerosis, and multiple myeloma in a patient in need of such treatment or prevention.

In another aspect, the present disclosure is also directed to the use of a compound of formula (I), or a pharmaceutically acceptable salt or solvate thereof, in the manufacture of a medicament for treating and/or preventing a disease or disorder selected from the group consisting of Parkinson's disease, Lewy body disease, dementia, multiple system atrophy, epilepsy, bipolar disorder, schizophrenia, an anxiety disorder, major depression, polycyctic kidney disease, type 2 diabetes, open angle glaucoma, multiple sclerosis, and multiple myeloma in a patient in need of such treatment or prevention.

In another aspect, the present disclosure provides a pharmaceutical composition comprising a compound of formula (I), or a pharmaceutically acceptable salt or solvate thereof, as defined herein, and at least one pharmaceutically acceptable excipient, for use in the treatment or prevention of a disease or disorder selected from the group consisting of Parkinson's disease, Lewy body disease, dementia, multiple system atrophy, epilepsy, bipolar disorder, schizophrenia, an anxiety disorder, major depression, polycyctic kidney disease, type 2 diabetes, open angle glaucoma, multiple sclerosis, and multiple myeloma.

Other aspects and advantages of the disclosure will be readily apparent from the following detailed description of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the disclosure as claimed.

DETAILED DESCRIPTION OF THE DISCLOSURE

One aspect of the disclosure is based on the use of Compounds of the Disclosure for binding to mutated β-glucocerebrosidase. In view of this property, Compounds of the Disclosure are expected to be useful for treating or preventing Gaucher's disease.

Compounds of the Disclosure useful in this aspect of the disclosure are compounds of formula (I):

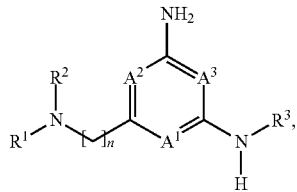

and the pharmaceutically acceptable salts and solvates thereof, wherein $A^1$, $A^2$, and $A^3$ are each independently selected from the group consisting of N, CH and C($R^4$), provided that at least one of $A^1$, $A^2$, or $A^3$ is N;

each $R^4$ is independently selected from the group consisting of halogen, —$C_{1-4}$ alkyl, —$C_{1-4}$ alkoxy, and —CN;

n is 1 or 2, wherein the alkylene chain can be optionally substituted with one or more —$C_{1-4}$ alkyl groups;

$R^1$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, —$C_{1-4}$ alkyl-(5- to 10-membered)-$C_{2-9}$ heterocyclyl, and —C(=O)Ra, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, -(5- to 10-membered)-$C_{2-9}$ heterocyclyl, and optionally substituted —O—($C_{6-10}$ aryl); and wherein said cycloalkyl, alkylcycloalkyl, aryl, alkylaryl, heteroaryl, alkylheteroaryl, heterocyclyl and alkylheterocyclyl is optionally fused to a further (second) ring; and $R^2$ is selected from the group consisting of hydrogen, —$C_{1-4}$ alkyl, and $C_{3-6}$ cycloalkyl, wherein said —$C_{1-4}$ alkyl is optionally substituted with —O($C_{1-4}$)alkyl optionally substituted with —O($C_{1-4}$)NH$_2$, hydroxy, —CN, halogen, or —N(Rb)$_2$; or $R^1$ and $R^2$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;

Ra is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, and —$C_{1-4}$ alkyl-(5- to 10-membered)-$C_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring;

each Rb is independently hydrogen, —$C_{1-4}$ alkyl, —$C_{3-10}$ cycloalkyl, or -(5- to 10-membered)-$C_{2-9}$ heterocyclyl, wherein said alkyl, cycloalkyl or heterocyclyl group is optionally substituted by 1, 2 or 3 fluorine atoms; and $R^3$ is selected from the group consisting of —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said aryl, heteroaryl, cycloalkyl, and heterocyclyl groups are optionally substituted with 1, 2 or 3 substituents each independently selected from the group consisting of halogen, hydroxy, —CN, —ORb, —SRb, —N(Rb)$_2$, —$C_{1-4}$alkyl optionally substituted with 1, 2, or 3 substituents each independently selected from the group consisting of halogen, —CN, —ORb, and —N(Rb)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl, and wherein said aryl, heteroaryl, cycloalkyl, and heterocyclyl is optionally fused to a further (second) ring.

In another embodiment, Compounds of the Disclosure useful in this aspect of the disclosure are compounds of formula (I):

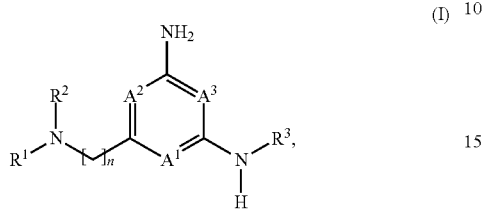

and the pharmaceutically acceptable salts and solvates thereof, wherein
- $A^1$, $A^2$, and $A^3$ are each independently selected from the group consisting of N, CH and C($R^4$), provided that at least one of $A^1$, $A^2$, or $A^3$ is N;
- each $R^4$ is independently selected from the group consisting of halogen, —$C_{1-4}$ alkyl, —$C_{1-4}$ alkoxy, and —CN;
- n is 1 or 2;
- $R^1$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, —$C_{1-4}$ alkyl-(5- to 10-membered)-$C_{2-9}$ heterocyclyl, and —C(=O)Ra, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring; and
- $R^2$ is hydrogen or —$C_{1-4}$ alkyl; or
- $R^1$ and $R^2$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;
- Ra is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, and —$C_{1-4}$ alkyl-(5- to 10-membered)-$C_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkyl heteroaryl, heterocyclyl and alkyl heterocyclyl is optionally fused to a further (second) ring;
- each Rb is independently hydrogen, —$C_{1-4}$ alkyl, —$C_{3-4}$ cycloalkyl, or -(5- to 10-membered)-$C_{2-9}$ heterocyclyl, wherein said alkyl, cycloalkyl or heterocyclyl group is optionally substituted by 1, 2 or 3 fluorine atoms; and
- $R^3$ is —$C_{6-10}$ aryl or -(5- to 10-membered)-$C_{1-9}$ heteroaryl, wherein said aryl and heteroaryl groups are optionally substituted with 1, 2 or 3 substituents each independently selected from the group consisting of halogen, hydroxy, —CN, —ORb, —SRb, —N(Rb)$_2$, —$C_{1-4}$alkyl optionally substituted with 1, 2, or 3 substituents each independently selected from the group consisting of halogen, —CN, —ORb, and —N(Rb)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

In another embodiment, Compounds of the Disclosure are compounds of formula (I), and the pharmaceutically acceptable salts and solvates thereof, wherein $A^1$, $A^2$ and $A^3$ are N.

In another aspect, useful Compounds of the Disclosure include compounds of formula (I), and the pharmaceutically acceptable salts and solvates thereof, wherein $R^1$, $R^2$, $R^3$, n, $A^1$, $A^2$, and $A^3$ are as described above, with the proviso that no more than two of $A^1$, $A^2$, or $A^3$ is N.

In another embodiment of this aspect of the disclosure, Compounds of the Disclosure are compounds of formula (I), and the pharmaceutically acceptable salts and solvates thereof, wherein $A^1$ is N and $A^2$ and $A^3$ are each independently selected from the group consisting of CH and C($R^4$). In another embodiment, $A^2$ and $A^3$ are both CH.

In another embodiment, Compounds of the Disclosure are compounds of formula (I), and their pharmaceutically acceptable salts and solvates thereof, wherein $A^2$ is N and $A^1$ and $A^3$ are each independently selected from the group consisting of CH and C($R^4$). In another embodiment, $A^1$ and $A^3$ are both CH.

In another embodiment, Compounds of the Disclosure are compounds of formula (I), and the pharmaceutically acceptable salts and solvates thereof, wherein $A^3$ is N and $A^1$ and $A^2$ are each independently selected from the group consisting of CH and C($R^4$). In another embodiment, $A^1$ and $A^2$ are both CH.

In another embodiment, Compounds of the Disclosure are compounds of formula (I), and the pharmaceutically acceptable salts and solvates thereof, wherein $A^1$ and $A^2$ are both N and $A^3$ is CH or C($R^4$). In another embodiment, $A^3$ is CH.

In another embodiment, Compounds of the Disclosure are compounds of formula (I), and the pharmaceutically acceptable salts and solvates thereof, wherein $A^1$ and $A^3$ are both N and $A^2$ is CH or C($R^4$). In another embodiment, $A^2$ is CH.

In another embodiment, Compounds of the Disclosure are compounds of formula (I), and the pharmaceutically acceptable salts and solvates thereof, wherein $A^2$ and $A^3$ are both N and $A^1$ is CH or C($R^4$). In another embodiment, $A^1$ is CH.

In another embodiment, Compounds of the Disclosure are compounds of formula (I), and the pharmaceutically acceptable salts and solvates thereof, wherein n is 1.

In another embodiment, Compounds of the Disclosure are compounds of formula (I), and the pharmaceutically acceptable salts and solvates thereof, wherein n is 2.

In another embodiment, Compounds of the Disclosure are compounds of formula (I), and the pharmaceutically acceptable salts and solvates thereof, wherein $R^3$ is —$C_{6-10}$ aryl optionally substituted with 1, 2 or 3 substituents each independently selected from the group consisting of halogen, hydroxy, —CN, —ORb, —SRb, —N(Rb)$_2$, —$C_{1-4}$alkyl optionally substituted with 1, 2, or 3 substituents each independently selected from the group consisting of halogen, —CN, —ORb, and —N(Rb), optionally substituted —$C_{6-10}$ aryl, optionally substituted -(5- to 10-membered)-$C_{1-9}$ heteroaryl and -(5- to 10-membered)-$C_{2-9}$ heterocyclyl. In another embodiment, $R^3$ is unsubstituted —$C_{6-10}$ aryl or —$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In one embodiment, $R^3$ is unsubstituted —$C_{6-10}$ aryl, and preferably unsubstituted phenyl. In another embodiment, $R^3$ is —$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In another embodiment, $R^3$ is —$C_{6-10}$ aryl, and preferably phenyl, substituted with 1 or 2 substituents each independently selected from the group consisting of halogen, hydroxy, —CN, methoxy, ethoxy, methylthio, ethylthio, dimethylamino, diethylamino, methylamino, ethylamino, halomethyl (such as fluoromethyl), di(halo)methyl (such as difluoromethyl), tri(halo)methyl (such as trifluoromethyl), cyanomethyl, methoxymethyl, methoxyethyl, dimethylaminomethyl, dimethylaminoethyl, methylaminomethyl, and methylaminoethyl. In another embodiment, $R^3$ is phenyl substituted with halogen, hydroxy, —CN, methyl, ethyl, methoxy, or ethoxy. In one embodiment, the substituent is attached to the meta-position of the phenyl group. In another embodiment, the substituent is attached to the ortho-position of the phenyl group. In another embodiment, the substituent is attached to the para-position of the phenyl group.

In another embodiment, Compounds of the Disclosure are compounds of formula (I), and the pharmaceutically acceptable salts and solvates thereof, wherein $R^3$ is (5- or 10-membered)-$C_{1-9}$ heteroaryl optionally substituted with 1, 2 or 3 substituents each independently selected from the group consisting of halogen, hydroxy, —CN, —ORb, —SRb, —N(Rb)$_2$, —$C_{1-4}$alkyl optionally substituted with 1, 2, or 3 substituents each independently selected from the group consisting of halogen, —CN, —ORb, and —N(Rb)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl. In one embodiment, $R^3$ is unsubstituted (5- or 10-membered)-$C_{1-9}$ heteroaryl or (5- or 10-membered)-$C_{1-9}$ heteroaryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In another embodiment, $R^3$ is unsubstituted -(5- or 10-membered)-$C_{1-9}$ heteroaryl. In another embodiment, $R^3$ is -(5- or 10-membered)-$C_{1-9}$ heteroaryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl).

In another embodiment, $R^3$ is —$C_{3-10}$ cycloalkyl or -(5- to 10-membered)-$C_{2-9}$ heterocyclyl, wherein said cycloalkyl and heterocyclyl groups are optionally substituted with 1, 2 or 3 substituents each independently selected from the group consisting of halogen, hydroxy, —CN, —ORb, —SRb, —N(Rb)$_2$, —$C_{1-4}$alkyl optionally substituted with 1, 2, or 3 substituents each independently selected from the group consisting of halogen, —CN, —ORb, and —N(Rb)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

In another embodiment, $R^3$ is selected from the group consisting of —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said aryl, heteroaryl, cycloalkyl, and heterocyclyl groups are optionally substituted with 1, 2 or 3 substituents each independently selected from the group consisting of halogen, hydroxy, —CN, —ORb, —SRb, —N(Rb)$_2$, —$C_{1-4}$alkyl optionally substituted with 1, 2, or 3 substituents each independently selected from the group consisting of halogen, —CN, —ORb, and —N(Rb)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl, and wherein said aryl, heteroaryl, cycloalkyl, and heterocyclyl is optionally fused with a cycloalkyl or heterocyclyl to give a bicyclic ring system, e.g.,

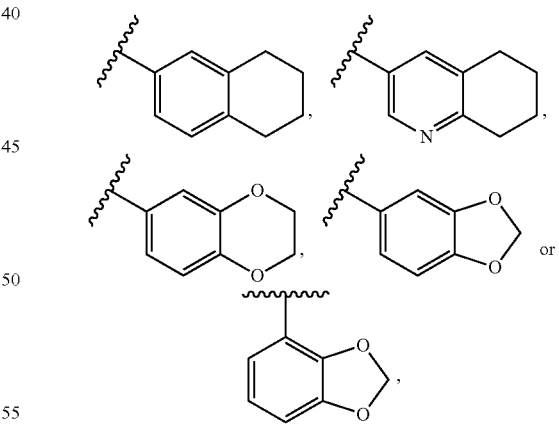

and said cycloalkyl or heterocyclyl is optionally fused with an aryl or heteroaryl to give a bicyclic ring system, e.g.,

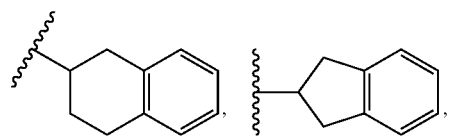

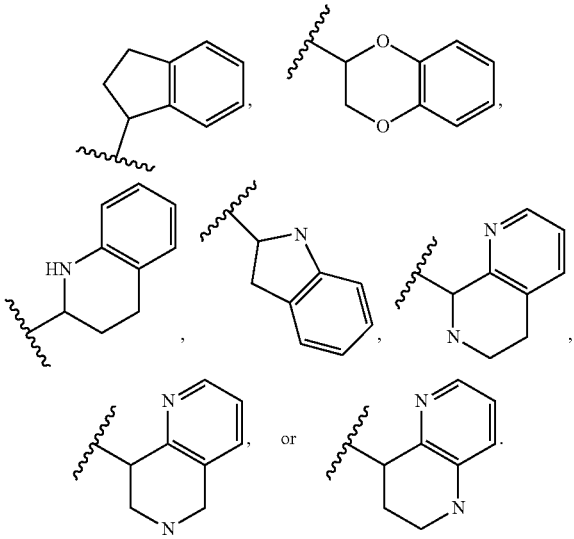

In another embodiment, Compounds of the Disclosure are compounds of formula (I), and the pharmaceutically acceptable salts and solvates thereof, wherein $R^2$ is H and $R^1$ is as defined above.

In another embodiment, Compounds of the Disclosure are compounds of formula (I), and the pharmaceutically acceptable salts and solvates thereof, wherein $R^2$ is —$C_{1-4}$ alkyl and $R^1$ is as defined above. In another embodiment, $R^2$ is methyl or ethyl. In another embodiment, $R^2$ is methyl.

In another embodiment, Compounds of the Disclosure are compounds of formula (I), and the pharmaceutically acceptable salts and solvates thereof, wherein $R^1$ is —$C_{6-10}$ aryl or —$C_{1-4}$ alkyl-$C_{6-10}$ aryl, wherein said aryl or alkylaryl is optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl, wherein Rb is as defined above.

In one embodiment, $R^1$ is unsubstituted —$C_{6-10}$ aryl optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 substituents each independently selected from the group consisting of halogen, —CN, —ORb, and —N(Rb)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl. In one embodiment, $R^1$ is unsubstituted —$C_{6-10}$ aryl or —$C_{6-10}$ aryl substituted with 1 or 2 substituents independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In another embodiment, $R^1$ is unsubstituted —$C_{6-10}$ aryl, and preferably unsubstituted phenyl. In another embodiment, $R^1$ is —$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In another embodiment, $R^1$ is —$C_{6-10}$ aryl, and preferably phenyl, substituted with 1 or 2 substituents each independently selected from the group consisting of halogen, hydroxy, —CN, methoxy, ethoxy, methylthio, ethylthio, dimethylamino, diethylamino, methylamino, ethylamino, halomethyl (such as fluoromethyl), di(halo)methyl (such as difluoromethyl), tri(halo)methyl (such as trifluoromethyl), cyanomethyl, methoxymethyl, methoxyethyl, dimethylaminomethyl, dimethylaminoethyl, methylaminomethyl, and methylaminoethyl. In another embodiment, $R^1$ is phenyl substituted with halogen, hydroxy, —CN, methyl, ethyl, methoxy, or ethoxy. In one embodiment, the substituent is attached to the meta-position of the phenyl group. In another embodiment, the substituent is attached to the ortho-position of the phenyl group. In another embodiment, the substituent is attached to the para-position of the phenyl group.

In another embodiment, $R^1$ is unsubstituted $C_{1-4}$ alkyl-$C_{6-10}$ aryl or $C_{1-4}$ alkyl-$C_{6-10}$ aryl optionally substituted with 1, 2 or 3 substituents each independently selected from the group consisting of halogen, hydroxy, —CN, —ORb, —SRb, —N(Rb)$_2$, —$C_{1-4}$alkyl optionally substituted with 1, 2, or 3 substituents each independently selected from the group consisting of halogen, —CN, —ORb, and —N(Rb)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl. In one embodiment, $R^1$ is unsubstituted $C_{1-4}$ alkyl-$C_{6-10}$ aryl or $C_{1-4}$ alkyl-$C_{6-10}$ aryl substituted with 1 or 2 substituents each independently selected from the group consisting of halogen, hydroxy, —CN, —O($C_{1-4}$)alkyl, —S($C_{1-4}$)alkyl, alkyl)$_2$, —NH($C_{1-4}$ alkyl), and alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In one embodiment, $R^1$ is unsubstituted $C_{1-4}$ alkyl-$C_{6-10}$ aryl, and preferably unsubstituted benzyl or phenethyl. In another embodiment, $R^1$ is $C_{1-4}$ alkyl-$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, CN, —O($C_{1-4}$)alkyl, —N($C_{1-4}$ alkyl)$_2$, and —NH($C_{1-4}$ alkyl). In another embodiment, $R^1$ is —$C_{1-4}$ alkyl-$C_{6-10}$ aryl, and preferably benzyl, substituted with 1 or 2 substituents each independently selected from the group consisting of halogen, hydroxy, —CN, methoxy, ethoxy, methylthio, ethylthio, dimethylamino, diethylamino, methylamino, ethylamino, halomethyl (such as fluoromethyl), di(halo)methyl (such as difluoromethyl), tri(halo)methyl (such as trifluoromethyl), cyanomethyl, methoxymethyl, methoxyethyl, dimethylaminomethyl, dimethylaminoethyl, methylaminomethyl, and methylaminoethyl. In another embodiment, $R^1$ is benzyl substituted with halogen, hydroxy, —CN, methyl, ethyl, methoxy, or ethoxy. In one embodiment, the substituent is attached to the meta-position of the phenyl group. In another embodiment, the substituent is attached to the ortho-position of the phenyl group. In another embodiment, the substituent is attached to the para-position of the phenyl group.

In another embodiment, Compounds of the Disclosure are compounds of formula (I), and the pharmaceutically acceptable salts and solvates thereof, wherein Rb is hydrogen or —$C_{1-4}$ alkyl.

In another embodiment, Compounds of the Disclosure are compounds of formula (I), and the pharmaceutically acceptable salts and solvates thereof, wherein $R^1$ and $R^2$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring. In another embodiment, $R^1$ and $R^2$ together with the nitrogen atom form a morpholinyl ring. In another embodiment, $R^1$ and $R^2$ together with the nitrogen atom form a piperidinyl ring optionally substituted at the nitrogen with —$C_{1-4}$ alkyl (such as methyl or ethyl), —$C_{6-10}$ aryl (such as phenyl) optionally substituted with $C_{1-4}$ alkyl or —O($C_{1-4}$ alkyl), or —C(=O)O($C_{1-4}$ alkyl).

In another embodiment, Compounds of the Disclosure are compounds of formula (I), and the pharmaceutically acceptable salts and solvates thereof, wherein $R^1$ and $R^2$ together with the nitrogen atom to which they are attached form a 5- or 6-membered ring optionally fused to a phenyl ring.

In another embodiment, the present disclosure provides a Compound of the Disclosure selected from the group consisting of

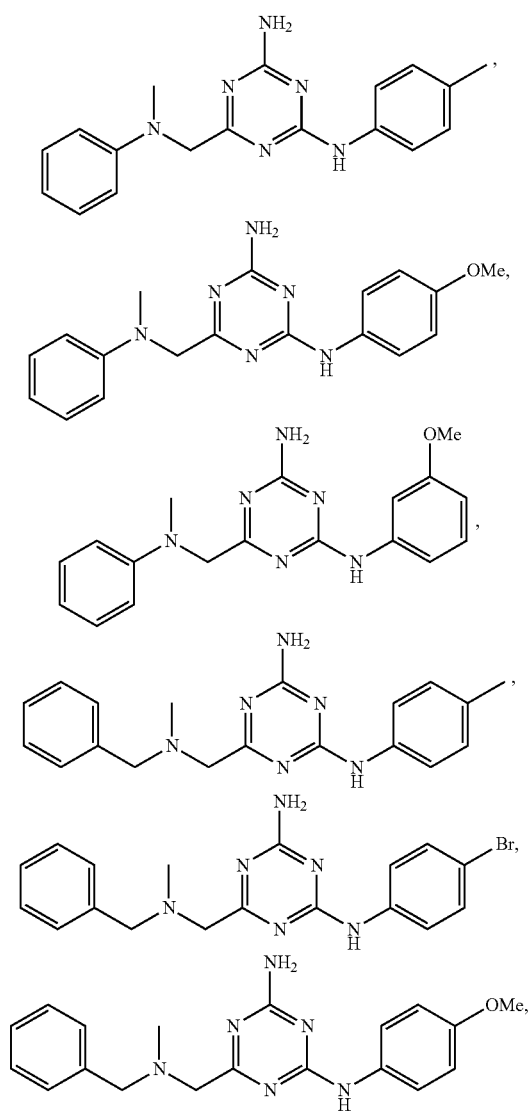

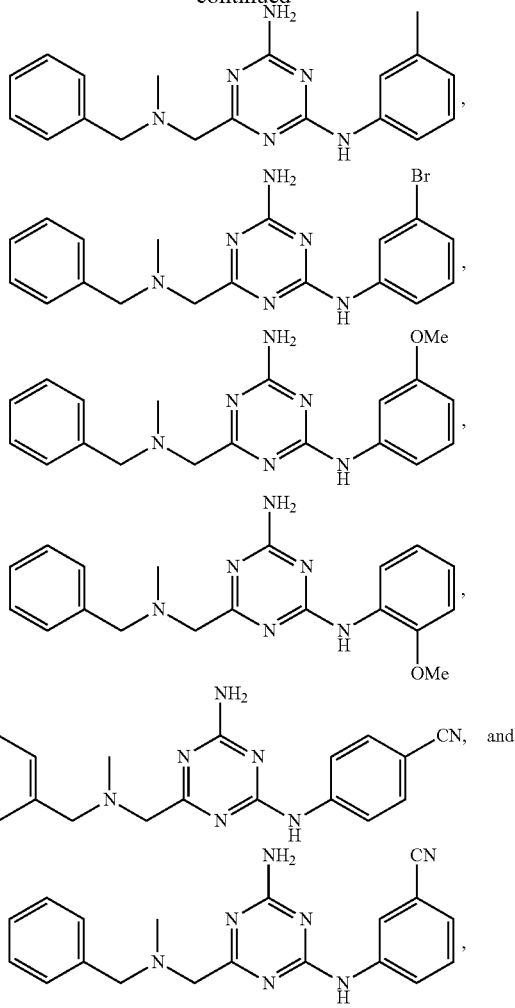

and the pharmaceutically acceptable salts and solvates thereof.

In another embodiment, the present disclosure provides a Compound of the Disclosure selected from the group consisting of

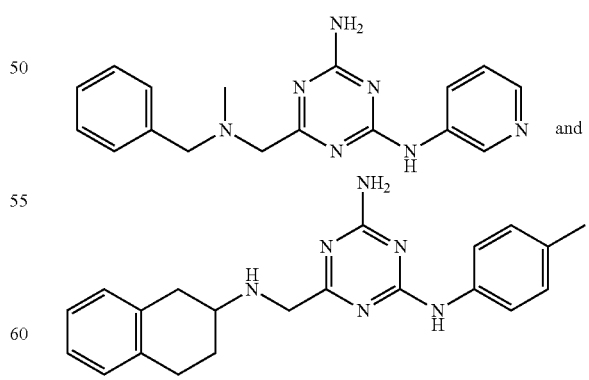

and the pharmaceutically acceptable salts thereof.

In another embodiment, the present disclosure provides a Compound of the Disclosure selected from the group consisting of

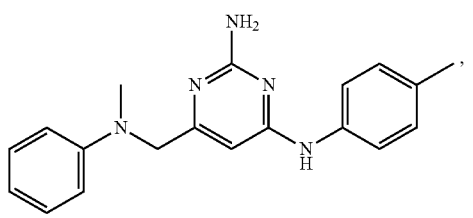
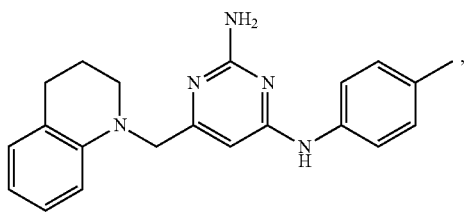
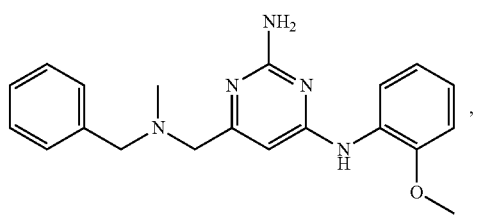
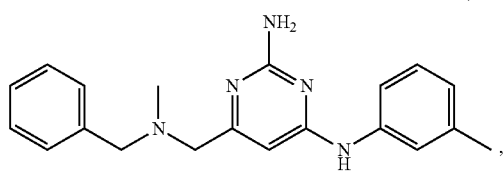
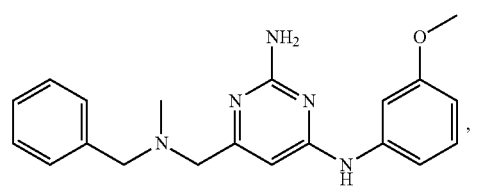
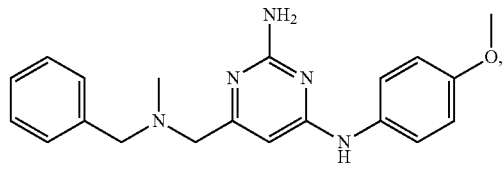
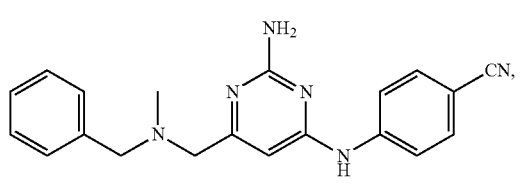
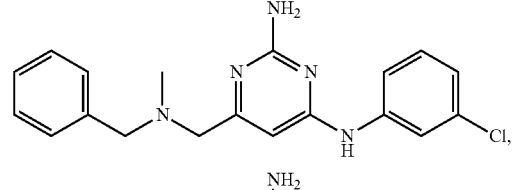
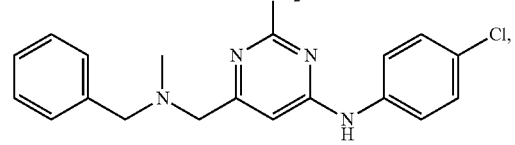
-continued
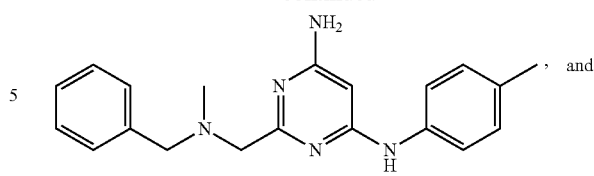
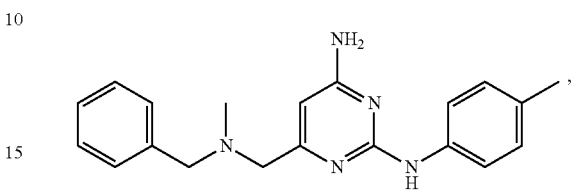
and the pharmaceutically acceptable salts and solvates thereof.
In another embodiment, the present disclosure provides a Compound of the Disclosure selected from the group consisting of
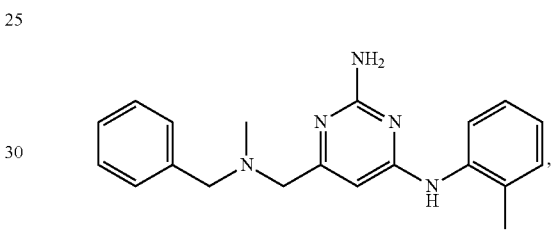
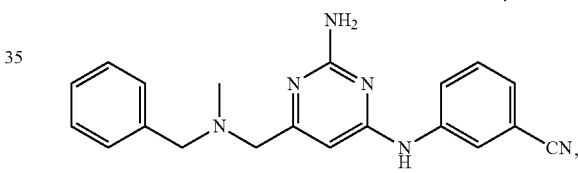
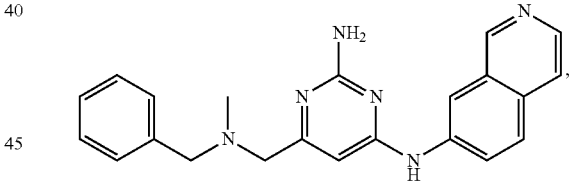
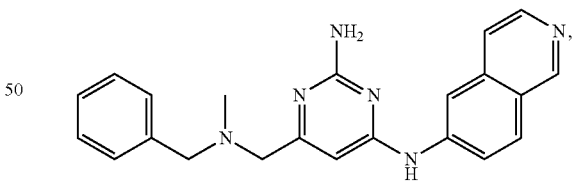
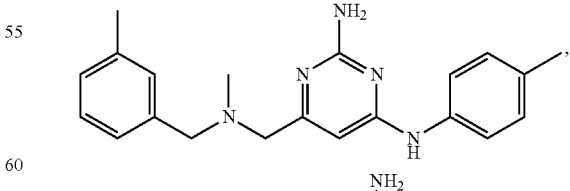
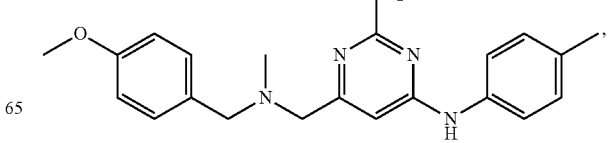

-continued

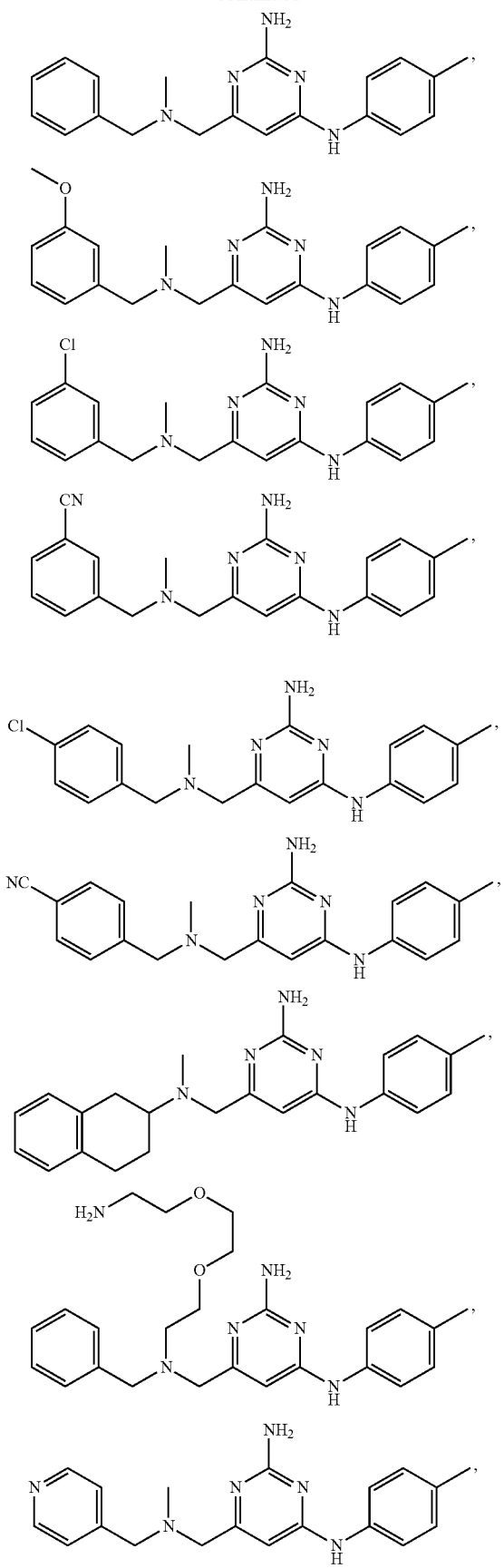
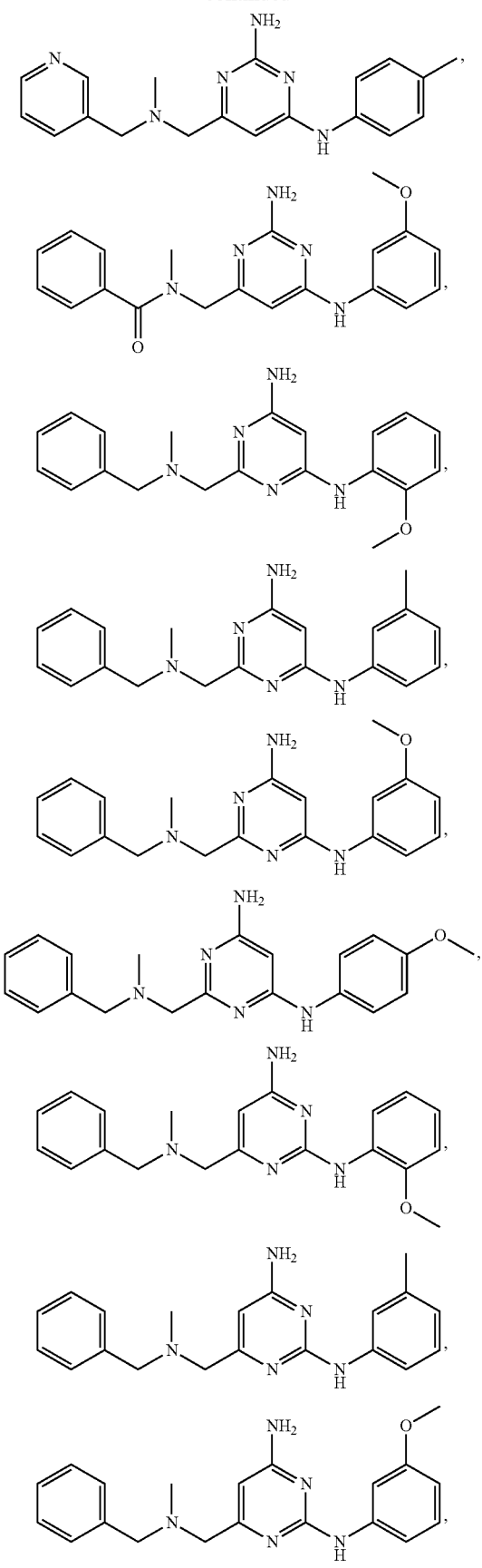

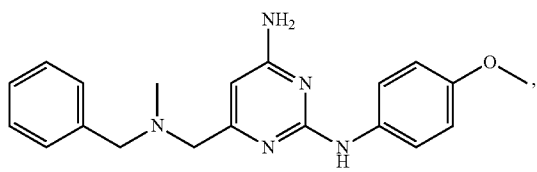

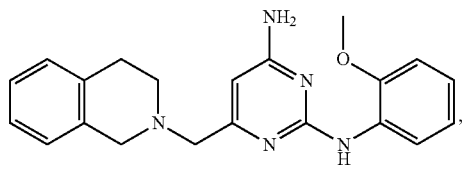

and the pharmaceutically acceptable salts and solvates thereof.

In another embodiment, the present disclosure provides a Compound of the Disclosure selected from the group consisting of

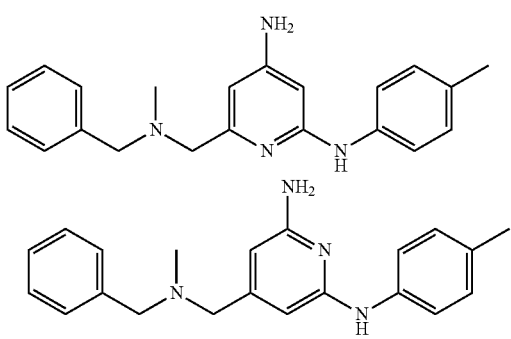

and the pharmaceutically acceptable salts and solvates thereof.

In another embodiment, Compounds of the Disclosure that may be employed in the method of the present disclosure include:

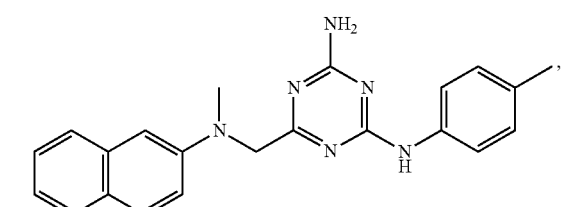

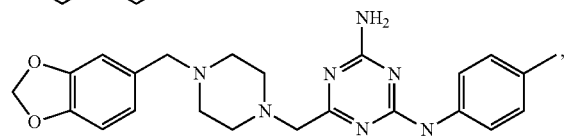

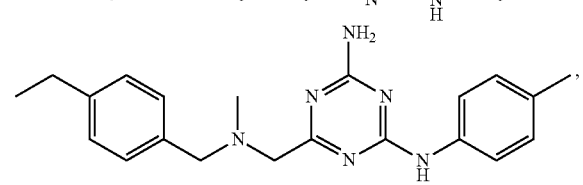

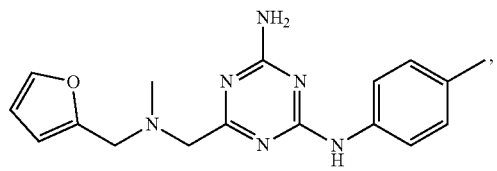

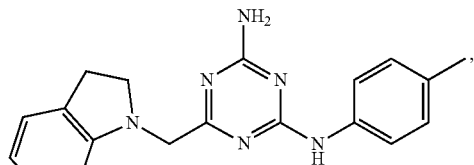

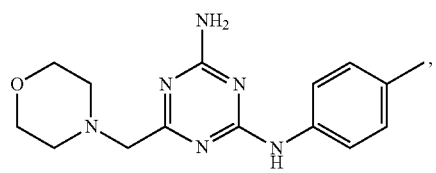

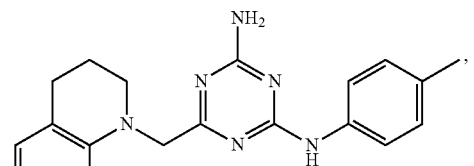

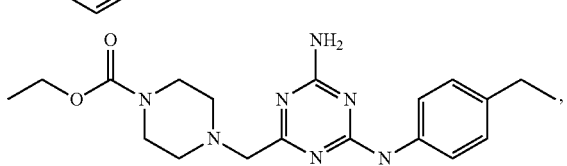

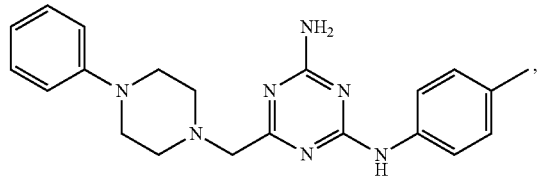

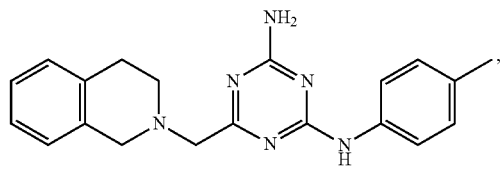

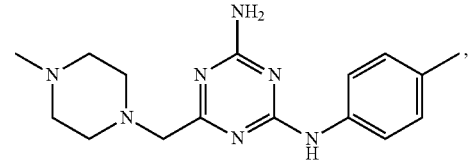

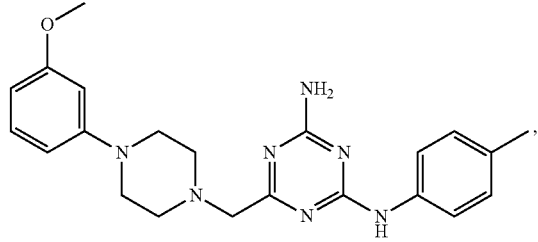

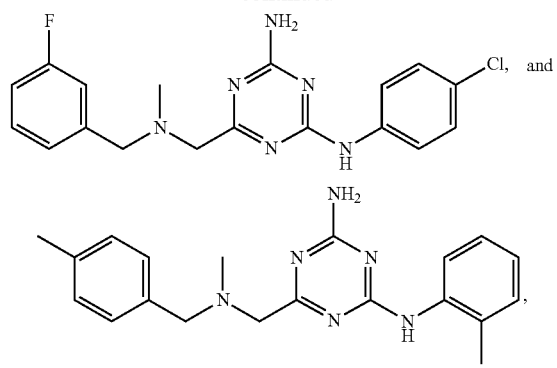
and the pharmaceutically acceptable salts and solvates thereof.
In another embodiment, Compounds of the Disclosure that may be employed in the method of the present disclosure include:
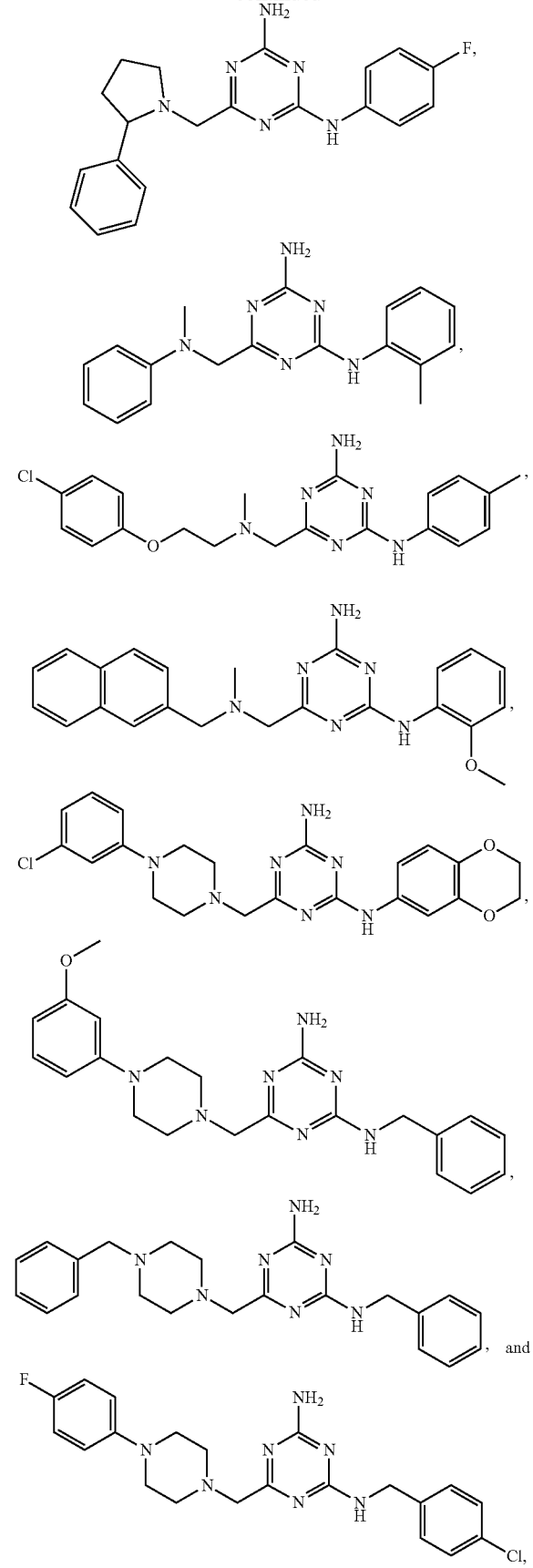

and the pharmaceutically acceptable salts and solvates thereof.

As used herein, the terms "halogen" or "halo" refer to —F, —Cl, —Br, or —I.

As used herein, the term "hydroxyl" or "hydroxy" refers to the group —OH.

As used herein, the term "alkyl" refers to a linear or branched hydrocarbon chain radical consisting of carbon and hydrogen atoms, containing no unsaturation, which is attached to the rest of the molecule by a single bond and, unless otherwise specified, an alkyl radical typically has from 1 to 4 carbon atoms, i.e., $C_{1-4}$ alkyl. Exemplary $C_{1-4}$ alkyl groups can be methyl, ethyl, n-propyl, i-propyl, n-butyl, tert-butyl, i-butyl and sec-butyl. In another embodiment, the alkyl is $C_{1-2}$ alkyl (methyl or ethyl).

As used herein, the term "$C_{1-4}$ alkoxy" refers to oxygen substituted by one of the $C_{1-4}$ alkyl groups mentioned above (e.g., methoxy, ethoxy, propoxy, iso-propoxy, butoxy, tert-butoxy, iso-butoxy, and sec-butoxy), for example by one of the $C_{1-2}$ alkyl groups.

As used herein, the term "cycloalkyl" embraces saturated cart cyclic radicals and, unless otherwise specified, a cycloalkyl radical typically has from 3 to 6 carbon atoms. Examples of cycloalkyl groups include cyclopropyl, cyclobutyl, cyclopentyl, cyclohexyl and cycloheptyl. It is, for example, cyclopropyl, cyclopentyl and cyclohexyl. In another embodiment, the cycloalkyl group is $C_{3-10}$ cycloalkyl.

As used herein, the term "alkylcycloalkyl" when employed in the definition of a substituent refers to a cycloalkyl group as defined above which is linked through an alkylene radical, such as $C_{1-4}$ alkylene, with the core structure which it substitutes. As an example, a cyclopentylethyl substituent is a substituent consisting of a cyclopentyl group linked through an ethylene group to the core structure which it substitutes.

As used herein, the terms "heterocyclyl" or "heterocyclic group" embrace typically a monocyclic or polycyclic, non-aromatic, saturated or unsaturated $C_{2-10}$ carbocyclic ring, such as a 5- to 10-membered radical, in which one or more, for example 1, 2, 3 or 4 of the carbon atoms, for example, 1 or 2 of the carbon atoms are replaced by a heteroatom selected from N, O and S. In one embodiment, the heterocyclyl is a $C_{3-7}$ heterocyclyl, i.e., a heterocycle having 3-7 carbon atoms and at least one heteroatom. In another embodiment, a heterocyclyl is a (5- to 10-membered)-$C_{2-9}$ heterocyclyl, i.e., a heterocycle having 5- to 10-members, of which 2-9 members are carbon. In another embodiment, the heteroatom is N. In another embodiment, the heteroatom is O.

In another embodiment, the heterocyclyl radicals are saturated. A heterocyclic radical can be a single ring or two or more fused rings wherein at least one ring contains a heteroatom. When a heterocyclyl radical carries one or more substituents, the substituents can be the same or different.

A said optionally substituted heterocyclyl is typically unsubstituted or substituted with 1, 2 or 3 substituents which can be the same or different. Examples of heterocyclic radicals include piperidyl, pyrrolidyl, pyrrolinyl, piperazinyl, morpholinyl, thiomorpholinyl, pyrazolinyl, pyrazolidinyl, quinuclidinyl, tetrazolyl, cromanyl, isocromanyl, imidazolidinyl, oxiranyl, azaridinyl, 4,5-dihydro-oxazolyl and 3-aza-tetrahydrofuranyl. The substituents are, for example, selected from halogen atoms, for example, fluorine or chlorine atoms, hydroxy groups, alkoxycarbonyl groups in which the alkyl moiety has from 1 to 4 carbon atoms, hydroxycarbonyl groups, carbamoyl groups, nitro groups, cyano groups, $C_{1-4}$ alkyl groups optionally substituted by one or more halogen atoms, $C_{1-4}$ alkoxy groups, optionally substituted by one or more halogen atoms and $C_{1-4}$ hydroxyalkyl groups.

As used herein, the term "alkylheterocyclyl" when employed in the definition of a substituent refers to a heterocyclyl group as defined above which is linked through an alkylene radical with the core structure which it substitutes. In one embodiment, the alkylheterocyclyl is a —$C_{1-4}$ alkyl-(5- to 10-membered)-$C_{2-9}$ heterocyclyl.

As used herein, the term "aryl" designates typically a $C_{6-10}$ monocyclic or polycyclic aryl radical such as phenyl and naphthyl. In another embodiment, the aryl is phenyl. A said optionally substituted aryl radical is typically unsubstituted or substituted with 1, 2 or 3 substituents which can be the same or different. The substituents are, for example, selected from halogen atoms, for example, fluorine or chlorine atoms, hydroxy groups, alkoxycarbonyl groups in which the alkyl moiety has from 1 to 4 carbon atoms, hydroxycarbonyl groups, carbamoyl groups, nitro groups, cyano groups, $C_{1-4}$ alkyl groups optionally substituted by one or more halogen atoms, $C_{1-4}$ alkoxy groups, optionally substituted by one or more halogen atoms and $C_{1-4}$ hydroxyalkyl groups. When an aryl radical carries 2 or more substituents, the substituents can be the same or different. Unless otherwise specified, the substituents on an aryl group are typically themselves unsubstituted.

As used herein, the term "alkylaryl" when employed in the definition of a substituent refers to an aryl group as defined above which is linked through an alkylene radical, such as $C_{1-4}$ alkylene, with the core structure which it substitutes.

As used herein, the term "heteroaryl" designates typically a 5- to 10-membered ring system, comprising at least one heteroaromatic ring and containing at least one heteroatom selected from O, S and N, typically 1, 2, 3, or 4 heteroatoms.

A heteroaryl group can comprise a single ring or two or more fused rings wherein at least one ring contains a heteroatom. A said optionally substituted heteroaryl group is typically unsubstituted or substituted with 1, 2 or 3 substituents which can be the same or different. The substituents are, for example, selected from halogen atoms, for example, fluorine, chlorine or bromine atoms, alkoxycarbonyl groups in which the alkyl moiety has from 1 to 4 carbon atoms, carbamoyl groups, nitro groups, hydroxy groups, $C_{1-4}$ alkyl groups, optionally substituted by one or more halogen atoms and $C_{1-4}$ alkoxy groups, optionally substituted by one or more halogen atoms. When a heteroaryl radical carries 2 or more substituents, the substituents can be the same or different. Unless otherwise specified, the substituents on a heteroaryl radical are typically themselves unsubstituted.

Examples of heteroaryl groups include pyridyl, pyrazinyl, pyrimidinyl, pyridazinyl, furyl, tetrazolyl, benzofuranyl, oxadiazolyl, oxazolyl, isoxazolyl, benzoxazolyl, imidazolyl, benzimidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo[3,4-d]pyrimidinyl, 1H-pyrazolo[3,4-d]pyrimidinyl, thieno[2,3-d]pyrimidinyl, and the various pyrrolopyridyl radicals.

In another embodiment, the heteroaryl is a (5- to 10-membered)-$C_{2-9}$ heteroaryl. In another embodiment, the heteroaryl is optionally substituted with 1, 2, or 3 groups independently selected from the group consisting of halogen, hydroxy, —CN, —ORb, —SRb, —N(Rb)$_2$, —$C_{1-}$ ₄alkyl optionally substituted with 1, 2, or 3 halogen atoms, optionally substituted $C_{6-10}$ aryl, optionally substituted (5- to 10-membered)-$C_{1-9}$ heteroaryl, and (5- to 10-membered)-$C_{2-9}$ heterocyclyl; said cycloalkyl, alkylcycloalkyl, aryl, alkylaryl, heteroaryl, alkylheteroaryl, heterocyclyl, and alkylheterocyclyl is optionally fused to a further (second) ring.

The mention of optionally substituted heteroaryl radicals or rests within the present disclosure is intended to cover the N-oxides obtainable from these radicals when they comprise N-atoms.

As used herein, the term "alkylheteroaryl" when employed in the definition of a substituent refers to an heteroaryl group as defined above which is linked through an alkylene radical with the core structure which it substitutes. In another embodiment, the alkylheteroaryl is a —$C_{1-4}$ alkyl-(5- to 10-membered)-$C_{1-9}$ heteroaryl.

The term "pharmaceutically acceptable" refers to compositions and molecular entities that are physiologically tolerable and do not typically produce an allergic reaction or a similar unfavorable reaction, such as gastric disorders, dizziness and suchlike, when administered to a human or animal. For example, the term "pharmaceutically acceptable" means it is approved by a regulatory agency of a state or federal government or is included in the U.S. Pharmacopoeia or other generally recognized pharmacopoeia for use in animals, and more particularly in humans.

The term "treatment" or "treating" refers to administering a therapy in an amount, manner or mode effective to improve a condition, symptom, or parameter associated with a condition or to prevent progression of a condition, to either a statistically significant degree or to a degree detectable to one skilled in the art. An effective amount, manner, or mode can vary depending on the subject and can be tailored to the patient.

The term "about", as used herein in connection with a measured quantity, refers to the normal variations in that measured quantity, as expected by the skilled artisan making the measurement and exercising a level of care commensurate with the objective of measurement and precision of the measuring equipment. Typically, the term "about" includes the recited number±10%. Thus, "about 10" means 9 to 11.

As used herein, the term "optionally substituted" refers to a group that can be unsubstituted or substituted.

The term "solvate" means any form of the active compound of the disclosure which has another molecule (for example a polar solvent such as water or ethanol, a cyclodextrin or a dendrimer) attached to it through noncovalent bonds. Methods of solvation are known within the art.

The disclosure also provides salts of the Compounds of the Disclosure. Non-limiting examples are sulphates; hydrohalide salts; phosphates; lower alkane sulphonates; arylsulphonates; salts of $C_{1-20}$ aliphatic mono-, di- or tribasic acids which can contain one or more double bonds, an aryl nucleus or other functional groups such as hydroxy, amino, or keto; salts of aromatic acids in which the aromatic nuclei may or may not be substituted with groups such as hydroxyl, lower alkoxyl, amino, mono- or di-lower alkylamino sulphonamido. Also included within the scope of the disclosure are quaternary salts of the tertiary nitrogen atom with lower alkyl halides or sulphates, and oxygenated derivatives of the tertiary nitrogen atom, such as the N-oxides. In preparing dosage formulations, those skilled in the art will select the pharmaceutically acceptable salts.

Solvates and salts can be prepared by methods known in the state of the art. Note that the non-pharmaceutically acceptable solvates also fall within the scope of the disclosure because they can be useful in preparing pharmaceutically acceptable salts and solvates.

The Compounds of the Disclosure also seek to include compounds that differ only in the presence of one or more isotopically enriched atoms. For example, compounds having the present structures except for the replacement of a hydrogen by a deuterium or tritium, or the replacement of a carbon by a carbon enriched in $^{11}C$, $^{13}C$ or $^{14}C$ or the replacement of a nitrogen by a $^{15}N$ enriched nitrogen are within the scope of this disclosure.

Some of the compounds disclosed herein can contain one or more asymmetric centers and can thus give rise to enantiomers, diastereomers, and other stereoisomeric forms, such as epimers. The present disclosure is meant to encompass the uses of all such possible forms, as well as their racemic and resolved forms and mixtures thereof. The individual enantiomers can be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "epimer" refers to diastereomers that have opposite configuration at only one of two or more tetrahedral streogenic centers present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

Some reactions for preparing Compounds of the Disclosure involve employing amino protecting groups. As used herein, an "amine protecting group" or "amino protecting group" refers to a group that blocks (i.e., protects) the amine functionality while reactions are carried out on other functional groups or parts of the molecule. Those skilled in the art will be familiar with the selection, attachment, and cleavage of amine protecting groups and will appreciate that many different protective groups are know in the art, the suitability of one protective group or another being dependent on the particular synthetic scheme planned. Treatises on the subject are available for consultation, such as Wuts, P. G. M. & Greene, T. W., *Greene's Protective Groups in Organic Synthesis,* 4rd Ed. (J. Wiley & Sons, 2007), herein incorporated by reference in its entirety. Suitable amine protecting groups include methyl carbamate, tert-butyloxycarbonyl (tert-butyl carbamate; BOC), 9-fluorenylmethyl carbamate, benzyl carbamate, 2-(trimethylsilyl)ethyl carbamate, trifluoroacetamide, benzylamine, allylamine, tritylamine, trichloroacetyl, trifluoroacetyl, p-toluenesulfonyl, and allyl carbamate. In another embodiment, the protected amino group can be a phthalimide-protected amino group (NPhth).

As used herein, the term "enzyme replacement therapy" or "ERT" refers to administering an exogenously-produced natural or recombinant enzyme or analog thereof to a patient in need thereof. In the case of a lyosomal storage disease, for example, the patient accumulates harmful levels of a substrate (i.e., material stored) in lysosomes due to a deficiency or defect in an enzyme responsible for metabolizing the substrate, or due to a deficiency in an enzymatic activator required for proper enzymatic function. Enzyme replacement therapy is provided to the patient to reduce the levels of (i.e., debulk) accumulated substrate in affected tissues. Enzyme replacement therapies for treating lysosomal storage diseases are known in the art. In accordance with a combination therapy of the disclosure, a lysosomal enzyme, e.g., β-glucocerebrosidase, can be used for enzyme replacement therapy to reduce the levels of corresponding substrate, e.g., β-glucocerebroside, in a patient having a lysosomal storage disease such as Gaucher's disease.

As used herein, the term "substrate reduction therapy" or "SRT" is a therapeutic approach used to treat certain metabolic disorders, e.g., lysosomal storage disorders, in which substrate, e.g., glycolipid, accumulation is counteracted not by replacing the deficient enzyme but by reducing the substrate level to better balance residual activity of the deficient enzyme. See, e.g., Coutinho et al., *Int. J. Mol. Sci.* 17:1065 (2016). Substrate reduction therapy and enzyme replacement therapy (see above) can have unique, independent, and potentially complementary mechanisms of action in the treatment of lyosomal storage disease and other diseases.

The general principle of SRT is that a substrate reduction agent is administered to a patient to partially inhibit the biosynthesis of the substrate, which accumulates in the absence of a specific lysosomal enzyme. As used herein, the term "substrate reduction agent" is a small molecule that reduces the number of substrate molecules requiring catabolism within the lysosome, thus contributing to balance the rate of synthesis with the impaired rate of catabolism. Substrate reduction agents are known in the art.

As used herein, an "effective amount" of an enzyme, when administered to a subject in a combination therapy of the disclosure, is an amount sufficient to improve the clinical course of a lyosomal storage disease, where clinical improvement is measured by any of the variety of defined parameters well known to the skilled artisan.

As used herein the term "small molecule chaperone" refers to a compound, other than a Compound of the Disclosure, that is capable of binding allosterically or competitively to a mutated enzyme, e.g., β-galactosidase, thereby stabilizing the enzyme against degradation. In some embodiments, the small molecule chaperone facilitates proper folding and transport of an enzyme to its site of action. Small molecule chaperones for the treatment of lysosomal storage diseases are known in the art. See, e.g., US 2016/0207933 A1 and WO 2011/049737 A1.

Synthesis of Compounds of the Disclosure

Another aspect of the disclosure refers to procedures to obtain compounds of formula (I). The following methods describe the procedures for obtaining compounds of general formula (I), or solvates or salts thereof.

Various synthetic routes for synthesizing compounds of formula (I) are summarized in the schemes below.

Scheme 1 illustrates the synthetic path to obtain compounds of formula (I) wherein $A^1=A^2=A^3=N$. These compounds have formula (Ia).

Scheme 2 illustrates the synthetic path to obtain compounds of formula (I). These compounds have formula (Ib).

Scheme 3 and 4 illustrates the synthetic path to obtain compounds of formula (I) wherein $A^1$, $A^2$ and $A^3$ can be nitrogen atoms in different combinations. These compounds have formula (Ib).

Scheme 5 illustrates the synthetic path to obtain compounds of formula (I). These compounds have formula (Ic).

Scheme 6 illustrates the synthetic path to obtain compounds of formula (I). These compounds have formula (Id).

Scheme 7 illustrates the synthetic path to obtain compounds of formula (I) wherein only one of $A^1$, $A^2$ and $A^3$ can be nitrogen atoms. These compounds have formula (Ie).

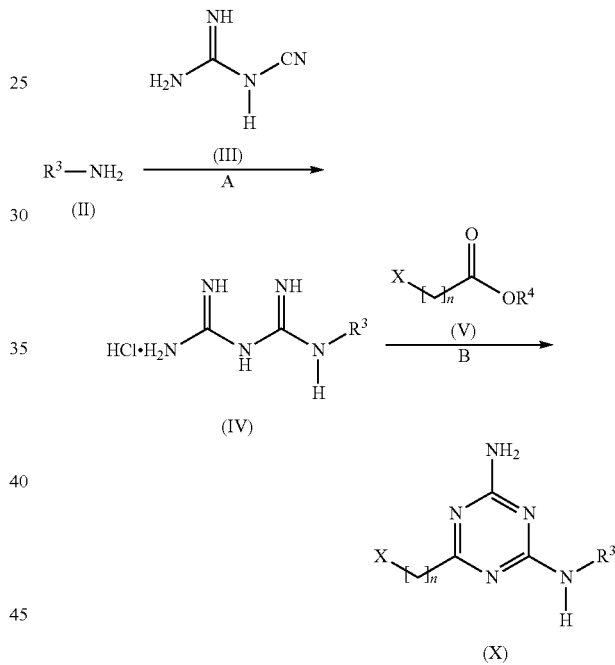

Scheme 1

$R^4$ = Me or Et
$X = $ —$NR^1R^2$, —OPG, —CN, —CHO, —$CO_2R^4$ $R^1$, $R^2$, $R^3$, and n are as defined above for formula (I).

Method 1

Step 1 (Reaction A)

In a first method, according to the disclosure, a compound of formula (II) wherein $R^3$ as defined above is reacted with a dicyandiamide (III) to yield a biguanidine compound of formula (IV) as illustrated in reaction A of the scheme above (Scheme 1).

Reaction A is used to prepare compounds of formula (IV) by reaction of compound of formula (II) with a compound of formula (III). Said reaction can be performed under standard conditions in the presence of a suitable acid or base (e.g., copper sulfate, sodium carbonate, ammonia, methanolic sodium methoxide, hydrogen chloride, hydrogen sulfide or mixtures thereof) and an appropriate solvent (e.g., butanol, water, tetrahydrofuran, xylene, acetone, methanol, ethanol, acetonitrile, 2-propanol, dichloromethane dimethylformamide, dimethylsulfoxide or mixture thereof) and, for example, at around room temperature, reflux temperature or microwave irradiation reaction conditions.

The reaction can also be carried out in the presence of an appropriate catalyst (or salt thereof) such as iron (III) chloride or copper (II) chloride and also optionally in the presence of an additive or protecting groups such as chlorotrimethylsilane or trimethylsilyl trifluoromethanesulfonate.

The reaction can be carried out with protecting groups present and those protecting groups can be removed after the reaction. Suitable protecting groups are known to the person skilled in the art (see T. W. Greene, "Protective Groups in Organic Synthesis," 3rd Edition, New York, 1999).

Step 2 (Reaction B)

The biguanidine (hydrochloride salt or not) compound of formula (IV) is subsequently reacted with a compound of formula (V), wherein X can be —NR$^1$R$^2$, —OPG, —CN, —CHO or —CO$_2$R$^4$, where PG is a protecting group and each of R$^1$ and R$^2$ is defined above and R$^4$ can be methyl or ethyl, to yield a compound of formula (X) as illustrated in reaction B of the scheme above (Scheme 1).

Reaction B is carried out under standard condensation conditions, for example in the presence of a suitable base (e.g., sodium hydride, sodium methoxide, sodium ethoxide, sodium tert-butoxide, 1,8-diazabicyclo(5.4.0)undec-7-ene or potassium carbonate) and an appropriate solvent (e.g., ethanol, methanol, dimethylformamide or mixture thereof) and for example at around room temperature or reflux temperature.

The reaction can be carried out with protecting groups present and those protecting groups can be removed after the reaction. Suitable protecting groups are known to the person skilled in the art (see T. W. Greene, "Protective Groups in Organic Synthesis," 3rd Edition, New York, 1999).

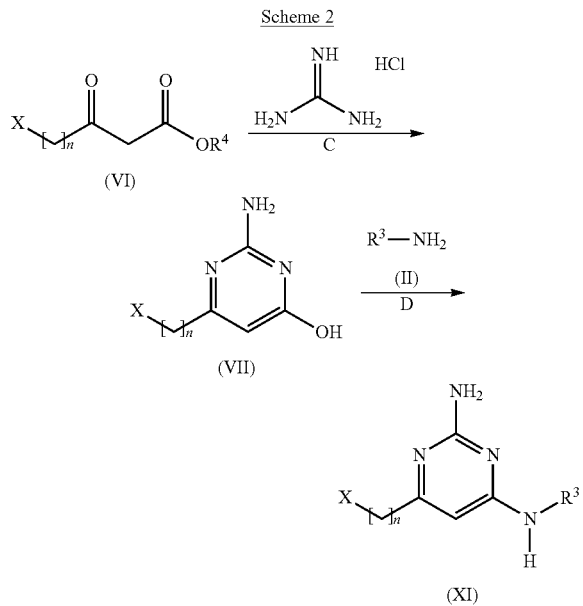

Scheme 2

R$^4$ = Me or Et
X = —NR$^1$R$^2$, —OPG, —CN, —CHO, —CO$_2$Me

R$^1$, R$^2$, R$^3$, and n are as defined above for formula (I).

Method 2
Step 1 (Reaction C)

In a third method, according to the disclosure, a compound of formula (VI), wherein X can be —NR$^1$R$^2$, —OPG, —CN, —CHO or CO$_2$Me, where PG is a protecting group and each of R$^1$ and R$^2$ is defined above and n is as defined above, is reacted with a guanidine source, preferably guanidine hydrochloride, to yield a compound of formula (VII) according to the disclosure as illustrated in reaction C of the scheme above (Scheme 2).

Reaction C is carried out under standard condensation conditions in a suitable solvent and in the presence of a suitable base, such as those explained for step 2 of method 1 described above (Scheme 1).

The compound of formula (VI) is commercially available or can be obtained by procedures described in the literature as is known by the person skilled in the art.

The reaction can be carried out with protecting groups present and those protecting groups can be removed after the reaction. Suitable protecting groups are known to the person skilled in the art (see T. W. Greene, "Protective Groups in Organic Synthesis," 3rd Edition, New York, 1999).

Step 2 (Reaction D)

The compound of formula (VII) is subsequently reacted with a compound of formula (II) wherein R$^3$ is as defined above to yield a compound of formula (XI) as illustrated in reaction D of the scheme above (Scheme 2).

Reaction D is carried out under standard coupling conditions, in the presence of a suitable coupling agent (e.g., (benzotriazol-1-yloxy)tripyrrolidinophosphonium hexafluorophosphate) and an appropriate base (e.g., N,N-diisopropylethylamine, dimethylaniline, diethylaniline, triethylamine, 1,8-diazabicyclo[5.4.0]undec-7-ene, or triethylamine) in a suitable solvent, such as 1,4-dioxane, tetrahydrofuran, dichloromethane, dimethylformamide, acetonitrile, or mixtures thereof.

The reaction mixture is stirred at low temperature, room temperature, or heated until the starting materials have been consumed. The reaction can be carried out with protecting groups present and those protecting groups can be removed after the reaction. Suitable protecting groups are known to the person skilled in the art (see T. W. Greene, "Protective Groups in Organic Synthesis", 3rd Edition, New York, 1999).

Alternatively, the hydroxyl group of the compound of formula (VII) can be transformed into a leaving group, such as a halogen, triflate, tosylate, or mesylate group. Said chlorination reaction can be performed under standard conditions in the presence of a suitable chloride source (e.g., N-chlorosuccinimide, phosphoryl chloride, phosphorous pentachloride or sulfonyl chloride), optionally in the presence of a suitable phase transfer catalyst (e.g., benzyltriethylammonium chloride or tetramethylammonium chloride) or of a suitable base (e.g. triethylamine, pyridine, N,N-diisopropylethylamine, ammonia, ammonium chloride or 4-dimethylaminopyridine) and an appropriate solvent (e.g., acetonitrile, dichloromethane, di methyl sulfoxide, dimethylformamide, chloroform, N,N-dimethylacetamide, carbon tetrachloride or mixture thereof), and for example, at around room temperature and reflux temperature.

Alternatively, the hydroxyl group of compound of formula (VII) can be transformed into a triflate, tosylate or mesylate group by reaction of compound of formula (VII) with trifluoromethanesulphonic anhydride in the presence of a suitable base (e.g., pyridine) or p-toluenesulfonyl chloride/ methanesulfonyl chloride in a suitable solvent (e.g., dichloromethane) in the presence of an appropriate base (e.g., triethylamine or pyridine), respectively.

The reaction mixture can be stirred at room temperature or heated until the starting materials have been consumed. The reaction can be carried out with protecting groups present and those protecting groups can be removed after the reaction. Suitable protecting groups are known to the person skilled in the art (see T. W. Greene, "Protective Groups in Organic Synthesis", 3rd Edition, New York, 1999).

The leaving group is subsequently substituted by reaction with amine (II) to form the corresponding amine group to yield the compound of formula (Ib). The reaction is carried out under standard nucleophilic substitution conditions, for example in the presence of a suitable base (e.g., triethylamine, dimethylaniline, diethylaniline pyridine, potassium carbonate or N,N-diisopropylethylamine) or acid (e.g., sulfuric acid, hydrogen chloride or acetic acid) or absence of base or acid, optionally in the presence of a suitable catalyst, ligand and base (e.g., Pd(dba)$_2$, XantPhos and cesium carbonate) and an appropriate solvent (e.g., ethanol, water, acetonitrile, N,N-dimethylacetamide, propanol, N-methylpyrrolidine, 1-methylpiperizine, dioxane, ethanol, methanol, butanol, dimethylformamide, dimethylsulphoxide, tetrahydrofuran, acetonitrile, toluene or mixture thereof).

The reaction mixture is stirred at low temperature, room temperature, reflux temperature, or microwave irradiation reaction conditions. The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).

Scheme 3

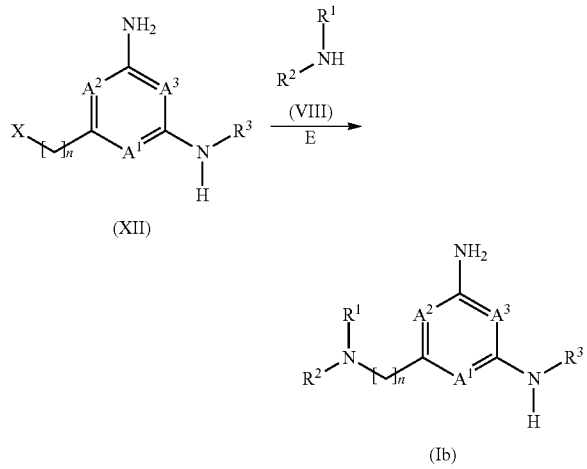

X = —OPG, —CN, —CHO, —CO$_2$R$^4$
R$^4$ = Me or Et

R$^1$, R$^2$, R$^3$, and n are as defined above for formula (I).
Method 3 (Reaction E)

In another method, according to the disclosure, a compound of formula (XII), wherein A$^1$, A$^2$, A$^3$, R$^3$ and n are as defined above and X can be different amine precursors, such as —OPG, —CHO, —CN or —CO$_2$R$^4$, where PG is a protecting group, is reacted with an amine (VIII), wherein R$^1$ and R$^2$ are as defined above, to yield a compound of formula (Ib) according to the disclosure as illustrated in reaction E of the scheme above (Scheme 3).

When X=—OPG and —CHO

The alcohol compound of formula (XII) is deprotected by standard methods and subsequently transformed in the corresponding aldehyde under standard oxidation conditions, for example, in the presence of a suitable oxidative agent (e.g., oxalyl chloride, manganese oxide or sulfur trioxide pyridine complex) and an appropriate base, such as triethylamine in a suitable solvent (e.g., dichloromethane, tetrahydrofuran, dimethylsulfoxide or mixtures thereof). The reaction mixture can be stirred at room temperature or heated until the starting materials have been consumed.

The aldehyde of the compound of formula (Ib) is subsequently converted by reaction with the amine (Viii) to a corresponding amine group to yield the compound of formula (Ib) according to the disclosure as illustrated in reaction E of the scheme above (Scheme 3). This transformation is carried out under standard condensation conditions, for example, in the presence of an appropriate reducing agent (e.g., sodium cyanoborohydride or sodium triacetoxyborohydride), alternatively in the presence of a suitable acid, such as acetic acid and appropriate solvent (e.g., dichloromethane, dichloroethane, methanol, toluene or mixture thereof).

The reaction can be carried out with protecting groups present and those protecting groups can be removed after the reaction. Suitable protecting groups are known to the person skilled in the art (see T. W. Greene, "Protective Groups in Organic Synthesis," 3rd Edition, New York, 1999).
When X=-LG The X group of the compound of formula (XII) is converted into a leaving group by standard methods, for instance the hydroxyl group of compound of formula (XII) can be transformed into a leaving group such as halogen, triflate, tosylate or a mesylate group.

The leaving group of the compound of formula (XII) is converted by reaction with an amine (VIII) to a corresponding amine group to yield the compound of formula (Ib) according to the disclosure as illustrated in reaction E of the scheme above (Scheme 3). Reaction E is carried out under standard nucleophilic substitution conditions, for example in the presence a suitable base (e.g., N,N-diisopropylethylamine, 4-dimethylaminopyridine, 2,6-lutidine, triethylamine, pyridine, ammonium chloride, sodium hydride, potassium carbonate, sodium carbonate, sodium hydrogen carbonate, sodium hydroxide, sodium acetate or sodium nitrite) and an appropriate solvent (e.g., acetonitrile, dichloromethane, tetrahydrofuran, benzene, diethyl ether, toluene, dimethylformamide, water, ethanol or mixture thereof). Such reactions can be used a base or acid in a further step such as, acetic acid, hydrogen chloride or sodium hydroxide.

The reaction mixture is stirred at a low temperature or room temperature, or heated until the starting materials have been consumed. The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).
When X=—CN The cyano group of the compound of formula (XII) is subsequently reduced in the appropriate aldehyde group under standard reductive conditions in the presence of a suitable reducing agent or catalyst (e.g., diisobutylaluminum hydride, sodium hypophosphite, lithium aluminum hydride, nickel, aluminum oxide, platinum oxide), an appropriate solvent (e.g., dichloromethane, tetrahydrofuran, ether, methanol, ethanol, water or mixture thereof) and for example, at around −78° C., room temperature, reflux or microwave irradiation reaction conditions. The reaction can also be carried out in the presence of an acid, such as acetic acid or base (e.g., pyridine) or under hydrogen atmosphere.

The aldehyde group can be subsequently converted to the corresponding amine under standard conditions, such as those explained for Method 3, when X is CHO.

The cyano compound can be prepared by reaction of the compound when X=−LG with a cyanide source. Said reaction can be performed under standard cyanation conditions in the presence of a suitable cyanide source (e.g., zinc cyanide) under the catalysis of a suitable catalyst, such as tetrakis(triphenylphosphine) palladium(0), in a suitable solvent (e.g., tetrahydrofuran, toluene, dimethylformamide, N-methylpyrrolidone or mixture thereof) at around room temperature or reflux temperature.

When $X=-CO_2R^4$

The ester of the compound of formula (XII) is subsequently converted to a substituted amide group to yield the compound of formula (Ib) according to the disclosure as illustrated in reaction E of the scheme above (Scheme 3).

Reaction E is carried out under standard amidation conditions, for example in the presence of a suitable metal or base catalyst (e.g., trimethylaluminum, antimony(III) ethoxide, indium(III) iodide, titanium(IV) isopropoxide, zirconium(IV) tert-butoxide, hafnium(IV) tert-butoxide, zinc dust, sodium methoxide, potassium methoxide, 1,8-Diazabicyclo[5.4.0]undec-7-ene, 1,3-bis(2,4,6-trimethylphenyl)-imidazolium, (PNN)Ru(II), Di-µ-chloro-bis[chloro-(pentamethyl-cyclopentadienyl)-iridium(III)], lanthanum(III) trifluoromethane-sulfonate, or magnesium nitride), optionally in the presence of a suitable additive (e.g., 1-hydroxy-7-azabenzotriazole, 1-hydroxybenzotriazole, hydroxyproline, or 4-trifluoromethylphenol) and an appropriate solvent (e.g., methanol, tetrahydrofuran, acetonitrile, 2-methyltetrahydrofuran, toluene, benzene, dichloromethane, water, chloroform dimethylformamide, or mixtures thereof) or absence of solvent. Such reactions can be performed in the presence of a further base, such as potassium tert-butoxide or sodium acetate.

This reaction can be carried out under microwave irradiation reaction conditions.

Alternatively, the ester group can be hydrolyzed to the carboxylic acid group following standard methods and then the acid can be converted to the amide under standard condensation or amide coupling conditions, for example in the presence of a suitable coupling agent (e.g., 1,1'-carbonyldiimidazole, N,N'-cyclohexylcarbodiimide, 1-(3-dimethylaminopropyl)-3-ethylcarbodiimide (or hydrochloride thereof), N,N'-disuccinimidyl carbonate, benzotriazol-1-yloxytris(dimethylamino)phosphonium hexafluoro-phosphate, 2-(1H-benzotriazol-1-yl)-1,1,3,3-tetramethyluronium hexafluorophosphate (i.e. O-(1H-benzotriazol-1-yl)-N,N,N',N'-tetramethyluronium hexafluorophosphate), benzotriazol-1-yloxytris-pyrrolidinophosphonium hexafluorophosphate, bromo-tris-pyrrolidinophosphonium hexafluorophosphate, 2-(1H-benzotriazol-1-yl)-1,1,3,3-tetramethyluronium tetrafluorocarbonate, 1-cyclohexylcarbodiimide-3-propyloxymethyl polystyrene, O-(7-azabenzotriazol-1-yl)-N,N,N',N'-tetramethyluronium hexafluorophosphate, or O-benzotriazol-1-yl-N,N,N',N'-tetramethyluronium hexfluoroborate), optionally in the presence of a suitable base (e.g., sodium hydride, sodium bicarbonate, potassium carbonate, pyridine, triethylamine, dimethylaminopyridine, diisopropylamine, sodium hydroxide, potassium tert-butoxide, and/or lithium diisopropylamide (or variants thereof)) and an appropriate solvent (e.g., tetrahydrofuran, pyridine, toluene, dichloromethane, chloroform, acetonitrile, dimethylformamide, trifluoromethylbenzene, dioxane, or triethylamine). Such reactions can be performed in the presence of a further additive, such as 1-hydroxybenzotriazole hydrate.

The reaction mixture is stirred at a low temperature or room temperature, or heated until the starting materials have been consumed. The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).

Subsequently, the amide group is reduced to the corresponding amine in the presence of a suitable reducing agent (e.g., aluminum hydride or borane) and an appropriate solvent, such as tetrahydrofuran, dichloromethane, dioxane, toluene or a mixture thereof, at around room temperature or reflux temperature. Every reaction can be carried out with protecting groups present and those protecting groups can be removed after the reaction. Suitable protecting groups are known to the person skilled in the art (see T. W. Greene, "Protective Groups in Organic Synthesis," 3rd Edition, New York, 1999).

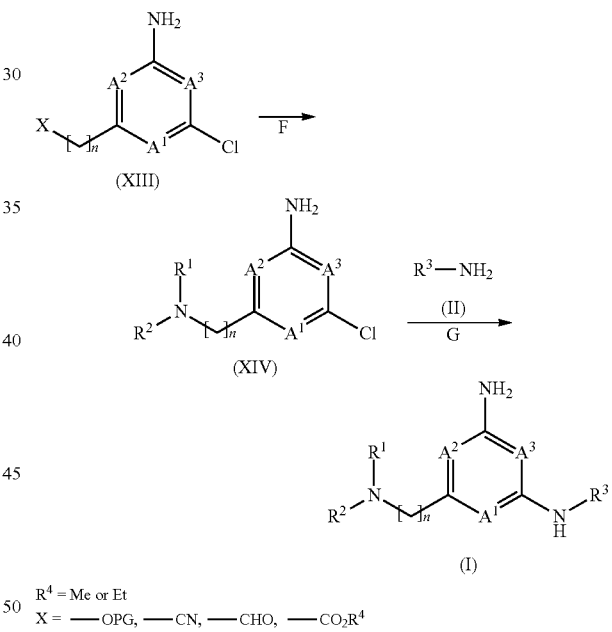

$R^4$ = Me or Et
X = —OPG, —CN, —CHO, —$CO_2R^4$ $R^1$, $R^2$, $R^3$, and n are as defined above.

Method 4

Step 1 (Reaction F)

In another method, according to the disclosure, in a compound of formula (XIII), wherein $A^1$, $A^2$, $A^3$ and n are defined above and X can be different amine precursors, such as —OPG, —CHO, —CN or —$CO_2R^4$, where PG is a protecting group, the group X can be transformed into the $NR^1R^2$ group before the final amine —$NHR^3$ to yield (Ib) according to the disclosure as illustrated in reaction F of the scheme above (Scheme 4) following standard conditions like the ones described in reaction E of Scheme 3.

The reaction can be carried out with protecting groups present, for instance on the —$NH_2$ moiety, and those protecting groups can be removed after reaction. Suitable protecting groups are known to the person skilled in the art, for instance 2,4,4-trimethylpentan (see T. W. Greene, "Protective Groups in Organic Synthesis," 3rd Edition, New York, 1999).

Step 2 (Reaction G)

Compound of formula (XIV) is subsequently reacted with compound of formula (II), wherein $R^3$ is defined above to yield a compound of formula (I) as illustrated in reaction G of the scheme above (Scheme 4).

Reaction G is carried out under standard nucleophilic substitution conditions in a suitable solvent and in the presence of a suitable base, such as those explained for reaction D (Scheme 2).

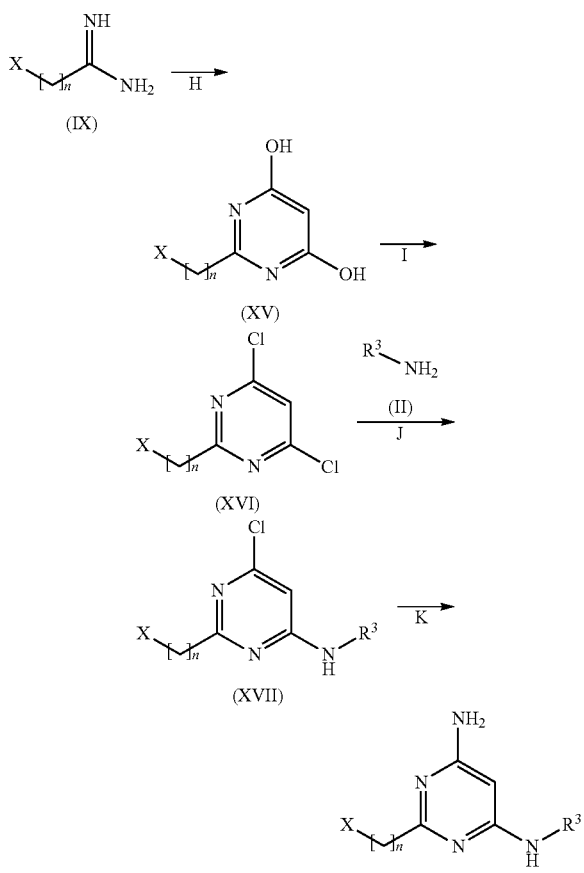

$R^4$ = Me or Et
X = —$NR^1R^2$, —OPG, —CN, —CHO, —$CO_2R^4$ $R^1$, $R^2$, $R^3$, and n are as defined above.

Method 5
Step 1 (Reaction H)

In another method, according to the disclosure, a compound of formula (IX), wherein X can be —$NR^1R^2$, —OPG, —CN, —CHO or $CO_2Me$, where PG is a protecting group and each of $R^1$ and $R^2$ and n is as defined above, is reacted with diethyl malonate to yield a compound of formula (XV) as illustrated in reaction H of the scheme above (Scheme 5).

Reaction H is carried out under standard condensation conditions in a suitable solvent and in the presence of a suitable) base, such as those explained for step 2 of method 1 described above (Scheme 1).

Compounds of formula (IX) are commercially available or can be obtained by procedures described in the literature as is known by the person skilled in the art.

Step 2 (Reaction I)

Subsequently, the hydroxyl groups of the compound of formula (XV) are transformed to chlorides to yield a compound of formula (XVI) according to the disclosure as illustrated in reaction I of the Scheme 5 above.

Reaction I is carried out Under standard chlorinated conditions, in the presence of appropriate chlorinated agents, such as phosphoryl chloride, phosphorus pentachloride, cobalt chloride or bis(trichloromethyl) carbonate, and a suitable base (e.g., triethylamine, N,N-diethylaniline, N,N-diisopropylethylamine or 4-(dimethylamino)pyridine) and an appropriate solvent, such as dimethylformamide, dichloromethane, tetrahydrofuran or mixture thereof.

The reaction mixture is stirred at a low temperature, room temperature, or heated until the starting materials have been consumed. The reaction can be carried out with protecting groups present and those protecting groups can be removed after reaction. Suitable protecting groups are known to the person spilled in the art (see T. W. Greene, "Protective Groups in Organic Synthesis," 3rd Edition, New York, 1999).

Step 3 (Reaction J)

One of the chlorides of the compound of formula (XVI) is subsequently substituted by reaction with an amine (II) to form the corresponding amino group to yield the compound of formula (XVII) according to the disclosure as illustrated in reaction J of the scheme above (Scheme 5).

Reaction J is carried out under standard nucleophilic substitution conditions, for example in the presence of a suitable base (e.g., triethylamine, pyridine, potassium carbonate or N,N-diisopropylethylamine) or acid (e.g., sulfuric acid, hydrogen chloride or acetic acid) or absence of base or acid, optionally in the presence of a suitable catalyst, ligand and base (e.g., Pd(dba)$_2$, XantPhos and cesium carbonate) and an appropriate solvent (e.g., ethanol, water, acetonitrile, N,N-di methyl net am ide, propanol, N-methylpyrrolidine, 1-methylpiperizine, dioxane, butanol or a mixture thereof).

The reaction mixture is stirred at a low temperature, room temperature, or heated until the starting materials have been consumed. The reaction can be carried out with protecting groups present and those protecting groups can be removed after reaction. Suitable protecting groups are known to the person skilled in the art (see T. W. Greene, "Protective Groups in Organic Synthesis," $3^{rd}$ Edition, New York, 1999).

Step 4 (Reaction K)

The remaining chloride of the compound of formula (XVII) is subsequently substituted by reaction with amine to form the corresponding amino group to yield the compound of formula (XVIII) according to the disclosure as illustrated in reaction K of the scheme above (Scheme 5). Reaction K is used to prepare compounds of formula (XVIII) by reaction of compound of formula (XVII) with the appropriate amine. Said reaction can be performed under standard conditions in the presence of a suitable palladium catalyst, such as Pd(dba)$_2$, palladium acetate or Pd$_2$(dba)$_3$, the appropriate base (cesium carbonate or triethylamine, among others) and a suitable ligand, such as 1,2,3,4,5-Pentaphenyl-1'-(di-tert-butylphosphino)ferrocene, Xantphos or XPhos, in the appropriate solvent (e.g., butanol, toluene, dioxane or mixture thereof) and, for example, at around room temperature or reflux temperature.

Alternatively, the transformation can be carried out in the presence of a suitable base (e.g., N,N-Diisopropylethylamine or triethylamine) and an appropriate solvent, such as dimethyl sulphoxide, tetrahydrofuran, dichloromethane, acetonitrile, dimethylformamide, methanol, ethanol, or a mixture thereof.

The reaction can be carried out with protecting groups present and those protecting groups can be removed after reaction. Suitable protecting groups are known to the person skilled in the art (see T. W. Greene, "Protective Groups in Organic Synthesis," 3$^{rd}$ Edition, New York, 1999).

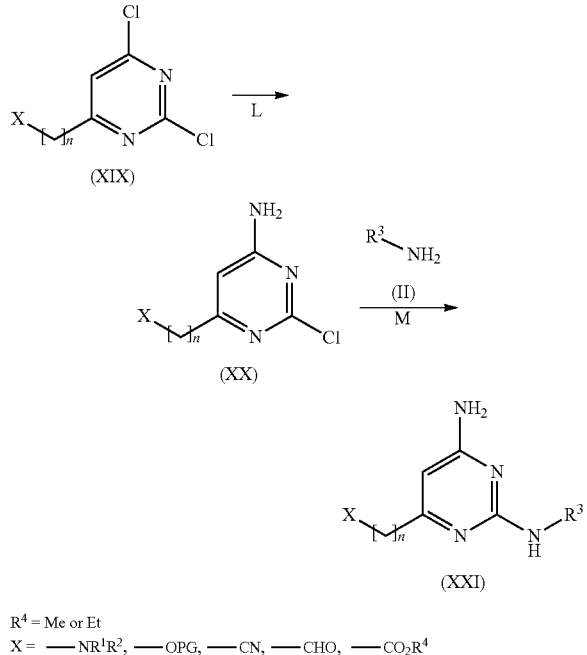

$R^4$ = Me or Et
X = —NR$^1$R$^2$, —OPG, —CN, —CHO, —CO$_2$R$^4$ $R^1$, $R^2$, $R^3$, and n are as defined above.

Method 6

Step 1 (Reaction L)

In another method, according to the disclosure, a compound of formula (XIX), wherein X can be —NR$^1$R$^2$, —OPG, —CN, —CHO or —CO$_2$Me, where PG is a protecting group and each of $R^1$ and $R^2$ and n are as defined above, is reacted with an amine source (for instance NH$_2$BOC) to yield a compound of formula (XX) as illustrated in reaction L of the scheme above (Scheme 6).

Reaction L is carried but under standard aromatic nucleophilic substitution conditions, such as those explained for step 4 of method 5 described above (Scheme 5).

Step 2 (Reaction M)

Subsequently, a compound of formula (XX), wherein X can be —NR$^1$R$^2$, —OPG, —CN, —CHO or —CO$_2$Me, where PG is a protecting group and each of $R^1$ and $R^2$ and n are as defined above, is reacted with an aniline group wherein $R^3$ is defined above to yield a compound of formula (XXI) as illustrated in reaction M of the scheme above (Scheme 6).

Reaction M is carried under standard aromatic nucleophilic substitution conditions, such as those explained for step 3 of method 5 described above (Scheme 5).

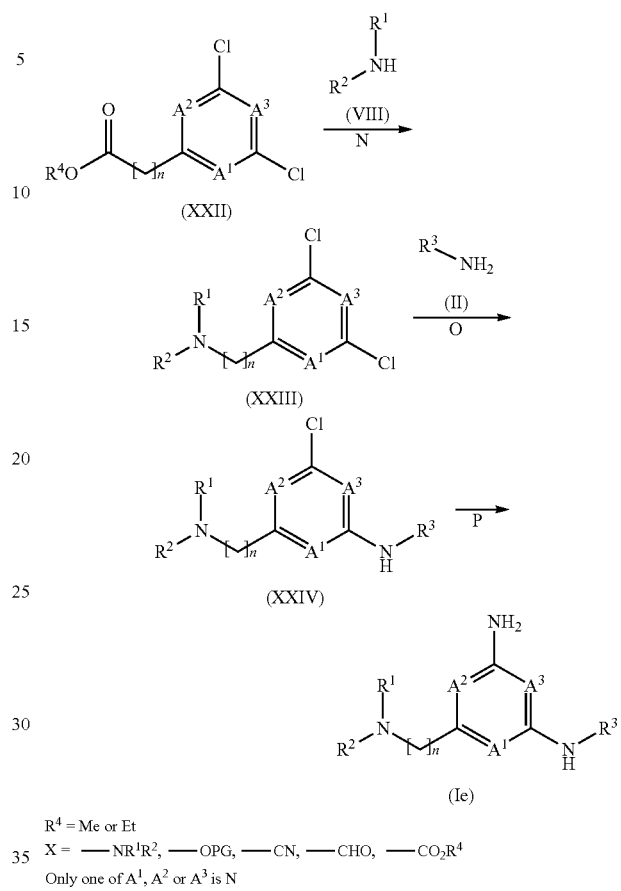

$R^4$ = Me or Et
X = —NR$^1$R$^2$, —OPG, —CN, —CHO, —CO$_2$R$^4$
Only one of A$^1$, A$^2$ or A$^3$ is N $R^1$, $R^2$, $R^1$, and n are as defined above.

Method 7

Step 1 (Reaction N)

In another method, according to the disclosure, a pyridine compound of formula (XXII), wherein n is as defined above and only one of A$^1$, A$^2$ or A$^3$ is N, is reacted with an aniline group of formula (VIII), wherein each of $R^1$ and $R^2$ are as defined above, to yield a compound of formula (XXIII) as illustrated in reaction N of the scheme above (Scheme 7).

Reaction N is carried out under conditions, such as those explained for method 3 when X is —CO$_2$R$^4$ described above (Scheme 3).

Step 2 (Reaction O)

The compound of formula (XXIII) is reacted with an aniline group (II), wherein $R^3$ is as defined above, to yield a compound of formula (XXIV) according to the disclosure as illustrated in reaction O of the scheme above (Scheme 7).

Reaction O is carried out under standard amine arylation conditions, such as those explained for step 3 of a method 5 described above (Scheme 5).

Step 3 (Reaction P)

The compound of formula (XXIV) is reacted with an amine source (for instance a NH$_2$BOC) to yield a compound of formula (Ie) according to the disclosure as illustrated in reaction P of the scheme above (Scheme 7).

Reaction P is carried out under standard amine arylation conditions, such as those explained for step 4 of a method 5 described above (Scheme 5).

Use of the Compounds of the Disclosure

Compounds of the Disclosure have the ability to increase β-glucocerebrosidase. Therefore, Compounds of the Disclosure can be used/administered to treat and/or prevent lysosomal storage diseases. In one embodiment, the lysosomal storage disease is Gaucher's disease.

Accordingly, the present disclosure is directed to a method of treating or preventing a lysosomal storage disease, comprising administering to a patient in need thereof an effective amount of a compound of formula (I), or a pharmaceutically acceptable salt or solvate thereof.

In another embodiment, the present disclosure is directed to a method of treating or preventing Gaucher's disease, comprising administering to a patient in need thereof an effective amount of a compound of formula (I), or a pharmaceutically acceptable salt or solvate thereof.

In another embodiment, the method of treating or preventing a lysosomal storage disease, such as Gaucher's disease, further comprises administering to the patient at least one other therapeutic agent. In another embodiment, the therapeutic agent is an effective amount of an enzyme for enzyme replacement therapy. In another embodiment, the enzyme is β-glucocerebrosidase or an analog thereof. In another embodiment, the enzyme is imiglucerase. In another embodiment, the therapeutic agent is an effective amount of a small molecule chaperone. In another embodiment, the small molecule chaperone binds competitively to an enzyme. In another embodiment, the small molecule chaperone is selected from the group consisting of iminoalditols, iminosugars, aminosugars, thiophenylglycosides, glycosidase, sulfatase, glycosyl transferase, phosphatase, and peptidase inhibitors. In another embodiment, the small molecule chaperone is selected from the group consisting of isofagomine, N-nonyl-1-deoxynojirimycin (NN-DNJ), ambroxol, and miglustat. In another embodiment, the small molecule chaperone is selected from the group consisting of isofagomine, N-nonyl-1-deoxynojirimycin (NN-DNJ), and ambroxol. In another embodiment, the small molecule chaperone is miglustat. In another embodiment, the therapeutic agent is an effective amount of substrate reduction agent for substrate reduction therapy. In another embodiment, the substrate reduction agent is miglustat.

The disclosure provides the following particular embodiments relating to methods of treating or preventing a disease, condition, or disorder in a patient designated as [I] for the first embodiment, [II] for the second embodiment, and so on.

[I]. A method of treating or preventing a disease, disorder, or condition in a patient, comprising administering to a patient in need thereof an effective amount of a compound of formula (I):

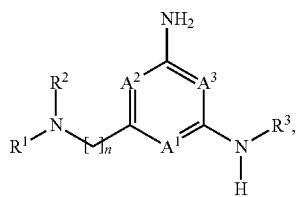

or a pharmaceutically acceptable salt or solvate thereof, wherein $A^1$, $A^2$, and $A^3$ are each independently selected from the group consisting of N, CH and $C(R^4)$, provided that at least one of $A^1$, $A^2$, or $A^3$ is N;

each $R^4$ is independent selected from the group consisting of halogen, —$C_{1-4}$ alkyl, —$C_{1-4}$ alkoxy, and —CN;

n is 1 or 2, wherein the alkylene chain can be optionally substituted with one or more —$C_{1-4}$ alkyl groups;

$R^1$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-4}$ heterocyclyl, —$C_{1-4}$ alkyl-(5- to 10-membered)-$C_{2-9}$ heterocyclyl, and C(=O)Ra, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, -(5- to 10-membered)-$C_{2-9}$ heterocyclyl, optionally substituted —O—($C_{6-10}$ aryl); and wherein said cycloalkyl, alkylcycloalkyl, aryl, alkylaryl, heteroaryl, alkylheteroaryl, heterocyclyl and alkylheterocyclyl is optionally fused to a further (second) ring; and $R^2$ is selected from the group consisting of hydrogen, —$C_{1-4}$ alkyl, and —$C_{3-6}$ cycloalkyl, wherein said —$C_{1-4}$ alkyl is optionally substituted with —O($C_{1-4}$) alkyl optionally substituted with —O($C_{1-4}$)NH$_2$, hydroxy, —CN, halogen, or —N(Rb)$_2$; or $R^1$ and $R^2$ together with idle nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocycle ring is optionally fused to a phenyl ring;

Ra is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, and —$C_{1-4}$ alkyl-(5- to 10-membered)-$C_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally Substituted with 1, 2, or 3 halogen atoms, optionally substituted —$C_{6-10}$ aryl, optionally Substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring;

each Rb is independently hydrogen, —$C_{1-4}$ alkyl, —$C_{3-10}$ cycloalkyl, or -(5- to 10-membered)-$C_{2-9}$ heterocyclyl, wherein said alkyl, cycloalkyl or heterocyclyl group is optionally substituted by 1, 2 or 3 fluorine atoms; and $R^3$ is selected from the group consisting of —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said aryl, heteroaryl, cycloalkyl, and heterocyclyl groups are optionally substituted with 1, 2 or 3 substituents each independently selected from the group consisting of halogen, hydroxy, —CN, —ORb, —SRb, —N(Rb)$_2$, —C$_{1-4}$alkyl optionally substituted with 1, 2, or 3 substituents each independently selected from the group consisting of halogen, —CN, —ORb, and —N(Rb)$_2$, optionally substituted —C$_{6-10}$ aryl, optionally substituted -(5- to 10-membered)-C$_{1-9}$ heteroaryl and -(5- to 10-membered)-C$_{2-9}$ heterocyclyl, and wherein said aryl, heteroaryl, cycloalkyl, and heterocyclyl is optionally fused to a further (second) ring.

[II]. The method of [I], wherein

A$^1$, A$^2$, and A$^3$ are each independently selected from the group consisting of N, CH and C(R$^4$), provided that at least one of A$^1$, A$^2$, or A$^3$ is N;

with the proviso that no more than two of A$^1$, A$^2$, or A$^3$ is N;

each R$^4$ is independently selected from the group consisting of halogen, —C$_{1-4}$ alkyl, —C$_{1-4}$ alkoxy, and —CN;

n is 1 or 2;

R$^1$ is selected from the group consisting of —C$_{1-4}$ alkyl, —C$_{3-10}$ cycloalkyl, —C$_{1-4}$ alkyl-C$_{3-10}$ cycloalkyl, —C$_{6-10}$ aryl, —C$_{1-4}$ alkyl-C$_{6-10}$ aryl, -(5- to 10-membered)-C$_{2-9}$ heteroaryl, —C$_{1-4}$ alkyl-(5- to 10-membered)-C$_{1-9}$ heteroaryl, -(5- to 10-membered)-C$_{2-9}$ heterocyclyl, —C$_{1-4}$ alkyl-(5- to 10-membered)-C$_{2-9}$ heterocyclyl, and —C(=O)Ra, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)), —C$_{1-4}$ alkyl optionally substituted with 1, 2, or 3 halogen atoms, optionally substituted —C$_{6-10}$ aryl, optionally Substituted -(5- to 10-membered)-C$_{1-9}$ heteroaryl, and -(5- to 10-membered)-C$_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring; and R$^2$ is hydrogen or —C$_{1-4}$ alkyl; or R$^1$ and R$^2$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;

Ra is selected from the group consisting of —C$_{1-4}$ alkyl, —C$_{3-10}$ cycloalkyl, —C$_{1-4}$ alkyl-C$_{3-10}$ cycloalkyl, —C$_{6-10}$ aryl, —C$_{1-4}$ alkyl-C$_{6-10}$ aryl, -(5- to 10-membered)-C$_{2-9}$ heteroaryl, —C$_{1-4}$ alkyl-(5- to 10-membered)-C$_{1-9}$ heteroaryl, -(5- to 10-membered)-C$_{2-9}$ heterocyclyl, and —C$_{1-4}$ alkyl-(5- to 10-membered)-C$_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —C$_{1-4}$ alkyl optionally Substituted with 1, 2, or 3 halogen atoms, optionally substituted —C$_{6-10}$ aryl, optionally substituted -(5- to 10-membered)-C$_{1-9}$ heteroaryl, and -(5- to 10-membered)-C$_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring;

each Rb is independently hydrogen, —C$_{1-4}$ alkyl, —C$_{3-10}$ cycloalkyl, or -(5- to 10-membered)-C$_{2-9}$ heterocyclyl, wherein said alkyl, cycloalkyl or heterocyclyl group is optionally substituted by 1, 2 or 3 fluorine atoms;

R$^3$ is —C$_{6-10}$ aryl or -(5- to 10-membered)-C$_{1-9}$ heteroaryl, wherein said aryl or heteroaryl group is optionally substituted with 1, 2 or 3 substituents each independently selected from the group consisting of halogen, hydroxy, —CN, —ORb, —SRb, —N(Rb)$_2$, —C$_{1-4}$ alkyl optionally substituted with 1, 2, or 3 substituents each independently selected from the group consisting of halogen, —CN, —ORb, and —N(Rb)$_2$, optionally substituted —C$_{6-10}$ aryl, optionally substituted -(5- to 10-Membered)-C$_1$ heteroaryl and -(5- to 10-membered)-C$_{2-9}$, heterocyclyl.

[III]. The method of [I] or [II], wherein A$^1$ is N and A$^2$ and A$^3$ are each independently selected from the group consisting of CH and C(R$^4$).

[IV]. The method of [I] or [II], wherein A$^2$ is N and A$^1$ and A$^3$ are each independently selected from the group consisting of CH and C(R$^4$).

[V]. The method of [I] or [II], wherein A$^3$ is N and A$^1$ and A$^2$ are each independently selected from the group consisting of CH and C(R$^4$).

[VI]. The method of [I] or [II], wherein A$^1$ and A$^2$ are both N and A$^3$ is CH or C(R$^4$).

[VII]. The method of [I] or [II], wherein A$^1$ and A$^3$ are both N and A$^2$ is CH or C(R$^4$).

[VIII]. The method of [1] or [II], wherein A$^2$ and A$^3$ are both N and A$^1$ is CH or C(R$^4$).

[IX]. The method of any one of [I]-[VIII], wherein n is 1.

[X]. The method of any one of [I]-[VIII], wherein n is 2.

[XI]. The method of any one of [I]-[X], or a pharmaceutically acceptable salt or solvate thereof, wherein R$^3$ is unsubstituted —C$_{6-10}$ aryl or —C$_{6-10}$ aryl substituted with 1 or 2 substituents each independently selected from the group consisting of halogen, hydroxy, —CN, —O(C$_{1-4}$)alkyl, —S(C$_{1-4}$)alkyl, —N(C$_{1-4}$ alkyl)$_2$, —NH(C$_{1-4}$ alkyl), and —C$_{1-4}$ alkyl optionally substituted with 1, 2, or 3 substituents each independently selected from the group consisting of halogen, —CN, —O(C$_{1-4}$)alkyl, —N(C$_{1-4}$ alkyl)$_2$, and —NH(C$_{1-4}$ alkyl).

[XII]. The method of any one of [I]-[XI], wherein R$^2$ is H.

[XIII]. The method of any one of [I]-[XI], wherein R$^2$ is —C$_{1-4}$ alkyl.

[XIV]. The method of any one of [I]-[XI] or [XIII], wherein R$^2$ is methyl.

[XV]. The method of any one of [I]-[XIV], wherein R$^1$ is —C$_{6-10}$ aryl or —C$_{1-4}$ alkyl-C$_{6-10}$ aryl, wherein said aryl or alkylaryl is optionally substituted with 1, 2 or 3 groups each independently selected from the group consisting of halogen, hydroxy, —CN, —ORb, —SRb, —N(Rb)$_2$, —C$_{1-4}$ alkyl optionally substituted with 1, 2, or 3 halogen atoms, optionally substituted —C$_{6-10}$ aryl, optionally substituted -(5- to 10-membered)-C$_{1-9}$ heteroaryl, and -(5- to 10-membered)-C$_{2-9}$ heterocyclyl, wherein Rb is as defined in [I].

[XVI]. The method of any one of [I]-[XV], wherein Rb is hydrogen or —C$_{1-4}$ alkyl.

[XVII]. The method of any one of [I]-[XI], wherein R$^1$ and R$^2$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring.

[XVIII]. The method of [XVII], wherein R¹ and R² together with the nitrogen atom to which they are attached form a 5- or 6-membered ring optionally fused to a phenyl ring.

[XIX]. The method of [1], wherein the compound of formula (I) is selected from the group consisting of

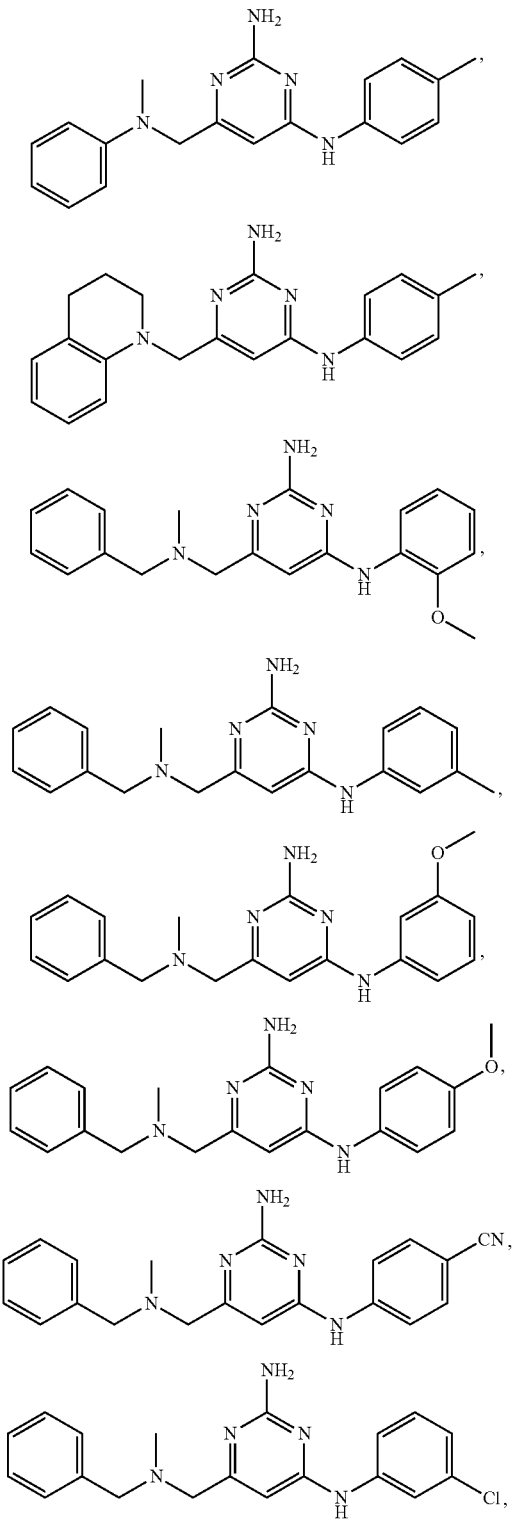

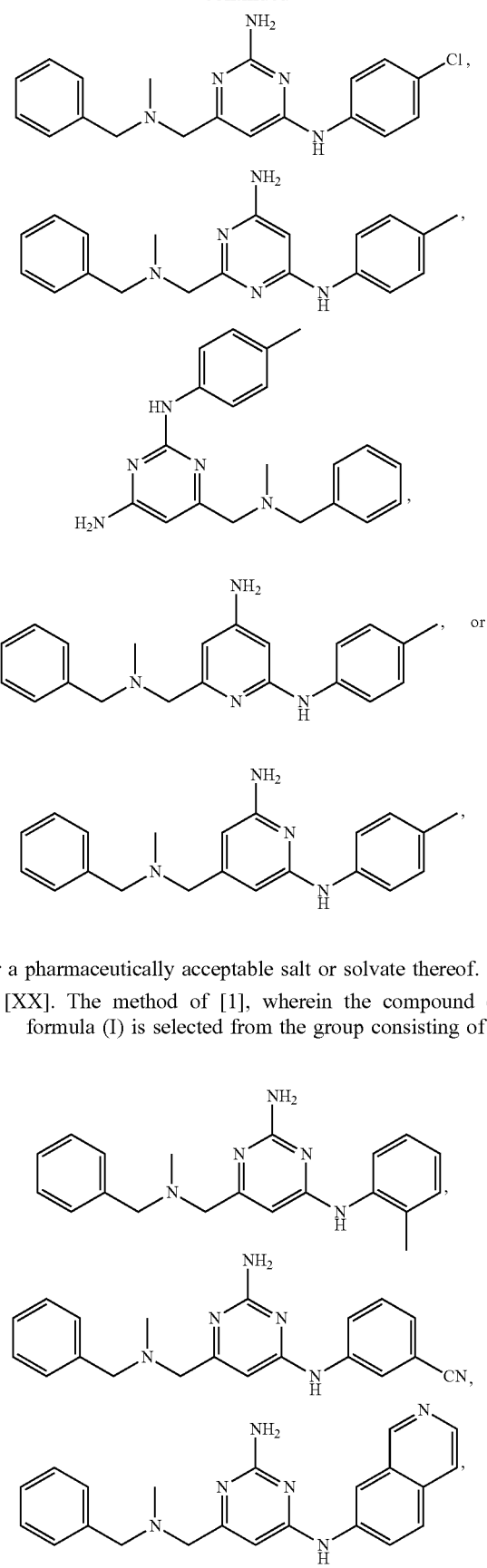

or a pharmaceutically acceptable salt or solvate thereof.

[XX]. The method of [1], wherein the compound of formula (I) is selected from the group consisting of

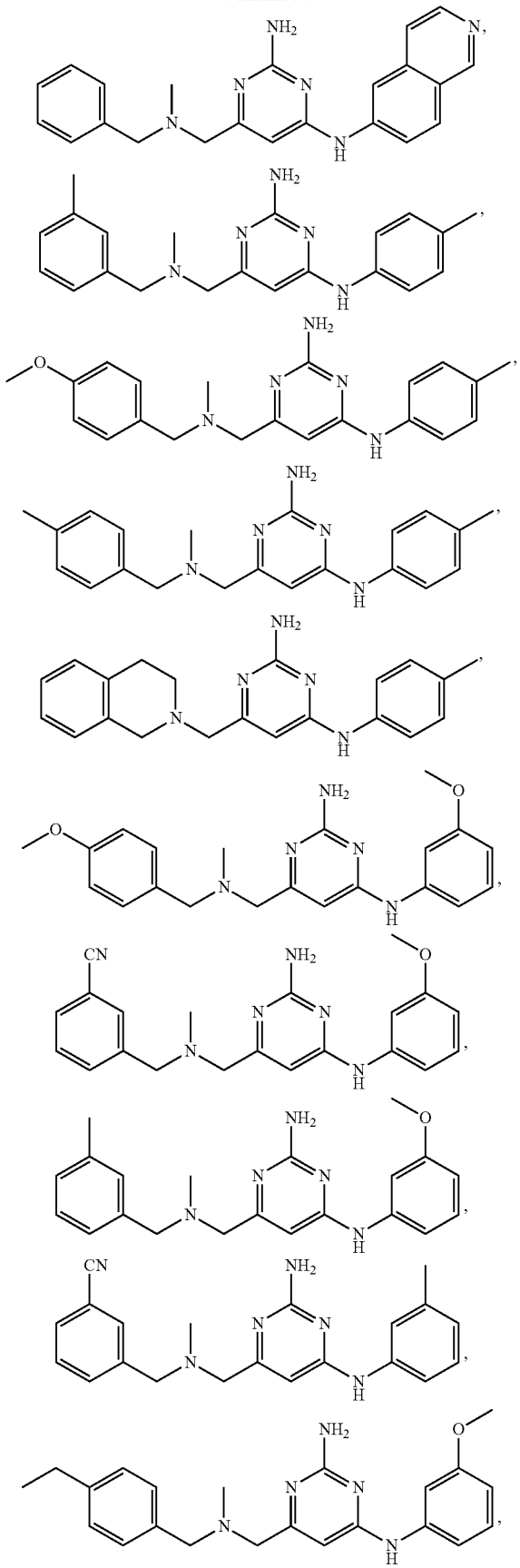
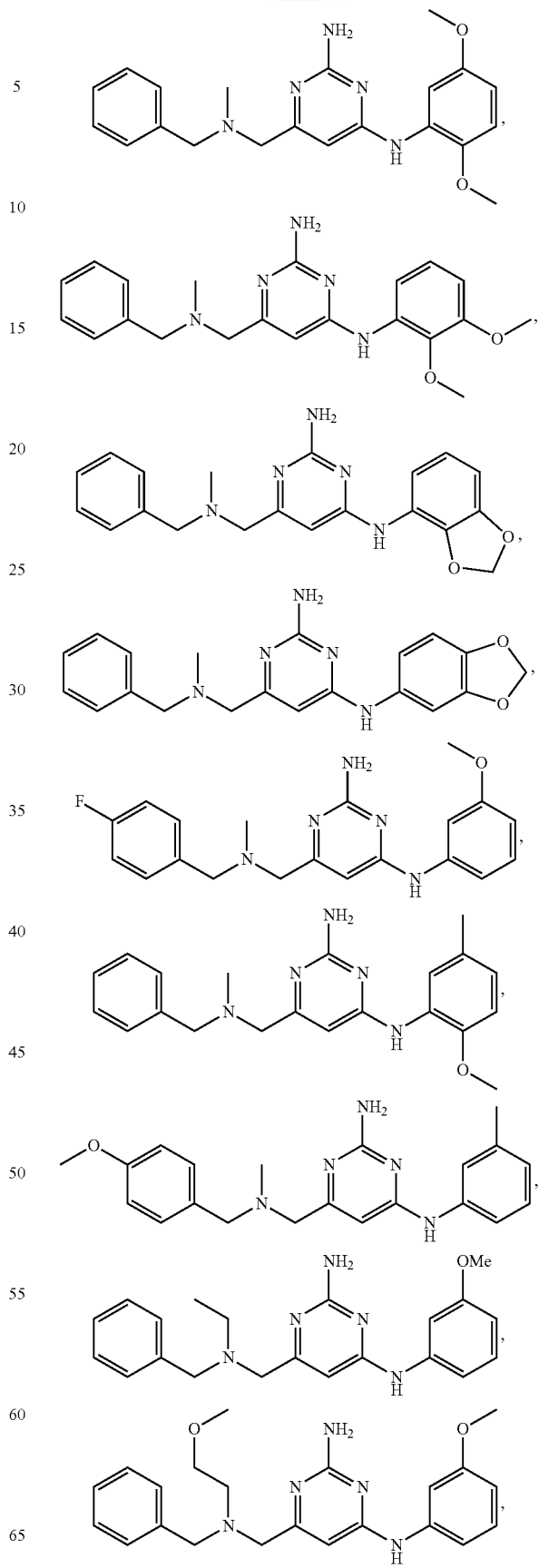

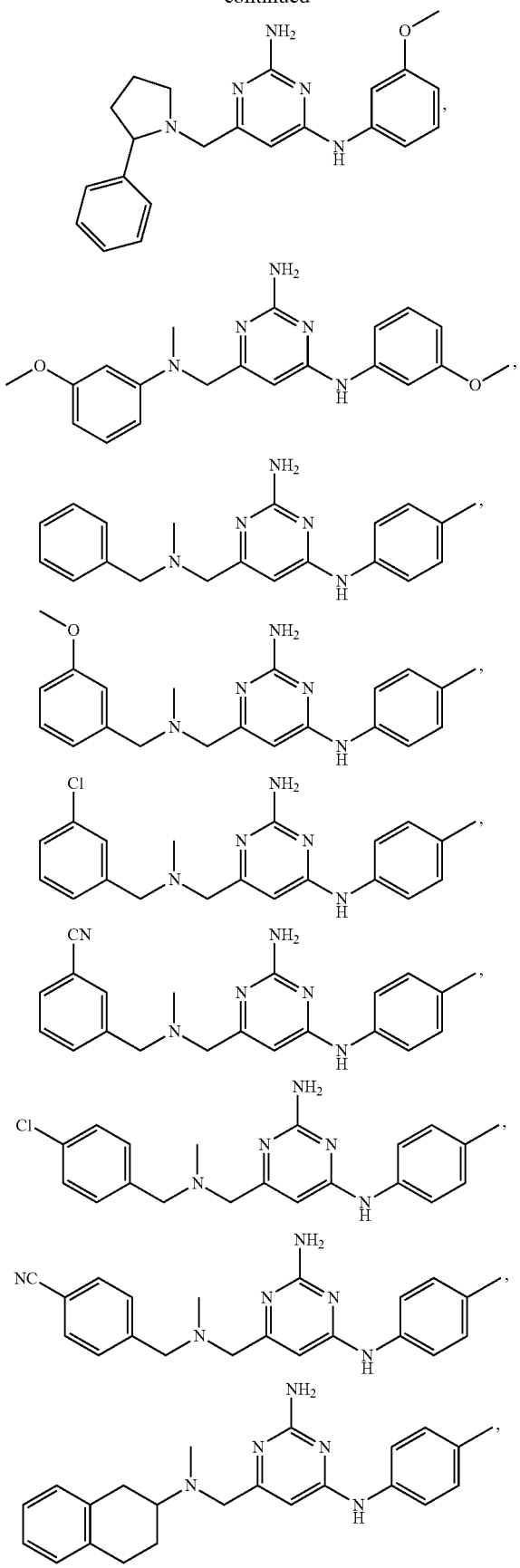
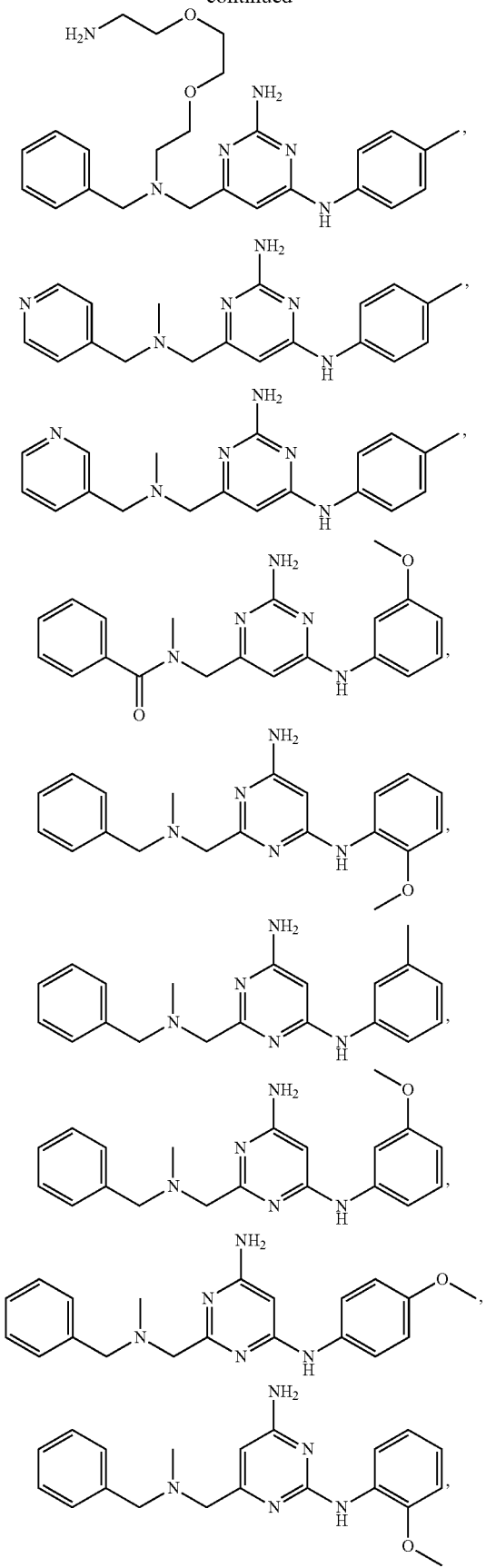

-continued

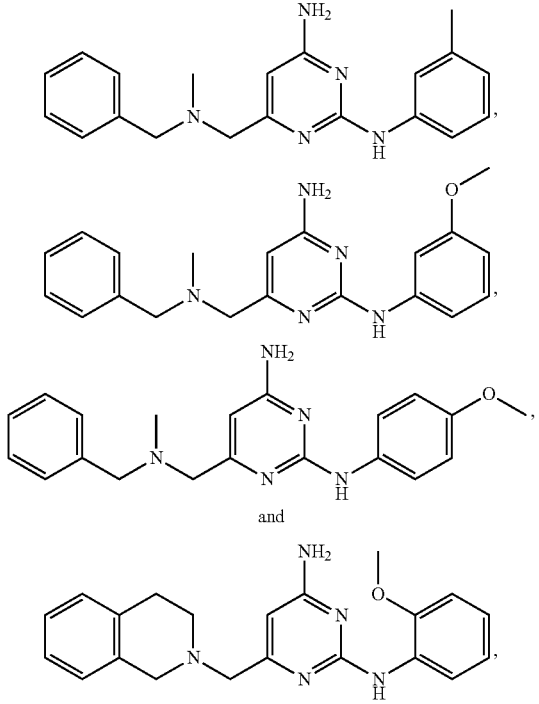

or a pharmaceutically acceptable salt or solvate thereof.

[XXI]. A method of treating or preventing a disease, disorder, or condition in a patient, comprising administering to a patient in need thereof an effective amount of a compound selected from the group consisting of

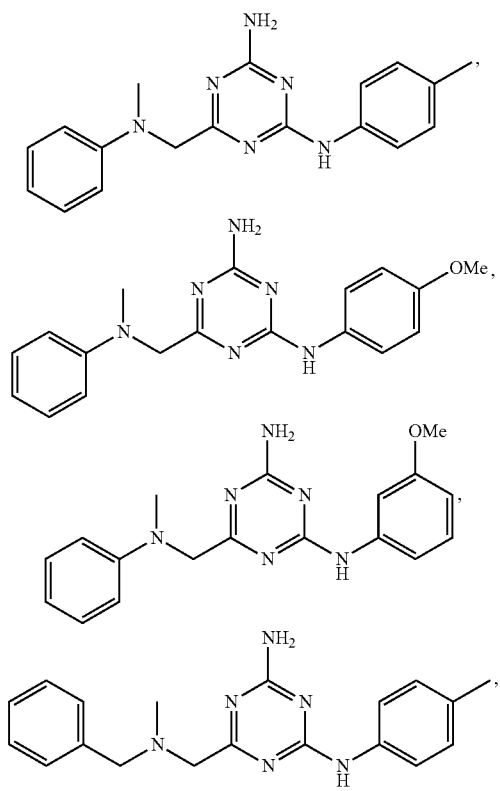

-continued

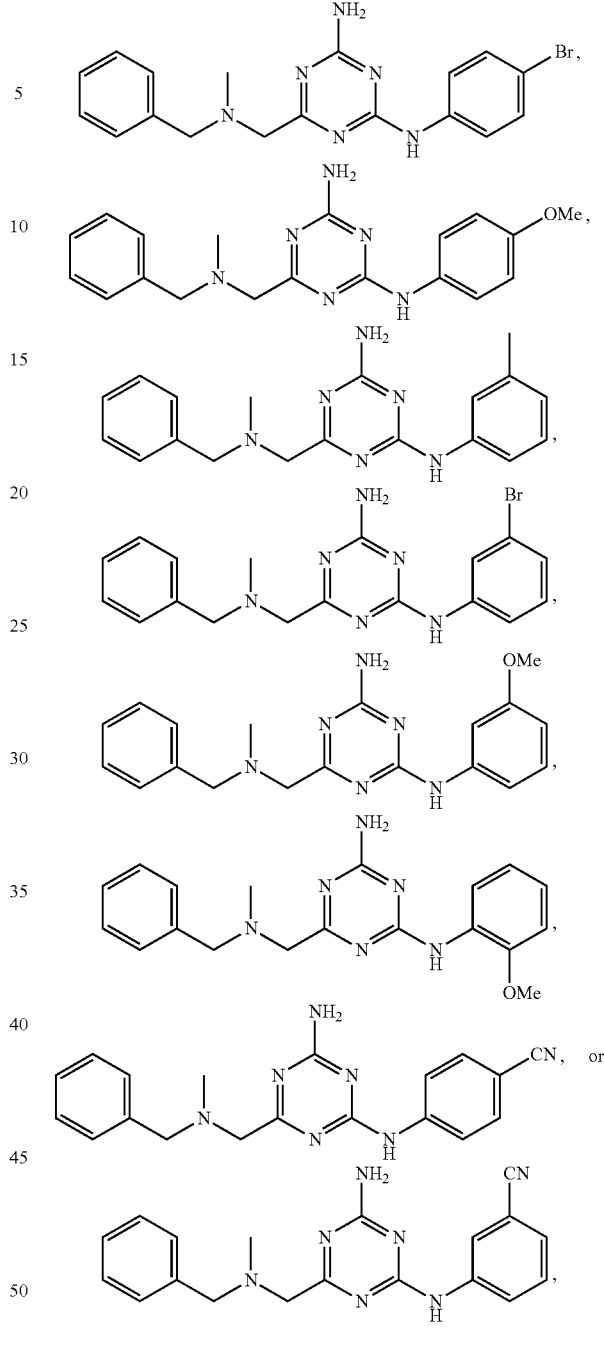

or a pharmaceutically acceptable salt or solvate thereof.

[XXII]. A method of treating or preventing a disease, disorder, or condition in a patient, comprising administering to a patient in need thereof an effective amount of a compound selected from the group consisting of

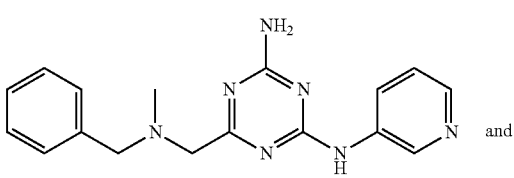

and

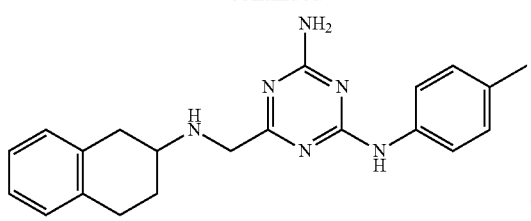

or a pharmaceutically acceptable salt or solvate thereof.

[XXIII]. The method of [I], wherein $A^1$, $A^2$ and $A^3$ are N.

[XXIV]. The method of [XXIII], wherein the compound administered is selected from the group consisting of

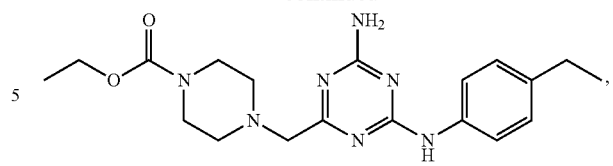

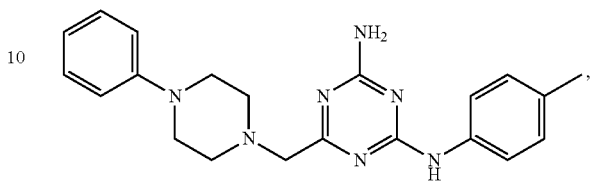

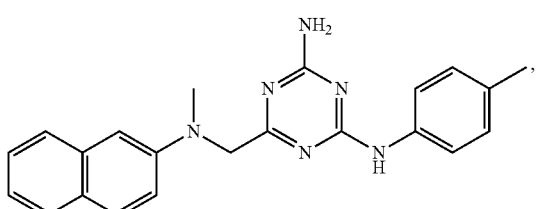

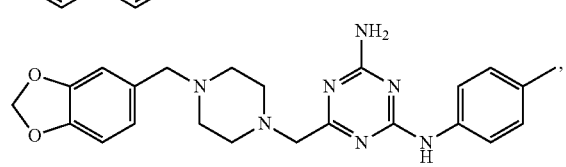

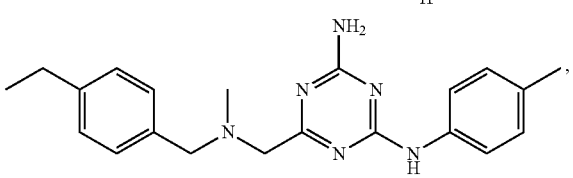

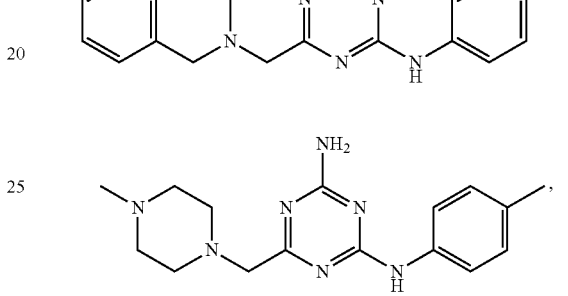

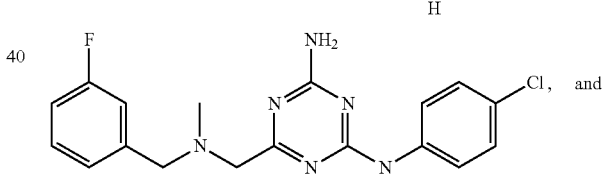

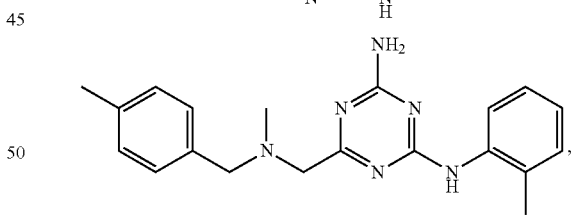

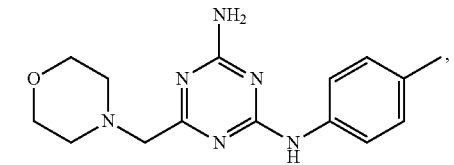

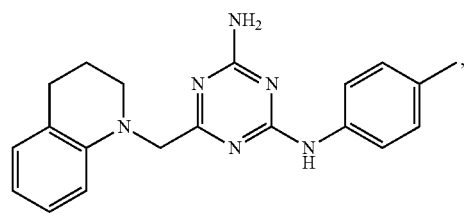

or a pharmaceutically acceptable salt or solvate thereof.

[XXV]. The method of [XXIII], wherein the compound administered is selected from the group consisting of

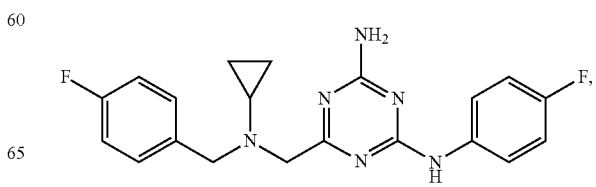

-continued

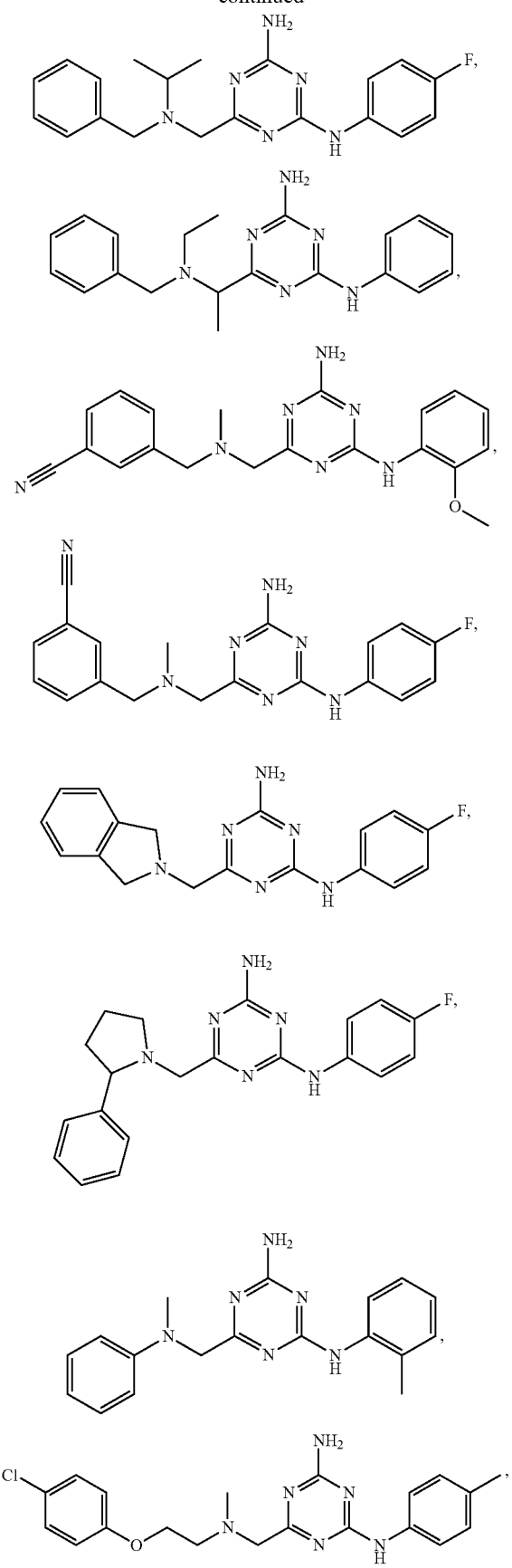

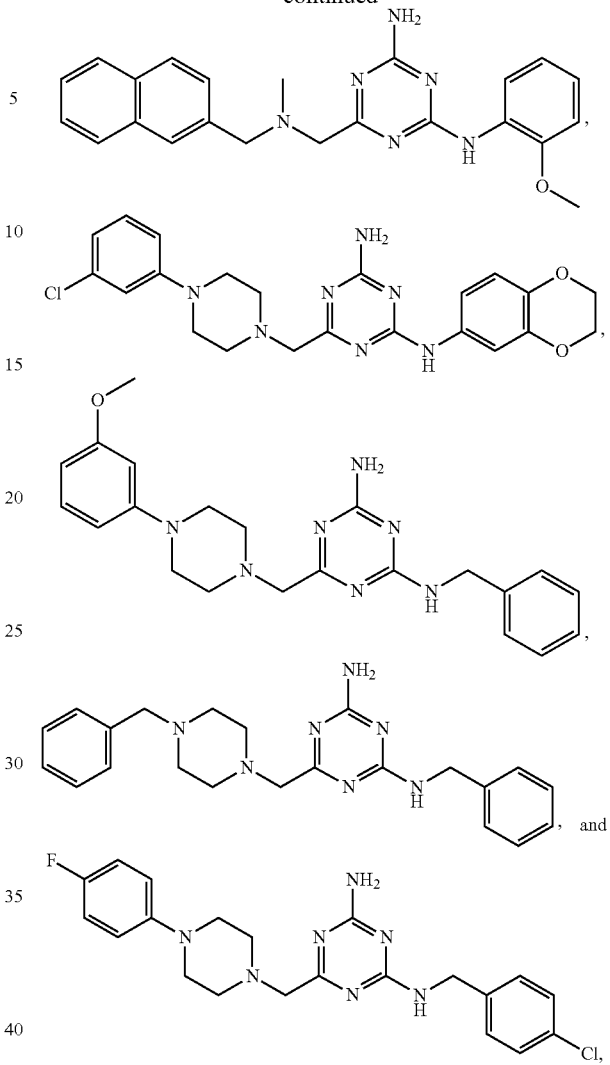

, and or a pharmaceutically acceptable salt or solvate thereof.

[XXVI]. The method of any one of [I]-[XXV], further comprising administering to the patient at least one other therapeutic agent.

[XXVII]. The method of [XXVI], wherein the therapeutic agent is an effective amount of an enzyme for enzyme replacement therapy.

[XXVIII]. The method of [XXVII], wherein the enzyme is β-glucocerebrosidase or an analog thereof.

[XXIX]. The method of [XXVIII], wherein the enzyme is imiglucerase.

[XXX]. The method of any one of [XXVI]-[XXIX], wherein the therapeutic agent is an effective amount of a small molecule chaperone.

[XXXI]. The method of [XXX], wherein the small molecule chaperone binds competitively to an enzyme.

[XXXII]. The method of [XXX] or [XXXI], wherein the small molecule chaperone is selected from the group consisting of iminoalditols, iminosugars, aminosugars, thiophenylglycosides, glycosidase, sulfatase, glycosyl transferase, phosphatase, and peptidase inhibitors.

[XXXIII]. The method of [XXXII], wherein the small molecule chaperone is selected from the group consisting of isofagomine, N-nonyl-1-deoxynojirimycin (NN-DNJ), ambroxol, and miglustat.

[XXXIV]. The method of any one of [XXVI]-[XXXIII], wherein the therapeutic agent is an effective amount of a substrate reduction agent for substrate reduction therapy.

[XXXV]. The method of [XXXIV], wherein the substrate reduction agent is miglustat.

[XXXVI]. The method of any one of [I]-[XXXV], wherein the disease, disorder, or condition is a lysosomal storage disease.

[XXXVII]. The method of [XXXVI], wherein the lysosomal storage disease is Gaucher's disease.

[XXXVIII]. The method of any one of [I]-[XXXV], wherein the disease, disorder, or condition is Parkinson's disease, Lewy body disease, dementia, multiple system atrophy, epilepsy, bipolar disorder, schizophrenia, an anxiety disorder, major depression, polycyctic kidney disease, type 2 diabetes, open angle glaucoma, multiple sclerosis, or multiple myeloma.

The present disclosure is also directed to a compound of formula (I), or a pharmaceutically acceptable salt or solvate thereof, for use in the treatment of prevention of a lysosomal storage disease, such as Gaucher's disease, in a patient in need of such treatment or prevention.

The present disclosure is also directed to the use of a compound of formula (I), or a pharmaceutically acceptable salt or solvate thereof, in the manufacture of a medicament for treating and/or preventing a lysosomal storage disease, such as Gaucher's disease, in a patient in need of such treatment or prevention.

The present disclosure is also directed to a compound of formula (I), or a pharmaceutically acceptable salt or solvate thereof, for use in treating or preventing a lysosomal storage disease, such as Gaucher's disease, in a patient. In one embodiment, the compound of formula (I), or a pharmaceutically acceptable salt or solvate thereof, is administered to the patient in combination with at least one other therapeutic agent. In another embodiment, the therapeutic agent is an effective amount of an enzyme for enzyme replacement therapy. In another embodiment, the enzyme is β-glucocerebrosidase or an analog thereof. In another embodiment, the enzyme is imiglucerase. In another embodiment, the therapeutic agent is an effective amount of a small molecule chaperone. In another embodiment, the small molecule chaperone binds competitively to an enzyme. In another embodiment, the small molecule chaperone is selected from the group consisting of iminoalditols, iminosugars, aminosugars, thiophenylglycosides, glycosidase, sulfatase, glycosyl transferase, phosphatase, and peptidase inhibitors. In another embodiment, the small molecule chaperone is selected from the group consisting of isofagomine, N-nonyl-1-deoxynojirimycin (NN-DNJ), ambroxol, and miglustat. In another embodiment, the small molecule chaperone is selected from the group consisting of isofagomine, N-nonyl-1-deoxynojirimycin (NN-DNJ), and ambroxol. In another embodiment, the small molecule chaperone is miglustat.

The present disclosure is also directed to a compound of formula (I), or a pharmaceutically acceptable salt or solvate thereof, for use in the treatment or prevention of a lysosomal storage disease, such as Gaucher's disease, in a patient in need of such treatment or prevention.

The present disclosure is also directed to the use of a compound of formula (I), or a pharmaceutically acceptable salt or solvate thereof, in the manufacture of a medicament for treating and/or preventing a lysosomal storage disease, such as Gaucher's disease, in a patient in need of such treatment or prevention.

Synucleinopathies are neurodegenerative diseases characterized by the abnormal accumulation of aggregates of α-synuclein protein in neurons, nerve fibres, or glial cells. There is a well-established clinical association between mutations in the glucocerebrosidase gene and the development of more prevalent multifactorial disorders including Parkinson's disease and other synucleinopathies. See, Siebert, M., et al., *Brain* 137:1304-1322 (2014). According to Siebert et al., there is a reciprocal relationship between glucocerebrosidase activity (wild-type and mutant) and α-synuclein in synucleinopathiesm such as Parkinson;s disease and dementia with Lewy bodies. This reciprocal relationship suggests that therapies for Gaucher's disease, which are targeted towards augmenting glucocerebrosidase activity or decreasing glucocerebrosides storage could prove to be provising strategies for modulating α-synuclein proteostasis and its subsequent aggregation and oligomerization.

Compounds of the Disclosure, based on their activities as described herein, can be used/administered to treat and/or prevent synucleinopathies, such as Parkinson's disease, Lewy body disease, dementia, multiple system atrophy, epilepsy, bipolar disorder, schizophrenia, an anxiety disorder, major depression, polycyctic kidney disease, type 2 diabetes, open angle glaucoma, multiple sclerosis, and multiple myeloma.

Accordingly, the present disclosure is also directed to a method of treating or preventing a disease or disorder selected from the group consisting of Parkinson's disease, Lewy body disease, dementia, multiple system atrophy, epilepsy, bipolar disorder, schizophrenia, an anxiety disorder, major depression, polycyctic kidney disease, type 2 diabetes, open angle glaucoma, multiple sclerosis, and multiple myeloma, comprising administering to a patient in need thereof an effective amount of a compound of formula (I), or a pharmaceutically acceptable salt or solvate thereof. In another embodiment, Parkinson's disease is treated or prevented. In another embodiment, the method further comprises administering to the patient at least one other therapeutic agent. In another embodiment, the therapeutic agent is an effective amount of an enzyme for enzyme replacement therapy. In another embodiment, the enzyme is β-glucocerebrosidase or an analog thereof. In another embodiment, the enzyme is imiglucerase. In another embodiment, the therapeutic agent is an effective amount of a small molecule chaperone. In another embodiment, the small molecule chaperone binds competitively to an enzyme. In another embodiment, the small molecule chaperone is selected from the group consisting of iminoalditols, iminosugars, aminosugars, thiophenylglycosides, glycosidase, sulfatase, glycosyl transferase, phosphatase, and peptidase inhibitors. In another embodiment, the small molecule chaperone is selected from the group consisting of isofagomine, N-nonyl-1-deoxynojirimycin (NN-DNJ), ambroxol, and miglustat. In another embodiment, the small molecule chaperone is selected from the group consisting of isofagomine, N-nonyl-1-deoxynojirimycin (NN-DNJ), and ambroxol. In another embodiment, the small molecule chaperone is miglustat.

The present disclosure is also directed to a compound of formula (I), or a pharmaceutically acceptable salt or solvate thereof, for use in treating or preventing a disease or disorder selected from the group consisting of Parkinson's disease, Lewy body disease, dementia, multiple system atrophy, epilepsy, bipolar disorder, schizophrenia, an anxiety disorder, major depression, polycyctic kidney disease, type 2 diabetes, open angle glaucoma, multiple sclerosis, and multiple myeloma, in a patient. In one embodiment, the compound of formula (I), or a pharmaceutically acceptable salt or solvate thereof, is administered to the patient in combination with at least one other therapeutic agent. In another embodiment, the compound of formula (I), or a pharmaceutically acceptable salt thereof, is for use in treating or preventing Parkinson's disease. In another embodiment, the therapeutic agent is an effective amount of an enzyme for enzyme replacement therapy. In another embodiment, the enzyme is β-glucocerebrosidase or an analog thereof. In another embodiment, the enzyme is imiglucerase. In another embodiment, the therapeutic agent is an effective amount of a small molecule chaperone. In another embodiment, the small molecule chaperone binds competitively to an enzyme. In another embodiment, the small molecule chaperone is selected from the group consisting of iminoalditols, iminosugars, aminosugars, thiophenylglycosides, glycosidase, sulfatase, glycosyl transferase, phosphatase, and peptidase inhibitors. In another embodiment, the small molecule chaperone is selected from the group consisting of isofagomine, N-nonyl-1-deoxynojirimycin (NN-DNJ), ambroxol, and miglustat. In another embodiment, the small molecule chaperone is selected from the group consisting of isofagomine, N-nonyl-1-deoxynojirimycin (NN-DNJ), and ambroxol. In another embodiment, the small molecule chaperone is miglustat.

The present disclosure is also directed to a compound of formula (I), or a pharmaceutically acceptable salt or solvate thereof, for use in the treatment or prevention of a disease or disorder selected from the group consisting of Parkinson's disease, Lewy body disease, dementia, multiple system atrophy, epilepsy, bipolar disorder, schizophrenia, an anxiety disorder, major depression, polycyctic kidney disease, type 2 diabetes, open angle glaucoma, multiple sclerosis, and multiple myeloma in a patient in need of such treatment or prevention.

The present disclosure is also directed to the use of a compound of formula (I), or a pharmaceutically acceptable salt or solvate thereof, in the manufacture of a medicament for treating and/or preventing a disease or disorder selected from the group consisting of Parkinson's disease, Lewy body disease, dementia, multiple system atrophy, epilepsy, bipolar disorder, schizophrenia, an anxiety disorder, major depression, polycyctic kidney disease, type 2 diabetes, open angle glaucoma, multiple sclerosis, and multiple myeloma in a patient in need of such treatment or prevention.

Pharmaceutical Compositions

The present disclosure is also directed to pharmaceutical compositions, comprising an effective amount of a Compound of the Disclosure, or a pharmaceutically acceptable salt or solvate thereof, and at least one pharmaceutically acceptable excipient.

Due to their activity, Compounds of the Disclosure can be used in human medicine. As described above, Compounds of the Disclosure are useful for treating or preventing Gaucher's disease. Compounds of the Disclosure can be administered to any patient suffering said condition. The term "patient" as used herein refers to any human that can experience the beneficial effects of a Compound of the Disclosure.

When administered to a patient, a Compound of the Disclosure can be administered as a component of a composition that comprises a pharmaceutically acceptable excipient or carrier.

The Compound of the Disclosure can be administered in combination with at least one other therapeutic agent. Administration of the Compound of the Disclosure with at least one other therapeutic agent can be sequential or concurrent. In one embodiment, the Compound of the Invention and the at least one other therapeutic agent are administered in separate dosage forms. In another embodiment, the Compound of the Invention and the at least one other therapeutic agent are administered concurrently in the same dosage form.

The term "excipient" refers to a vehicle, diluent, or adjuvant that is administered with the active ingredient. Such pharmaceutical excipients can be sterile liquids, such as water and oils, including those of petroleum, animal, vegetable, or synthetic origin, such as peanut oil, soybean oil, mineral oil, sesame oil, and similar. Water or saline aqueous solutions and aqueous dextrose and glycerol solutions, for example, for injectable solutions, can be used as vehicles. Suitable pharmaceutical vehicles are described in "Remington's Pharmaceutical Sciences" by E. W. Martin, $21^{st}$ Edition, 2005; or "Handbook of Pharmaceutical Excipients," Rowe C. R.; Paul J. S.; Marian E. Q., sixth Edition, incorporated herein by reference.

Examples of pharmaceutical compositions include any solid composition (tablets, pills, capsules, granules, etc.) or liquid compositions (solutions, suspensions, or emulsions) for oral, topical, or parenteral administration.

In another embodiment, the pharmaceutical compositions are in an oral delivery form. Pharmaceutical forms suitable for oral administration can be tablets and capsules, and can contain conventional excipients known in the art, such as binders, for example syrup, gum Arabic, gelatin, sorbitol, tragacanth, or polyvinylpyrrolidone; fillers, for example lactose, sugar, cornstarch, calcium phosphate, sorbitol, or glycine; lubricants for the preparation of tablets, for example magnesium stearate; disintegrants, for example starch, polyvinylpyrrolidone, sodium starch glycolate, or microcrystalline cellulose; or pharmaceutically acceptable wetting agents, such as sodium lauryl sulphate.

Solid oral compositions can be prepared by conventional methods of blending, filling, or preparation of tablets. Repeated blending operations can be used to distribute the active ingredient in all the compositions that use large amounts of fillers. Such operations are conventional in the art. The tablets can be prepared, for example, by dry or wet granulation and optionally can be coated by well known methods in normal pharmaceutical practice, in particular using enteric coating.

Pharmaceutical compositions can also be adapted for parenteral administration, such as sterile solutions, suspensions, or lyophilized products in the appropriate unit dosage form. Suitable excipients, such as fillers, buffering agents, or surfactants can be used.

The mentioned formulations can be prepared using standard methods, such as those described or referred to in the Spanish and U.S. Pharmacopoeias and similar reference texts.

In general, the effective amount of a Compound of the Disclosure to be administered depends on the relative efficacy of the compound chosen, the severity of the condition or disorder being treated, and the patient's weight. The active compound can be administered one or more times a day, for example 1, 2, 3, or 4 times daily, with typical total daily doses in the range from about 0.01 mg/kg of body weight/day to about 1000 mg/kg of body weight/day. In another embodiment, the effective dosage amount of a Compound of the Disclosure is about 500 mg/kg of body weight/day or less. In another embodiment, the effective dosage amount of a Compound of the Disclosure is about 100 mg/kg of body weight/day or less. In another embodiment, the effective dosage amount ranges from about 0.01 mg/kg of body weight/day to about 100 mg/kg of body weight/day of a Compound of the Disclosure; in another embodiment, from about 0.02 mg/kg of body weight/day to about 50 mg/kg of body weight/day of a Compound of the Disclosure; and in another embodiment, from about 0.025 mg/kg of body weight/day to about 20 mg/kg of body weight/day of a Compound of the Disclosure.

A composition of the disclosure can be prepared by a method comprising admixing a Compound of the Disclosure with a pharmaceutically acceptable excipient or carrier. Admixing can be accomplished using methods known for admixing a compound and a pharmaceutically acceptable excipient or carrier. In another embodiment, the Compound of the Disclosure is present in the composition in an effective amount.

The following examples are illustrative, but not limiting, of the compounds, compositions and methods of the present disclosure. Suitable modifications and adaptations of the variety of conditions and parameters normally encountered in clinical therapy and which are obvious to those skilled in the art in view of this disclosure are within the spirit and scope of the disclosure.

General Experimental Conditions

The compound IUPAC names given herein were generated with ChemBioDraw Ultra 12.0., 12.0.2., or 16.0.

Hereinafter, the term "h" means hours, "eq" means equivalents, "min." means minutes, "$Pd_2(dba)_3$" means tris (dibenzylideneacetone)-dipalladium(0), "$Pd(PPh_3)_4$" means palladium-tetrakis(triphenylphosphine), "DavePhos" means 2-dicyclohexylphosphino-2'-(N,N-dimethylamino)biphenyl; "XPhos" means 2-Dicyclohexylphosphino-2',4',6'-triisopropylbiphenyl, "$Zn(CN)_2$" means zinc(II) cyanide, "HPLC" means high-performance liquid chromatography, "TLC" means thin layer chromatography, "LC-MS" or "HPLC-MS" means Liquid chromatography-mass spectrometry, "$CD_3OD$" means deuterated methanol, "$CDCl_3$" means deuterated chloroform, "DMSO-$d_6$" means deuterated dimethyl sulfoxide, "BOC group" means tert-butyloxycarbonyl group, and "HATU" means 1-[Bis(dimethylamino)methylene]-1H-1,2,3-triazolo[4,5-b]pyridinium 3-oxid hexafluoro-phosphate.

$^1$H NMR spectra were recorded in a Bruker (400 MHz and 500 MHz) and in a Varian Mercury 400 MHz spectrometer (at room temperature).

HPLC spectra were recorded on Waters 2695, Agilent 1260 Infibity-2^ Waters UPLC-H class.

MW calculated is an isotopic average and the "found mass" is referring to the most abundant isotope detected in the LC-MS.

LC-MS analysis of the compounds was conducted as per one of the following methods.

Method A: X-BRIDGE C18 (4.6 mm×75 mm, 3.5 μm); wavelength: 215 nm; flow: 2.0 mL/min; run time: 5.0 min; Mobile phase A: 10 mM ammonium acetate in water and B: 100% acetonitrile; Time and mobile phase-gradient (time in min/% B): 0.0/10, 0.2/10, 2.5/75, 3.0/100, 4.8/100, 5.0/10; MASS: Agilent 1200 SERIES, Mass: 6130SQD (ESI/APCI).

Method B: Aquity UPLC BEH C18 (50 mm×2.1 mm, 1.7 μm); wavelength: 215 nm; flow: 0.8 mL/min; run time: 3.0 min; Mobile phase A: 0.1% of formic acid in water and B: 1.0% formic acid in acetonitrile; Time and mobile phase-gradient (time in min/% B): 0.0/2, 0.2/2, 1.5/98, 2.6/98, 2.61/2, 3.2/2; MASS: Agilent 1290 infinity, Mass: 6150 SQD (ESI/APCI).

Method C: YMC-Pack ODS-AQ (50 mm×4.6 mm, S-3 μm, 12 mm); wavelength: 215 nm; flow: 1.6 mL/min at 50° C.; run time: 3.5 min; mobile phase A: 0.1% of formic acid in water and B: 0.1% formic acid in acetonitrile; Time and mobile phase-gradient (time in min/% B): 5% B-100% B in 3.5 min; MASS: micromass ZQ4000.

Method D: Aquity UPLC BEH C18 (50 mm×2.1 mm, 1.7 μm); wavelength: 215 nm; flow: 0.6 mL/min; run time: 3.2 min; Mobile phase A: 10 mM ammonium acetate in water and B: 100% acetonitrile; Time and mobile phase-gradient (time in min/% B): 0.0/98, 0.5/98, 8.5/2.9, 2/2, 9.5/98, 10/98; MASS: Agilent 1290 infinity, Mass: 6150 SQD (ESI/APCI).

Method E: Aquity UPLC BEH C18 (50 mm×2.1 mm, 1.7 μm); wavelength: 215 nm; flow: 0.6 mL/min; run time: 3.2 min; Mobile phase A: 0.1% of formic acid in water and B: 0.1% formic acid in acetonitrile; Time and mobile phase-gradient (time in mini % A): 0/97, 0.3/97, 3.0/2, 4.0/2, 4.2/97, 4.5/97; MASS: Waters Acquity UPLC with SQD (ESI/APCI).

Method F: Aquity UPLC BEH C18 (50 mm×2.1 mm, 1.7 μm); wavelength: 215 nm; flow: 0.8 mL/min; run time: 3.2 min; Mobile phase A: 0.1% of formic acid in water and B: 1.0% formic acid in acetonitrile; Time and mobile phase-gradient (time in min/% A): 0.0/98, 0.5/98, 3.4/2, 4.2/2, 4.5/98, 5/98; MASS: Waters Acquity UPLC with SQD(ESI/APCI).

Method G: Aquity UPLC BEH C18 (50 mm×2.1 mm, 1.7 μm); wavelength: 215 nm; flow: 0.6 mL/min; run time: 3.2 min; Mobile phase A: 0.1% of formic acid in water and B: Acetonitrile; Time and mobile phase-gradient (time in min/% A): 0.0/98, 0.5/98, 3.4/2, 4.2/2, 4.5/98; MASS: Waters Acquity UPLC with SQD(ESI/APCI).

Method H: X-BRIDGE C18 (2.5 mm×50 mm 1.7 μm); wavelength: 220 nm; flow: 0.6 mL/min; run time: 4.0 min: Mobile phase A: 10 mM ammonium acetate in water and B: 100% acetonitrile; Time and mobile phase-gradient (time in min/% B): 0.0/5, 0.3/5, 2.0/98, 3.5/98, 3.6/5: MASS: Agilent 1200 SERIES, Mass: 6130SQD (ESI/APCI).

Intermediate 1

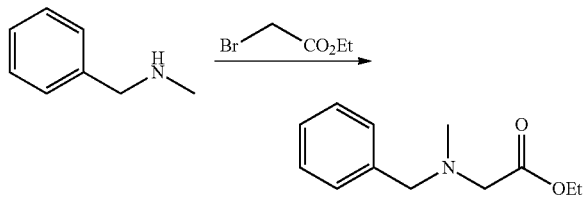

To a stirred solution of ethyl bromoacetate (1 eq) in dichloromethane (1.25 mL/mmol) at 0° C. were added N-methylbenzylamine (1 eq) and diisopropylamine (2.4 eq). The reaction mixture was warmed to room temperature and stirred for 6 h. After reaction completion, the reaction mixture was poured into saturated sodium bicarbonate solution and the organic product was extracted with dichloromethane. The organic layer was dried over anhydrous sodium sulfate and the solvent was evaporated under vacuum to get the crude product, which was purified by flash column chromatography (15-17% ethyl acetate-petroleum ether as eluent) to get product (ethyl N-benzyl-N-methylglycinate) as a yellow liquid. Yield: 66%.

ES-MS [M+H]$^+$: 208.2; Rt=1.27 min (Method B).

$^1$H NMR (400 MHz, CDCl$_3$) δ: 7.35-7.30 (m, 5H), 7.27-7.26 (m, 1H), 4.20-4.16 (m, 2H), 3.67 (s, 2H), 3.25 (s, 2H), 2.38 (s, 3H), 1.26 (t, J=5.6 Hz, 3H).

General Procedure I

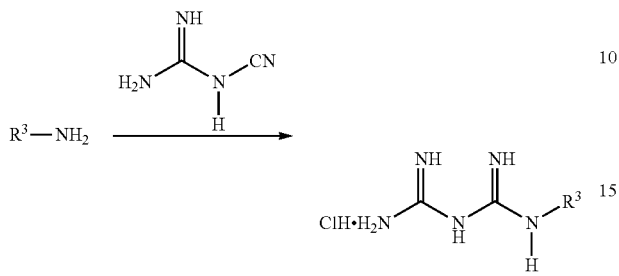

A mixture of an aromatic amine (ex: p-toluidine) (1 eq) and dicyandiamide (1 eq) in 3M hydrogen chloride (aq) (1 eq) was heated at 90° C. for 16 h. After reaction completion, the mixture was cooled to room temperature and during this process a solid compound precipitate (in some cases, the crude compound was co-distilled with toluene (3×). The crude was collected by vacuum filtration and washed with cold water and triturated with ethyl acetate and diethyl ether to give the compound as hydrochloride salt (ex: p-tolyl-biguanide hydrochloride).

In some cases, the intermediate salt was then added to a mixture of methanol and methanolic sodium methoxide (25% solution, 12 mmol), and the mixture was stirred at room temperature for 1 h. Following filtration, the filtrate was evaporated under vacuum and the precipitate was re-dissolved in hot ethanol. Further precipitate was removed by filtration, then ethanol was evaporated under vacuum and the resulting residue was collected and dried to give the desired product (ex: N(1)-(4-Methylphenyl)biguanide).

Intermediate 2

N(1)-(4-Methylphenyl)biguanide

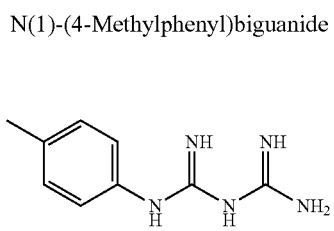

Yield: 86%
HPLC-MS [M+H]$^+$: 191; Rt=1.03 min (Method C).

Intermediate 3

N(I)-(4-Bromophenyl)-1-biguanide hydrochloride

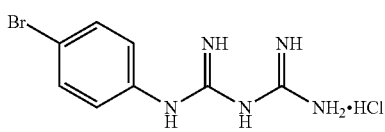

Yield: 59%
ES-MS [M+H]$^+$: 256; Rt=1.36 min (Method B). .

$^1$H NMR (500 MHz, MeOD) δ: 7.46-7.44 (m, 2H), 7.31-7.29 (m, 2H).

Intermediate 4

N(1)-(4-Methoxyphenyl)biguanide hydrochloride

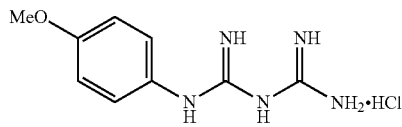

Yield: 90%
ES-MS [M+H-36.5]$^+$: 208.2; Rt=0.47 min (Method B).

Intermediate 5

N(1)-(3-Methylphenyl)biguanide hydrochloride

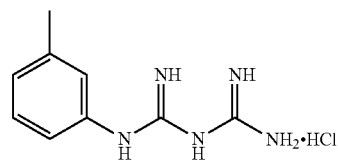

Yield: 60%
ES-MS [M+H-36.5]$^+$: 192; Rt=1.14 min (Method B).

Intermediate 6

N(1)-(3-Bromophenyl)biguanide hydrochloride

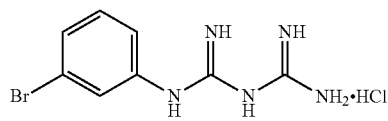

Yield: 42%
ES-MS [M+H-36.5]$^+$: 255.01; Rt=1.32 min (Method B).

Intermediate 7

N(I)-(3-Methoxyphenyl)biguanide hydrochloride

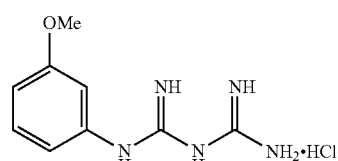

Yield: 76%
ES-MS [M+H-36.5]$^+$: 208; Rt=1.22 min (Method A).

Intermediate 8

N(I)-(2-Methoxyphenyl)biguanide hydrochloride

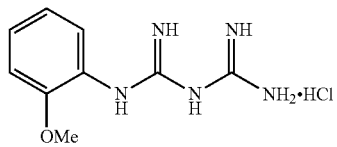

Yield: 66%
ES-MS [M+H-36.5]$^+$: 208.2; Rt=1.10 min (Method A).

General Procedure II

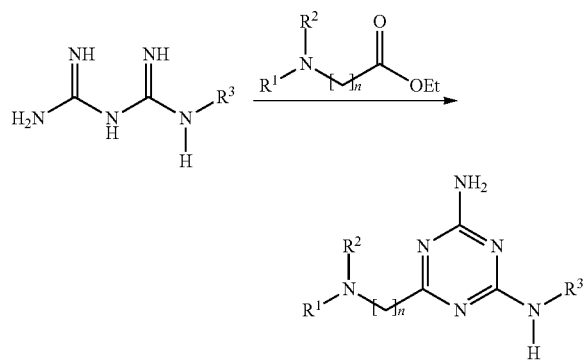

Freshly prepared appropriate biguanide (ex: p-tolylbiguanide) (1 eq) in methanol (19 mL/mmol) was placed in a Schlenk. An appropriate ester (ex: ethyl N-methyl-N-phenylglycinate) (1 eq) was added and the mixture was stirred at 40° C. or 90° C. for 16 h. The resultant crude was purified by flash column chromatography (hexane/acetate or dichloromethane/methanol) to obtain the desired product (ex: 6-((methyl(phenyl)amino)methyl)-N$^2$-(p-tolyl)-1,3,5-triazine-2,4-diamine).

Example 1

6-((Methyl(phenyl)amino)methyl)-N$^2$-(p-tolyl)-1,3,5-triazine-2,4-diamine

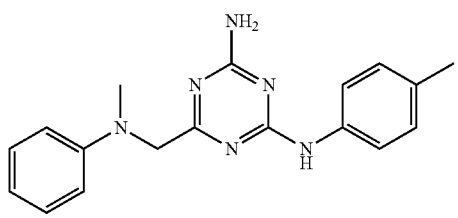 [SMILES: Cc1ccc(Nc2nc(N)nc(CN(C)c3ccccc3)n2)cc1]

Yield: 9%
HPLC-MS [M+H]$^+$: 321; Rt=2.72 min (Method C).
$^1$H NMR (400 MHz, CDCl$_3$) δ: 7.28 (s, 2H), 7.15 (ddd, J=7.3, 5.9, 2.3 Hz, 2H), 7.00 (d, J=7.4 Hz, 2H), 6.84 (s, 1H), 6.71 (dd, J=8.8, 0.9 Hz, 2H), 6.65 (td, J=7.3, 1.0 Hz, 1H), 5.04 (s, 2H), 4.26 (s, 2H), 3.07 (s, 3H), 2.24 (s, 3H).

Example 2

N$^2$-(4-Methoxyphenyl)-6-((methyl(phenyl)amino)methyl)-1,3,5-triazine-2,4-diamine

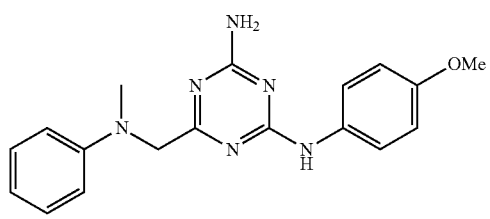 [SMILES: COc1ccc(Nc2nc(N)nc(CN(C)c3ccccc3)n2)cc1]

Yield: 6%
HPLC-MS [M+H]$^+$: 337; Rt=2.43 min (Method C).
$^1$H NMR (400 MHz, CDCl$_3$) δ: 7.24 (d, J=20.0 Hz, 2H), 7.18-7.13 (m, 2H), 6.79 (s, 1H), 6.75 (s, 2H), 6.72-6.68 (m, 2H), 6.67-6.62 (m, 1H), 5.05 (s, 2H), 4.25 (s, 2H), 3.72 (s, 3H), 3.05 (s, 3H).

Example 3

N$^2$-(3-Methoxyphenyl)-6-((methyl(phenyl)amino)methyl)-1,3,5-triazine-2,4-diamine

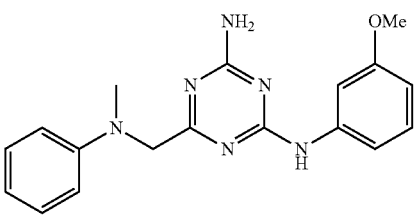 [SMILES: COc1cccc(Nc2nc(N)nc(CN(C)c3ccccc3)n2)c1]

Yield: 21%.
HPLC-MS [M+H]$^+$: 337; Rt=2.65 min (Method C).
$^1$H NMR (400 MHz, CDCl$_3$) δ: 7.19 (d, J=2.1 Hz, 1H), 7.17-7.13 (m, 2H), 7.10 (t, J=8.5 Hz, 1H), 6.97 (s, 1H), 6.93 (dd, J=8.2, 1.4 Hz, 1H), 6.69 (dt, J=3.5, 1.8 Hz, 2H), 6.64 (tt, J=5.0, 2.5 Hz, 1H), 6.57-6.51 (m, 1H), 5.16 (s, 2H), 4.26 (s, 2H), 3.70 (s, 3H), 3.07 (s, 3H).

General Procedure III

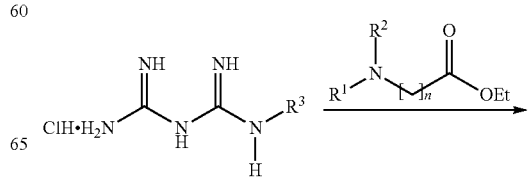

-continued

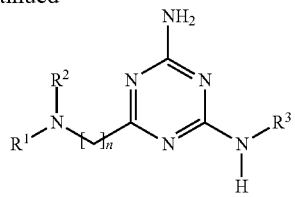

To a stirred solution of the appropriate biguanide hydrochloride salt (ex: p-tolylbiguanide) (1.0 eq) in methanol (2.4 mL/mmol) was added sodium methoxide (1.0 eq, 25 wt % in methanol) at room temperature and it was stirred for 30 min. The appropriate ester was added to the reaction mixture (ex: ethyl N-benzyl-N-methylglycinate) (1.2 eq) and heated to 70° C. for 18 h. After reaction completion, the reaction mixture was poured into cold water and the organic product was extracted with ethyl acetate. Organic extracts were dried over anhydrous sodium sulfate and the solvent was evaporated under vacuum to get the crude mixture. The crude product was purified by flash column chromatography (ethyl acetate-petroleum ether as eluent) to get the desired triazine product (ex: 6-((benzyl(methyl)amino)methyl)-$N^2$-p-tolyl-1,3,5-trizine-2,4-diamine).

Example 4

6-((Benzyl(methyl)amino)methyl)-$N^2$-p-tolyl-1,3,5-trizine-2,4-diamine

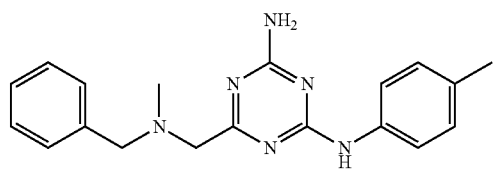

Yield: 14%.

ES-MS [M+H]$^+$: 335.2; Rt=1.59 min (Method B).

$^1$H NMR (400 MHz, DMSO-d$_6$) δ: 9.35 (br s, 1H), 7.66 (d, J=8.0 Hz, 2H), 7.36-7.30 (m, 4H), 7.26-7.22 (m, 1H), 7.06 (d, J=8.0 Hz, 2H), 7.00 (br s, 2H), 3.63 (s, 2H), 3.33 (m, 2H), 2.24 (s, 3H), 2.21 (s, 3H).

Example 5

6-((Benzyl(methyl)amino)methyl)-$N^2$-(4-bromophenyl)-1,3,5-triazine-2,4-diamine

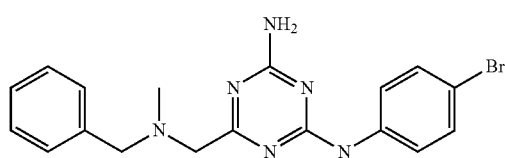

Yield: 25%

ES-MS [M+H]$^+$: 399.1; Rt=1.63 min (Method B).

$^1$H NMR (400 MHz, DMSO-d$_6$) δ: 9.62 (br s, 1H), 7.79 (d, J=8.8 Hz, 2H), 7.41 (d, J=9.6 Hz, 2H), 7.36-7.29 (m, 4H), 7.26-7.22 (m, 1H), 7.14-7.04 (m, 2H), 3.63 (s, 2H), 3.35 (s, 2H), 2.21 (s, 3H).

Example 6

6-((Benzyl(methyl)amino)methyl)-$N^2$-(4-methoxyphenyl)-1,3,5-triazine-2,4-diamine

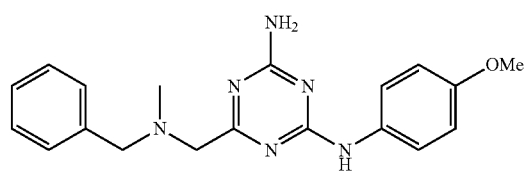 [SMILES: COc1ccc(Nc2nc(N)nc(CN(C)Cc3ccccc3)n2)cc1]

Yield: 3%

ES-MS [M+H]$^+$: 351.2; Rt=1.53 min (Method B).

$^1$H NMR (400 MHz, DMSO-d$_6$) δ: 9.28 (br s, 1H), 7.66 (d, J=8.8 Hz, 2H), 7.35-7.29 (m, 4H), 7.25-7.22 (m, 1H), 6.94 (br s, 2H), 6.83 (d, J=8.8 Hz, 2H), 3.72 (s, 3H), 3.63 (s, 2H), 3.32 (s, 2H), 2.21 (s, 3H).

Example 7

6-((Benzyl(methyl)amino)methyl)-$N^2$-m-tolyl-1,3,5-triazine-2,4-diamine

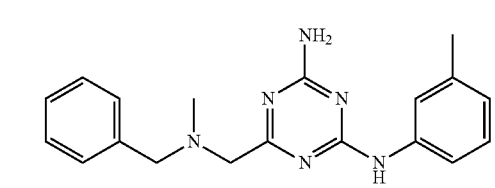

Yield: 8%

ES-MS [M+H]$^+$: 208.2; Rt=1.27 min (Method B).

$^1$H NMR (400 MHz, DMSO-d$_6$) δ: 9.37 (br s, 1H), 7.63-7.59 (m, 2H), 7.36-7.29 (m, 4H), 7.25-7.22 (m, 1H), 7.14-7.10 (m, 1H), 7.02 (br s, 2H), 6.77 (d, J=7.6 Hz, 1H), 3.64 (s, 2H), 3.35 (s, 2H), 2.26 (s, 3H), 2.22 (s, 3H).

Example 8

6-((Benzyl(methyl)amino)methyl)-$N^2$-(3-bromophenyl)-1,3,5-triazine-2,4-diamine

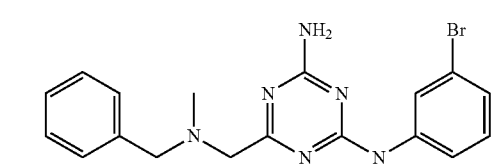

Yield: 15%

ES-MS [M+H]$^+$: 399.1: Rt=1.62 min (Method B).

$^1$H NMR (400 MHz, DMSO-d$_6$) δ: 9.65 (s, 1H), 8.11 (s, 1H), 7.79 (d, J=8.0 Hz, 1H), 7.36-7.29 (m, 4H), 7.25-7.11 (m, 5H), 3.64 (s, 2H), 3.37 (s, 2H), 2.23 (s, 3H).

Example 9

6-(Benzyl(methyl)amino)methyl)-N$^2$-(3-methoxyphenyl)-1,3,5-triazine-2,4-diamine

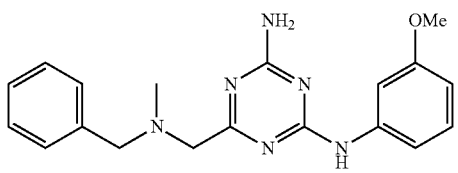 [SMILES: COc1cccc(Nc2nc(N)nc(CN(C)Cc3ccccc3)n2)c1]

Yield: 3%
ES-MS [M+H]$^+$: 351.2; Rt=1.55 min (Method B).
$^1$H NMR (400 MHz, DMSO-d$_6$) δ: 9.43 (br s, 1H), 7.57 (s, 1H), 7.36-7.29 (m, 5H), 7.25-7.22 (m, 1H), 7.12 (br s, 3H), 6.55-6.52 (m, 1H), 3.72 (s, 3H), 3.63 (s, 2H), 3.54 (s, 2H), 2.21 (s, 3H).

Example 10

6-((Benzyl (methyl) amino) methyl)-N$^2$-(2-methoxyphenyl)-1,3,5-triazine-2,4-diamine

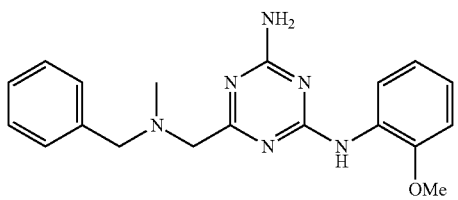 [SMILES: COc1ccccc1Nc1nc(N)nc(CN(C)Cc2ccccc2)n1]

Yield: 6.9%
ES-MS [M+H]$^+$: 351.2; Rt=1.56 min (Method B).
$^1$H NMR (400 MHz, DMSO-d$_6$) δ: 8.14 (d, J=8.0 Hz, 1H), 7.87 (s, 1H), 7.35-7.29 (m, 4H), 7.26-7.22 (m, 1H), 7.06-7.02 (m, 4H), 6.93-6.89 (m, 1H), 3.83 (s, 3H), 3.63 (s, 2H), 3.34 (s, 2H), 2.21 (s, 3H).

General Procedure IV

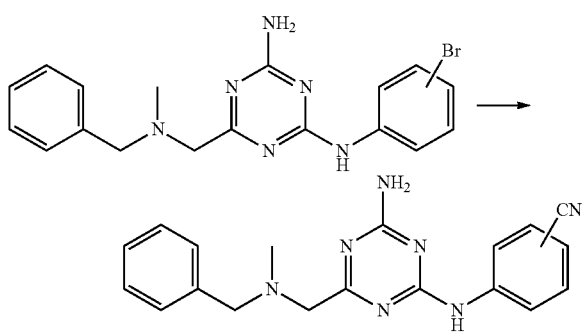

To a stirred and degassed (with argon) solution of bromo phenyl triazine (ex: 6-((benzyl(methyl)amino)methyl)-N$^2$-(4-bromophenyl)-1,3,5-triazine-2,4-diamine) (1 eq), Zn(CN)$_2$ (2.05 eq) in dimethyl formamide (9 mL/mmol) at room temperature were added DavePhos (0.026 eq) and Pd(PPh$_3$)$_4$ (0.05 eq). The reaction mixture was irradiated under microwave at 160° C. for 0.5 h. After reaction completion, the reaction mixture was cooled to room temperature and slowly poured into water and the organic product was extracted with ethyl acetate. The organic layer was washed with water, brine solution and dried over anhydrous sodium sulfate. The solvent was evaporated under vacuum to get the crude product, which was purified by flash column chromatography purification using 20% to 60%© ethyl acetate-petroleum ether as eluent to get the wanted product (ex: (44(4-amino-6-((benzyl(methyl)amino)methyl)-1,3,5-triazin-2-yl)amino)benzonitrile).

Example 11

4-(4-Amino-6-((benzyl(methyl)amino)methyl)-1,3,5-triazin-2-ylamino)benzonitrile

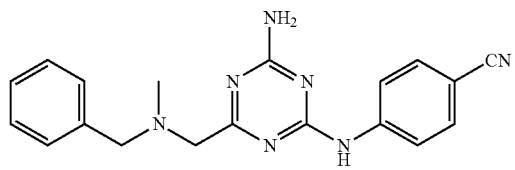 [SMILES: CN(Cc1ccccc1)Cc1nc(N)nc(Nc2ccc(C#N)cc2)n1]

Yield: 11%
ES-MS [M+H]$^+$: 346.2; Rt=1.53 min (Method B).
$^1$H NMR (500 MHz, DMSO-d$_6$) δ: 10.02 (s, 1H), 8.03 (d, J=8.5 Hz, 2H), 7.70 (d, J=9.0 Hz, 2H), 7.30 (s, 7H), 3.60 (s, 2H), 3.39 (s, 2H), 2.22 (s, 3H).

Example 12

3-(4-Amino-6-((benzyl(methyl)amino)methyl)-1,3,5-triazin-2-ylamino)benzonitrile

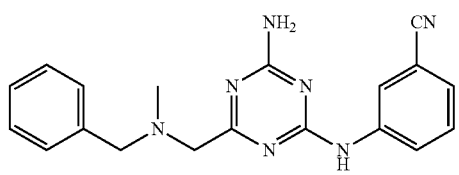 [SMILES: CN(Cc1ccccc1)Cc1nc(N)nc(Nc2cccc(C#N)c2)n1]

Yield: 8%
ES-MS [M+H]$^+$: 346.2; Rt=1.54 min (Method B).
$^1$H NMR (500 MHz, DMSO-d$_6$) δ: 9.85 (s, 1H), 8.38 (s, 1H), 8.02-8.00 (m, 1H), 7.48-7.45 (m, 1H), 7.40-7.39 (m, 1H), 7.36-7.30 (m, 4H), 7.26-7.24 (m, 3H), 3.63 (s, 2H), 3.37 (s, 2H), 2.22 (s, 3H).

Intermediate 9 tert-butyl 4-(benzyl(methyl)amino)-3-oxobutanoate

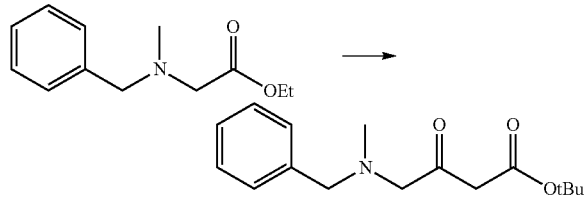

To a stirring solution of t-butyl acetate (5.0 g, 43.4 mmol, 3.0 eq) in tetrahydrofuran (25 mL) was added lithium diisopropylamide (2 M in tetrahydrofuran) (24.63 mL, 49.2 mmol, 3.4 eq) at −78° C. under nitrogen atmosphere and stirred for 60 min at −78° C. To the reaction mixture was added a solution of compound ethyl N-benzyl-N-methyl-glycinate (3.0 g, 14.5 mmol, 1.0 eq) in tetrahydrofuran (10 mL) at −78° C. and stirred for another 1 h. The reaction mixture was quenched with saturated ammonium chloride solution and stirred for 10-15 min at room temperature. The organic product was extracted with ethyl acetate. The organic layer was washed with water followed by brine solution. The organic layer was dried over anhydrous sodium sulfate and the solvent was evaporated under reduced pressure to afford crude compound tert-butyl 4-(benzyl(methyl)amino)-3-oxobutanoate (4.0 g, 14.4 mmol). The crude product was used for the next step without further purification. Yield: 95%.

ES-MS [M+H]$^+$: 278.2; Rt=1.52 min (Method B).

Intermediate 10 ethyl 4-(benzyl(methyl)amino)-3-oxobutanoate

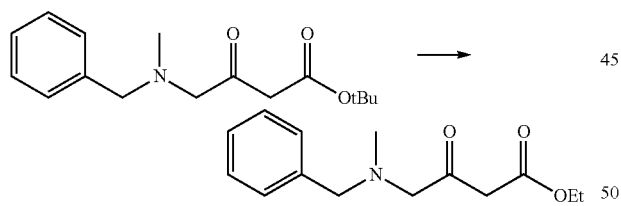

In a sealed tube compound tert-butyl 4-(benzyl(methyl) amino)-3-oxobutanoate (4.0 g, 14.4 mmol, 1.0 eq) was dissolved in ethanol (25 mL). The reaction mixture was heated to 100° C. for 16 h. The reaction mixture was cooled to room temperature and solvent was concentrated under reduced pressure to afford the residue. The residue was dissolved in ethyl acetate and the organic layer was washed with water followed by brine. The organic layer was dried over anhydrous sodium sulfate and the solvent was concentrated under reduced pressure to afford crude mixture. The crude was purified by column chromatography (silica gel 100-200 mesh; using 20% ethyl acetate in petroleum ether) to get the compound ethyl 4-(benzyl(methyl)amino)-3-oxobutanoate (1.3 g) as off white solid. Yield: 36%.

ES-MS [M+H]$^+$: 250.2; Rt=1.36 min (Method B).

$^1$H NMR (400 MHz, DMSO-d$_6$) δ: 7.35-7.24 (m, 5H), 4.21-4.14 (m, 2H), 3.58 (s, 2H), 3.51 (s, 2H), 3.25 (s, 2H), 2.28 (s, 3H), 1.29-1.26 (t, 3H).

General Procedure V

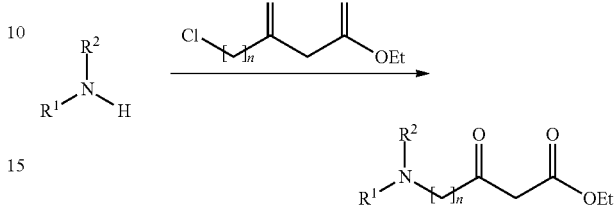

Under nitrogen atmosphere, a mixture of the appropriate phenyl amine (1 eq), wherein R$^1$ and R$^2$ are as defined above (ex: N-methylaniline), sodium bicarbonate (2 eq), the corresponding oxobutanone (2 eq) (ex: ethyl 4-chloro-3-oxobutanoate) and potassium iodide (2 eq) in dry acetonitrile (0.2 mL/mmol) was heated at 80° C. for 16 h. After cooling at room temperature, sodium thiosulfate saturated solution was added and the organic layer was separated. The aqueous layer was extracted with ethyl acetate (×3) and the combined organic layers were adjusted to pH=3 with aqueous hydrochloric acid 1M. The aqueous phase was cleaned with ethyl acetate (×2) and basified carefully with sodium hydroxide (1M) until pH=8. Ethyl acetate was added and organic layer was separated, dried over magnesium sulfate, filtrated, and concentrated under vacuum. The crude was purified by flash column chromatography (dichloromethane/methanol) to obtain the desired product (ex: ethyl 4-(methyl(phenyl) amino)-3-oxobutanoate).

Intermediate 11

Ethyl 4-(methyl(phenyl)amino)-3-oxobutanoate

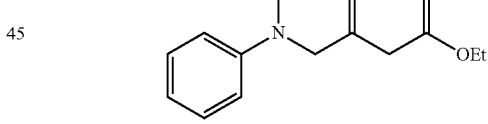

Yield: 22%
HPLC-MS [M+H]$^+$: 236; Rt=2.93 min (Method C).

Intermediate 12

Ethyl 4-(3,4-dihydroquinolin-1(2H)-yl)-3-oxobutanoate

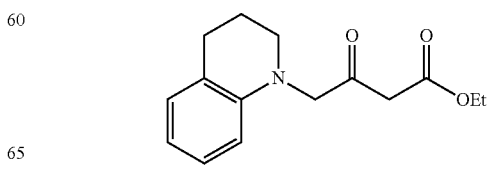

Yield: 51%
HPLC-MS [M+H]+: 262; Rt=3.15 min (Method C).

General Procedure VI

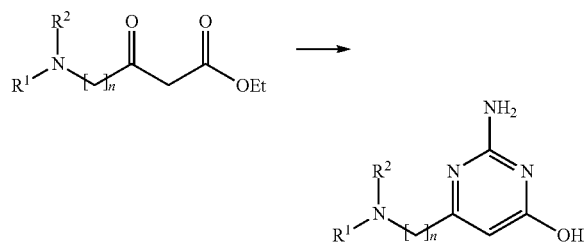

The appropriate amino oxobutanoate (1.1 eq), wherein R¹, R², and n are as defined above, (ex: ethyl 4-(methyl (phenyl)amino)-3-oxobutanoate), guanidine hydrochloride (1 eq) and potassium carbonate (1.1 eq) in ethanol were stirred at reflux temperature for 16 h. After cooling, the appeared precipitate was filtered off and the resultant crude was purified by flash column chromatography (dichloromethane/methanol) to obtain the desired pyrimidine product (ex: 2-amino-6-((methyl(phenyl)amino)methyl)pyrimidin-4-01).

Intermediate 13

2-Amino-6-((methyl(phenyl)amino)methyl)pyrimidin-4-ol

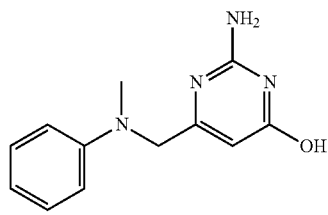 [SMILES: CN(Cc1cc(O)nc(N)n1)c1ccccc1]

Yield: 74%
HPLC-MS [M+H]+: 231; Rt=1.80 min (Method C).

Intermediate 14

2-Amino-6-((3,4-dihydroquinolin-1(2H)-yl)methyl) pyrimidin-4-ol

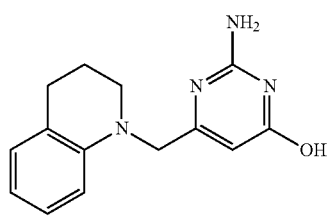 [SMILES: Nc1nc(O)cc(CN2CCCc3ccccc32)n1]

Yield: 37%
HPLC-MS [M+H]+: 257; Rt=2.05 min (Method C).

Intermediate 15

2-amino-6-((benzyl(methyl)amino)methyl)pyrimidin-4-ol

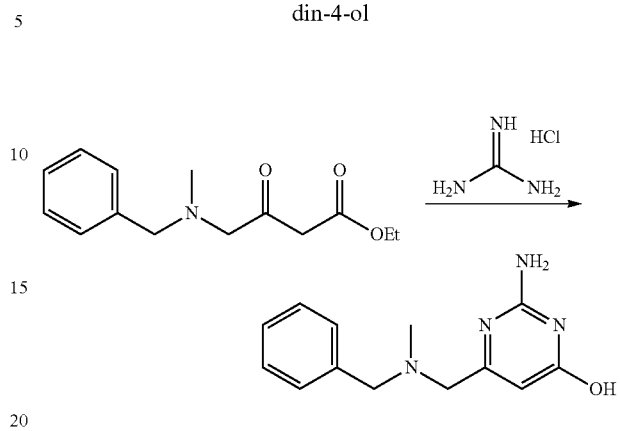

In a sealed tube 30% sodium methoxide in methanol (6 mL) was added to a stirred solution of compound ethyl 4-(benzyl(methyl)amino)-3-oxobutanoate (1.2 g, 4.8 mmol, 1.0 eq) in ethanol (10 mL) and stirred for 10 min at room temperature. Guanidine hydrochloride was added to (0.91 g, 9.6 mmol, 2 eq) the reaction mixture at room temperature. The reaction mixture was heated to 100° C. under stirring condition for 16 h. Reaction mixture was cooled to room temperature and the solvent was evaporated under reduced pressure to get the crude product. The crude product was purified by reverse phase flash column chromatography using 0.1% formic acid in water and acetonitrile as eluent to get pure compound 2-amino-6-((benzyl(methyl)amino) methyl)pyrimidin-4-ol (0.9 g, 3.7 mmol). Yield: 77%.

ES-MS [M+H]+: 245.2; Rt=1.042 min (Method B).

General Procedure VII

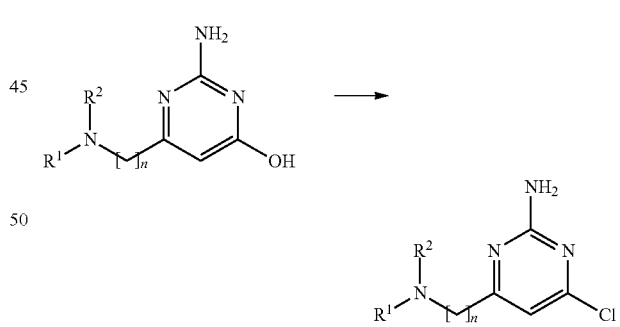

A heterogeneous solution of the corresponding pyrimidin-4-ol (1 eq) (ex: 2-amino-6-((methyl(phenyl)amino)methyl) pyrimidin-4-ol) in phosphoryl chloride (10 eq) was heated to reflux temperature during 1 h. The reaction mixture was cooled and concentrated under vacuum to remove excess of phosphoryl chloride. The residue was taken-up into dichloromethane, neutralized and subsequently basified carefully with sodium hydroxide (1M) until pH=8. The organic layer was separated, washed with water, dried over magnesium sulfate and concentrated under vacuum. The resultant crude was purified by flash column chromatography (dichloromethane/methanol) to obtain the desired product (ex: 4-chloro-6-((methyl(phenyl)amino)methyl)pyrimidin-2-amine).

Intermediate 16

4-Chloro-6-((methyl(phenyl)amino)methyl)pyrimidin-2-amine

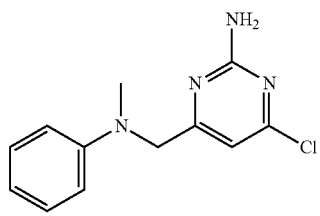 [SMILES: CN(Cc1cc(Cl)nc(N)n1)c1ccccc1]

Yield: 7%
HPLC-MS [M+H]$^+$: 249/251: Rt=2.93 min (Method C).

Intermediate 17

4-Chloro-6-((3,4-dihydroquinolin-1(2H)-yl)methyl)pyrimidin-2-amine

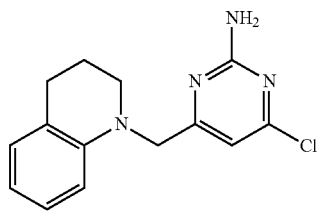 [SMILES: Nc1nc(Cl)cc(CN2CCCc3ccccc32)n1]

Yield: 52%
HPLC-MS [M+H]$^+$: 275; Rt=3.15 min (Method C).

General Procedure VIII

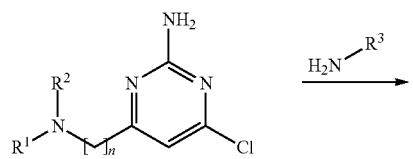

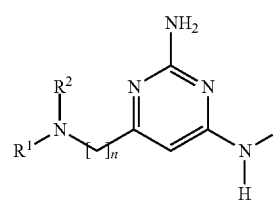

The appropriate chloride (1 eq) (ex: 4-chloro-6-((methyl(phenyl)amino)methyl)-pyrimidin-2-amine) and the corresponding aromatic amine (2 eq) (ex: p-toluidine) were stirred at 140° C. for 1-5 h. The resultant crude was purified by flash column chromatography (dichloromethane/methanol) to obtain the desired product (ex: 6-((methyl(phenyl)amino)methyl)-N$^4$-(p-tolyl)pyrimidine-2,4-diamine).

Example 13

6-Methyl(phenyl)amino)methyl)-N$^4$-(p-tolyl)pyrimidine-2,4-diamine

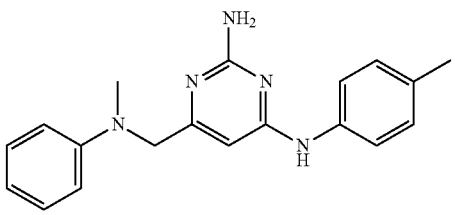 [SMILES: Cc1ccc(Nc2cc(CN(C)c3ccccc3)nc(N)n2)cc1]

Yield: 50%
HPLC-MS [M+H]$^+$: 320; Rt=2.35 min (Method C).
$^1$H NMR (400 MHz, CDCl$_3$) δ: 7.23 (dd, J=8.8, 7.3 Hz, 2H), 7.07 (dd, J=20.5, 8.4 Hz, 4H), 6.74 (t, J=7.2 Hz, 1H), 6.68 (d, J=7.9 Hz, 2H), 6.40 (s, 1H), 5.93 (s, 1H), 4.30 (s, 2H), 3.49 (s, 3H), 2.30 (s, 3H).

Example 14

6-((3,4-Dihydroquinolin-1(2H)-yl)methyl)-N$^1$-(p-tolyl)pyrimidine-2,4-diamine

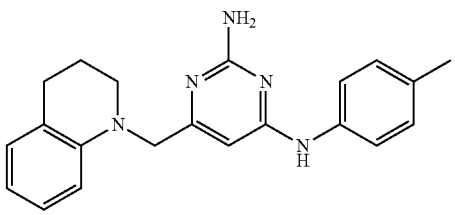 [SMILES: Cc1ccc(Nc2cc(CN3CCCc4ccccc43)nc(N)n2)cc1]

Yield: 10%.
HPLC-MS [M+H]$^+$: 346; Rt=2.38 min (Method C).
$^1$H NMR (400 MHz, CDCl$_3$) δ; 7.37 (s, 2H), 7.10 (d, J=8.3 Hz, 2H), 6.93 (t, J=8.2 Hz, 2H), 6.64 (t, J=7.1 Hz, 1H), 6.32-6.11 (m, 2H), 4.22 (s, 2H), 3.46-3.19 (m, 2H), 2.74 (t, J=6.2 Hz, 2H), 2.29 (d, J=10.2 Hz, 3H), 2.06-1.91 (m, 2H).

General Procedure IX

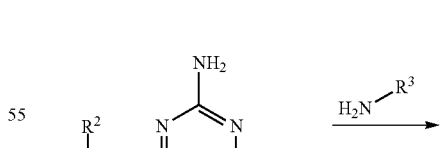

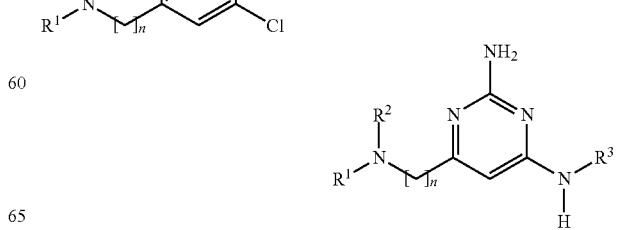

To a stirred solution of a chloride compound (ex: 4-((benzyl(methyl)amino)methyl)-6-chloropyrimidin-2-amine) (1.0 eq) in 1-butanol (13 mL/mmol) were added the corresponding aniline (ex. o-anisidine) (2.0 eq), sulfuric acid (catalytic, 2 drops) at room temperature and heated to 100° C. for 16 h. After completion of the reaction, the reaction mixture was allowed to cool to room temperature and diluted with water and basified with saturated sodium bicarbonate (~pH=8). The aqueous layer was extracted twice with ethyl acetate, dried over anhydrous sodium sulfate and solvent was evaporated under reduced pressure to get crude compound. The crude was purified by flash column chromatography instrument using 2% to 15% methanol in dichloromethane as eluent to get the product (ex: 6-((benzyl(methyl) amino) methyl)-$N^4$-(2-methoxyphenyl) pyrimidine-2,4-diamine).

Example 15

6-((benzyl(methyl)amino)methyl)-$N^4$-(2-methoxyphenyl)pyrimidine-2,4-diamine

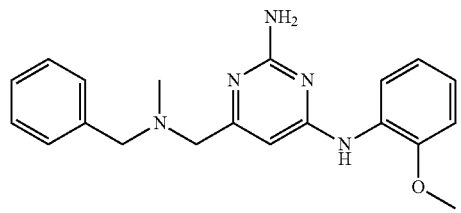 [SMILES: COc1ccccc1Nc1cc(CN(C)Cc2ccccc2)nc(N)n1]

Yield: 7% (over 2 steps from intermediate 16).
ES-MS [M+H]$^+$: 350.32; Rt=1.96 min (Method E).
$^1$H NMR (400 MHz, DMSO-d$_6$) δ: 8.15 (s, 1H), 8.06-8.04 (d, J=7.6 Hz, 1H), 7.34-7.24 (m, 5H), 7.03-7.01 (m, 2H), 6.92-6.88 (m, 1H), 6.34 (s, 1H), 6.05 (br s, 2H), 3.80 (s, 3H), 3.51 (s, 2H), 3.24 (s, 2H), 2.12 (s, 3H).

Example 16

6-((benzyl(methyl)amino)methyl)-$N^4$-m-tolylpyrimidine-2,4-diamine

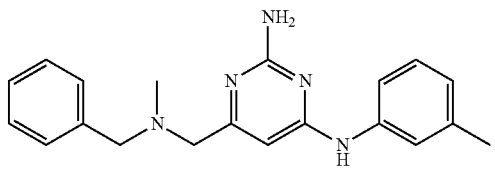 [SMILES: Cc1cccc(Nc2cc(CN(C)Cc3ccccc3)nc(N)n2)c1]

Yield: 4% (over 2 steps from intermediate 16).
ES-MS [M+H]$^+$: 334.3; Rt=2.31 min (Method F).
$^1$H NMR (400 MHz, DMSO-d$_6$) δ: 8.98 (s, 1H), 7.54 (d, J=8.4 Hz, 1H), 7.47 (s, 1H), 7.37-7.31 (m, 4H), 7.28-7.26 (m, 1H), 7.15-7.11 (m, 1H), 6.75 (d, J=7.6 Hz, 1H), 6.27 (s, 1H), 6.13 (br s, 2H), 3.53 (s, 2H), 3.25 (s, 2H), 2.28 (s, 3H), 2.14 (s, 3H).

Example 17

6-((benzyl(methyl)amino)methyl)-$N^4$-(3-methoxyphenyl)pyrimidine-2,4-diamine

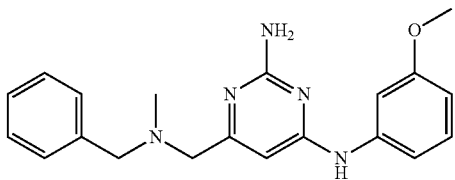 [SMILES: COc1cccc(Nc2cc(CN(C)Cc3ccccc3)nc(N)n2)c1]

Yield: 7% (over 2 steps from intermediate 16).
ES-MS [M+H]$^+$: 350.32: Rt=1.96 min (Method E).
$^1$H NMR (400 MHz, DMSO-d$_6$): 9.07 (s, 1H), 7.45-7.44 (m, 1H), 7.38-7.31 (m, 4H), 7.28-7.20 (m, 2H), 7.16-7.12 (m, 1H), 6.52-6.49 (m, 1H), 6.28 (s, 1H), 6.16 (br s, 2H), 3.74 (s, 3H), 3.54 (s, 2H), 3.26 (s, 2H), 2.15 (s, 3H).

Example 18

6-((benzyl(methyl)amino)methyl)-$N^4$-(4-methoxyphenyl)pyrimidine-2,4-diamine

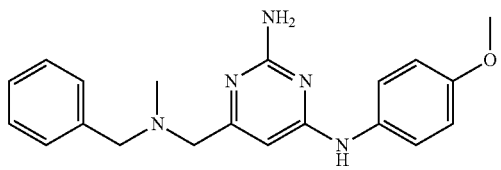 [SMILES: COc1ccc(Nc2cc(CN(C)Cc3ccccc3)nc(N)n2)cc1]

Yield: 6% (over 2 steps from intermediate 16).
ES-MS [M+H]$^+$: 350.40; Rt=2.18 min (Method F).
$^1$H NMR (400 MHz, DMSO-d$_6$) δ: 8.86 (s, 1H), 7.55 (d, J=9.2 Hz, 2H), 7.34-7.24 (m, 5H), 6.87-6.83 (m, 2H), 6.19 (s, 1H), 6.04 (br s, 2H), 3.72 (s, 3H), 3.52 (s, 2H), 3.24 (s, 2H), 2.13 (s, 3H).

Example 19

4-(2-amino-6-((benzyl(methyl)amino)methyl)pyrimidin-4-ylamino)benzonitrile

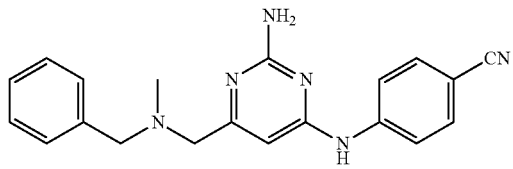 [SMILES: CN(Cc1ccccc1)Cc1cc(Nc2ccc(C#N)cc2)nc(N)n1]

Yield: 7% (over 2 steps from intermediate 16).
ES-MS [M+H]$^+$: 345.40: Rt=1.91 min (Method G).
$^1$H NMR (400 MHz, DMSO-d$_6$) δ: 9.63 (s, 1H), 7.98-7.96 (m, 2H), 7.67-7.65 (m, 2H), 7.38-7.26 (m, 5H), 6.38 (s, 2H), 6.35 (s, 2H), 3.55 (s, 2H), 3.29 (s, 2H), 2.15 (s, 3H).

Example 20

6-((benzyl(methyl)amino)methyl)-N⁴-(3-chlorophenyl)pyrimidine-2,4-diamine

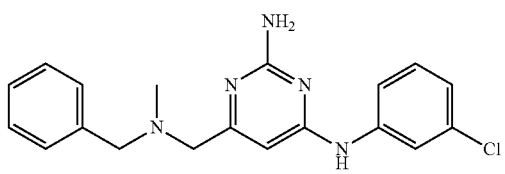 [SMILES: CN(Cc1ccccc1)Cc1cc(Nc2cccc(Cl)c2)nc(N)n1]

Yield: 5% (over 2 steps from intermediate 16).
ES-MS [M+H]⁺: 354.24; Rt=2.11 min (Method E).
¹H NMR (400 MHz, DMSO-$d_6$) δ: 9.28 (s, 1H), 7.92 (s, 1H), 7.63 (d, J=8.4 Hz, 1H), 7.36-7.24 (m, 6H), 6.95 (d, J=7.6 Hz, 1H), 6.29-6.26 (m, 3H), 3.54 (s, 2H), 3.27 (s, 2H), 2.15 (s, 3H).

Example 21

6-((benzyl(methyl)amino)methyl)-N⁴-(4-chlorophenyl)pyrimidine-2,4-diamine

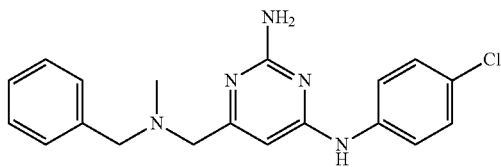 [SMILES: CN(Cc1ccccc1)Cc1cc(Nc2ccc(Cl)cc2)nc(N)n1]

Yield: 4% (over 2 steps from intermediate 16).
ES-MS [M+H]⁺: 354.36: Rt=2.12 min (Method E).
¹H NMR (400 MHz, DMSO-$d_6$) δ: 9.23 (s, 1H), 7.79-7.77 (m, 2H), 7.36-7.34 (m, 4H), 7.28-7.26 (m, 3H), 6.27 (s, 1H), 6.21 (br s, 2H), 3.54 (s, 2H), 3.26 (s, 2H), 2.14 (s, 3H).

Intermediate 18

2-(benzyl(methyl)amino)acetonitrile

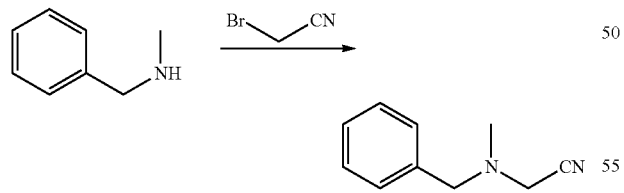

To a stirring solution of N-methyl-1-phenylmethanamine (5.0 g, 41.3 mmol, 1.0 eq) in dichloromethane (50 mL) was added N,N-Diisopropylethylamine (16.5 mL, 98.4 mmol, 2.4 eq) under nitrogen atmosphere. To the reaction mixture was added 2-bromo acetonitrile (5.44 g, 45.9 mmol, 1.1 eq) drop wise at 0° C. The reaction mixture was allowed to come to room temperature and stirred for 16 h. Reaction mixture was quenched with ice water and then the dichloromethane layer was separated. The organic layer was washed with water followed by brine. The organic layer was dried over anhydrous sodium sulfate and solvent was concentrated under reduced pressure to afford crude product. Crude product was purified by column chromatography (silica gel 100-200 mesh; using 10% ethyl acetate in petroleum ether) to get the product 2-(benzyl (methyl) amino) acetonitrile (5.0 g) as yellow liquid. Yield: 75%.
ES-MS [M+H]⁺: 161.2; Rt=1.70 min (Method B).
¹H NMR (400 MHz, CDCl₃) δ: 7.4-7.25 (m, 5H), 3.60 (s, 2H), 3.45 (s, 2H), 3.43 (s, 3H).

Intermediate 19

2-(benzyl(methyl)amino)acetimidamide

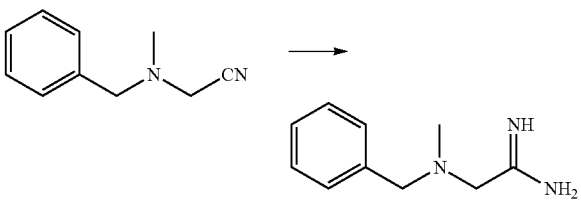

To a stirred suspension of ammonium chloride (0.33 g, 6.2 mmol, 2.0 eq) in toluene at 0° C. was added trimethyl aluminum (2.0 M in toluene) (3.15 mL, 6.2 mmol, 2.0 eq) and stirred at room temperature for 1 h. To the reaction mixture was added a solution of compound 2-(benzyl (methyl)amino)acetonitrile (0.5 g, 3.1 mmol, 1.0 eq) in toluene and heated to 110° C. for 16 h. After completion of the reaction, the reaction mixture was cooled to room temperature and slowly poured into the emulsion of silica (~3.0 g) in chloroform at 0° C. The mixture was stirred for 30 min and filtered. The silica bed was washed thoroughly with chloroform\methanol\aqueous ammonia (40:10:1 v/v/v). The combined filtrate was evaporated under reduced pressure and co-distilled with toluene to get the crude compound 2-(benzyl(methyl)amino)acetimidamide (0.5 g) which was used for the next step without further purification. Yield: 90%.
ES-MS [M+H]⁺: 178.2; Rt=1.679 min (Method A).

Intermediate 20

2-((benzyl(methyl)amino)methyl)pyrimidine-4,6-diol

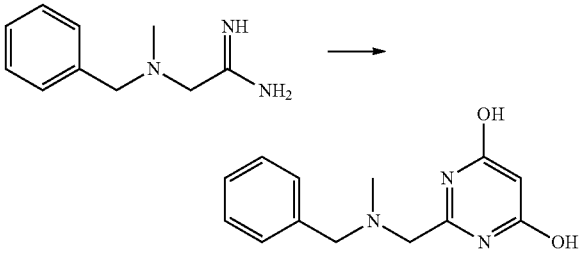

To a stirred solution of compound 2-(benzyl(methyl) amino)acetimidamide (0.5 g, 2.8 mmol, 1.0 eq) and diethylmalonate (0.5 mL, 0.54 mmol, 1.2 eq) in methanol was added 30% sodium methoxide in methanol (0.76 mL, 4.2 mmol, 1.5 eq) at room temperature and heated to 70° C. for 16 h. After completion of the reaction, the reaction mixture was cooled to room temperature and concentrated under reduced pressure to get the crude product. The crude product was purified by reverse phase purification in flash column chromatography using 0.01 M aqueous formic acid and methanol as eluent to get compound 2-((benzyl(methyl)amino)methyl)pyrimidine-4,6-diol as thick yellow gummy solid. Yield: 36% (over 2 steps from intermediate 18).

ES-MS [M+H]$^+$: 246.1; Rt=1.331 min (Method A).

$^1$H NMR (400 MHz, DMSO-d$_6$) δ: 12.0-11.75 (br s, 2H), 7.41-7.24 (m, 5H), 5.16 (s, 1H), 3.63-3.60 (m, 2H), 3.45 (s, 2H), 2.16-2.15 (m, 3H).

Intermediate 21

N-benzyl-1-(4,6-dichloropyrimidin-2-yl)-N-methyl-methanamine

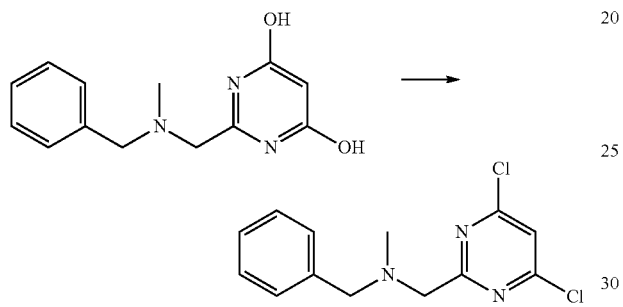

Phosphoryl chloride (0.6 mL, 1 g, 6.4 mmol, 2.6 eq) was added to compound 2-((benzyl(methyl)amino)methyl)pyrimidine-4,6-diol (0.6 g, 2.4 mmol, 1.0 eq) and heated to 100° C. for 3 h. After completion of the reaction, the reaction mixture was evaporated under reduced pressure and co-distilled twice with toluene to get the crude compound N-benzyl-1-(4,6-dichloropyrimidin-2-yl)-N-methylmethanamine as brown color liquid (0.6 g). The crude was used directly to next step without further purification. Yield: 89%.

ES-MS [M+H]$^+$: 282.1; Rt=1.51 min (Method B).

Intermediate 22

2-((benzyl(methyl)amino)methyl)-6-chloro-N-(p-tolyl)pyrimidin-4-amine

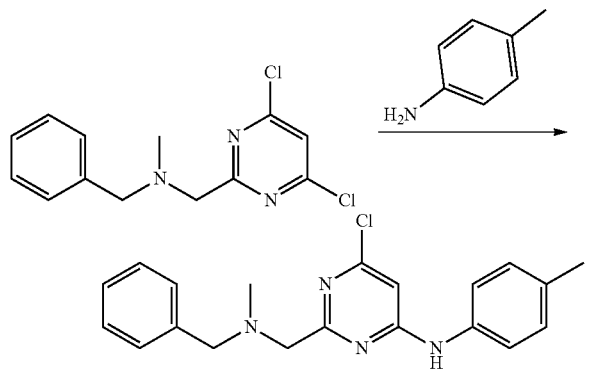

To a stirred solution of compound N-benzyl-1-(4,6-dichloropyrimidin-2-yl)-N-methylmethanamine (0.6 g, 2.1 mmol, 1.0 eq) in concentrated hydrochloric acid (0.192 mL) and water (1.92 mL) at room temperature were added p-toluidine (0.258 g, 2.41 mmol, 1.0 eq), sodium iodide (0.367 g, 2.41 mmol, 1.0 eq) and heated to 100° C. for 16 h. The reaction mixture was allowed to cool to room temperature and basified with saturated sodium bicarbonate (~pH=8) and the organic product was extracted into ethyl acetate. The organic layer was dried over anhydrous sodium sulfate and the solvent was evaporated under reduced pressure to get the crude mixture. The crude was purified by flash column chromatography using 10% to 60% ethyl acetate in petroleum ether as eluent to get compound 2-((benzyl(methyl)amino)methyl)-6-chloro-N-(p-tolyl)pyrimidin-4-amine (0.43 g) as pale brown thick liquid. Yield: 50% (over 2 steps from intermediate 20).

ES-MS [M+H]$^+$: 353.2; Rt=1.69 min (Method B).

$^1$H NMR (500 MHz, CDCl$_3$) δ: 7.39-7.13 (m, 9H), 7.00 (br s, 1H), 6.51 (s, 1H), 3.72-3.66 (m, 2H), 3.61-3.56 (m, 2H), 2.36 (s, 6H).

Intermediate 23

Tert-butyl (2-((benzyl(methyl)amino)methyl)-6-(p-tolylamino)pyrimidin-4-yl)carbamate

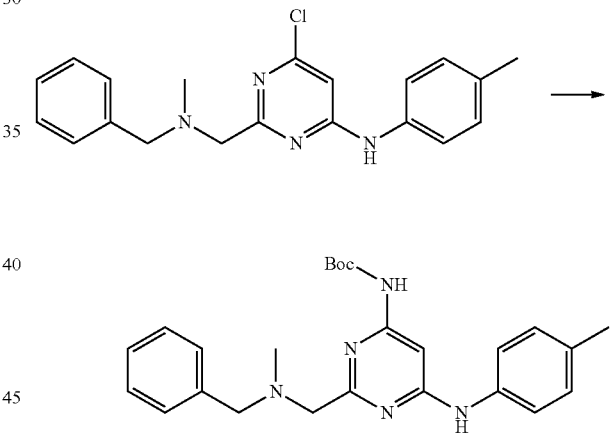

To a stirred and degassed solution of 2-((benzyl(methyl)amino)methyl)-6-chloro-N-(p-tolyl)pyrimidin-4-amine (0.5 g, 1.42 mmol, 1.0 eq), tert-butyl carbamate (0.332 g, 2.8 mmol, 2.0 eq) in 1,4-dioxane (6 mL) were added cesium carbonate (1.38 g, 4.2 mmol, 3.0 eq) XPhos (0.033 g, 0.07 mmol, 0.05 eq), Pd$_2$(dba)$_3$ (0.13 g, 0.142 mmol, 0.1 eq) and heated to 90° C. for 16 h. After completion of the reaction, the reaction mixture was allowed to cool to room temperature and diluted with water and the organic product was extracted with ethyl acetate. The organic layer was dried over anhydrous sodium sulfate and solvent was evaporated under reduced pressure. The crude was purified by flash column chromatography using 20% to 60% ethyl acetate in petroleum ether as eluent to get the product tert-butyl (2-((benzyl(methyl)amino)methyl)-6-(p-tolylamino)pyrimidin-4-yl)carbamate (0.38 g) as pale yellow thick liquid. Yield: 61%.

ES-MS [M+H]$^+$: 434.3; Rt=1.84 min (Method B).

Example 22

2-((Benzyl(methyl)amino)methyl)-N⁴-(p-tolyl)pyrimidine-4,6-diamine

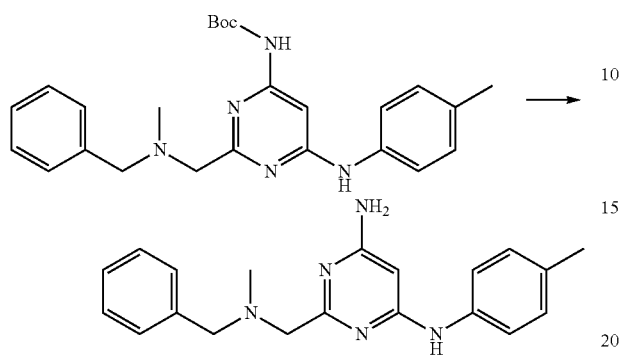

A solution of compound tert-butyl 2-((benzyl(methyl)amino)methyl)-6-(p-tolylamino)pyrimidin-4-ylcarbamate (0.38 g, 1 eq) in 4N hydrochloric acid in 1,4-dioxane (10 eq) was stirred at room temperature for 16 h. After completion of the reaction, the reaction mixture was evaporated under reduced pressure. The crude was basified with saturated sodium bicarbonate and the product was extracted with dichloromethane. The organic layer was dried over anhydrous sodium sulfate and evaporated. The crude was purified by preparative HPLC (reverse phase) to get the product 2-((benzyl(methyl)amino)methyl)-N⁴-(p-tolyl)pyrimidine-4,6-diamine as pale yellow solid. Yield: 5% (over 2 steps from intermediate 22).

ES-MS [M+H]⁺: 334.44; Rt=4.44 min (Method D).

¹H NMR (400 MHz, DMSO-$d_6$) δ: 8.72 (s, 1H), 7.41 (d, J=8.4 Hz, 2H), 7.37-7.29 (m, 4H), 7.25-7.23 (m, 1H), 7.06 (d, J=8.4 Hz, 2H), 6.24 (s, 2H), 5.64 (s, 1H), 3.62 (s, 2H), 3.37 (s, 2H), 2.24 (s, 3H), 2.19 (s, 3H).

Intermediate 24

Methyl 2-chloro-6-(2,4,4-trimethylpentan-2-ylamino)pyrimidine-4-carboxylate

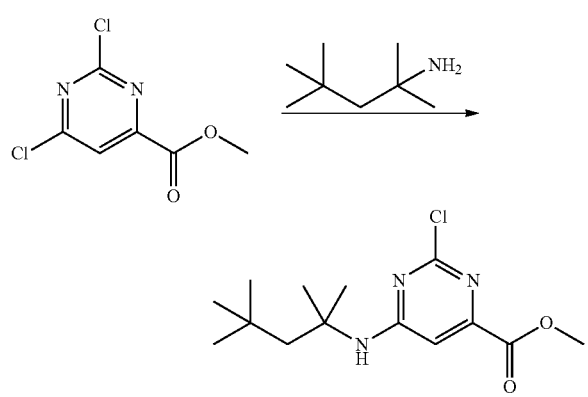

A mixture of compound methyl 2,6-dichloropyrimidine-4-carboxylate (5.0 g, 24.2 mmol, 1.0 eq), tert-octylamine (6.71 mL, 36.4 mmol, 1.5 eq) and N,N-diisopropylethylamine (6.71 mL, 36.4 mmol, 1.5 eq) in tetrahydrofuran (5 mL) was stirred at room temperature for 24 h. After completion of the reaction, the reaction mixture was diluted with water and the organic product was extracted with ethyl acetate. The organic layer was dried over anhydrous sodium sulfate and the solvent was evaporated under reduced pressure to get crude product. The crude was purified by flash column chromatography column using 10% to 40% ethyl acetate in petroleum ether as eluent to get methyl 2-chloro-6-(2,4,4-trimethylpentan-2-ylamino)pyrimidine-4-carboxylate (3.0 g) as white solid. Yield: 41%.

ES-MS [M+H]⁺: 300.2: Rt=2.167 min (Method B).

Intermediate 25

N-benzyl-2-chloro-N-methyl-6-(2,4,4-trimethylpentan-2-ylamino)pyrimidine-4-carboxamide

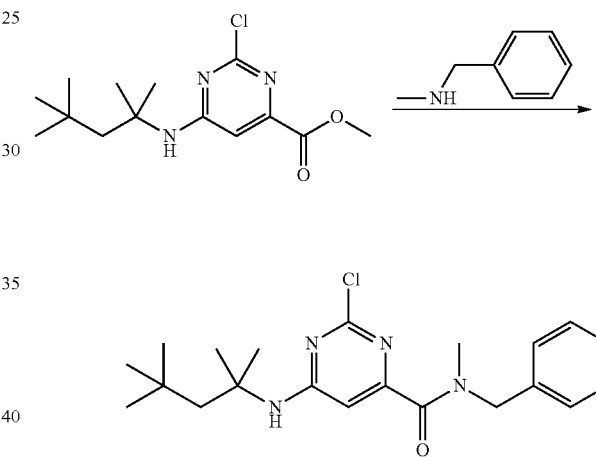

To a stirred solution of compound methyl 2-chloro-6-(2,4,4-tri methylpentan-2-ylamino)pyrimidine-4-carboxylate (0.5 g, 1.67 mmol, 1.0 eq), N-methylbenzylamine (0.202 g, 1.67 mmol, 1.0 eq) in tetrahydrofuran (10 mL) at room temperature was added 1,5,7-triazabicyclo[4.4.0]dec-5-ene (69.6 mg, 0.5 mmol, 0.3 eq) and stirred for 3 h at room temperature. After completion of the reaction, the reaction mixture was diluted with water and the organic product was extracted with ethyl acetate. The organic layer was dried over anhydrous sodium sulfate and solvent was evaporated under reduced pressure to get crude product. The crude product was purified by flash column chromatography column using 10% to 50% ethyl acetate in petroleum ether as eluent to get compound N-benzyl-2-chloro-N-methyl-6-(2,4,4-trimethylpentan-2-ylamino)pyrimidine-4-carboxamide (0.21 g) as a pale yellow thick liquid. Yield: 32%.

ES-MS [M+H]⁺: 289.3; Rt=2.281 min (Method B).

¹H NMR (400 MHz, DMSO-$d_6$) δ: 7.74-7.73 (d, J=6.4 Hz, 1H), 7.40-7.25 (m, 5H), 6.55 (s, 1H), 4.61 (s, 1H), 4.50 (s, 1H), 2.83-2.82 (m, 3H), 3.37 (s, 2H), 1.88-1.86 (m, 2H), 1.42-1.41 (m, 6H), 0.92-0.88 (m, 9H).

Intermediate 26

6-((Benzyl(methyl)amino)methyl)-2-chloro-N-(2,4,4-trimethylpentan-2-yl)pyrimidin-4-amine

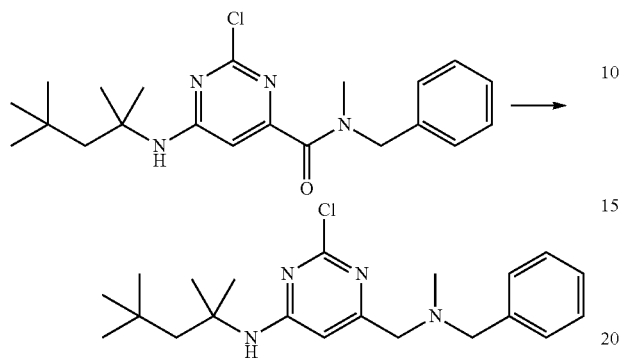

To a stirred solution of compound N-benzyl-2-chloro-N-methyl-6-(2,4,4-trimethylpentan-2-ylamino)pyrimidine-4-carboxamide (0.21 g, 0.5 mmol, 1.0 eq) in tetrahydrofuran at 0° C. was added borane dimethyl sulfide complex (0.16 mL, 1.5 mmol, 3.0 eq) and stirred at 70 for 4 h. The reaction mixture was allowed to cool to 0° C., quenched with 2N hydrochloric acid, basified with saturated sodium bicarbonate solution (pH~8) and the organic product was extracted into dichloromethane. The organic layer was dried over anhydrous sodium sulfate and solvent was evaporated under reduced pressure to get crude product. The crude product was purified by flash column chromatography column using 10% to 50% ethyl acetate in petroleum ether as eluent to get compound 6-((benzyl(methyl)amino)methyl)-2-chloro-N-(2,4,4-trimethylpentan-2-yl)pyrimidin-4-amine (0.08 g) as thick liquid. Yield: 39%.

ES-MS [M+H]$^+$: 375.3; Rt=1.90 min (Method B).

$^1$H NMR (400 MHz, DMSO-d$_6$) δ: 9.66 (s, 1H), 8.11 (s, 1H), 7.80 (d, J=8.4 Hz, 1H), 7.37-7.11 (m, 10H), 3.64 (s, 2H), 3.37 (s, 2H), 2.22 (s, 3H).

Intermediate 27

6-((Benzyl(methyl)amino)methyl)-N$^2$-p-tolyl-N$^4$-(2,4,4-trimethylpentan-2-yl)pyrimidine-2,4-diamine

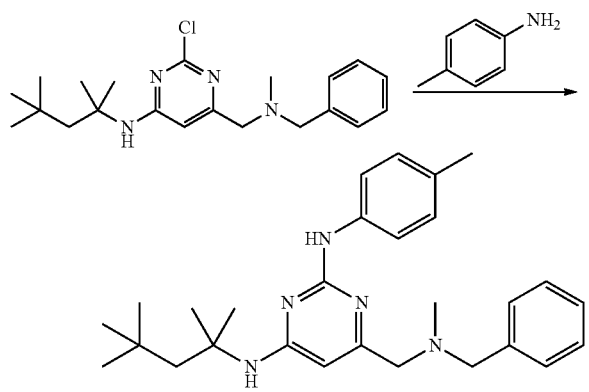

To a stirred solution of compound 6-((benzyl(methyl)amino)methyl)-2-chloro-N-(2,4,4-trimethylpentan-2-yl)pyrimidin-4-amine (0.08 g, 0.2 mmol, 1.0 eq) in 1-butanol (0.2 mL) at room temperature were added p-toluidine (0.04 g, 0.4 mmol, 2.0 eq), catalytic sulfuric acid (2 drops) and heated to 110° C. for 16 h. After completion of the reaction, the reaction mixture was cooled to room temperature and slowly basified with saturated sodium bicarbonate and the organic product was extracted into ethyl acetate. The organic layer was dried over anhydrous sodium sulfate and solvent was evaporated under reduced pressure to get crude product. The crude product was purified by flash column chromatography using 10% to 60% ethyl acetate in petroleum ether as eluent to get compound 6-((benzyl(methyl)amino)methyl)-N$^2$-p-tolyl-N$^4$-(2,4,4-trimethylpentan-2-yl)pyrimidine-2,4-diamine (0.07 g) as pale brown thick liquid. Yield: 78%.

ES-MS [M+H]$^+$: 446.4; Rt=2.028 min (Method B).

Example 23

6-((benzyl(methyl)amino)methyl)-N$^2$-p-tolylpyrimidine-2,4-diamine

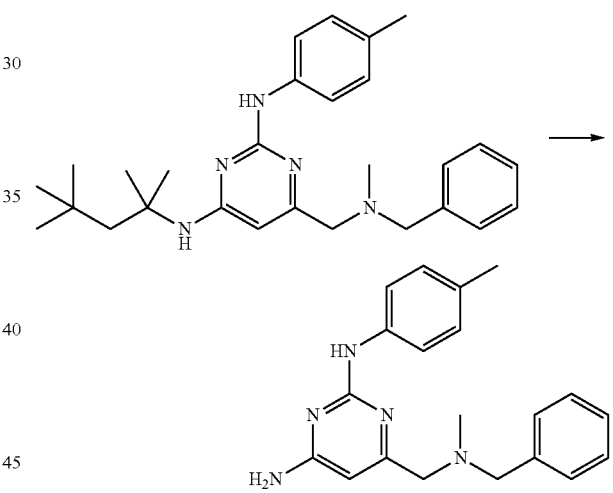

To a stirred solution of compound 6-((benzyl(methyl)amino)methyl)-N$^2$-p-tolyl-N-(2,4,4-trimethylpentan-2-yl)pyrimidine-2,4-diamine in dichloromethane (3 mL) at room temperature was added trifluoro acetic acid (7 eq) and heated to 40° C. for 16 h. The reaction mixture was evaporated completely to get the residue which was basified with saturated sodium bicarbonate and the organic product was extracted into dichloromethane. The organic layer was dried over anhydrous sodium sulfates and solvent was evaporated under reduced pressure. The crude product was purified by flash column chromatography using 20% to 60% ethyl acetate in petroleum ether as eluent to get 6-((benzyl(methyl)amino)methyl)-N$^2$-p-tolylpyrimidine-2,4-diamine (0.04 g) as pale yellow solid. Yield: 16%.

ES-MS [M+H]$^+$: 334.2: Rt=1.615 min (Method B).

$^1$H NMR (400 MHz, DMSO-d$_6$) δ: 9.31 (s, 1H), 7.57-7.41 (m, 9H), 7.10 (d, J=8.4 Hz, 1H), 6.03 (s, 1H), 4.14 (s, 2H), 3.84 (s, 2H), 2.55 (s, 2H), 2.26 (s, 3H).

Intermediate 28

4,6-dichloropicolinic acid

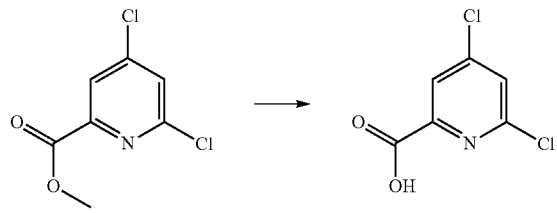

Lithium hydroxide monohydrate (1.46 g, 34.9 mmol) was added to a solution of methyl 4,6-dichloropicolinate (4.8 g, 23.3 mmol) in methanol:water (100 mL, 1:0.1 v/v) at 0° C. The reaction mixture was warmed to room temperature and stirred for 16 h. The reaction mixture was concentrated under reduced pressure to get crude product which was diluted with water. The crude was acidified by 2N hydrochloric acid at 0° C. to get white precipitate. The precipitate was filtered and dried under vacuum to get 3.0 g of 4,6-dichloropicolinic acid. Yield: 67%.

ES-MS [M+H]$^+$: 190.02; Rt=1.55 min (Method B).

Intermediate 29

N-benzyl-4,6-dichloro-N-methylpicolinamide

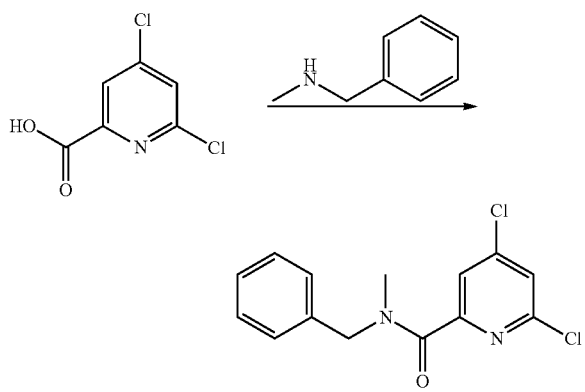

50% Propylphosphonic anhydride solution in ethyl acetate (20.0 mL, 31.5 mmol) was added to a suspension of 4,6-dichloropicolinic acid (3.0 g, 15.7 mmol), N-methyl-1-phenylmethanamine (2.8 g, 23.6 mmol) and diisopropylethylamine (13.5 mL, 78.9 mmol) in dichloromethane (50 mL) at 0° C. The reaction mixture was warmed to room temperature and stirred for 16 h. The reaction mixture was quenched with saturated sodium bicarbonate solution, the organic product was extracted with dichloromethane (3×40 mL). The combined organic extracts were washed with water, brine, dried over anhydrous sodium sulfate and solvent was evaporated under reduced pressure to get crude product. The crude product was purified by column chromatography (silica gel 230-400 mesh, 30% ethyl acetate in petroleum ether as eluent) to afford 3.5 g of N-benzyl-4,6-dichloro-N-methylpicolinamide as pale yellow oil. Yield: 75%.

ES-MS [M+H]$^+$: 295.1; Rt=1.99 min (Method B).

$^1$H NMR (400 MHz, DMSO-d$_6$) δ: 7.93-7.90 (m, 1H), 7.85-7.80 (m, 1H), 7.40-7.27 (m, 5H), 4.67 (s, 1H), 4.49 (s, 1H), 2.84 (d, J=14 Hz, 3H).

Intermediate 30

N-benzyl-1-(4,6-dichloropyridin-2-yl)-N-methyl-methanamine

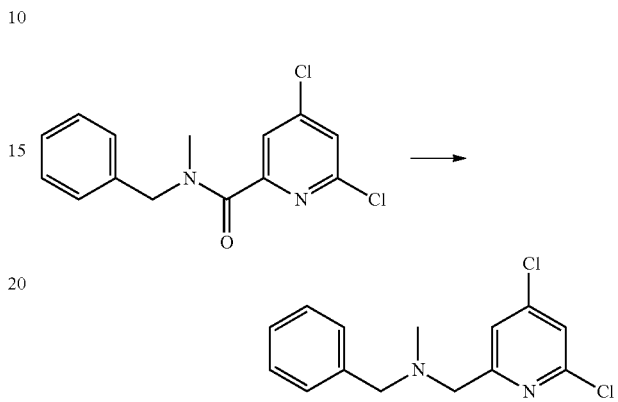

Borane dimethyl sulphide complex solution (33.2 mL, 66.4 mmol; 2.0M in tetrahydrofuran) was added to the solution of N-benzyl-4,6-dichloro-N-methylpicolinamide (3.1 g, 11.0 mmol) in tetrahydrofuran (70 mL) at 0° C. The reaction mixture was warmed to room temperature and stirred for 16 h. The reaction mixture was cooled to 0° C. and quenched with saturated sodium bicarbonate solution. The organic product was extracted with dichloromethane (3×60 mL). The combined organic extracts were washed with water, brine, dried over anhydrous sodium sulfate and solvent was evaporated under reduced pressure to get crude product. The crude product was purified by column chromatography (silica gel 230-400 mesh, 10% ethyl acetate in petroleum ether as eluent) to get 2.1 g of N-benzyl-4,6-dichloro-N-methylpicolinamide as yellow oil. Yield: 71%.

$^1$H NMR (400 MHz, DMSO-d$_6$) δ: 7.85 (d, J=1.6 Hz, 1H), 7.73 (d, J=2 Hz, 1H), 7.66-7.58 (m, 2H), 7.42-7.33 (m, 3H), 4.03-3.99 (m, 2H), 3.78 (d, J=12.4 Hz, 1H), 3.62-3.57 (m, 1H), 2.47 (s, 3H).

Intermediate 31

2-((benzyl(methyl)amino)methyl)-6-chloropyridin-4-amine

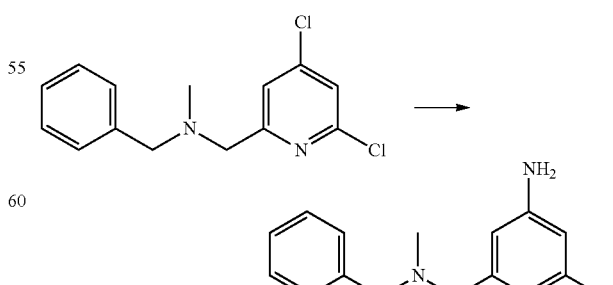

Sodium azide (1.38 g, 21.3 mmol) was added to a solution of N-benzyl-1-(4,6-dichloropyridin-2-yl)-N-methylmethanamine (2.0 g, 7.1 mmol) in anhydrous dimethylformamide (50 mL) at 0° C. The reaction mixture was warmed to room temperature and heated at 90° C. for 24 h. After completion of reaction (monitored by TLC), reaction mixture was quenched with water and organic product was extracted using ethyl acetate (3×50 mL). The combined organic extracts were washed with water, brine, dried over anhydrous sodium sulfate and solvent was evaporated under reduced pressure to get crude product. The crude product was dissolved in methanol (50 mL) and sodium borohydride (0.5 g, 14.2 mmol) was added at 0° C. The reaction mixture was warmed to room temperature and stirred for 2 h. After completion of reaction, solvent was evaporated under reduced pressure to obtain residue which was diluted with water and extracted using ethyl acetate (3×60 mL). The combined organic extracts were washed with water, brine, dried over anhydrous sodium sulfate and solvent was evaporated under reduced pressure to get crude product. The crude product was purified by column chromatography (silica gel 230-400 mesh, 70% ethyl acetate in petroleum ether as eluent) to get 1.0 g of 2-((benzyl(methyl)amino)methyl)-6-chloropyridin-4-amine as yellow oil. Yield: 53%.

ES-MS [M+H]⁺: 262.1; Rt=1.44 min (Method B).

¹H NMR (400 MHz, CDCl₃) δ: 7.37-7.30 (m, 5H), 7.24-7.22 (m, 1), 6.74 (d, J=2.0 Hz 1H), 6.42 (d, J=2.0 Hz, 1H), 4.22 (br s, 2H), 3.58 (s, 2H), 3.54 (s, H), 2.23 (s, 3H).

Example 24

6-((benzyl(methyl)amino)methyl)-N²-(p-tolyl)pyridine-2,4-diamine

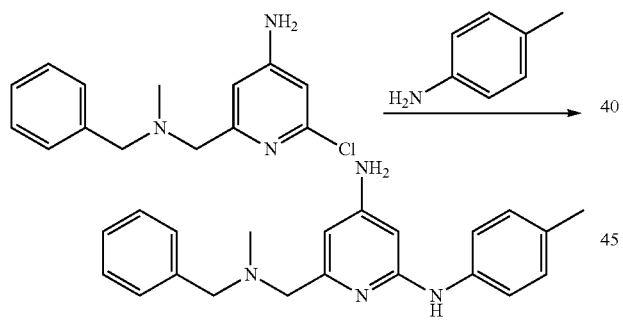

p-Toluidine (6.0 g) and 2-((benzyl(methyl)amino) methyl)-6-chloropyridin-4-amine were mixed and heated at 200° C. for 16 h. After completion of starting material (monitored by TLC) the crude was purified by column chromatography (silica gel 230-400 mesh, 2-3% methanol in dichloromethane as eluent) to get 0.4 g of 6-((benzyl (methyl)amino)methyl)-N²-(p-tolyl)pyridine-2,4-diamine as dark brown solid. The crude product was further purified by reverse phase prep HPLC to afford 0.17 g of compound 6-((benzyl(methyl)amino)methyl)-N²-(p-tolyl)pyridine-2,4-diamine. Yield: 44%.

ES-MS [M+H]⁺: 333.33; Rt=1.61 min (Method B).

¹H NMR (400 MHz, DMSO-d₆) δ: 8.24 (s, 1H), 7.44 (d, J=8.4 Hz, 2H), 7.38-7.31 (m, 4H), 7.26 (d, J=6.8 Hz, 1H), 6.99 (d, J=8.4 Hz, 2H), 6.21 (s, 1H), 5.83 (d, J=0.8 Hz, 1H), 5.68 (br s, 2H), 3.54 (s, 2H), 3.36 (s, 2H), 2.21 (s, 3H), 2.14 (s, 3H).

Intermediate 32

N-benzyl-2,6-dichloro-N-methyl isonicotinamide

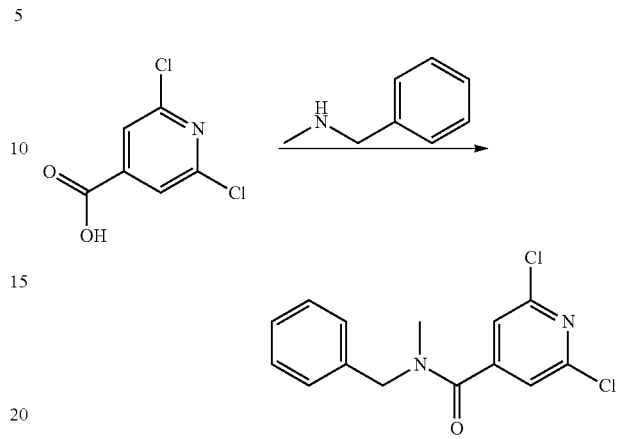

50% Propylphosphonic anhydride solution in ethyl acetate (33.1 mL, 52.0 mmol) was added to a suspension of 2,6-dichloroisonicotinic acid (5.0 g, 26.0 mmol), N-methyl-1-phenylmethanamine (4.7 g, 39.0 mmol) and diisopropylethylamine (22.3 mL, 130.0 mmol) in dichloromethane (80 mL) at 0° C. The reaction mixture was warmed to room temperature and stirred for 16 h. The reaction mixture was quenched with saturated sodium bicarbonate solution. The organic product was extracted with dichloromethane (3×50 mL). The combined organic extracts were washed with water, brine, dried over anhydrous sodium sulfate and solvent was evaporated under reduced pressure to get crude product. The crude product was purified by column chromatography (silica gel 230-400 mesh, 30% ethyl acetate in petroleum ether as eluent) to afford 6.0 g of N-benzyl-2,6-dichloro-N-methylisonicotinamide as pale yellow oil. Yield: 78%.

ES-MS [M+H]⁺: 295.1; Rt=1.99 min (Method B).

Intermediate 33

N-benzyl-1-(2,6-dichloropyridin-4-yl)-N-methyl-methanamine

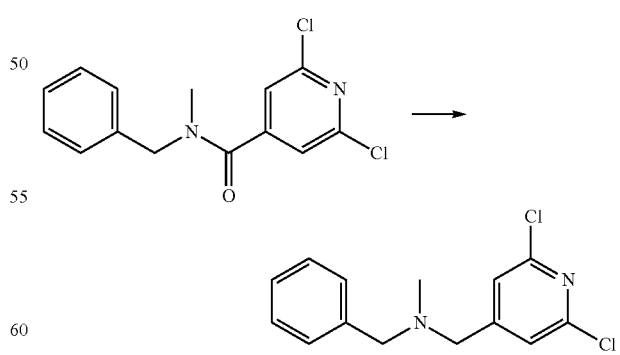

Borane dimethyl sulphide complex solution (56.1 mL, 112.0 mmol; 2.0M in tetrahydrofuran) was added to the solution of N-benzyl-2,6-dichloro-N-methylisonicotinamide (5.5 g, 18.7 mmol) in tetrahydrofuran (80 mL) at 0° C. The reaction mixture was warmed to room temperature and stirred for 16 h. The reaction mixture was cooled to 0° C. and quenched with saturated sodium bicarbonate solution. The organic product was extracted with dichloromethane (3×60 mL). The combined organic extracts were washed with water, brine, dried over anhydrous sodium sulfate and solvent was evaporated under reduced pressure to get crude product. The crude product was purified by column chromatography (silica gel 230-400 mesh, 10% ethyl acetate in petroleum ether as eluent) to get 2.8 g of N-benzyl-1-(2,6-dichloropyridin-4-yl)-N-methylmethanamine as yellow oil. Yield: 49%.

ES-MS [M+H]⁺: 281.1; Rt=1.61 min (Method B).

¹H NMR (400 MHz, DMSO-d₆) δ: 7.51 (s, 2H), 7.35-7.32 (m, 4H), 7.28-7.24 (m, 1H), 3.57 (m, 2H), 3.54 (s, 2H), 2.10 (s, 3H).

Intermediate 34 di-tert-butyl (4-((benzyl(methyl)amino)methyl)pyridine-2,6-diyl)dicarbamate

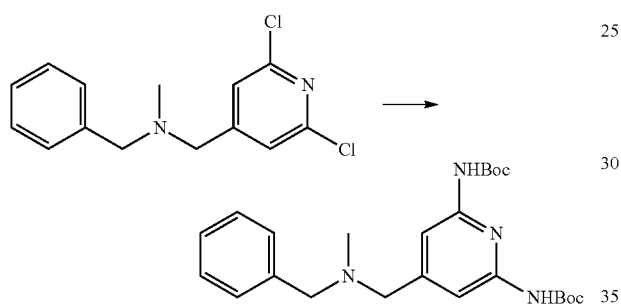

Cesium carbonate (1.39 g, 4.2 mmol) was added to a stirred solution of N-benzyl-1-(2,6-dichloropyridin-4-yl)-N-methylmethanamine (0.4 g, 1.4 mmol) and tert-butyl carbamate (0.5 g, 4.2 mmol) in 1,4-dioxane (10 mL). The reaction mixture was purged with argon for 10 min and added Pd₂(dba)₃ (0.065 g, 0.07 mmol) and XPhos (0.033 g, 0.07 mmol). The mixture was purged again with argon for 10 min. The reaction mixture was heated to 100° C. for 16 h in a sealed tube. After consumption of starting materials (monitored by TLC), reaction mixture was cooled to room temperature and filtered through a pad of celite. The solvent was concentrated under reduced pressure to get 0.42 g of crude di-tort-butyl (4-((benzyl(methyl)amino)methyl)pyridine-2,6-diyl)dicarbamate as yellow oil which was used in the next step without purification. Yield: 66%.

ES-MS [M+H]⁺: 443.3; Rt=1.79 min (Method B).

Intermediate 35

4-((benzyl(methyl)amino)methyl)pyridine-2,6-diamine

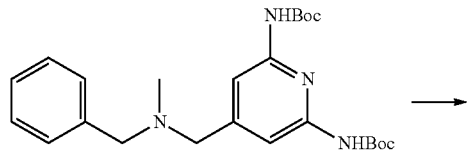

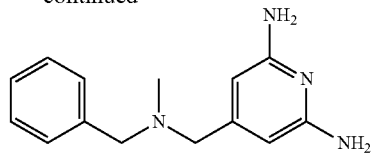

4N Hydrogen chloride in 1,4-dioxane (5 mL) was added to the solution of di-tert-butyl (4-((benzyl(methyl)amino)methyl)pyridine-2,6-diyl)dicarbamate (0.95 mmol) in methanol (10 mL) at 0° C. The reaction mixture was warmed to room temperature and stirred for 16 h. The reaction mixture was concentrated under reduced pressure to get crude product. The crude was basified with saturated sodium bicarbonate solution and the organic product was extracted with dichloromethane (3×30 mL). The combined organic extracts were washed with water, brine, dried over anhydrous sodium sulfate and solvent was evaporated under reduced pressure to get 0.38 g of crude 4-((benzyl(methyl)amino)methyl)pyridine-2,6-diamine as yellow oil which was used for next step as such without any purification. Yield: 95%.

ES-MS [M+H]⁺: 243.2; Rt=1.97 min (Method A).

Example 25

4-((benzyl(methyl)amino)methyl)-N²-(p-tolyl)pyridine-2,6-diamine

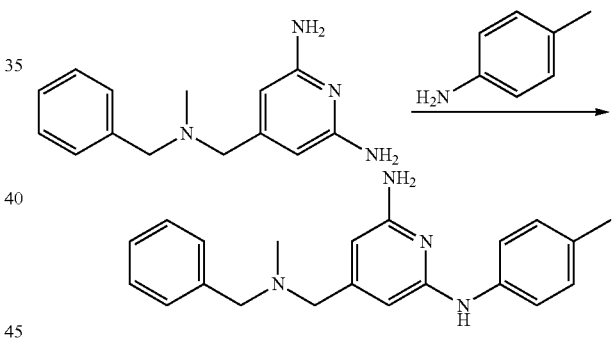

Copper(II)acetate (0.67 g, 3.7 mmol) was added to a solution of 4-((benzyl(methyl)amino)methyl)pyridine-2,6-diamine (0.3 g, 1.2 mmol), 4-methylphenyl boronic acid (0.25 g, 1.8 mmol) and triethylamine (0.4 mL, 2.4 mmol) in dichloromethane (8 mL) at room temperature under oxygen atmosphere. The reaction mixture was stirred at room temperature for 16 h. The reaction mixture was filtered through a pad of celite and clear filtrate was evaporated to get crude product. The crude product was purified by column chromatography (silica gel 230-400 mesh, 2-4% methanol in dichloromethane as eluent) to get the impure product 4-((benzyl(methyl)amino)methyl)-N²-(p-tolyl)pyridine-2,6-diamine which was further purified by reverse phase prep HPLC to afford 14 mg of 4-((benzyl(methyl)amino)methyl)-N²-(p-tolyl)pyridine-2,6-diamine as off-white solid. Yield: 3%.

ES-MS [M+H]⁺: 333.31; Rt=1.77 min (Method D).

¹H NMR (400 MHz, DMSO-d₆) δ: δ 8.37 (s, 1H), 7.50 (d, J=8.0 Hz, 2H), 7.34-7.25 (m, 5H), 6.99 (d, J=8.0 Hz, 2H), 6.03 (s, 1H), 5.85 (s, 1H), 5.57 (br s, 2H), 3.47 (s, 2H), 3.24 (s, 2H), 2.22 (s, 3H), 2.08 (s, 3H).

Example 26

6-((Benzyl(methyl)amino)methyl)-N²-(pyridin-3-yl)-1,3,5-triazine-2,4-diamine was Prepared According to the General Procedure III Above

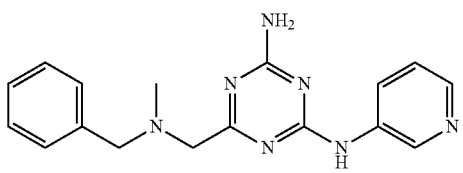 [SMILES: CN(Cc1ccccc1)Cc1nc(N)nc(Nc2cccnc2)n1]

Yield: 3%.
HPLC-MS [M+H]⁺: 320.2; Rt=1.23 min (Method B).
¹H NMR (500 MHz, DMSO-d₆) δ: 9.68 (br s, 1H), 8.96-8.95 (d, J=2.0 Hz, 1H), 8.25-8.20 (m, 1H), 8.18-8.16 (m, 1H), 7.35-7.22 (m, 8H), 3.63 (s, 2H), 3.36 (s, 2H), 2.22 (s, 3H).

Example 27

6-(((1,2,3,4-Tetrahydronaphthalen-2-yl)amino) methyl)-N²-(p-tolyl)-1,3,5-triazine-2,4-diamine was Prepared According to the General Procedure III Above

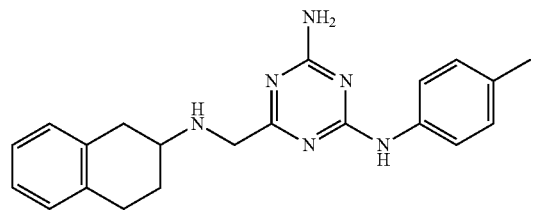 [SMILES: Cc1ccc(Nc2nc(N)nc(CNC3CCc4ccccc4C3)n2)cc1]

Yield: 13%.
HPLC-MS [M+H]⁺: 361: Rt=2.07 min (Method A).
¹H NMR (400 MHz, CD₃OD) δ 7.49 (d, J=8.1 Hz, 2H), 7.17-7.04 (m, 6H), 3.89 (s, 2H), 3.25-3.14 (m, 2H), 2.93-2.91 (m, 2H), 2.79-2.76 (m, 1H), 2.30 (s, 3H), 2.25-2.21 (m, 1H), 1.75-1.73 (m, 1H).

General Procedure X

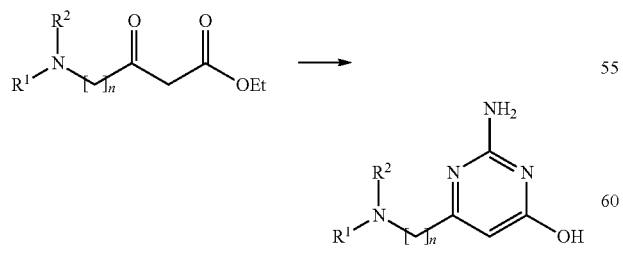

In a sealed tube, sodium methoxide (30%, 1.5 eq) in methanol (6 mL) and guanidine hydrochloride (1-1.5 eq) were added to a stirred solution of the appropriate amino oxobutanoate (prepared following literature procedures) (ex: ethyl 4-(benzyl(methyl)amino)-3-oxobutanoate) (1.0 eq) in ethanol (10 mL). The reaction mixture was heated to 90-100° C. under stirring condition for 16 h. Reaction mixture was cooled to room temperature and the solvent was evaporated under reduced pressure to get the crude product. The crude product was purified by flash column chromatography (20% dichloromethane/methanol) or HPLC (0.1% formic acid in water/acetonitrile) to obtain the desired pyrimidine product (ex: 2-amino-6-((benzyl(methyl)amino) methyl)pyrimidin-4-ol.

Intermediate 36

2-Amino-6-(((4-methoxybenzyl)(methyl)amino) methyl)pyrimidin-4-ol

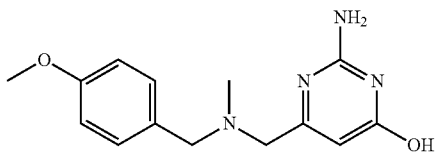 [SMILES: COc1ccc(CN(C)Cc2cc(O)nc(N)n2)cc1]

Yield: 36%
HPLC-MS [M+H]⁴: 275.15; Rt=0.23 min (Method A).
¹H NMR (400 MHz, DMSO-d₆) δ: 11.5 (br s, H), 7.24-7.22 (m, 2H), 6.90-6.85 (m, 4H), 5.61 (s, 1H), 3.72 (s, 3H), 3.44 (s, 2H), 3.11 (s, 2H), 2.11 (s, 3H).

Intermediate 37

2-Amino-6-((methyl(3-methylbenzyl)amino)methyl) pyrimidin-4-ol

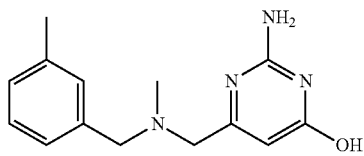 [SMILES: Cc1cccc(CN(C)Cc2cc(O)nc(N)n2)c1]

Yield: 77%
HPLC-MS [M+H]⁺: 259.06; Rt=1.22 min (Method A).

Intermediate 38

2-Amino-6-((methyl(4-methylbenzyl)amino)methyl) pyrimidin-4-ol

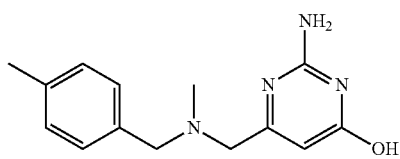 [SMILES: Cc1ccc(CN(C)Cc2cc(O)nc(N)n2)cc1]

Yield: 65%
HPLC-MS [M+F1]⁴": 259.10; Rt=1.20 min (Method A).

Intermediate 39

2-Amino-6-((3,4-dihydroisoquinolin-2(1H)-yl)methyl)pyrimidin-4-ol

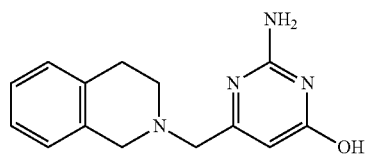 [SMILES: Nc1nc(O)cc(CN2CCc3ccccc3C2)n1]

Yield: 90%.
¹H NMR (400 MHz, DMSO-d₆) δ: 10.66 (s, 1H), 7.10-7.02 (m, 4H), 6.50 (br s, 2H), 5.62 (s, 1H), 3.58 (s, 2H), 3.32 (s, 2H), 2.82 (m, 2H), 2.70 (m, 2H).

Intermediate 40

2-Amino-6-(benzyloxymethyl)pyrimidin-4-ol

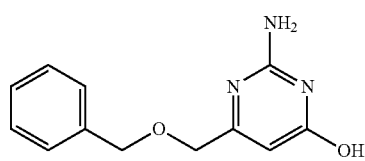 [SMILES: Nc1nc(O)cc(COCc2ccccc2)n1]

Yield: 71%
¹H NMR (400 MHz, DMSO-d₆) δ: 10.68 (s, 1H), 7.39-6.97 (m, 5H), 6.51 (s br, 2H), 5.60 (s, 1H), 4.55 (s, 2H), 4.15 (s, 2H).

Intermediate 41

3-((((2-Amino-6-hydroxypyrimidin-4-yl)methyl)(methyl)amino)methyl)benzonitrile

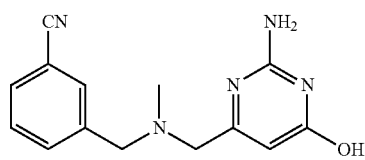 [SMILES: CN(Cc1cccc(C#N)c1)Cc1cc(O)nc(N)n1]

Yield: 99%
HPLC-MS [M+H]⁺: 270.16; Rt=0.44 min (Method B).

Intermediate 42

2-Amino-6-(((4-ethylbenzyl)(methyl)amino)methyl)pyrimidin-4-ol

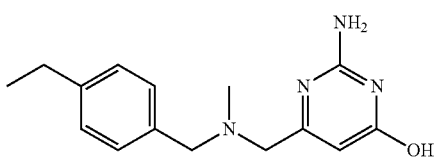 [SMILES: CCc1ccc(CN(C)Cc2cc(O)nc(N)n2)cc1]

Yield: 99%
HPLC-MS [M+H]⁺: 273.14; Rt=1.41 min (Method B).

Intermediate 43

2-Amino-6-(((4-fluorobenzyl)(methyl)amino)methyl)pyrimidin-4-ol

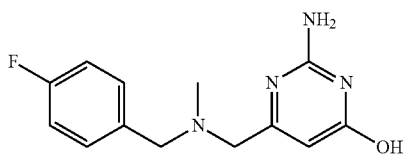 [SMILES: CN(Cc1ccc(F)cc1)Cc1cc(O)nc(N)n1]

Yield: 64%
HPLC-MS [M+H]⁺: 263.1: Rt=1.74 min (Method H).

Intermediate 44

2-Amino-6-((benzyl(ethyl)amino)methyl)pyrimidin-4-ol

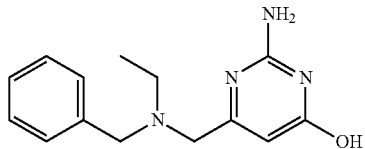 [SMILES: CCN(Cc1ccccc1)Cc1cc(O)nc(N)n1]

Yield: 24%
HPLC-MS [M+H]⁺: 259.21; Rt=1.92 min (Method B).
¹H NMR (400 MHz, DMSO-d₆) δ: 10.62 (s, 1H), 7.35-7.30 (m, 4H), 7.24-7.23 (m, 1H), 6.46 (br, s, 2H), 5.72 (s, 1H), 3.57 (s, 2H), 3.18 (s, 2H), 2.51-2.42 (m, 2H), 1.02-0.98 (m, 3H).

Intermediate 45

2-Amino-6-((benzyl(2-methoxyethyl)amino)methyl)pyrimidin-4-ol

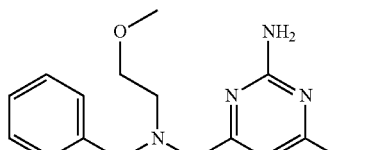

Yield: 63%
HPLC-MS [M+H]⁺: 287.1; Rt=2.02 min (Method B).

Intermediate 46

2-Amino-6-((2-phenylpyrrolidin-1-yl)methyl)pyrimidin-4-ol

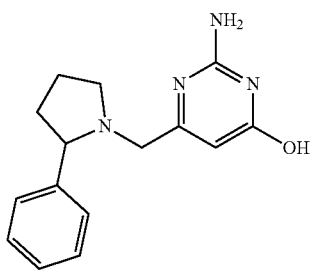 [SMILES: Nc1nc(O)cc(CN2CCCC2c2ccccc2)n1]

Yield: 28%
HPLC-MS [M+H]⁺: 271.2; Rt=0.97 min (Method B).

Intermediate 47

2-Amino-6-(((3-methoxyphenyl)(methyl)amino)methyl)pyrimidin-4-ol

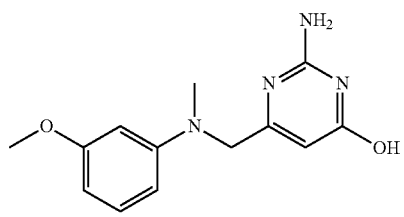 [SMILES: COc1cccc(N(C)Cc2cc(O)nc(N)n2)c1]

Yield: 77%
HPLC-MS [M+H]+: 261.1; Rt=1.95 min (Method A).

General Procedure XI

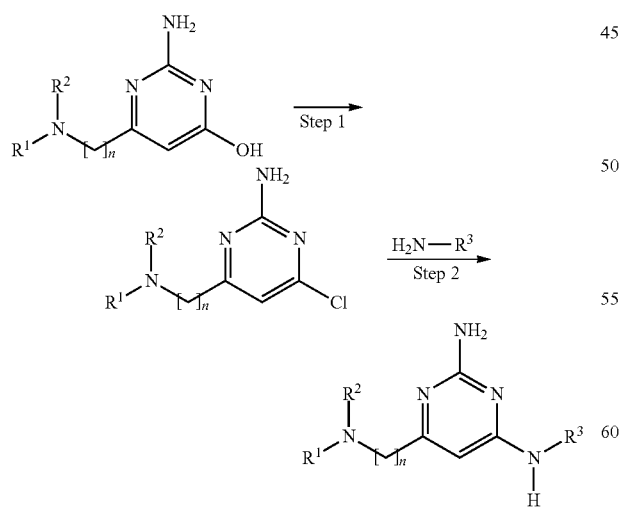

Step 1:
Phosphoryl chloride (3 mL/mmol) was added to the appropriate pyrimidin-4-ol (1 eq) (ex: 2-amino-6-((methyl(phenyl)amino)methyl)pyrimidin-4-01) under nitrogen atmosphere. The reaction mixture was heated to 100° C. under stirring condition for 1 h. The reaction mixture was cooled to room temperature and evaporated under reduced pressure and co-distilled twice with toluene to afford the desired crude product. The crude product was used as such for the next step.

In same cases, the reaction was performed using phosphoryl chloride (10 eq) as chlorinating agent.

Step 2:
To a stirred solution of the appropriate chloride (1 eq) (ex: 4-chloro-6-((methyl(phenyl)amino)methyl)-pyrimidin-2-amine) in 1-butanol (13 mL/mmol) were added the corresponding aromatic amine (2 eq) (ex: p-toluidine) and sulphuric acid (catalytic, 2 drops) at room temperature. The reaction mixture was stirred at 100° C. for 16 h. The reaction mixture was allowed to cool to room temperature and quenched with saturated sodium bicarbonate (pH~8). The aqueous layer was extracted with ethyl acetate (2×), dried over anhydrous sodium sulphate and the solvent evaporated under reduced pressure. The resultant crude was purified by flash column chromatography (dichloromethane/methanol) to obtain the desired product (ex: 6-((methyl(phenyl)amino)methyl)-N⁴-(p-tolyl)pyrimidine-2,4-diamine).

In same cases, isopropyl alcohol was used as solvent.

Example 28

6-((Benzyl(methyl)amino)methyl)-N⁴-o-tolylpyrimidine-2,4-diamine

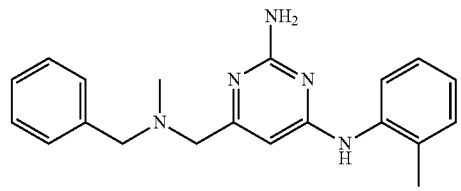 [SMILES: Cc1ccccc1Nc1cc(CN(C)Cc2ccccc2)nc(N)n1]

Yield: 4.7% (over two steps).
HPLC-MS [M+H]⁺: 334.48; Rt=1.97 min (Method B).
¹H NMR (400 MHz, DMSO-d₆) δ: 8.32 (s, 1H), 7.40-7.38 (d, J=7.2 Hz, 1H), 7.32-7.18 (m, 7H), 7.11-7.09 (m, 1H), 6.07 (s, 1H), 5.95 (s, 2H), 3.47 (s, 2H), 3.22 (s, 2H), 2.18 (s, 3H), 2.10 (s, 3H).

Example 29

3-(2-Amino-6-((benzyl(methyl)amino)methyl)pyrimidin-4-ylamino)benzonitrile

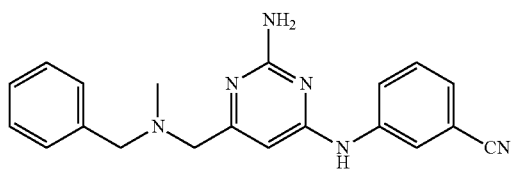 [SMILES: CN(Cc1ccccc1)Cc1cc(Nc2cccc(C#N)c2)nc(N)n1]

Yield: 13% (over two steps).
HPLC-MS [M+H]⁺: 345.22; Rt=1.60 min (Method E).

¹H NMR (400 MHz, DMSO-d₆) δ: 9.45 (s, 1H), 8.37-8.36 (m, 1H), 7.90-7.87 (m, 1H), 7.45 (t, J=8 Hz, 1H), 7.39-7.20 (m, 6H), 6.37 (br s, 2H), 6.30 (s, 1H), 3.55 (s, 2H), 3.8 (s, 2H), 2.15 (s, 3H).

Example 30

6-((Benzyl(methyl)amino)methyl)-N⁴-(isoquinolin-7-yl)pyrimidine-2,4-diamine

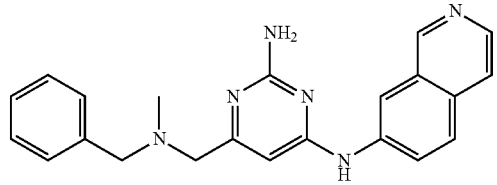 [SMILES: CN(Cc1ccccc1)Cc1cc(Nc2ccc3ccncc3c2)nc(N)n1]

Yield: 5% (over two steps).
HPLC-MS [M+H]⁺: 371.33; Rt=6.29 min (Method E).
¹H NMR (400 MHz, DMSO-d₆) δ: 9.54 (s, 1H), 9.19 (s, 1H), 8.89 (s, 1H), 8.33-8.32 (d, J=4 Hz, 1H), 7.84-7.83 (m, 2H), 7.70-7.68 (d, J=8 Hz, 1H), 7.39-7.26 (m, 5H), 6.38-6.37 (d, J=4 Hz, 3H), 3.57 (s, 2H), 3.31 (s, 2H), 2.17 (s, 3H).

Example 31

6-((Benzyl(methyl)amino)methyl)-N⁴-(isoquinolin-6-yl)pyrimidine-2,4-diamine

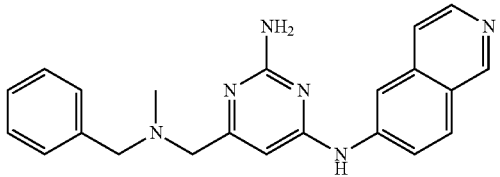 [SMILES: CN(Cc1ccccc1)Cc1cc(Nc2ccc3cnccc3c2)nc(N)n1]

Yield: 4% (over two steps).
HPLC-MS [M+H]⁺: 371.21; Rt=1.24 min (Method E).
¹H NMR (400 MHz, DMSO-d₆) δ: 9.61 (s, 1H), 9.08 (s, 1H), 8.73 (s, 1H), 8.37-8.36 (d, J=4 Hz, 1H), 7.98-7.95 (d, J=12 Hz, 11-1), 7.74-7.72 (d, J=8 Hz, 1H), 7.66-7.65 (d, J=4 Hz, 1H), 7.40-7.26 (m, 5H), 6.41 (s, 3H), 3.57 (s, 2H), 3.31 (s, 2H), 2.17 (s, 3H).

Example 32

6-((Methyl(3-methylbenzyl)amino)methyl)-N⁴-p-tolylpyrimidine-2,4-diamine

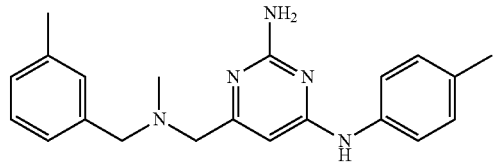

Yield: 5.4% (over two steps).
HPLC-MS [M+H]⁺: 348.25; Rt=1.78 min (Method A).

¹H NMR (400 MHz, DMSO-d₆) δ: 9.05 (s br, 1H), 7.55 (d, J=8 Hz, 2H), 7.24-7.20 (m, 1H), 7.15 (m, 2H), 7.07 (m, 3H), 6.23 (m, 3H), 3.50 (s, 2H), 3.27 (s, 2H), 2.30 (s, 3H), 2.25 (s, 3H), 2.14 (s, 3H).

Example 33

6-(((4-Methoxybenzyl)(methyl)amino)methyl)-N⁴-p-tolylpyrimidine-2,4-diamine

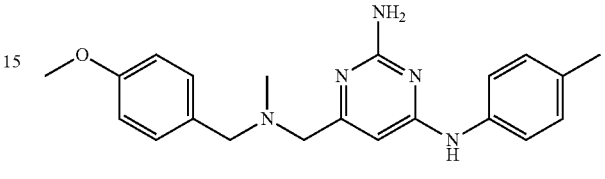

Yield: 7% (over two steps).
HPLC-MS [M+H]⁺: 364.26; Rt=1.61 min (Method A).
¹H NMR (400 MHz, DMSO-d₆) δ: 8.95 (s, 1H), 7.56 (d, J=8.4 Hz, 2H), 7.25 (d, J=8.4 Hz, 2H), 7.06 (d, J=8.4 Hz, 2H), 6.88 (d, J=8.4 Hz, 2H), 6.22 (s, 1H), 6.09 (s, 2H), 3.74 (s, 3H), 3.45 (s, 2H), 3.22 (s, 2H), 2.25 (s, 3H), 2.12 (s, 3H).

Example 34

6-((Methyl(4-methylbenzyl)amino)methyl)-N⁴-p-tolylpyrimidine-2,4-diamine

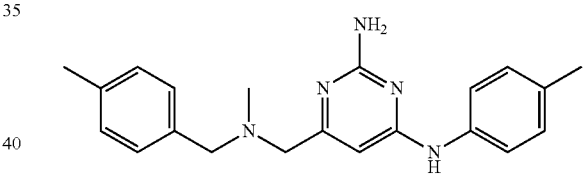

Yield: 16% (over two steps).
HPLC-MS [M+H]⁺: 348.29; Rt=1.80 min (Method A).
¹H NMR (400 MHz, DMSO-d₆) δ: 7.56 (d, J=8.4 Hz, 2H), 7.22 (d, J=8 Hz, 2H), 7.13 (d, J=7.6 Hz, 2H), 7.06 (d, J=8.4 Hz, 2H), 6.23 (s, 1H), 6.08 (s, 1H), 3.41 (s, 2H), 3.22 (s, 2H), 2.28 (s, 3H), 2.25 (s, 3H), 2.12 (s, 3H).

Example 35

6-((3,4-Dihydroisoquinolin-2(1H)-yl)methyl)-N⁴-p-tolylpyrimidine-2,4-diamine

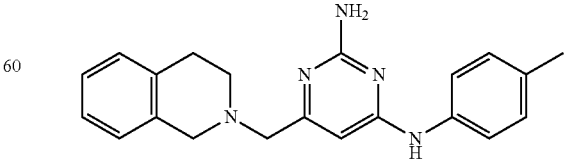

Yield: 3.5% (over two steps).
HPLC-MS [M+H]⁺: 346.21; Rt=1.74 min (Method A).

$^1$H NMR (400 MHz, DMSO-d$_6$) δ: 8.93 (s, 1H), 7.56 (d, J=8.4 Hz, 2H), 7.11-7.03 (m, 6H), 6.18 (s, 2H), 6.13 (s, 2H), 3.60 (s, 2H), 3.40 (s, 2H), 2.86-2.84 (m, 2H), 2.75-2.72 (m, 2H), 2.23 (s, 3H).

Intermediate 48

6-(Benzyloxymethyl)-N$^4$-p-tolylpyrimidine-2,4-diamine

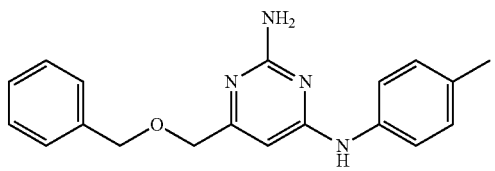 [SMILES: Cc1ccc(Nc2cc(COCc3ccccc3)nc(N)n2)cc1]

Yield: 57% (over two steps).
HPLC-MS [M+H]$^+$: 321.15: Rt=1.73 min (Method A).
$^1$H NMR (400 MHz, DMSO-d$_6$) δ: 9.00 (s, 1H), 7.57 (d, J=8.4 Hz, 1H), 7.38-7.37 (m, 4H), 7.33-7.31 (m, 1H), 7.06 (d, J=8.4 Hz, 2H), 6.14 (s, 3H), 4.57 (s, 2H), 4.25 (s, 2H), 2.24 (s, 3H).

Example 36

6-(((4-Methoxybenzyl)(methyl)amino)methyl)-N$^4$-(3-methoxyphenyl)pyrimidine-2,4-diamine

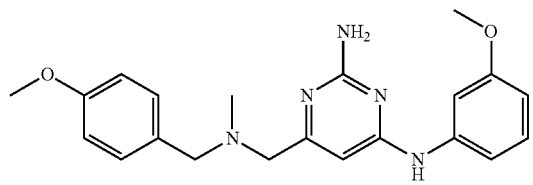 [SMILES: COc1ccc(CN(C)Cc2cc(Nc3cccc(OC)c3)nc(N)n2)cc1]

Yield: 36% (over two steps).
HPLC-MS [M+H]$^+$: 380.33; Rt=1.63 min (Method G).
$^1$H NMR (400 MHz, DMSO-d$_6$) δ: 9.06 (s, 1H), 7.44 (m, 1H), 7.27-7.25 (d, J=8.4 Hz, 2H), 7.20-7.12 (m, 2H), 6.90-6.88 (d, J=8.8 Hz, 2H), 6.51-6.49 (m, 1H), 6.26 (s, 1H), 6.15 (br s, 2H), 3.74 (s, 6H), 3.46 (s, 2H), 3.23 (s, 2H), 2.12 (s, 3H).

Example 37

3-((((2-Amino-6-(3-methoxyphenylamino)pyrimidin-4-yl)methyl)(methyl)amino)methyl) benzonitrile

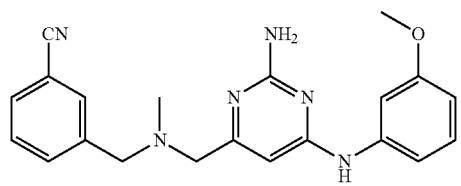 [SMILES: COc1cccc(Nc2cc(CN(C)Cc3cccc(C#N)c3)nc(N)n2)c1]

Yield: 21.5% (over two steps).
HPLC-MS [M+H]$^+$: 375.32; Rt=1.68 min (Method-A).

$^1$H NMR (400 MHz, DMSO-d$_6$) δ: 9.07 (s, 1H), 7.79 (s, 1H), 7.75-7.71 (m, 2H), 7.58-7.55 (m, 1H), 7.44 (m, 1H), 7.22-7.20 (m, 1H), 7.16-7.12 (m, 1H), 6.52-6.49 (m, 1H), 6.24 (s, 1H), 6.17 (br s, 2H), 3.74 (s, 3H), 3.61 (s, 2H), 3.29 (s, 2H), 2.15 (s, 3H).

Example 38

N$^4$-(3-Methoxyphenyl)-6-((methyl(3-methylbenzyl)amino)methyl)pyrimidine 2,4-diamine

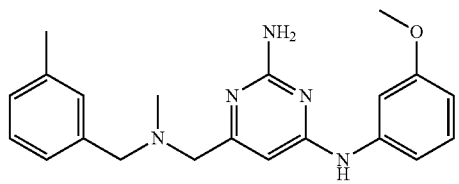 [SMILES: COc1cccc(Nc2cc(CN(C)Cc3cccc(C)c3)nc(N)n2)c1]

Yield: 22% (over two steps).
HPLC-MS [M+H]$^+$: 364.29: Rt=1.70 min (Method A).
$^1$H NMR (400 MHz, DMSO-d$_6$) δ: 9.06 (s, 1H), 7.44 (m, 1H), 7.24-7.05 (m, 6H), 6.52-6.49 (m, 1H), 6.27 (s, 1H), 6.15 (br s, 2H), 3.73 (s, 3H), 3.49 (s, 2H), 3.25 (s, 2H), 2.30 (s, 3H), 2.13 (s, 3H).

Example 39

3-((((2-Amino-6-(m-tolylamino)pyrimidin-4-yl)methyl)(methyl)amino)methyl) benzonitrile

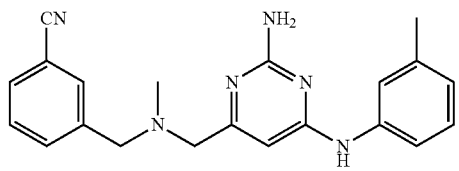 [SMILES: Cc1cccc(Nc2cc(CN(C)Cc3cccc(C#N)c3)nc(N)n2)c1]

Yield: 21% (over two steps).
HPLC-MS [M+H]$^+$: 359.20; Rt=1.72 min (Method A).
$^1$H NMR (400 MHz, DMSO-d$_6$) δ: 8.99 (s, 1H), 7.78-7.70 (m, 3H), 7.58-7.53 (m, 2H), 7.46 (s, 1H), 7.15-7.11 (t, J=5.0 Hz, 1H), 6.76-6.74 (d, J=7.6 Hz, 1H), 6.24 (s, 1H), 6.15 (br s, 2H), 3.60 (s, 2H), 3.29 (s, 2H), 2.28 (s, 3H), 2.15 (s, 3H).

Example 40

6-(((4-Ethylbenzyl)(methyl)amino)methyl)-N$^4$-(3-methoxyphenyl)pyrimidine-2,4-diamine

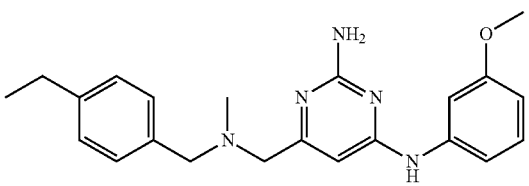 [SMILES: CCc1ccc(CN(C)Cc2cc(Nc3cccc(OC)c3)nc(N)n2)cc1]

Yield: 43% (over two steps).
HPLC-MS [M+H]$^+$: 378.32; Rt=1.83 (Method A).

¹H NMR (400 MHz, DMSO-d₆) δ: 9.06 (s, 1H), 7.45-7.43 (m, 1H), 7.27-7.12 (m, 6H), 6.52-6.49 (m, 1H), 6.27 (s, 1H), 6.15 (br s, 2H), 3.74 (s, 3H), 3.49 (s, 2H), 3.24 (s, 2H), 2.61-2.52 (m, 2H), 2.14 (s, 3H), 1.19-1.15 (t, J=7.6 Hz, 3H).

Example 41

6-((Benzyl(methyl)amino)methyl)-N⁴-(2,5-dimethoxyphenyl)pyrimidine-2,4-diamine

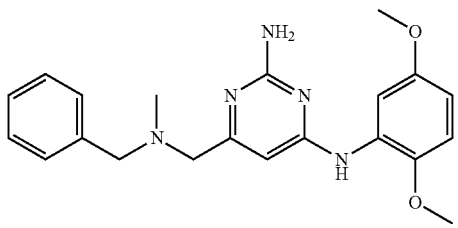 [SMILES: COc1ccc(OC)c(Nc2cc(CN(C)Cc3ccccc3)nc(N)n2)c1]

Yield: 16% (over two steps).
HPLC-MS [M+H]⁺: 380.29; Rt=1.61 min (Method E).
¹H NMR (400 MHz, DMSO-d₆) δ: 8.16 (s, 1H), 7.84-7.83 (d, J=4 Hz, 1H), 7.36-7.25 (m, 5H), 6.92-6.90 (d, J=8 Hz, 1H), 6.55-6.52 (m, 1H), 6.42 (s, 1H), 6.10 (br s, 2H), 3.76 (s, 3H), 3.71 (s, 3H), 3.53 (s, 2H), 3.24 (s, 2H), 2.13 (s, 3H).

Example 42

6-((Benzyl(methyl)amino)methyl)-N⁴-(2,3-dimethoxyphenyl)pyrimidine-2,4-diamine

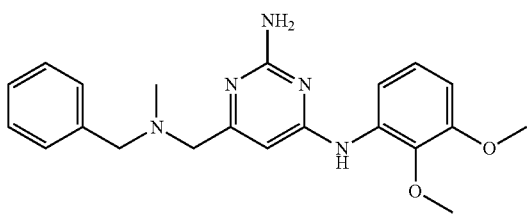 [SMILES: COc1cccc(Nc2cc(CN(C)Cc3ccccc3)nc(N)n2)c1OC]

Yield: 16% (over two steps).
HPLC-MS [M+H]⁺: 380.30; Rt=1.62 min (Method E).
¹H NMR (400 MHz, DMSO-d₆) δ: 8.28 (s, 1H), 7.79-7.77 (d, J=8 Hz, 1H), 7.36-7.25 (m, 5H), 6.99-6.95 (t, J=8.4 Hz, 1H), 6.74-6.72 (m, 1H), 6.44 (s, 1H), 6.08 (br s, 2H), 3.80 (s, 3H), 3.70 (s, 3H), 3.51 (s, 2H), 3.25 (s, 2H), 2.13 (s, 3H).

Example 43

N⁴-(Benzo[d][1,3]dioxol-4-yl)-6-((benzyl(methyl)amino)methyl)pyrimidine-2,4-diamine

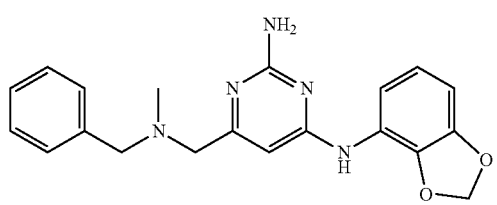 [SMILES: CN(Cc1ccccc1)Cc1cc(Nc2cccc3c2OCO3)nc(N)n1]

Yield: 9% (over two steps).
HPLC-MS [M+H]⁺: 364.35; Rt=2.64 min (Method A).
1H NMR (400 MHz, DMSO-d₆) δ: 8.68 (s, 1H), 7.33-7.24 (m, 6H), 6.81-6.77 (t, J=8.0 Hz, 1H), 6.69-6.67 (m, 1H), 6.26 (s, 1H), 6.05 (br s, 2H), 5.97 (s, 2H), 3.51 (s, 2H), 3.24 (s, 2H), 2.12 (s, 3H).

Example 44

N⁴-(Benzo[d][1,3]dioxol-4-yl)-6-((benzyl(methyl)amino)methyl)pyrimidine-2,4-diamine

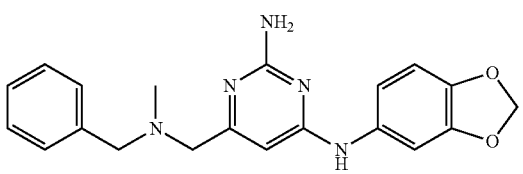 [SMILES: CN(Cc1ccccc1)Cc1cc(Nc2ccc3c(c2)OCO3)nc(N)n1]

Yield: 17% (over two steps).
HPLC-MS [M+H]⁺: 364.3; Rt=1.58 min (Method E).
¹H NMR (400 MHz, DMSO-d₆) δ: 8.95 (s, 1H), 7.53 (s, 1H), 7.36-7.25 (m, 5H), 6.96-6.94 (d, J=8 Hz, 1H), 6.82-6.80 (d, J=8 Hz, 1H), 6.20 (s, 1H), 6.12 (br, s, 2H), 5.96 (s, 2H), 3.52 (s, 2H), 3.24 (s, 2H), 2.14 (s, 3H).

Example 45

6-(((4-Fluorobenzyl)(methyl)amino)methyl)-N⁴-(3-methoxyphenyl)pyrimidine-2,4-diamine

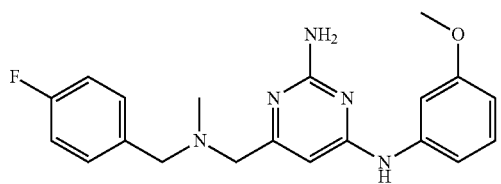 [SMILES: COc1cccc(Nc2cc(CN(C)Cc3ccc(F)cc3)nc(N)n2)c1]

Yield: 25% (over two steps).
HPLC-MS [M+H]⁺: 368.32; Rt=1.67 min (Method E).
¹H NMR (400 MHz, DMSO-d₆) δ: 9.06 (s, 1H), 7.45-7.37 (m, 3H), 7.20-7.13 (m, 4H), 6.51-6.49 (m, 1H), 6.25 (s, 1H), 6.16 (hr, s, 2H), 3.74 (s, 3H), 3.52 (s, 2H), 3.26 (s, 2H), 2.13 (s, 3H).

Example 46

6-((Benzyl(methyl)amino)methyl)-N⁴-(2-methoxy-5-methylphenyl)pyrimidine-2,4-diamine

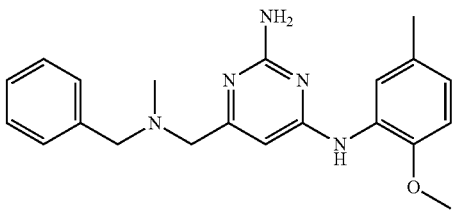 [SMILES: COc1ccc(C)cc1Nc1cc(CN(C)Cc2ccccc2)nc(N)n1]

Yield: 49% (over two steps).
HPLC-MS [M+H]+: 364.33; Rt=1.74 min (Method E).
$^1$H NMR (400 MHz, DMSO-d$_6$) δ: 8.06 (s, 1H), 7.80 (s, 1H), 7.34-7.24 (m, 5H), 6.90-6.88 (m, 1H), 6.84-6.81 (m, 1H), 6.30 (s, 1H), 6.04 (br s, 2H), 3.75 (s, 3H), 3.51 (s, 2H), 3.23 (s, 2H), 2.25 (s, 3H), 2.12 (s, 3H).

Example 47

6-4(4-Methoxybenzyl)(methyl)amino)methyl)-N$^4$-m-tolylpyrimidine-2,4-diamine

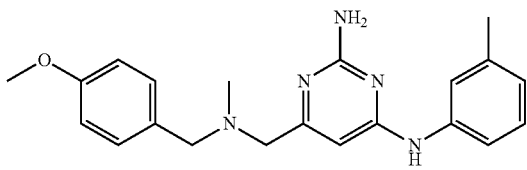 [SMILES: COc1ccc(CN(C)Cc2cc(Nc3cccc(C)c3)nc(N)n2)cc1]

Yield: 15% (over two steps).
HPLC-MS [M+H]+: 364.38; Rt=2.83 min (Method B).
$^1$H NMR (400 MHz, DMSO-d$_6$) δ: 8.98 (s, 1H), 7.55-7.53 (d, J=8.0 Hz, 1H), 7.47 (s, 1H), 7.27-7.25 (d, J=8.0 Hz, 2H), 7.15-7.11 (t, J=8.0 Hz, 1H), 6.90-6.88 (d, J=8.0 Hz, 2H), 6.76-6.74 (d, J=8.0 Hz, 1H), 6.25 (s, 1H), 6.13 (br, s, 2H), 3.74 (s, 3H), 3.46 (s, 2H), 3.23 (s, 2H), 2.28 (s, 3H), 2.12 (s, 3H).

Example 48

6-((Benzyl(ethyl)amino)methyl)-N$^4$-(3-methoxyphenyl)pyrimidine-2,4-diamine

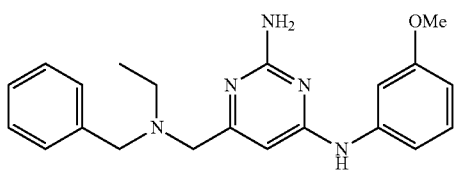 [SMILES: CCN(Cc1ccccc1)Cc1cc(Nc2cccc(OC)c2)nc(N)n1]

Yield: 21% (over two steps).
HPLC-MS [M+H]+: 364.3; Rt=1.71 min (Method A).
$^1$H NMR (400 MHz, DMSO-d$_6$) δ: 9.06 (s, 1H), 7.44-7.43 (t, J=4.4 Hz, 1H), 7.38-7.30 (m, 4H), 7.25-7.21 (m, 2H), 7.16-7.12 (t, J=8.0 Hz, 1H), 6.51-6.49 (m, 1H), 6.32 (s, 1H), 6.13 (br, s, 2H), 3.74 (s, 3H), 3.58 (s, 2H), 3.29 (s, 2H), 2.47-2.45 (m, 2H), 1.04-1.00 (t, J=14 Hz, 3H).

Example 49

6-((Benzyl(2-methoxyethyl)amino)methyl)-N$^4$-(3-methoxyphenyl)pyrimidine-2,4-diamine

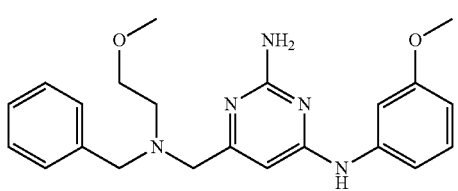 [SMILES: COCCN(Cc1ccccc1)Cc1cc(Nc2cccc(OC)c2)nc(N)n1]

Yield: 39% (over two steps).
HPLC-MS [M+H]+: 394.36; Rt=1.80 min (Method A).
$^1$H NMR (400 MHz, DMSO-d$_6$) δ: 9.07 (s, 1H), 7.43-7.42 (t, J=4.4 Hz, 11-1), 7.38-7.30 (m, 4H), 7.26-7.21 (m, 2H), 7.16-7.12 (t, J=8.0 Hz, 1H), 6.52-6.49 (m, 1H), 6.31 (s, 1H), 6.14 (br, s, 2H), 3.74 (s, 3H), 3.64 (s, 2H), 3.46-3.43 (t, J=12.4 Hz, 2H), 3.36 (s, 2H), 3.19 (s, 3H), 2.16-2.58 (t, J=2.0 Hz, 2H).

Example 59

N$^4$-(3-Methoxyphenyl)-6-((2-phenylpyrrolidin-1-yl)methyl)pyrimidine-2,4-diamine

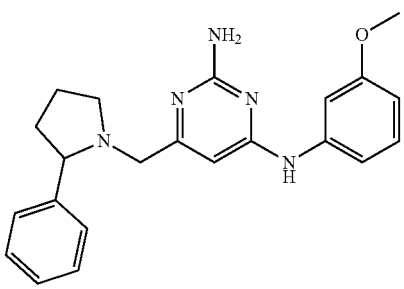 [SMILES: COc1cccc(Nc2cc(CN3CCCC3c3ccccc3)nc(N)n2)c1]

Yield: 15% (over two steps).
HPLC-MS [M+H]+: 376.41; Rt=3.02 min (Method A).
$^1$H NMR (400 MHz, DMSO-d$_6$) δ: 9.08 (s, 1H), 7.47-7.46 (t, J=4.4 Hz, 11-1), 7.42-7.40 (d, J=6.8 Hz, 2H), 7.35-7.31 (t, J=7.0 Hz, 2H), 7.25-7.21 (t, J=8.0 Hz, 2H), 7.16-7.11 (t, J=8.0 Hz, 1H), 6.51-6.48 (m, 1H), 6.22 (s, 1H), 6.12 (br s, 2H), 3.74 (s, 3H), 3.47-3.41 (m, 2H), 3.27-3.23 (m, 1H), 2.89-2.85 (d, J=15.2 Hz, 1H), 2.25-2.15 (m, 2H), 1.83-1.80 (m, 2H), 1.60-1.55 (m, 1H).

Example 51

N$^4$-(3-Methoxyphenyl)-6-(((3-methoxyphenyl)(methyl)amino)methyl)pyrimidine-2,4-diamine

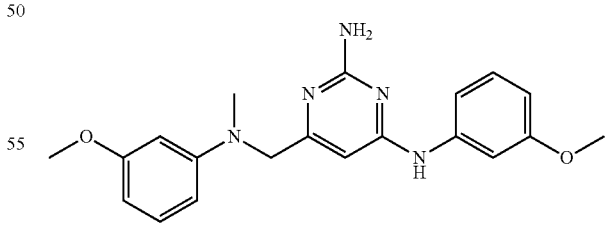

Yield: 6% (over two steps).
HPLC-MS [M+H]+: 366.38; Rt=3.08 min (Method B).
$^1$H NMR (400 MHz, DMSO-d$_6$) δ: 9.00 (s, 1H), 7.40-7.39 (t, J=4 Hz, 1H), 7.17-7.15 (d, J=8 Hz, 1H), 7.11-7.02 (m, 2H), 6.48-6.46 (dd, J=8 Hz, 1H), 6.25-6.20 (m, 4H), 6.15-6.14 (t, J=4 Hz, 1H), 5.78 (s, 1H), 4.21 (s, 2H), 3.70 (s, 3H), 3.67 (s, 3H), 3.05 (s, 3H).

Example 52

6-((Benzyl(methyl)amino)methyl)-N⁴-p-tolylpyrimidine-2,4-diamine

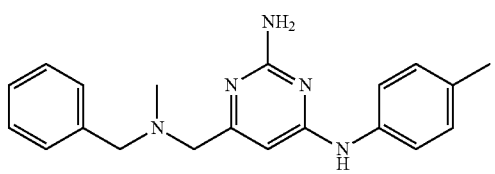 [SMILES: Cc1ccc(Nc2cc(CN(C)Cc3ccccc3)nc(N)n2)cc1]

To a stirred solution of compound 4-((benzyl(methyl)amino)methyl)-6-chloropyrimidin-2-amine (120 mg, 0.4 mmol, 1.0 eq) in tetrahydrofurane (5 mL) was added N,N-diisopropylethylamine (0.385 mL, 2.28 mmol, 5 eq) at room temperature and it was stirred for 20 min. To the reaction mixture, was added p-toluidine (0.068 g, 6.35 mmol, 1.5 eq) and the mixture was stirred for 16 h at room temperature and further stirred for 4 h at 70° C. After completion of the reaction, reaction mixture was poured into cold water and extracted with ethyl acetate. Organic extracts were dried over anhydrous sodium sulfate and solvent was evaporated under reduced pressure to get crude compound. The crude was purified by preparative reverse phase prep HPLC to get the product 6-((benzyl(methyl)amino)methyl)-N⁴-p-tolylpyrimidine-2,4-diamine as pale yellow solid. Yield: 4% (over two steps).

HPLC-MS [M+H]⁺: 334.3; Rt=1.63 min (Method B).

¹H NMR (400 MHz, DMSO-d₆) δ: 8.97 (br s, 1H), 7.57-7.55 (d, J=8.4 Hz, 2H), 7.36-7.31 (m, 4H), 7.28-7.26 (m, 1H), 7.07-7.05 (d, J=8.0 Hz, 2H), 6.24 (s, 1H), 6.10 (br s, 2H), 3.53 (s, 2H), 3.25 (s, 2H), 2.25 (s, 3H), 2.15 (s, 3H).

Intermediate 49

Tert-butyl (tert-butoxycarbonyl)(4-((tert-butoxycarbonyl)(p-tolyl)amino)-6-formylpyrimidin-2-yl)carbamate

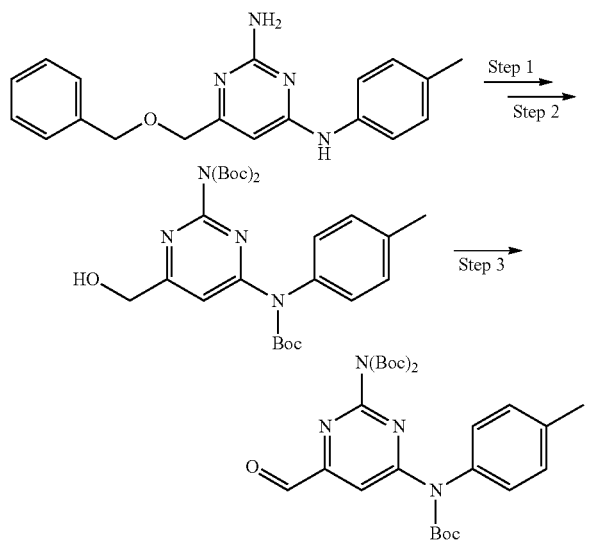

Step 1:

Boc anhydride (43 ml, 188.4 mmol, 6 eq) was added to a stirred solution of 6-(benzyloxymethyl)-N⁴-p-tolylpyrimidine-2,4-diamine (Intermediate 48) (10 g, 31.4 mmol, 1 eq) and dimethylaminopyridine (0.383 g, 3.14 mmol, 0.1 eq) in tetrahydrofurane at 0° C., then the reaction mixture was heated at 90° C. for 6 h. The reaction mixture was diluted with water and extracted with ethyl acetate (3×25 mL). The combined organic extracts were washed with water and brine, and dried over anhydrous sodium sulfate. The solvent was evaporated under reduced pressure to get the crude product which was purified by flash column chromatography (2-4% methanol/dichloromethane) to get 14 g of product tert-butyl (4-((benzyloxy)methyl)-6-((tert-butoxycarbonyl)(p-tolyl)amino)pyrimidin-2-yl)(tert-butoxycarbonyl)carbamate (yield: 72%).

HPLC-MS [M+H]⁺: 621.55; Rt=1.61 min (Method B).

¹H NMR (400 MHz, DMSO-d₆) δ: 7.83 (s, 1H), 7.39-7.38 (m, 1H), 7.1.9 (d, J=8 Hz, 2H), 7.05 (d, J=8 Hz, 2H), 4.65 (s, 2H), 4.60 (s, 2H), 2.31 (s, 3H), 1.44-1.39 (m, 27H).

Step 2:

10% Palladium on Charcoal (5 g) was added under nitrogen to a stirred solution of compound tert-butyl (4-((benzyloxy)methyl)-6-((tert-butoxycarbonyl)(p-tolyl)amino)pyrimidin-2-yl)(tert-butoxycarbonyl)carbamate (16 g, 25.5 mmol, 1 eq) in methanol (100 ml) at room temperature. The reaction mixture was stirred at same temperature under hydrogen pressure for 16 h. The reaction mixture was filtered through celite bed, washed with methanol and evaporated under reduced pressure to afford 12.4 g of pure product tert-butyl (tert-butoxycarbonyl)(4-((tert-butoxycarbonyl)(p-tolyl)amino)-6-(hydroxymethyl)pyrimidin-2-yl)carbamate (yield: 92%).

HPLC-MS [M+H]⁺: 531.61: Rt=2.46 min (Method A).

Step 3:

Dess-Martin periodinane was slowly added to a solution of compound tert-butyl (tert-butoxycarbonyl)(4-((tert-butoxycarbonyl)(p-tolyl)amino)-6-(hydroxymethyl)pyrimidin-2-yl)carbamate in dichloromethane at 0° C. Then reaction mixture was warmed to room temperature and stirred for 3 h. The reaction mixture was quenched with saturated solution of sodium thiosulphate and sodium bicarbonate and organic product was extracted with dichloromethane. Combined organics were dried over anhydrous sodium sulfate, filtered and evaporated under reduced pressure to get crude product. The crude product was purified by flash column chromatography (2-3% methanol/dichloromethane) to afford 8 g of compound tert-butyl (tert-butoxycarbonyl)(4-((tert-butoxycarbonyl)(p-tolyl)amino)-6-formylpyrimidin-2-yl)carbamate (yield: 73%).

HPLC-MS [M+H]⁺: 529.44; Rt=2.67 min (Method A).

¹H NMR (400 MHz, DMSO-d₆) δ: 9.91 (s, 1H), 8.24 (s, 1H), 7.21 (d, J=8 Hz, 1H), 7.09 (d, J=8.4 Hz, 1H), 2.32 (s, 3H), 1.38-1.29 (m, 27H).

General Procedure XII

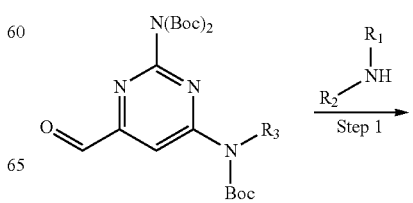

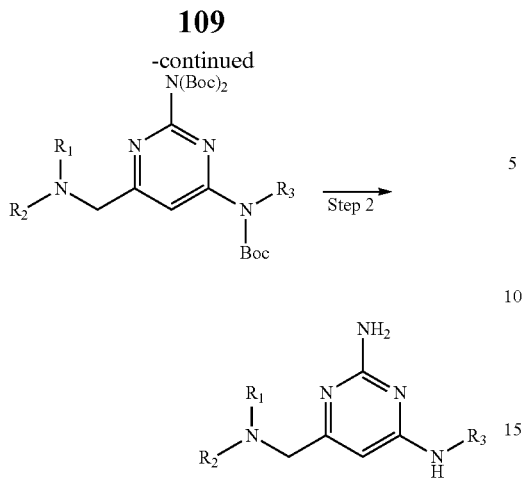

Step 1:

Catalytic acetic acid was added to a stirred solution of the appropriate formyl pyrimidine (1 eq) (ex: tert-butyl (tert-butoxycarbonyl)(4-((tert-butoxycarbonyl)(p-tolyl)amino)-6-formylpyrimidin-2-yl)carbamate) and the appropriate benzyl amine (1.5 eq) (ex: 1-(3-methoxyphenyl)-N-methyl-methanamine) in 1,2-dichloroethane at 0° C. then followed by sodium cyanoborohydride (2 eq) was added then the reaction mixture was stirred at room temperature for 16 h. After completion of the reaction, the reaction mixture was quenched with minimum amount of saturated sodium bicarbonate solution, the organic product was extracted with dichloromethane (3×). The combined organic extracts were dried over anhydrous sodium sulfate. Solvent was distilled under reduced pressure to give the crude compound. The crude was purified by flash column chromatography (10-20% ethyl acetate/petroleum ether or 2-5% methanol/dichloromethane) to get the desired BOC protected product (ex: tert-butyl (tert-butoxycarbonyl)(4-((tert-butoxycarbonyl)(p-tolyl)amino)-6-(((3-methoxybenzyl)(methyl)amino)methyl) pyrimidin-2-yl)carbamate).

In some examples, the reaction was carried out with trimethyl orthoformate (10 eq) and sodium triacetoxyborohydride (2.5 eq).

Step 2:

To a stirred dioxane solution of the BOC-protected compound (ex: tert-butyl (tert-butoxycarbonyl)(4-((tert-butoxycarbonyl)(p-tolyl)amino)-6-(((3-methoxybenzyl)(methyl)-amino)methyl)pyrimidin-2-yl)carbamate) at 0° C. was added 4M HCl and the mixture was stirred at room temperature for 48 h. The reaction mixture was further heated at 50° C. for 2 h. The reaction mixture was evaporated under reduced pressure to get crude which was quenched with minimum amount of aqueous sodium bicarbonate solution. The organic product was extracted with dichloromethane (3×). The combined organic extracts were dried over anhydrous sodium sulfate. Solvent was distilled under reduced pressure to give the crude compound The crude was purified by flash column chromatography (neutral alumina, 15% methanol/dichloromethane) and further purified by reverse phase preparative HPLC to get the final desired de-protected product (ex: 6-(((3-methoxybenzyl)(methyl)amino)methyl)-$N^4$-p-tolylpyrimidine-2,4-diamine).

In same cases, trifluoroacetic acid was used instead HCl and with dichloromethane as solvent.

Example 53

6-(((3-Methoxybenzyl)(methyl)amino)methyl)-$N^4$-p-tolylpyrimidine-2,4-diamine

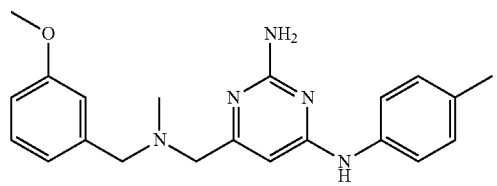 [SMILES: COc1cccc(CN(C)Cc2cc(Nc3ccc(C)cc3)nc(N)n2)c1]

Yield: 10%.

HPLC-MS [M+H]$^+$: 364.24; Rt=1.69 min (Method A).

$^1$H NMR (400 MHz, DMSO-$d_6$) δ: 8.95 (s, 1H), 7.55 (d, J=8.4 Hz, 2H), 7.26-7.22 (m, 1H), 6.93-6.91 (d, J=7.6 Hz 2H), 6.83-6.81 (m, 1H), 6.24 (s, 1H), 6.09 (s, 2H), 3.73 (s, 3H), 3.51 (s, 2H), 3.24 (s, 2H), 2.24 (s, 3H), 2.15 (s, 3H).

Example 54

6-(((3-Chlorobenzyl)(methyl)amino)methyl)-$N^4$-p-tolylpyrimidine-2,4-diamine

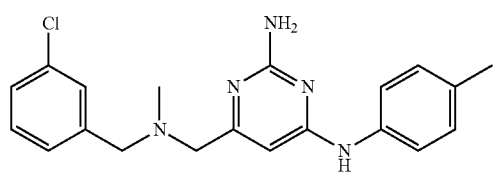

Yield: 36%.

HPLC-MS [M+H]$^+$: 368.23; Rt=1.80 min (Method A).

$^1$H NMR (400 MHz, DMSO-$d_6$) δ: 8.96 (s, 1H), 7.55 (d, J=8.4 Hz, 2H), 7.40-7.30 (m, 4H), 7.06 (d, J=8 Hz, 2H), 6.22 (s, 1H), 6.10 (br s, 2H), 3.55 (s, 2H), 3.26 (s, 2H), 2.24 (s, 3H), 2.14 (s, 3H).

Example 55

3-((((2-Amino-6-(p-tolylamino)pyrimidin-4-yl) methyl)(methyl)amino)methyl)benzonitrile

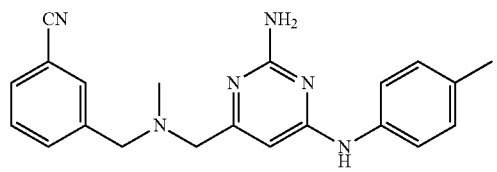 [SMILES: Cc1ccc(Nc2cc(CN(C)Cc3cccc(Cl)c3)nc(N)n2)cc1]

Yield: 21%

HPLC-MS [M+H]$^+$; 359.21; Rt=1.77 min (Method A).

$^1$H NMR (400 MHz, DMSO-$d_6$) δ: 8.96 (s, 1H), 7.78-7.69 (m, 3H), 7.58-7.54 (m, 3H), 7.06 (d, J=8 Hz, 2H), 6.21 (s, 1H), 6.11 (br s, 1H), 3.60 (s, 2H), 3.28 (s, 2H), 2.24 (s, 3H), 2.14 (s, 3H).

Example 56

6-(((4-Chlorobenzyl)(methyl)amino)methyl)-N$^4$-p-tolylpyrimidine-2,4-diamine

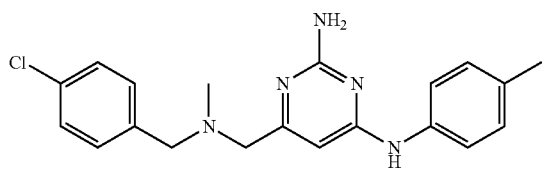 [SMILES: Cc1ccc(Nc2cc(CN(C)Cc3ccc(Cl)cc3)nc(N)n2)cc1]

Trifluoroacetic acid and dichloromethane were used in the second step
Yield: 42%.
HPLC-MS [M+H]$^+$: 368.21; Rt=1.85 min (Method A).
$^1$H NMR (400 MHz, DMSO-d$_6$) δ: 8.95 (s, 1H), 7.54 (d, J=8.4 Hz, 2H), 7.38 (m, 4H), 7.06 (d, J=8.4 Hz, 2H), 6.21 (s, 1H), 6.10 (br s, 2H), 3.52 (s, 2H), 3.23 (s, 2H), 2.25 (s, 3H), 2.14 (s, 3H).

Example 57

4-((((2-Amino-6-(p-tolylamino)pyrimidin-4-yl)methyl)(methyl)amino)methyl)benzonitrile

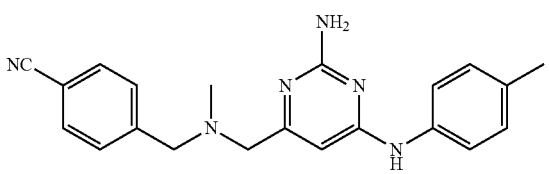 [SMILES: Cc1ccc(Nc2cc(CN(C)Cc3ccc(C#N)cc3)nc(N)n2)cc1]

Trifluoroacetic acid and dichloromethane were used
Yield: 23%.
HPLC-MS [M+H]$^+$: 359.28; Rt=1.76 min (Method A).
$^1$H NMR (400 MHz, DMSO-d$_6$) δ: 8.96 (s, 1H), 7.81 (d, J=8 Hz, 2H), 7.57-7.55 (m, 4H), 7.06 (d, J=8 Hz, 2H), 6.21 (s, 1H), 6.11 (s, 2H), 3.63 (s, 2H), 3.27 (s, 2H), 2.25 (s, 3H), 2.16 (s, 3H).

Example 58

6-((Methyl(1,2,3,4-tetrahydronaphthalen-2-yl)amino)methyl)-N$^4$-(p-tolyl)pyrimidine-2,4-diamine

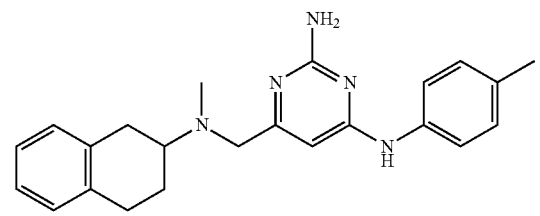 [SMILES: Cc1ccc(Nc2cc(CN(C)C3CCc4ccccc4C3)nc(N)n2)cc1]

Yield: 44%.
HPLC-MS [M+H]$^+$: 374; Rt=2.13 min (Method A).
$^1$H NMR (400 MHz, CDCl$_3$) δ 7.14 (d, J=8.5 Hz, 2H), 7.08 (d, J=8.3 Hz, 2H), 7.04-6.96 (m, 4H), 6.47 (s, 1H), 6.23 (s, 1H), 4.89 (s, 2H), 3.44 (s, 2H), 2.94-2.65 (m, 5H), 2.28 (s, 6H), 2.03-1.97 (m, 1H), 1.70-1.64 (m, 1H).

Example 59

6-(((2-(2-(2-Aminoethoxy)ethoxy)ethyl)(benzyl)amino)methyl)-N$^4$-(p-tolyl)pyrimidine-2,4-diamine

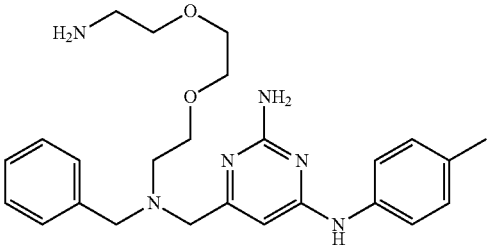 [SMILES: Cc1ccc(Nc2cc(CN(CCOCCOCCN)Cc3ccccc3)nc(N)n2)cc1]

Yield: 30%.
HPLC-MS [M+H]$^+$: 451; Rt=1.75 min (Method A).
$^1$H NMR (400 MHz, CD$_3$OD) δ 7.40 (d, J=8.3 Hz, 2H), 7.34 (d, J=6.9 Hz, 2H), 7.29 (d, J=7.0 Hz, 2H), 7.22 (t, J=7.1 Hz, 1H), 7.13 (d, J=8.2 Hz, 2H), 6.38 (s, 1H), 3.67 (s, 2H), 3.59-3.57 (m, 4H), 3.54-3.52 (m, 2H), 3.46 (s, 2H), 3.30 (dt, J=3.3, 1.6 Hz, 2H), 2.99-2.92 (m, 2H), 2.69 (t, J=5.8 Hz, 2H), 2.31 (s, 3H).

Example 60

6-((Methyl(pyridin-4-ylmethyl)amino)methyl)-N$^4$-p-tolylpyrimidine-2,4-diamine

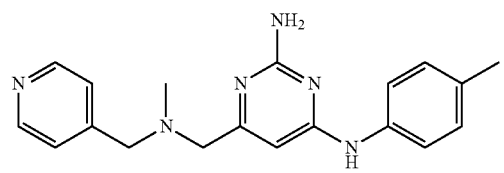 [SMILES: Cc1ccc(Nc2cc(CN(C)Cc3ccncc3)nc(N)n2)cc1]

Trifluoroacetic acid and dichloromethane were used in the second step
Yield: 5%.
HPLC-MS [M+H]$^+$: 335.23; Rt=1.39 min (Method A).
$^1$H NMR (400 MHz, DMSO-d$_6$) δ: 8.96 (s, 1H), 8.53-8.52 (m, 2H), 7.57-7.55 (d, J=8.4 Hz, 2H). 7.38-7.36 (m, 2H), 7.07-7.05 (d, J=8.4 Hz, 2H), 6.23 (s, 1H), 6.11 (s, 2H), 3.58 (s, 2H), 3.31 (s, 2H), 2.25 (s, 3H), 2.17 (s, 3H).

Example 61

6-((Methyl(pyridin-3-ylmethyl)amino)methyl)-N$^4$-p-tolylpyrimidine-2,4-diamine

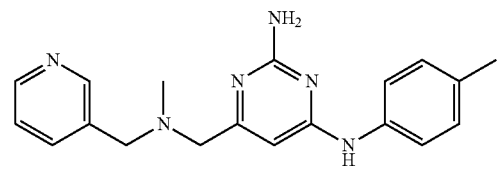 [SMILES: Cc1ccc(Nc2cc(CN(C)Cc3cccnc3)nc(N)n2)cc1]

Trifluoroacetic acid and dichloromethane were used in the second step

Yield: 38%.

HPLC-MS [M+H]$^+$: 335.25 Rt=1.37 min (Method-A).

$^1$H NMR (400 MHz, DMSO-d$_6$) δ: 8.97 (s, 1H), 8.57 (s, 1H), 8.49-8.47 (m, 1H), 7.75-7.73 (d, J=8 Hz, 1H). 7.58-7.56 (d, J=8 Hz, 2H), 7.38-7.35 (m, 1H), 7.07-7.05 (d, J=8.4 Hz, 2H), 6.23 (s, 1H), 6.11 (br s, 2H), 3.57 (s, 2H), 3.27 (s, 2H), 2.24 (s, 3H), 2.15 (s, 3H).

Example 62

N-((2-Amino-6-(3-methoxyphenylamino)pyrimidin-4-yl)methyl)-N-methylbenzamide

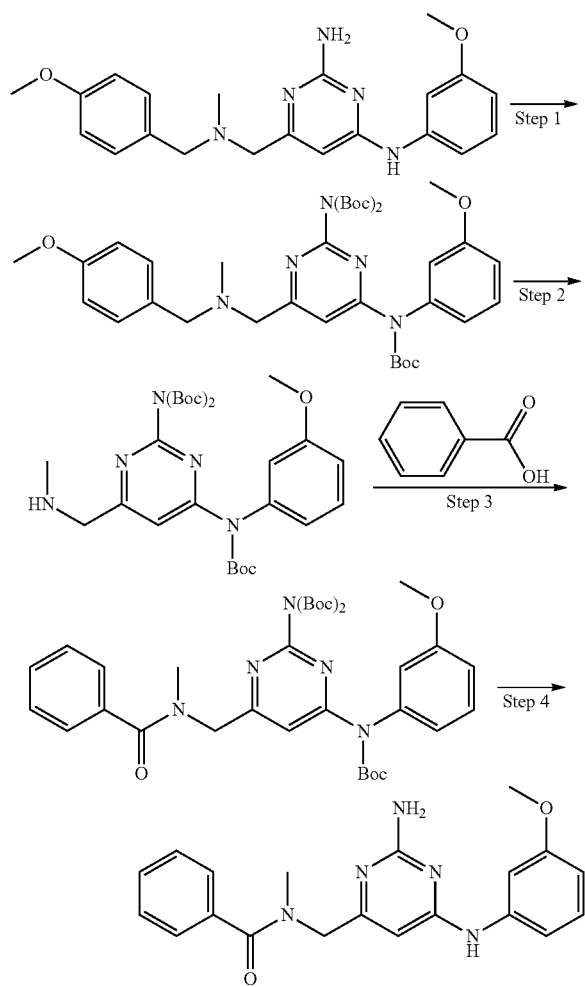

Step 1:

Boc anhydride (1.7 mL, 7.9 mmol, 6 eq) was added to a stirred solution of 6-(((4-methoxybenzyl)(methyl)amino) methyl)-N$^4$-(3-methoxyphenyl)pyrimidine-2,4-diamine (0.5 g, 1.3 mmol, 1 eq) and dimethylaminopyridine (0.016 g, 0.13 mmol, 0.1 eq) in tetrahydrofuran at 0° C. and the reaction mixture heated to 100° C. for 6 h. The reaction mixture was diluted with water, extracted with ethyl acetate (3×10 mL). The combined organic extracts were washed with water, brine, dried over anhydrous sodium sulfate and solvent was evaporated under reduced pressure to get crude product. The crude product was purified by flash column chromatography (15-20% ethyl acetate/petroleum ether) to get 0.75 g of product tert-butyl (tert-butoxycarbonyl)(4-((tert-butoxycarbonyl)(3-methoxyphenyl)amino)-6-(((4-methoxybenzyl)(methyl)amino)methyl)pyrimidin-2-yl)carbamate (yield: 83.7%).

HPLC-MS [M+H]$^+$: 364.33; Rt=3.71 min (Method H).

Step 2:

10% Pd/C (0.4 g) was added to a stirred solution of compound tert-butyl (tert-butoxycarbonyl)(4-((tert-butoxycarbonyl)(3-methoxyphenyl)amino)-6-(((4-methoxybenzyl)(methyl)amino)methyl)pyrimidin-2-yl)carbamate (0.75 g, 1.1 mmol, 1 eq) in methanol (20 mL) under nitrogen at room temperature. The reaction mixture was stirred at same temperature under hydrogen pressure for 16 h. The reaction mixture was filtered through celite bed, washed with methanol and filtrate was evaporated under reduced pressure to afford 0.35 g of crude product tert-butyl (tert-butoxycarbonyl)(4-((tert-butoxycarbonyl)(3-methoxyphenyl)amino)-6-((methylamino)methyl)pyrimidin-2-yl)carbamate which was used for next step as such without any purification.

ES-MS [M+H]$^+$: 560.3; Rt=2.68 min (Method H).

Step 3:

HATU (0.24 g, 0.64 mmol, 1.2 eq) was added portion wise to a solution of N,N-diisopropylethylamine (0.18 mL, 1.0 mmol, 2 eq) and compound tert-butyl (tert-butoxycarbonyl)(4-((tert-butoxycarbonyl)(3-methoxyphenyl)amino)-6-((methylamino)methyl)pyrimidin-2-yl)carbamate (0.3 g, 0.53 mmol, 1 eq) in dimethyl formamide (3 mL) at 0° C. The reaction mixture was stirred for 10 minutes at same temperature. To the reaction mixture was added benzoic acid (0.078 g, 0.64 mmol, 1.2 eq) at 0° C. and the reaction mixture was stirred at room temperature for 16 h. The reaction mixture was quenched with minimum amount of saturated sodium bicarbonate solution, the organic product was extracted with ethyl acetate (2×10 mL). The combined organic extracts were dried over anhydrous sodium sulfate. Solvent was distilled under reduced pressure to give the crude compound. The crude product was purified by flash column chromatography (20-30% ethyl acetate/petroleum ether) to get 0.25 g of product tert-butyl (tert-butoxycarbonyl)(4-((tert-butoxycarbonyl)(3-methoxyphenyl)amino)-6-((N-methylbenzamido)methyl)pyrimidin-2-yl)carbamate (yield: 70%).

HPLC-MS [M+H]$^+$: 664.3; Rt=3.17 min (Method H).

Step 4:

Trifluoroacetic acid (3 mL) was added to a stirred solution of compound cert-butyl (tert-butoxycarbonyl)(4-((tert-butoxycarbonyl)(3-methoxyphenyl)amino)-6-((N-methylbenzamido)methyl)pyrimidin-2-yl)carbamate (0.25 g, 0.37 mmol, 1 eq) in dichloromethane (5 mL) 0° C. and then the reaction mixture was stirred at room temperature for 3 h. The reaction mixture was evaporated under reduced pressure to obtain crude. The crude product was purified by reverse phase prep HPLC to afford 70 mg of pure compound N-((2-amino-6-(3-methoxyphenylamino)pyrimidin-4-yl) methyl)-N-methylbenzamide (yield: 51%).

HPLC-MS [M+H]$^+$: 364.33; Rt=1.60 min (Method E).

$^1$H NMR (400 MHz, VT, DMSO-d$_6$) δ: 8.86 (s, 1H), 7.42-7.34 (m, 6H), 7.18-7.12 (m, 2H), 6.55-6.52 (m, 1H), 5.99 (s, 1H), 5.92 (br, s, 2H), 4.26 (br, s, 2H), 3.75 (s, 3H), 2.69 (s, 3H).

General Procedure XIII

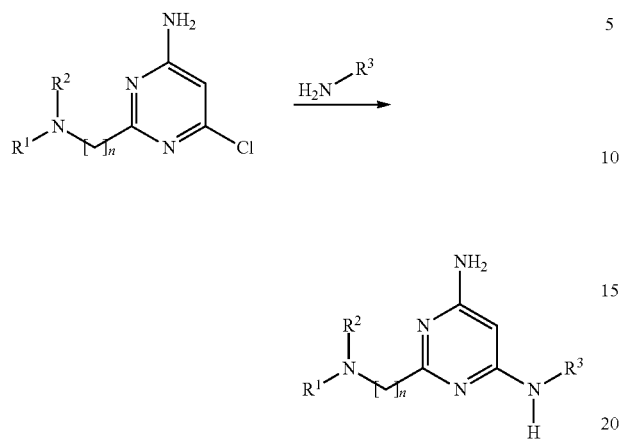

To a stirred solution of the dichloro compound (ex: N-benzyl-1-(4,6-dichloropyrimidin-2-yl)-N-methylmethanamine; Intermediate 21) (1 eq) in 1-butanol (13 mL/mmol) were added the corresponding aniline (ex. 2-methoxyaniline) (0.7 eq), sulfuric acid (catalytic, 2 drops) at room temperature and heated to 100° C. for 16 h. After completion of the reaction, the reaction mixture was allowed to cool to room temperature and diluted with water and basified with saturated sodium bicarbonate (pH~8). The aqueous layer was extracted twice with ethyl acetate, dried over anhydrous sodium sulfate and solvent was evaporated under reduced pressure to get crude compound. The crude was purified by flash column chromatography (2-15% methanol/dichloromethane or 10-60% ethyl acetate/heptanes) to get the product (ex: 2-((benzyl(methyl)amino) methyl)-6-chloro-N-(2-methoxyphenyl)pyrimidin-4-amine).

In same examples, the reaction was carried using concentrated hydrochloric acid and sodium iodide (1 eq) and water as solvent.

Intermediate 50

2-((Benzyl(methyl)amino)methyl)-6-chloro-N-(2-methoxyphenyl)pyrimidin-4-amine

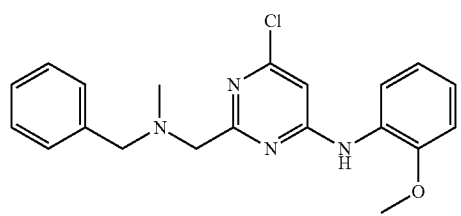 [SMILES: COc1ccccc1Nc1cc(Cl)nc(CN(C)Cc2ccccc2)n1]

Yield: 43%
HPLC-MS [M+H]$^+$: 369.18; Rt=1.76 min (Method B).

Intermediate 51

2-((Benzyl(methyl)amino)methyl)-6-chloro-N-m-tolylpyrimidin-4-amine

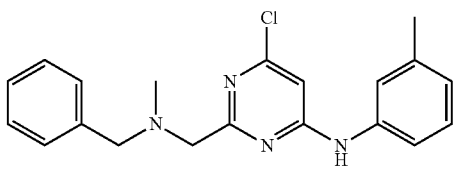 [SMILES: Cc1cccc(Nc2cc(Cl)nc(CN(C)Cc3ccccc3)n2)c1]

Yield: 37%
HPLC-MS [M+H]$^+$: 353.38; Rt=2.80 min (Method A).

Intermediate 52

2-((Benzyl(methyl)amino)methyl)-6-chloro-N-(3-methoxyphenyl)pyrimidin-4-amine

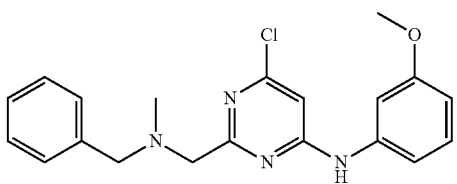 [SMILES: COc1cccc(Nc2cc(Cl)nc(CN(C)Cc3ccccc3)n2)c1]

Yield: 3
HPLC-MS [M+H]$^+$: 369.27; Rt=1.77 min (Method B).

Intermediate 53

2-((Benzyl(methyl)amino)methyl)-6-chloro-N-(4-methoxyphenyl)pyrimidin-4-amine

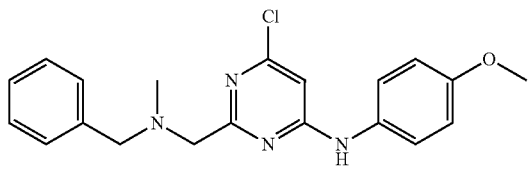 [SMILES: COc1ccc(Nc2cc(Cl)nc(CN(C)Cc3ccccc3)n2)cc1]

Yield: 33%
HPLC-MS [M+H]$^+$: 369.18; Rt=1.76 min (Method B).

General Procedure XIV

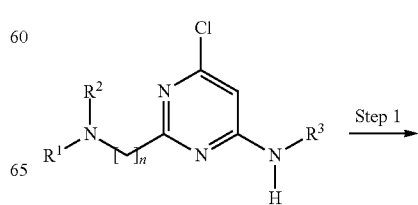

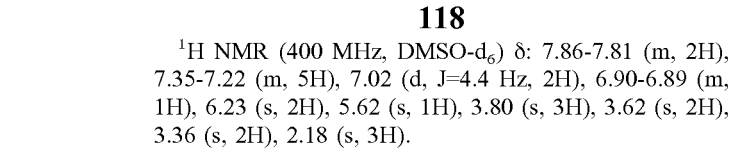

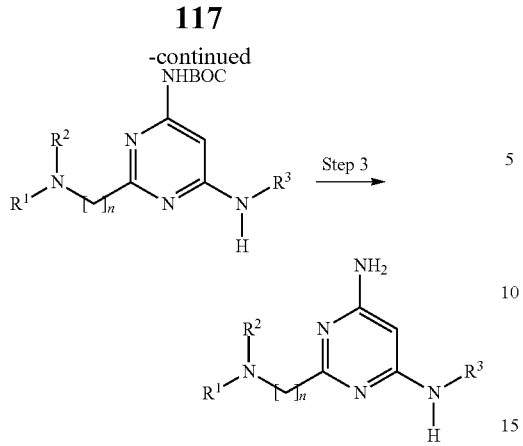

Step 1:

To a stirred and degassed solution of the chloro pyrimidine intermediate (ex: 2-((benzyl(methyl)amino)methyl)-6-chloro-N-(2-methoxyphenyl)pyrimidin-4-amine; Intermediate 50) (1.0 eq), tert-butyl carbamate (2.0 eq) in 1,4-dioxane (6 mL) were added cesium carbonate (3.0 eq) XPhos (0.05 eq), Pd$_2$(dba)$_3$ (0.1 eq) and heated to 90° C. for 16 h. After completion of the reaction; the reaction mixture was allowed to cool to room temperature and diluted with water and the organic product was extracted with ethyl acetate. The organic layer was dried over anhydrous sodium sulfate and solvent was evaporated under reduced pressure. The crude was purified by flash column chromatography (20/60% ethyl acetate/petroleum ether) to get the Boc-protected amine product (ex: tert-butyl (2-((benzyl(methyl)amino)methyl)-6-(p-tolylamino)pyrimidin-4-yl)carbamate).

Step 2:

A solution of the BOC-protected compound (ex: tert-butyl 2-((benzyl (methyl) amino) methyl)-6-(p-tolylamino) pyrimidin-4-ylcarbamate) (1 eq) in 4N hydrochloric acid in 1,4-dioxane (10 eq) was stirred at room temperature for 16 h. After completion of the reaction, the reaction mixture was evaporated under reduced pressure. The crude was basified with saturated sodium bicarbonate and the product was extracted with dichloromethane. The organic layer was dried over anhydrous sodium sulfate and evaporated. The crude was purified by preparative HPLC (reverse phase) to get the amine product (ex: 2-((benzyl(methyl)amino)methyl)-N$^4$-(2-methoxyphenyl)pyrimidine-4,6-diamine; Example 63)

Example 63

2-((Benzyl(methyl)amino)methyl)-N$^4$-(2-methoxyphenyl)pyrimidine-4,6-diamine

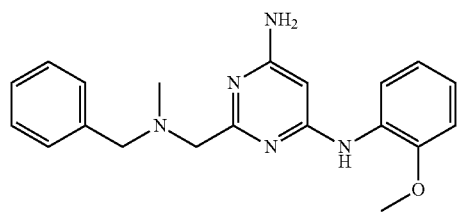 [SMILES: COc1ccccc1Nc1cc(N)nc(CN(C)Cc2ccccc2)n1]

Yield: 21% (over two steps).
HPLC-MS [M+H]$^+$: 350.23; Rt=1.67 min (Method A).
$^1$H NMR (400 MHz, DMSO-d$_6$) δ: 7.86-7.81 (m, 2H), 7.35-7.22 (m, 5H), 7.02 (d, J=4.4 Hz, 2H), 6.90-6.89 (m, 1H), 6.23 (s, 2H), 5.62 (s, 1H), 3.80 (s, 3H), 3.62 (s, 2H), 3.36 (s, 2H), 2.18 (s, 3H).

Example 64

2-((Benzyl(methyl)amino)methyl)-N4-m-tolylpyrimidine-4,6-diamine

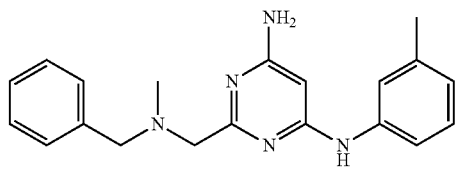 [SMILES: Cc1cccc(Nc2cc(N)nc(CN(C)Cc3ccccc3)n2)c1]

Trifluoroacetic acid and dichloromethane were used.
Yield: 5% (over two steps).
HPLC-MS [M+H]$^+$: 334.1; Rt=2.09 min (Method A).
$^1$H NMR (400 MHz, DMSO-d$_6$) δ: 8.77 (s, 1H), 7.39-7.23 (m, 7H), 7.12 (1, J=7.6 Hz, 1H), 6.73 (d, J=4.0 Hz 1H), 6.27 (s, 2H), 5.68 (s, 1H), 3.64 (s, 2H), 3.39 (s, 2H), 2.25 (s, 3H), 2.20 (s, 3H).

Example 65

2-((Benzyl(methyl)amino)methyl)-N$^4$-(3-methoxyphenyl)pyrimidine-4,6-diamine

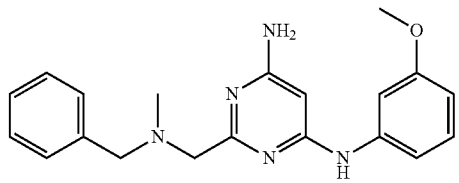 [SMILES: COc1cccc(Nc2cc(N)nc(CN(C)Cc3ccccc3)n2)c1]

Trifluoroacetic acid and dichloromethane were used.
Yield: 4% (over two steps).
HPLC-MS [M+H]$^+$: 350.29; Rt=1.91 min (Method A).
$^1$H NMR (400 MHz, DMSO-d$_6$) δ: 8.86 (s, 1H), 7.38-7.23 (m, 6H), 7.15-7.05 (m, 2H), 6.49-6.47 (m, 1H), 6.31 (s, 2H), 5.70 (s, 1H), 3.71 (s, 3H), 3.62 (s, 2H), 3.39 (s, 2H), 2.19 (s, 3H).

Example 66

2-((Benzyl(methyl)amino)methyl)-N$^4$-(4-methoxyphenyl)pyrimidine-4,6-di amine

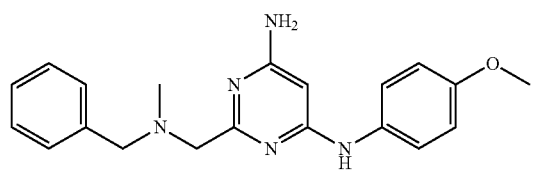 [SMILES: COc1ccc(Nc2cc(N)nc(CN(C)Cc3ccccc3)n2)cc1]

Trifluoroacetic acid and dichloromethane were used.
Yield: 6% (over two steps).

HPLC-MS [M+H]$^+$: 350.29; Rt=1.84 min (Method A).
$^1$H NMR (400 MHz, DMSO-d$_6$) δ: 8.60 (s, 1H), 7.40-7.23 (m, 7H), 6.86-6.84 (d, J=8.0 Hz, 2H), 6.20 (s, 2H), 5.55 (s, 1H), 3.73 (s, 3H), 3.62 (s, 2H), 3.36 (s, 2H), 2.19 (s, 3H).

Intermediate 54

6-((Benzyl(methyl)amino)methyl)-2-chloro-N-(2,4,4-trimethylpentan-2-yl)pyrimidin-4-amine

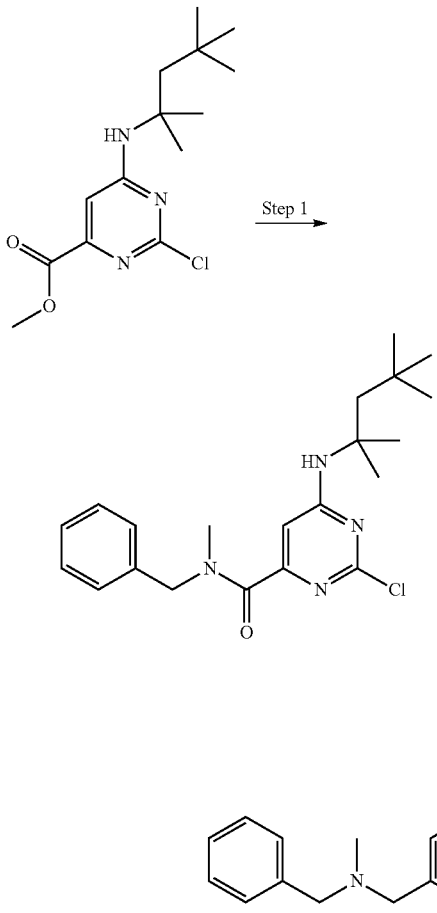

Step 1:
To a stirred solution of compound methyl 2-chloro-6-(2,4,4-trimethylpentan-2-ylamino)pyrimidine-4-carboxylate (0.5 g, 1.67 mmol, 1 eq), N-methylbenzylamine (0.202 g, 1.67 mmol, 1.0 eq) in tetrahydrofuran (10 mL) at room temperature was added 1,5,7-triazabicyclo[4.4.0]dec-5-ene (69.6 mg, 0.5 mmol, 0.3 eq) and stirred for 3 h at room temperature. After completion of the reaction, the reaction mixture was diluted with water and the organic product was extracted with ethyl acetate. The organic layer was dried over anhydrous sodium sulfate and solvent was evaporated under reduced pressure to get crude product. The crude product was purified by flash column chromatography (10-50% ethyl acetate/petroleum ether) to get compound N-benzyl-2-chloro-N-methyl-6-(2,4,4-trimethylpentan-2-ylamino)pyrimidine-4-carboxamide (0.21 g, yield: 32%) as a pale yellow thick liquid.

HPLC-MS [M+H]$^+$: 289.3; Rt=2.281 min (Method B).
$^1$H NMR (400 MHz, DMSO-d$_6$) δ: 7.74-7.73 (d, J=6.4 Hz, 1H), 7.40-7.25 (m, 5H), 6.55 (s, 1H), 4.61 (s, 1H), 4.50 (s, 1H), 2.83-2.82 (m, 3H), 3.37 (s, 2H), 1.88-1.86 (m, 2H), 1.42-1.41 (m, 6H), 0.92-0.88 (m, 9H).

Step 2:
To a stirred solution of compound N-benzyl-2-chloro-N-methyl-6-(2,4,4-trimethylpentan-2-ylamino)pyrimidine-4-carboxamide (0.21 g, 0.5 mmol, 1 eq) in tetrahydrofuran at 0° C. was added borane dimethyl sulfide complex (0.16 mL, 1.5 mmol, 3 eq) and stirred at 70° C. for 4 h. The reaction mixture was allowed to cool to 0° C., quenched with 2N hydrochloric acid, basified with saturated sodium bicarbonate solution (pH~8) and the organic product was extracted into dichloromethane. The organic layer was dried over anhydrous sodium sulfate and solvent was evaporated under reduced pressure to get crude product. The crude product was purified by flash column chromatography (10-50% ethyl acetate/petroleum ether) to get compound 6-((benzyl(methyl)amino)methyl)-2-chloro-N-(2,4,4-trimethylpentan-2-yl)pyrimidin-4-amine (80 mg, yield: 39%) as thick liquid.

HPLC-MS [M+H]$^+$: 375.3; Rt=1.90 min (Method B).
$^1$H NMR (400 MHz, DMSO-d$_6$) δ: 9.66 (s, 1H), 8.11 (s, 1H), 7.80 (d, J=8.4 Hz, 1H), 7.37-7.11 (m, 10H), 3.64 (s, 2H), 3.37 (s, 2H), 2.22 (s, 3H).

General Procedure XV

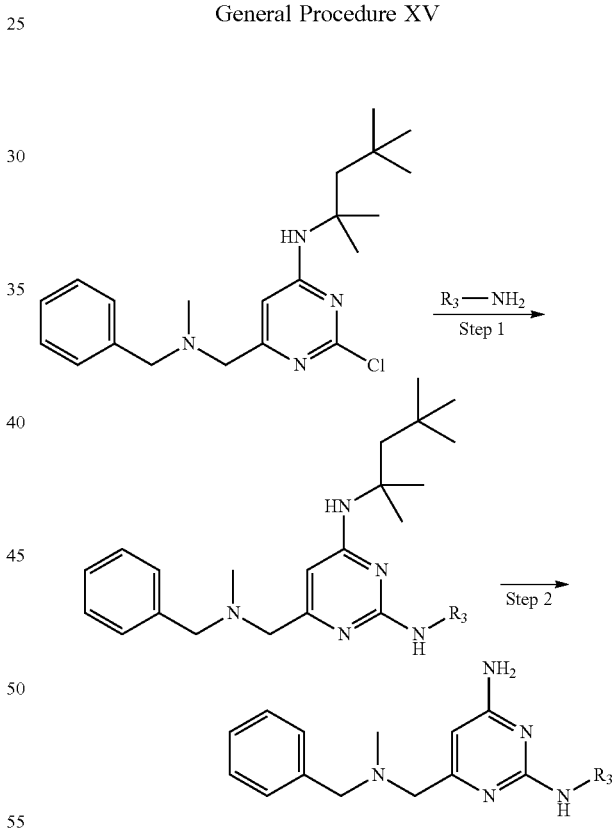

Step 1:
To a stirred solution of compound 6-((benzyl(methyl)amino)methyl)-2-chloro-N-(2,4,4-trimethylpentan-2-yl)pyrimidin-4-amine (1 eq) in 1-butanol (13 mL/mmol) at room temperature were added the appropriate amine (ex: p-toluidine) (0.04 g, 0.4 mmol, 2.0 eq), catalytic sulfuric acid (2 drops) and heated to 110° C. for 16 h. After completion of the reaction, the reaction mixture was cooled to room temperature and slowly basified with saturated sodium bicarbonate and the organic product was extracted into ethyl acetate. The organic layer was dried over anhydrous sodium sulfate and solvent was evaporated under reduced pressure to get crude product. The crude product was purified by flash column chromatography (10-60% ethyl acetate/petroleum ether or 2-8% methanol/dichloromethane) to get the desired compound (ex: 6-((benzyl(methyl)amino)methyl)-N$^2$-p-tolyl-N$^4$-(2,4,4-trimethylpentan-2-yl)pyrimidine-2,4-diamine).

Step 2:

To a stirred solution of the appropriate protected compound (ex: 6-((benzyl(methyl)amino)methyl)-N$^2$-p-tolyl-N$^4$-(2,4,4-trimethylpentan-2-yl)pyrimidine-2,4-diamine) in dichlormethane (3 mL) at room temperature was added trifluoro acetic acid (7 eq) and heated to 40° C. for 16 h. The reaction mixture was evaporated completely to get the residue which was basified with saturated sodium bicarbonate and the organic product was extracted into dichloromethane. The organic layer was dried over anhydrous sodium sulfate and solvent was evaporated under reduced pressure. The crude product was purified by flash column chromatography (20-60% ethyl acetate/petroleum ether or 2-8% methanol/dichloromethane) to get the desired free amine compound (ex: 6-((benzyl(methyl)amino)methyl)-N$^2$-p-tolylpyrimidine-2,4-diamine; Example 23; yield 13% over two steps).

Example 67

6-((Benzyl(methyl)amino)methyl)-N$^2$-(2-methoxyphenyl) pyrimidine-2,4-diamine

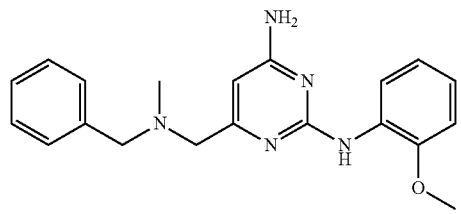 [SMILES: COc1ccccc1Nc1nc(N)cc(CN(C)Cc2ccccc2)n1]

Yield: 14% (over two steps).
HPLC-MS [M+H]$^+$: 350.44; Rt=1.95 min (Method E).
$^1$H NMR (400 MHz, DMSO-d$_6$) δ: 8.52-8.49 (m, 1H), 7.39-7.32 (m 4H), 7.27-7.26 (m, 2H), 6.99-6.96 (m, 1H), 6.89-6.87 (m, 2H), 6.64 (br s, 2H), 6.17 (s, 1H), 3.86 (s, 3H), 3.56 (s, 2H), 3.28 (s, 2H), 2.16 (s, 3H).

Example 68

6-((Benzyl(methyl)amino)methyl)-N$^2$-m-tolylpyrimidine-2,4-diamine

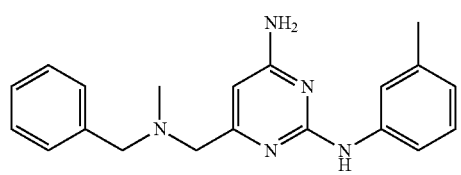 [SMILES: Cc1cccc(Nc2nc(N)cc(CN(C)Cc3ccccc3)n2)c1]

Yield: 11% (over two steps).
HPLC-MS [M+H]$^+$: 334.24; Rt=1.64 min (Method E).
$^1$H NMR (400 MHz, DMSO-d$_6$) δ: 8.77 (s, 1H), 7.66-7.64 (d, J=8 Hz, 1H), 7.56 (s, 1H), 7.38-7.32 (m, 4H), 7.28-7.26 (m, 1H), 7.08-7.04 (t, J=8 Hz, 1H), 6.66-6.64 (d, J=8 Hz, 1H), 6.50 (br s, 2H), 6.13 (s, 1H), 3.55 (s, 2H), 3.32-3.31 (m, 2H), 2.24 (s, 3H), 2.16 (s, 3H).

Example 69

6-((Benzyl(methyl)amino)methyl)-N$^2$-(3-methoxyphenyl)pyrimidine-2,4-diamine

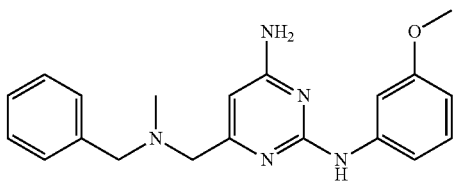 [SMILES: COc1cccc(Nc2nc(N)cc(CN(C)Cc3ccccc3)n2)c1]

Yield: 30% (over two steps).
HPLC-MS [M+H]$^+$: 350.74; Rt=1.91 min (Method E).)
$^1$H NMR (400 MHz, DMSO-d$_6$) δ: 8.86 (s, 1H), 7.62-7.61 (m, 3H), 7.38-7.26 (m, 6H), 7.09-7.05 (t, J=8.0, 1H), 6.52 (br s, 2H), 6.43-6.40 (dd, J=8.2, 1.8 Hz, 1H), 6.15 (s, 1H), 3.71 (s, 3H), 3.55 (s, 2H), 3.31 (s, 2H), 2.16 (s, 3H).

Example 70

6-((Benzyl(methyl)amino)methyl)-N$^2$-(4-methoxyphenyl) pyrimidine-2,4-diamine

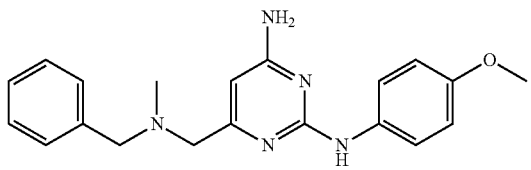 [SMILES: COc1ccc(Nc2nc(N)cc(CN(C)Cc3ccccc3)n2)cc1]

Yield: 7% (over two steps).
HPLC-MS [M+H]$^+$: 350.28; Rt=1.54 min (Method E).
$^1$H NMR (400 MHz, DMSO-d$_6$) δ: 8.66 (s, 1H), 7.68-7.66 (d, J=6.8 Hz, 2H), 7.38-7.32 (m, 4H), 7.27-7.26 (m, 1H), 6.79-6.77 (d, J=8 Hz, 2H), 6.44 (br s, 2H), 6.10 (s, 1H), 3.69 (s, 3H), 3.55 (s, 2H), 3.28 (s, 2H), 2.15 (s, 3H).

Example 71

(6-((3,4-Dihydroisoquinolin-2(1H)-yl)methyl)-N$^2$-(2-methoxyphenyl)pyrimidine-2,4-diamine)

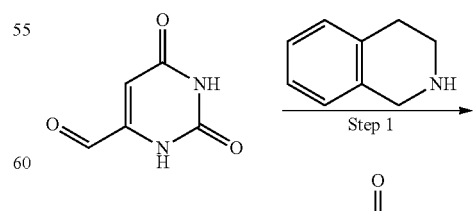

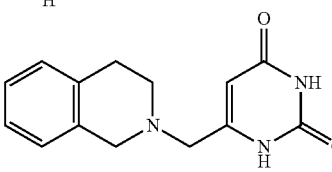

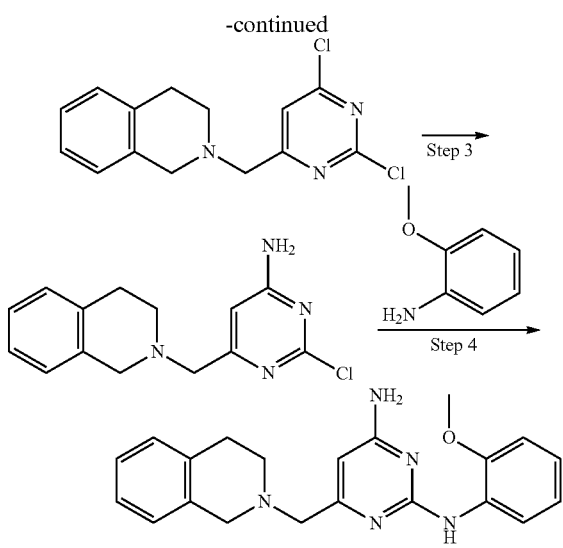

Step 1:

(6-((3,4-dihydroisoquinolin-2(1H)-yl)methyl)pyrimidine-2,4(1H,3H)-dione)

1,2,3,4-tetrahydroisoquinoline (3.4 g, 25.7 mmol, 1.2 eq) was added to a stirred solution of 2,6-dioxo-1,2,3,6-tetrahydropyrimidine-4-carbaldehyde (3 g, 21.4 mmol, 1 eq) and acetic acid (cat.) in 1,2-dichloroethane-methanol (25:25 mL) at 0° C. and stirred at room temperature for 2 h. The reaction mixture was cooled to 0° C. and NaCNBH$_3$ (2.7 g, 42.8 mmol, 2 eq) was added and further allowed to come to room temperature and stirred for 16 h. After completion of the reaction, the reaction mixture was evaporated under reduced pressure then quenched with minimum amount of saturated sodium bicarbonate solution and extracted with dichloromethane (3×100 mL). The combined organic extracts were dried over anhydrous sodium sulfate. Solvent was distilled under reduced pressure to give the crude compound. The crude product purified by flash column chromatography (10-20% methanol/dichloromethane) as eluent to afford 0.8 g pure compound (6-((3,4-dihydroisoquinolin-2(1H)-yl)methyl)pyrimidine-2,4(1H,3H)-dione as yellow solid (yield: 14.5%).

HPLC-MS [M+H]$^+$: 258.2; Rt=2.17 min (Method B).

$^1$H NMR (400 MHz, DMSO-d$_6$) δ: 10.95 (s, 1H), 10.71 (s, 1H), 7.11-7.03 (m, 4H), 5.50 (s, 1H), 3.61 (s, 2H), 3.35 (s, 2H), 2.84-2.81 (t, J=4 Hz, 2H), 2.73-2.70 (t, J=4 Hz, 4H).

Step 2:

Phosphoryl chloride (10 mL) was added to (6-((3,4-dihydroisoquinolin-2(1H)-yl)methyl)pyrimidine-2,4(1H,3H)-dione (0.8 g, 3.1 mmol, 1 eq) at room temperature under nitrogen atmosphere and then heated to 120° C. for 16 h. The reaction mixture was evaporated under reduced pressure to get the crude product. The crude was quenched with ice water and then basified (up to pH-8) using 10% sodium bicarbonate solution. The organic product was extracted with dichloromethane (2×20 mL). The organic layer was washed with water, brine, dried over anhydrous sodium sulfate and solvent was concentrated under reduced pressure to afford 0.5 g of crude product 2-((2,6-dichloropyrimidin-4-yl)methyl)-1,2,3,4-tetrahydroisoquinoline.

HPLC-MS [M+H]+: 294.00; Rt=1.95 min (Method C).

Step 3:

Ammonia gas was purged to compound 2-((2,6-dichloropyrimidin-4-yl)methyl)-1,2,3,4-tetrahydroisoquinoline (0.4 g, 1.36 mmol, 1 eq) at −78° C. in sealed tube and stirred at room temperature for 4 h. The reaction mixture was then cooled and solvent was concentrated under reduced pressure to afford 0.2 g of crude product 2-chloro-6-((3,4-dihydroisoquinolin-2(1H)-yl)methyl)pyrimidin-4-amine.

ES-MS [M+H]$^+$: 275.1; Rt=2.31 min (Method A).

Step 4:

To a stirred solution of compound 2-chloro-6-((3,4-dihydroisoquinolin-2(1H)-yl)methyl)pyrimidin-4-amine (0.4 g, 0.68 mmol, 1 eq) in isopropyl alcohol (10 mL) was added 2-methoxyaniline (0.146 g, 1.36 mmol, 2.0 eq) at room temperature and heated to 100° C. for 16 h. After completion of the reaction, the reaction mixture was allowed to cool to room temperature. Solvent was concentrated under reduced pressure to get crude. The crude was diluted with water and the aqueous layer was extracted twice with ethyl acetate, dried over anhydrous sodium sulfate and solvent was evaporated under reduced pressure to get crude compound. The crude was purified by reverse phase preparative HPLC to get 0.04 g of the pure compound (6-((3,4-dihydroisoquinolin-2(1H)-yl)methyl)-N$^2$-(2-methoxyphenyl) pyrimidine-2,4-diamine) as brown solid (yield: 15% over 2 steps).

HPLC-MS [M+H]$^+$: 362.39; Rt=2.83 min (Method B).

$^1$H NMR (400 MHz, DMSO-d$_6$) δ: 8.52-8.50 (m, 1H), 7.30 (s, 1H), 7.11-7.08 (m, 3H), 7.04-7.03 (m, 1H), 6.99-6.97 (m, 1H), 6.89-6.87 (m, 2H), 6.61 (br, s, 2H), 6.13 (s, 1H), 3.86 (s, 3H), 3.62 (s, 2H), 3.47 (s, 2H), 2.86-2.84 (s, J=4 Hz, 2H), 2.76-2.75 (t, J=4 Hz, 2H).

Intermediate 31

2-((Benzyl(methyl)amino)methyl)-6-chloropyridin-4-amine

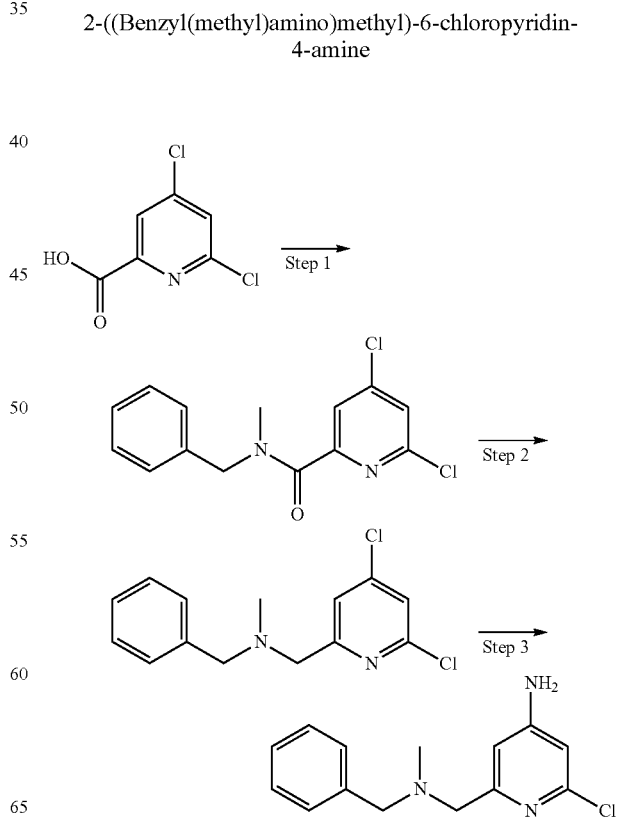

Step 1:

50% Propylphosphonic anhydride solution in ethyl acetate (20 mL, 31.5 mmol) was added to a suspension of 4,6-dichloropicolinic acid (3 g, 15.7 mmol; Intermediate 28), N-methyl-1-phenylmethanamine (2.8 g, 23.6 mmol) and diisopropylethylamine (13.5 mL, 78.9 mmol) in dichloromethane (50 mL) at 0° C. The reaction mixture was warmed to room temperature and stirred for 16 h. The reaction mixture was quenched with saturated sodium bicarbonate solution, the organic product was extracted with dichloromethane (3×40 mL). The combined organic extracts were washed with water, brine, dried over anhydrous sodium sulfate and solvent was evaporated under reduced pressure to get crude product. The crude product was purified by flash column chromatography (30% ethyl acetate/petroleum ether) to afford 3.5 g of N-benzyl-4,6-dichloro-N-methylpicolinamide as pale yellow oil (yield: 75%; Intermediate 29).

HPLC-MS [M+H]$^1$: 295.1; Rt=1.99 min (Method B).

$^1$H NMR (400 MHz, DMSO-$d_6$) δ: 7.93-7.90 (m, 1H), 7.85-7.80 (m, 1H), 7.40-7.27 (m, 5H), 4.67 (s, 1H), 4.49 (s, 1H), 2.84 (d, J=14 Hz, 3H).

Step 2:

Borane dimethyl sulphide complex solution (33.2 mL, 66.4 mmol; 2.0 M in tetrahydrofuran) was added to the solution of N-benzyl-4,6-dichloro-N-methylpicolinamide (3.1 g, 11.0 mmol) in tetrahydrofuran (70 mL) at 0° C. The reaction mixture was warmed to room temperature and stirred for 16 h. The reaction mixture was cooled to 0° C. and quenched with saturated sodium bicarbonate solution. The organic product was extracted with dichloromethane (3×60 mL). The combined organic extracts were washed with water, brine, dried over anhydrous sodium sulfate and solvent was evaporated under reduced pressure to get crude product. The crude product was purified by flash column chromatography (10% ethyl acetate/petroleum ether) to get 2.1 g of N-benzyl-4,6-dichloro-N-methylpicolinamide as yellow oil (yield: 71%; Intermediate 30).

$^1$H NMR (400 MHz, DMSO-$d_6$) δ: 7.85 (d, J=1.6 Hz, 1H), 7.73 (d, J=2 Hz, 1H), 7.66-7.58 (m, 2H), 7.42-7.33 (m, 3H), 4.03-3.99 (m, 2H), 3.78 (d, J=12.4 Hz, 1H), 3.62-3.57 (m, 1H), 2.47 (s, 3H).

Step 3:

Sodium azide (1.38 g, 21.3 mmol) was added to a solution of N-benzyl-1-(4,6-dichloropyridin-2-yl)-N-methylmethanamine (2 g, 7.1 mmol) in anhydrous dimethylformamide (50 mL) at 0° C. The reaction mixture was warmed to room temperature and heated at 90° C. for 24 h. After completion of reaction (monitored by TLC), reaction mixture was quenched with water and organic product was extracted using ethyl acetate (3×50 mL). The combined organic extracts were washed with water, brine, dried over anhydrous sodium sulfate and solvent was evaporated under reduced pressure to get crude product. The crude product was dissolved in methanol (50 mL) and sodium borohydride (0.5 g, 14.2 mmol) was added at 0° C. The reaction mixture was warmed to room temperature and stirred for 2 h. After completion of reaction, solvent was evaporated under reduced pressure to obtain residue which was diluted with water and extracted using ethyl acetate (3×60 mL). The combined organic extracts were washed with water, brine, dried over anhydrous sodium sulfate and solvent was evaporated under reduced pressure to get crude product. The crude product was purified by flash column chromatography (70% ethyl acetate/petroleum ether) to get 1 g of 2-((benzyl (methyl)amino)methyl)-6-chloropyridin-4-amine as yellow oil (yield: 53%).

HPLC-MS 262.1: Rt=1.44 min (Method B).

$^1$H NMR (400 MHz, CDCl$_3$) δ: 7.37-7.30 (m, 5H), 7.24-7.22 (m, 1H), 6.74 (d, J=2.0 Hz 1H), 6.42 (d, J=2.0 Hz, 1H), 4.22 (br s, 2H), 3.58 (s, 2H), 3.54 (s, H), 2.23 (s, 3H).

Biological Assays

Compounds of the Disclosure are capable of binding allosterically to mutated β-glucocerebrosidase enzyme thereby stabilizing the enzyme against denaturation and enhancing its catalytic activity.

Enhancement of β-Glucocerebrosidase Activity Measured in Gaucher Disease Fibroblasts Materials Human fibroblasts from a patient with Gaucher disease homozygous for p.L444P mutation (GM08760A) were purchased from Coriell Institute for Medical Research (Camden, N.J., USA).

Cell Culture and Compound Treatment

Fibroblasts were seeded at $5×10^3$ cells per well in 96-well cell culture plates (Corning, N.Y., USA) in Dulbecco's Modified Eagle's Media (DMEM) supplemented with 10% of fetal bovine serum (FBS), 1% penicillin/streptomycin (P/S) (Thermo Fisher Scientific, Waltham, Mass., USA) and grown at 37° C., 5% $CO_2$ overnight for cell attachment. Subsequently, cells were incubated in the absence or presence of the compounds at the desired concentration for 4 days. After incubation, cells were washed twice with phosphate-buffered saline (PBS) and enzyme activity assay was performed.

Enzyme Activity Assay

β-glucocerebrosidase activity in intact cultured cells was measured by using 4-methylumbelliferyl-β-D-glucopyranoside substrate (Apollo Scientific, UK). Briefly, cells were incubated with 4-MU-β-D-glucopyranoside in 0.1 M acetate buffer pH=4 at 37° C. for 1 hour. The reaction was stopped by adding 200 mM glycine-NaOH pH=10.7. The liberated 4-MU was measured on a GloMax Discover plate reader (Promega, Madison, Wis., USA) with and excitation at 340 nm and emission at 460 nm. Enzyme activities were expressed in treated cells as X-fold increase in comparison with non-treated cells (X=1 represents no enhancement).

The capacity of the compounds of the disclosure to produce an increase in enzyme activity in GBA fibroblasts bearing L444P at concentrations between 6 and 50 μM is denoted as follows:

Increase in comparison with non-treated of >2.0 fold is shown as A

Increase in comparison with non-treated of >1.7-2.0 fold is shown as B

Increase in comparison with non-treated of 1.2-1.7 fold is shown as C

D means that no increase compared with non-treated cells was detected in this method ND means "not determined"

TABLE 1

| Example | Activity L444P | Activity Wild Type (WT) |
|---|---|---|
| 1 | C | B |
| 2 | C | ND |
| 3 | C | B |
| 4 | C | A |
| 5 | C | C |
| 6 | B | B |
| 7 | B | B |
| 8 | B | B |
| 9 | C | B |
| 10 | C | B |
| 11 | C | ND |

TABLE 1-continued

| Example | Activity L444P | Activity Wild Type (WT) |
|---|---|---|
| 12 | C | B |
| 13 | B | B |
| 14 | C | B |
| 15 | B | ND |
| 16 | B | A |
| 17 | B | ND |
| 18 | B | B |
| 19 | B | B |
| 20 | B | B |
| 21 | B | ND |
| 22 | B | D |
| 23 | B | ND |
| 24 | D | ND |
| 25 | ND | ND |
| 26 | C | B |
| 27 | C | ND |
| 28 | B | B |
| 29 | B | ND |
| 30 | A | B |
| 31 | D | A |
| 32 | C | ND |
| 33 | B | B |
| 34 | B | ND |
| 35 | B | ND |
| 36 | D | ND |
| 37 | C | B |
| 38 | B | ND |
| 39 | C | ND |
| 40 | B | ND |
| 41 | B | C |
| 42 | C | B |
| 43 | C | C |
| 44 | B | C |
| 45 | C | C |

TABLE 1-continued

| Example | Activity L444P | Activity Wild Type (WT) |
|---|---|---|
| 46 | B | B |
| 47 | C | C |
| 48 | C | B |
| 49 | C | ND |
| 50 | C | C |
| 51 | C | ND |
| 52 | C | C |
| 53 | C | ND |
| 54 | ND | ND |
| 55 | B | ND |
| 56 | ND | ND |
| 57 | C | ND |
| 58 | ND | ND |
| 59 | D | ND |
| 60 | C | ND |
| 61 | C | ND |
| 62 | D | ND |
| 63 | C | ND |
| 64 | B | B |
| 65 | B | A |
| 66 | B | ND |
| 67 | A | B |
| 68 | B | A |
| 69 | A | C |
| 70 | A | B |
| 71 | C | ND |

Enzyme Activity Assay for Commercially Available Compounds

The following compounds listed in Table 2 were purchased (from Enamine, Princeton, Asinex, Vistas-M, and OSSK_541352) and tested in the assay as described above.

TABLE 2

| Compound Structure | Name | Activity L444P | Activity WT |
|---|---|---|---|
| [structure] | 6-((methyl(naphthalen-2-yl)amino)methyl)-N2-(p-tolyl)-1,3,5-triazine-2,4-diamine | A | C |
| [structure] | 6-((4-(benzo[d][1,3]dioxol-5-ylmethyl)piperazin-1-yl)methyl)-N2-(p-tolyl)-1,3,5-triazine-2,4-diamine | C | B |
| [structure] | 6-(((4-ethylbenzyl)(methyl)amino)methyl)-N2-(p-tolyl)-1,3,5-triazine-2,4-diamine | C | B |
| [structure] | 6-(((furan-2-ylmethyl)(methyl)amino)methyl)-N2-(p-tolyl)-1,3,5-triazine-2,4-diamine | C | ND |

TABLE 2-continued

| Compound Structure | Name | Activity L444P | Activity WT |
|---|---|---|---|
| 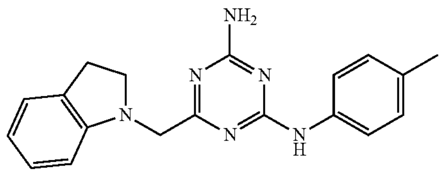 [SMILES: Cc1ccc(Nc2nc(N)nc(CN3CCc4ccccc43)n2)cc1] | 6-(indolin-1-ylmethyl)-N2-(p-tolyl)-1,3,5-triazine-2,4-diamine | D | D |
| 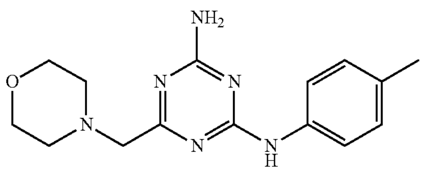 [SMILES: Cc1ccc(Nc2nc(N)nc(CN3CCOCC3)n2)cc1] | 6-(morpholinomethyl)-N2-(p-tolyl)-1,3,5-triazine-2,4-diamine | D | ND |
| 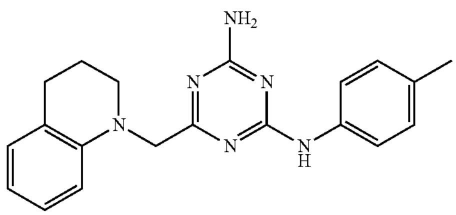 [SMILES: Cc1ccc(Nc2nc(N)nc(CN3CCCc4ccccc43)n2)cc1] | 6-((3,4-dihydroquinolin-1(2H)-yl)methyl)-N2-(p-tolyl)-1,3,5-triazine-2,4-diamine | C | C |
| 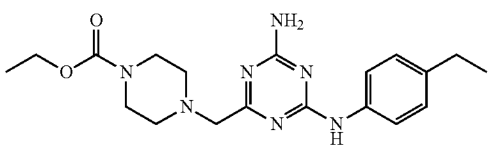 [SMILES: CCOC(=O)N1CCN(Cc2nc(N)nc(Nc3ccc(CC)cc3)n2)CC1] | ethyl 4-((4-amino-6-((4-ethylphenyl)amino)-1,3,5-triazin-2-yl)methyl)piperazine-1-carboxylate | D | ND |
| 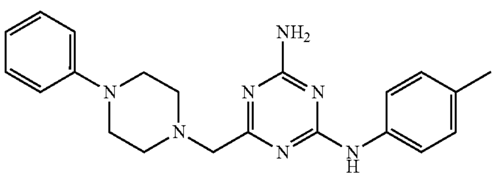 [SMILES: Cc1ccc(Nc2nc(N)nc(CN3CCN(c4ccccc4)CC3)n2)cc1] | 6-((4-phenylpiperazin-1-yl)methyl)-N2-(p-tolyl)-1,3,5-triazine-2,4-diamine | C | ND |
| 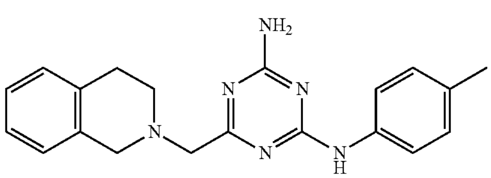 [SMILES: Cc1ccc(Nc2nc(N)nc(CN3CCc4ccccc4C3)n2)cc1] | 6-((3,4-dihydroisoquinolin-2(1H)-yl)methyl)-N2-(p-tolyl)-1,3,5-triazine-2,4-diamine | B | B |
| 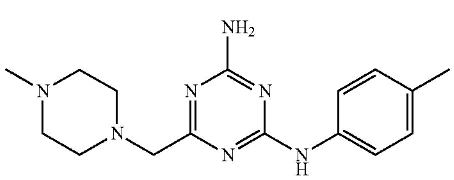 | 6-((4-methylpiperazin-1-yl)methyl)-N2-(p-tolyl)-1,3,5-triazine-2,4-diamine | D | ND |
| 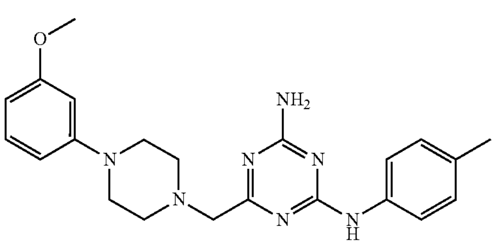 [SMILES: COc1cccc(N2CCN(Cc3nc(N)nc(Nc4ccc(C)cc4)n3)CC2)c1] | 6-((4-(3-methoxyphenyl)piperazin-1-yl)methyl)-N2-(p-tolyl)-1,3,5-triazine-2,4-diamine | C | ND |

TABLE 2-continued

| Compound Structure | Name | Activity L444P | Activity WT |
|---|---|---|---|
| 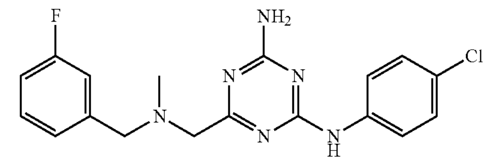 [SMILES: CN(Cc1cccc(F)c1)Cc1nc(N)nc(Nc2ccc(Cl)cc2)n1] | N2-(4-chlorophenyl)-6-(((3-fluorobenzyl)(methyl)amino)methyl)-1,3,5-triazine-2,4-diamine | C | ND |
| 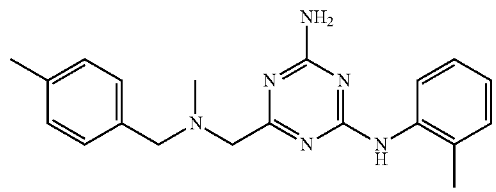 [SMILES: Cc1ccc(CN(C)Cc2nc(N)nc(Nc3ccccc3C)n2)cc1] | 6-((methyl(4-methylbenzyl)amino)methyl)-N2-(o-tolyl)-1,3,5-triazine-2,4-diamine | C | ND |
| 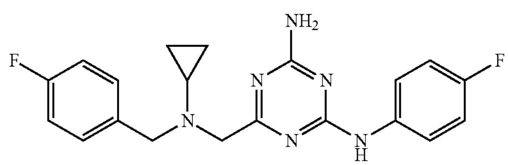 [SMILES: Nc1nc(CN(Cc2ccc(F)cc2)C2CC2)nc(Nc2ccc(F)cc2)n1] | 6-((cyclopropyl(4-fluorobenzyl)amino)methyl)-N2-(4-fluorophenyl)-1,3,5-triazine-2,4-diamine | C | ND |
| 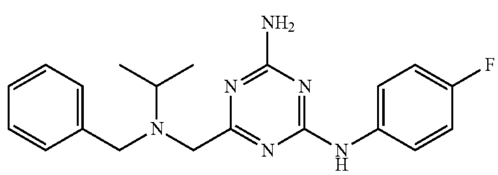 [SMILES: CC(C)N(Cc1ccccc1)Cc1nc(N)nc(Nc2ccc(F)cc2)n1] | 6-((benzyl(isopropyl)amino)methyl)-N2-(4-fluorophenyl)-1,3,5-triazine-2,4-diamine | D | ND |
| 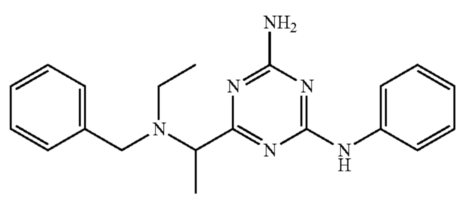 [SMILES: CCN(Cc1ccccc1)C(C)c1nc(N)nc(Nc2ccccc2)n1] | 6-(1-(benzyl(ethyl)amino)ethyl)-N2-phenyl-1,3,5-triazine-2,4-diamine | B | B |
| 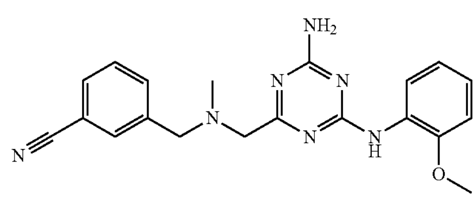 [SMILES: COc1ccccc1Nc1nc(N)nc(CN(C)Cc2cccc(C#N)c2)n1] | 3-((((4-amino-6-((2-methoxyphenyl)amino)-1,3,5-triazin-2-yl)methyl)(methyl)amino)methyl)benzonitrile | D | ND |
| 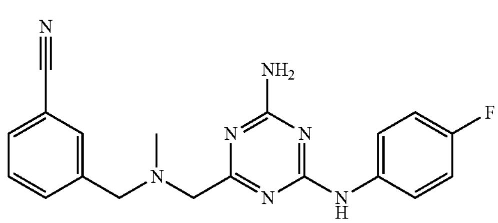 [SMILES: CN(Cc1cccc(C#N)c1)Cc1nc(N)nc(Nc2ccc(F)cc2)n1] | 3-((((4-amino-6-((4-fluorophenyl)amino)-1,3,5-triazin-2-yl)methyl)(methyl)amino)methyl)benzonitrile | D | ND |
| 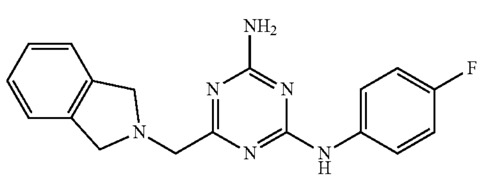 [SMILES: Nc1nc(CN2Cc3ccccc3C2)nc(Nc2ccc(F)cc2)n1] | N2-(4-fluorophenyl)-6-(isoindolin-2-ylmethyl)-1,3,5-triazine-2,4-diamine | B | C |

TABLE 2-continued

| Compound Structure | Name | Activity L444P | Activity WT |
|---|---|---|---|
| 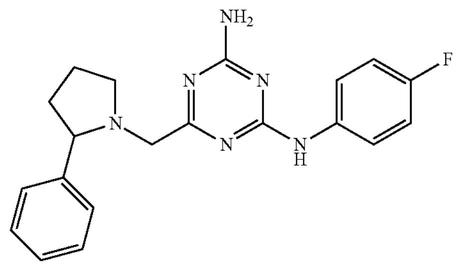 [SMILES: Nc1nc(CN2CCCC2c2ccccc2)nc(Nc2ccc(F)cc2)n1] | N2-(4-fluorophenyl)-6-((2-phenylpyrrolidin-1-yl)methyl)-1,3,5-triazine-2,4-diamine | B | ND |
| 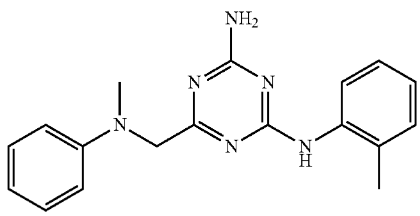 [SMILES: Cc1ccccc1Nc1nc(N)nc(CN(C)c2ccccc2)n1] | 6-((methyl(phenyl)amino)methyl)-N2-(o-tolyl)-1,3,5-triazine-2,4-diamine | C | ND |
| 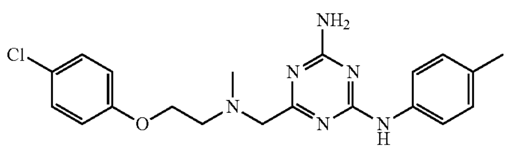 [SMILES: Cc1ccc(Nc2nc(N)nc(CN(C)CCOc3ccc(Cl)cc3)n2)cc1] | 6-(((2-(4-chlorophenoxy)ethyl)(methyl)amino)methyl)-N2-(p-tolyl)-1,3,5-triazine-2,4-diamine | C | ND |
| 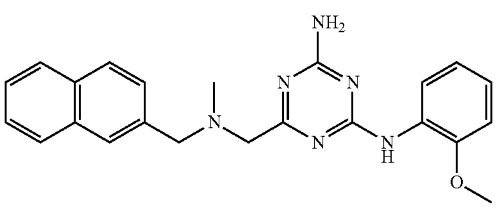 [SMILES: COc1ccccc1Nc1nc(N)nc(CN(C)Cc2ccc3ccccc3c2)n1] | N2-(2-methoxyphenyl)-6-((methyl(naphthalen-2-ylmethyl)amino)methyl)-1,3,5-triazine-2,4-diamine | B | ND |
| 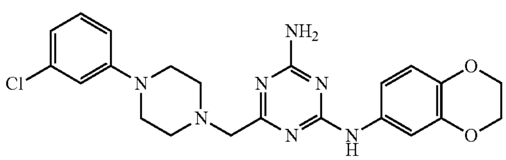 [SMILES: Nc1nc(CN2CCN(c3cccc(Cl)c3)CC2)nc(Nc2ccc3c(c2)OCCO3)n1] | 6-((4-(3-chlorophenyl)piperazin-1-yl)methyl)-N2-(2,3-dihydrobenzo[b][1,4]dioxin-6-yl)-1,3,5-triazine-2,4-diamine | B | C |
| 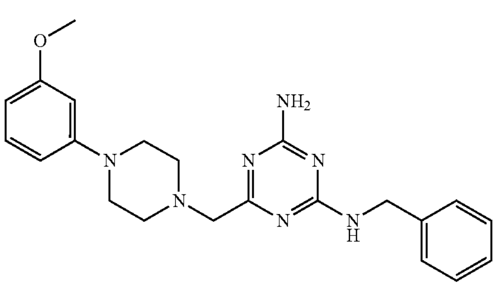 [SMILES: COc1cccc(N2CCN(Cc3nc(N)nc(NCc4ccccc4)n3)CC2)c1] | N2-benzyl-6-((4-(3-methoxyphenyl)piperazin-1-yl)methyl)-1,3,5-triazine-2,4-diamine | C | C |
| 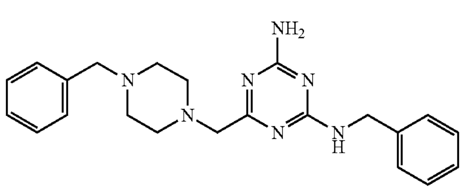 [SMILES: Nc1nc(CN2CCN(Cc3ccccc3)CC2)nc(NCc2ccccc2)n1] | N2-benzyl-6-((4-benzylpiperazin-1-yl)methyl)-1,3,5-triazine-2,4-diamine | D | ND |

TABLE 2-continued

| Compound Structure | Name | Activity L444P | Activity WT |
|---|---|---|---|
| 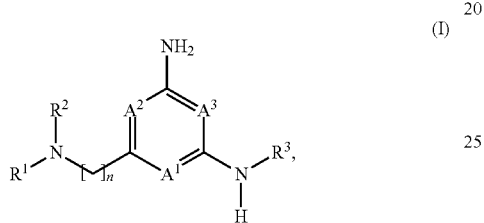 | N2-(4-chlorobenzyl)-6-((4-(4-fluorophenyl)piperazin-1-yl)methyl)-1,3,5-triazine-2,4-diamine | D | ND |

The disclosure also relates to the following particular embodiments designated as [1] for the first embodiment, [2] for the second embodiment, and so on:

[1] A compound of formula (I):

$$\text{(I)}$$

or a pharmaceutically acceptable salt or solvate thereof, wherein $A^1$, $A^2$, and $A^3$ are each independently selected from the group consisting of N, CH and C($R^4$), provided that at least one of $A^1$, $A^2$, or $A^3$ is N;

with the proviso that no more than two of $A^1$, $A^2$, or $A^3$ is N;

each $R^4$ is independently selected from the group consisting of halogen, $C_{1-4}$ alkyl, $C_{1-4}$ alkoxy, and CN;

n is 1 or 2;

$R^1$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{2-9}$ heterocyclyl, alkyl-(5- to 10-membered)-$C_{2-9}$ heterocyclyl, and C(=O)Ra, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted $C_{6-10}$ aryl, optionally substituted (5- to 10-membered)-$C_{1-9}$ heteroaryl, and (5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring; and $R^2$ is hydrogen or $C_{1-4}$ alkyl; or $R^1$ and $R^2$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;

Ra is selected from the group consisting of alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{2-9}$ heterocyclyl, and —$C_{1-4}$ alkyl-(5- to 10-membered)-$C_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted $C_{6-10}$ aryl, optionally substituted (5- to 10-membered)-$C_{1-9}$ heteroaryl, and (5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring;

each Rb is independently hydrogen, —$C_{1-4}$ alkyl, —$C_{3-10}$ cycloalkyl, or -(5- to 10-membered)-$C_{2-9}$ heterocyclyl, wherein said alkyl, cycloalkyl or heterocyclyl group is optionally substituted by 1, 2 or 3 fluorine atoms;

$R^3$ is —$C_{6-10}$ aryl or -(5- to 10-membered)-$C_{1-9}$ heteroaryl, wherein said aryl or heteroaryl group is optionally substituted with 1, 2 or 3 substituents each independently selected from the group consisting of halogen, hydroxy, CN, —ORb, —SRb, —N(Rb)$_2$, —$C_{1-4}$ alkyl optionally substituted with 1, 2, or 3 substituents each independently selected from the group consisting of halogen, CN, —ORb, and —N(Rb)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

[2] The compound of [1], or a pharmaceutically acceptable salt or solvate thereof, wherein $A^1$ is N and $A^2$ and $A^3$ are each independently selected from the group consisting of CH and C($R^4$).

[3] The compound of [1], or a pharmaceutically acceptable salt or solvate thereof, wherein $A^2$ is N and $A^1$ and $A^3$ are each independently selected from the group consisting of CH and C($R^4$).

[4] The compound of [1], or a pharmaceutically acceptable salt or solvate thereof, wherein $A^3$ is N and $A^1$ and $A^2$ are each independently selected from the group consisting of CH and C($R^4$).

[5] The compound of [1], or a pharmaceutically acceptable salt or solvate thereof, wherein $A^1$ and $A^2$ are both N and $A^3$ is CH or C($R^4$).

[6] The compound of [1], or a pharmaceutically acceptable salt or solvate thereof, wherein $A^1$ and $A^3$ are both N and $A^2$ is CH or C($R^4$).

[7] The compound of [1], or a pharmaceutically acceptable salt or solvate thereof, wherein $A^2$ and $A^3$ are both N and $A^1$ is CH or $C(R^4)$.

[8] The compound of any one of [1] to [7], or a pharmaceutically acceptable salt or solvate thereof, wherein n is 1.

[9] The compound of any one of [1] to [7], or a pharmaceutically acceptable salt or solvate thereof, wherein n is 2.

[10] The compound of any one of [1] to [9], or a pharmaceutically acceptable salt or solvate thereof, wherein $R^3$ is unsubstituted $C_{6-10}$ aryl or $C_{6-10}$ aryl substituted with 1 or 2 substituents each independently selected from the group consisting of halogen, hydroxy, CN, —O($C_{1-4}$)alkyl, —S($C_{1-4}$)alkyl, —NH($C_{1-4}$ alkyl), and $C_{1-4}$ alkyl optionally substituted with 1, 2, or 3 substituents each independently selected from the group consisting of halogen, CN, —O($C_{1-4}$)alkyl, alkyl)$_2$, and —NH($C_{1-4}$ alkyl).

[11] The compound of any one of [1] to [10], or a pharmaceutically acceptable salt or solvate thereof, wherein $R^2$ is H.

[12] The compound of any one of [1] to [10], or a pharmaceutically acceptable salt or solvate thereof, wherein $R^2$ is $C_{1-4}$ alkyl.

[13] The compound of any one of [1] to [10] or [12], or a pharmaceutically acceptable salt or solvate thereof, wherein $R^2$ is methyl.

[14] The compound of any one of [1] to [13], or a pharmaceutically acceptable salt or solvate thereof, wherein $R^1$ is —$C_{6-10}$ aryl or —$C_{1-4}$ alkyl-$C_{6-10}$ aryl, wherein said aryl or alkylaryl is optionally substituted with 1, 2 or 3 groups each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl, wherein Rb is as defined in claim 1.

[15] The compound of any one of [1] to [14], or a pharmaceutically acceptable salt or solvate thereof, wherein Rb is hydrogen or $C_{1-4}$ alkyl.

[16] The compound of any one of [1] to [10], or a pharmaceutically acceptable salt or solvate thereof, wherein $R^1$ and $R^2$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring.

[17] The compound of [16], or a pharmaceutically acceptable salt or solvate thereof, wherein $R^1$ and $R^2$ together with the nitrogen atom to which they are attached form a 5- or 6-membered ring optionally fused to a phenyl ring.

[18] The compound of [1], which is selected from the group consisting of

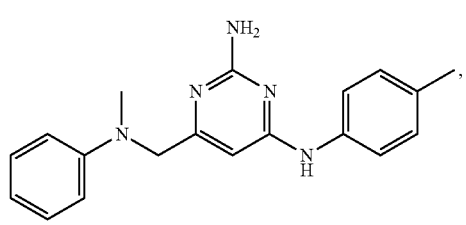

-continued

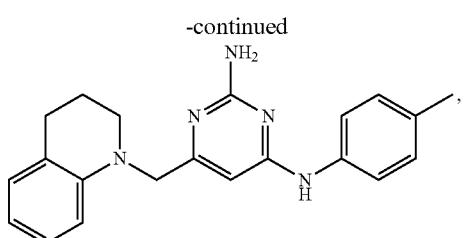

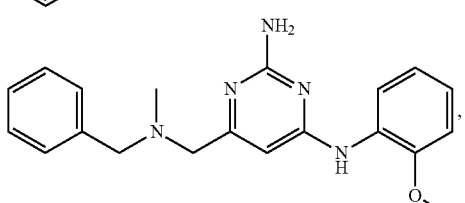

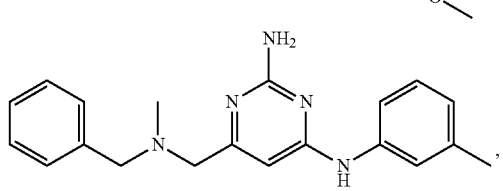

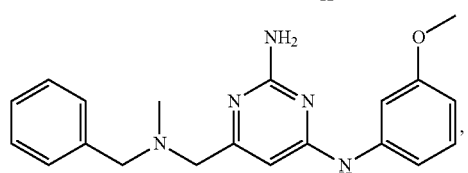

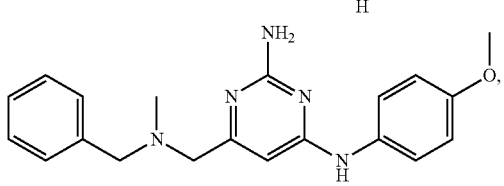

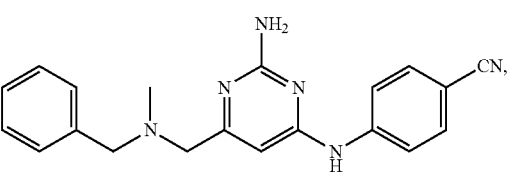

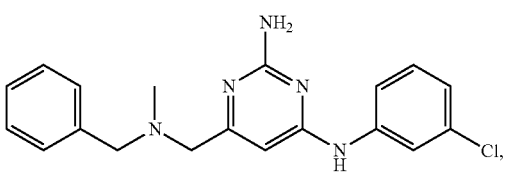

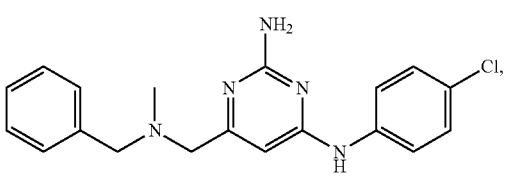

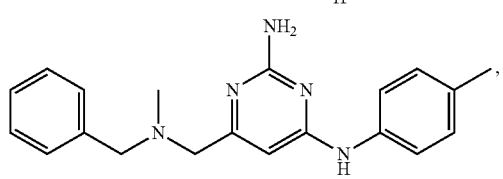

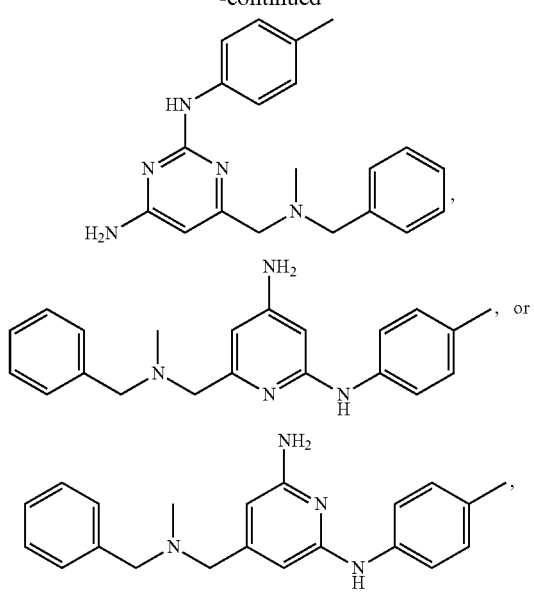

or a pharmaceutically acceptable salt or solvate thereof.

[19] A compound selected from the group consisting of

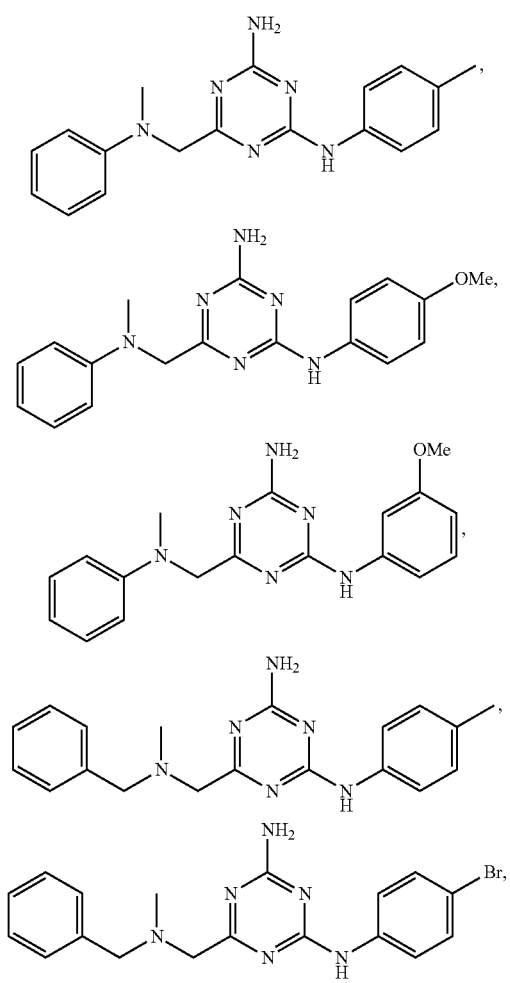

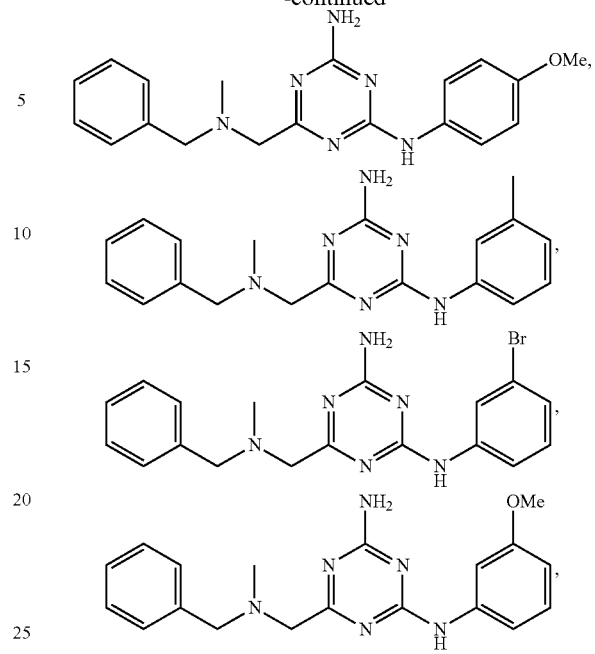

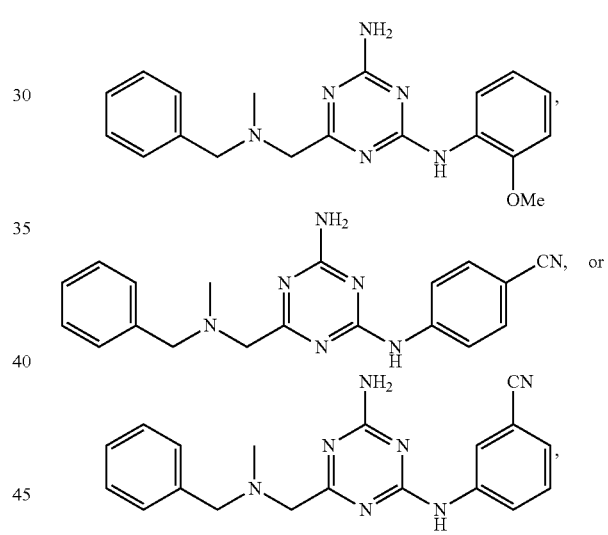

or a pharmaceutically acceptable salt thereof.

[20] A pharmaceutical composition, comprising an effective amount of a compound of any one of [1] to [19], or a pharmaceutically acceptable salt or solvate thereof, and at least one pharmaceutically acceptable excipient.

[21] A method of treating or preventing Gaucher's disease, comprising administering to a patient in need thereof an effective amount of a compound of formula (I):

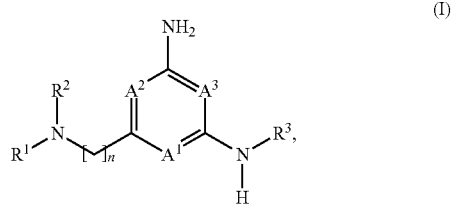

or a pharmaceutically acceptable salt or solvate thereof, wherein $A^1$, $A^2$, and $A^3$ are each independently selected from the group consisting of N, CH and $C(R^4)$, provided that at least one of $A^1$, $A^2$, or $A^3$ is N;

each $R^4$ is independent selected from the group consisting of halogen, $C_{1-4}$ alkyl, $C_{1-4}$ alkoxy, and CN;

n is 1 or 2;

$R^1$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-C)—, heteroaryl, —$C_{1-4}$ alkyl-(5- to 10-membered)-$C_{1-9}$ heteroaryl, (5- to 10-membered)-$C_{2-9}$ heterocyclyl, —$C_{1-4}$ alkyl-(5- to 10-membered)-$C_{2-9}$ heterocyclyl, and C(=O)Ra, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring; and $R^2$ is hydrogen or $C_{1-4}$ alkyl; or $R^1$ and $R^2$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;

Ra is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{2-9}$ heterocyclyl, and —$C_{1-4}$ alkyl-(5- to 10-membered)-$C_{1-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted $C_{6-10}$ aryl, optionally substituted (5- to 10-membered)-$C_{1-9}$ heteroaryl, and (5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring;

each Rb is independently hydrogen, —$C_{1-4}$ alkyl, —$C_{3-10}$ cycloalkyl, or (5- to 10-membered)-$C_{2-9}$ heterocyclyl, wherein said alkyl, cycloalkyl or heterocyclyl group is optionally substituted by 1, 2 or 3 fluorine atoms;

$R^3$ is —$C_{6-10}$ aryl or -(5- to 10-membered)-$C_{1-9}$ heteroaryl, wherein said aryl or heteroaryl group is optionally substituted with 1, 2 or 3 substituents each independently selected from the group consisting of halogen, hydroxy, CN, —ORb, —SRb, —N(Rb)$_2$, —$C_{1-4}$alkyl optionally substituted with 1, 2, or 3 substituents each independently selected from the group consisting of halogen, CN, —ORb, and —N(Rb)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

[22] The method of [21], wherein $A^1$, $A^2$ and $A^3$ are N.

[23] The method of [21], wherein the compound administered is as claimed in any one of [1] to [20].

[24] The method of [21], wherein the compound administered is selected from the group consisting of

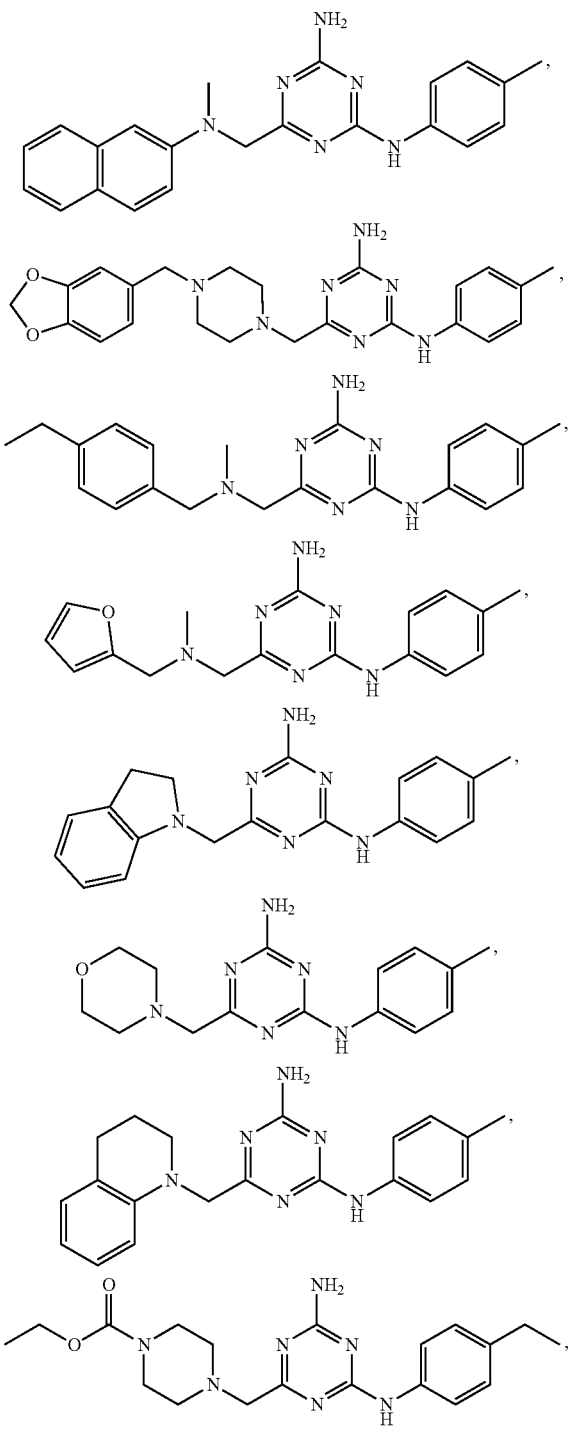

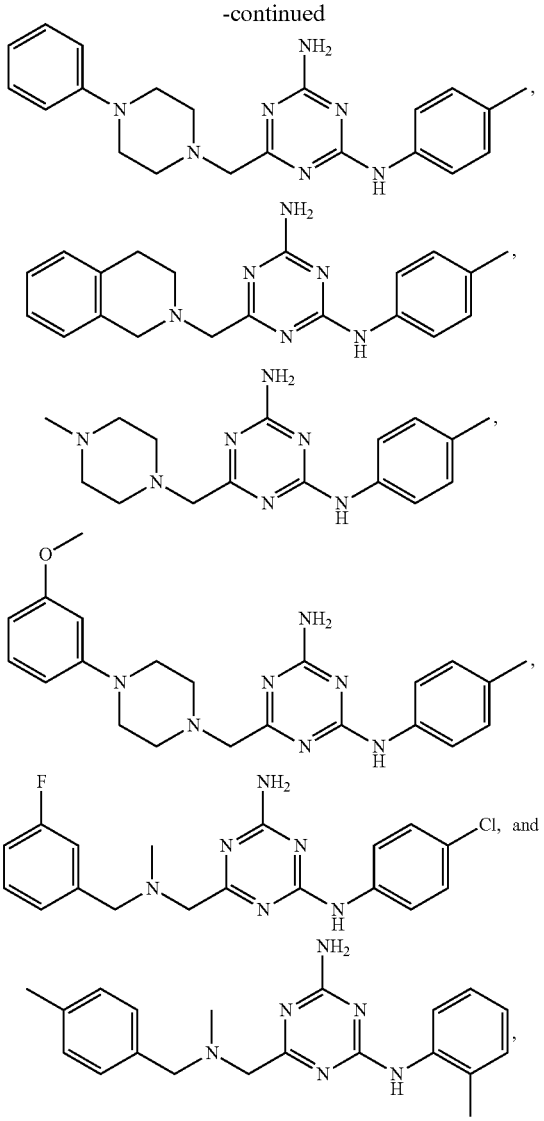

or a pharmaceutically acceptable salt or solvate thereof.

[25] A compound as defined in any one of [1] to [20], or a pharmaceutically acceptable salt or solvate thereof, for use as a medicament.

[26] A compound of formula (I), or a pharmaceutically acceptable salt or solvate thereof, for use in the treatment or prevention of Gaucher's disease, the compound of formula (I) having the structure:

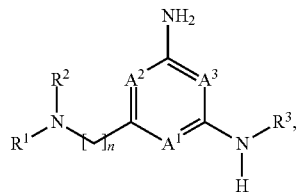

wherein $A^1$, $A^2$, and $A^3$ are each independently selected from the group consisting of N, CH and $C(R^4)$, provided that at least one of $A^1$, $A^2$, or $A^3$ is N;

each $R^4$ is independently selected from the group consisting of halogen, $C_{1-4}$ alkyl, $C_1$-4 alkoxy, and CN;

n is 1 or 2;

$R^1$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{3-9}$ heterocyclyl, —$C_{1-4}$ alkyl-(5- to 10-membered)-$C_{2-9}$ heterocyclyl, and C(=O)Ra, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted $C_{6-10}$ aryl, optionally substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring; and $R^2$ is hydrogen or $C_{1-4}$ alkyl; or $R^1$ and $R^2$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;

Ra is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C)_{2-9}$ heterocyclyl, and —$C_{1-4}$ alkyl-(5- to 10-membered)-$C_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted $C_{6-10}$ aryl, optionally substituted (5- to 10-membered)-$C_{1-9}$ heteroaryl, and (5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring;

each Rb is independently, hydrogen, —$C_{1-4}$ alkyl, —$C_{3-10}$ cycloalkyl, or (5- to 10-membered)-$C_{2-9}$ heterocyclyl, wherein said alkyl, cycloalkyl or heterocyclyl group is optionally substituted by 1, 2 or 3 fluorine atoms;

$R^3$ is —$C_{6-10}$ aryl or -(5- to 10-membered)-$C_{1-9}$ heteroaryl, wherein said aryl or heteroaryl group is optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 groups each independently selected from the group consisting of halogen, CN, —ORb, and —N(Rb)$_2$, optionally substituted —$C_{6-10}$ aryl, optionally substituted -(5- to 10-membered)-$C_{4-9}$ heteroaryl and -(5- to 10-membered)-$C_{2-9}$ heterocyclyl.

[27] The compound for use of [26], wherein the compound is as claimed in any one of claims 1-20.

[28] The compound for use of [26], wherein the compound is selected from the group consisting of

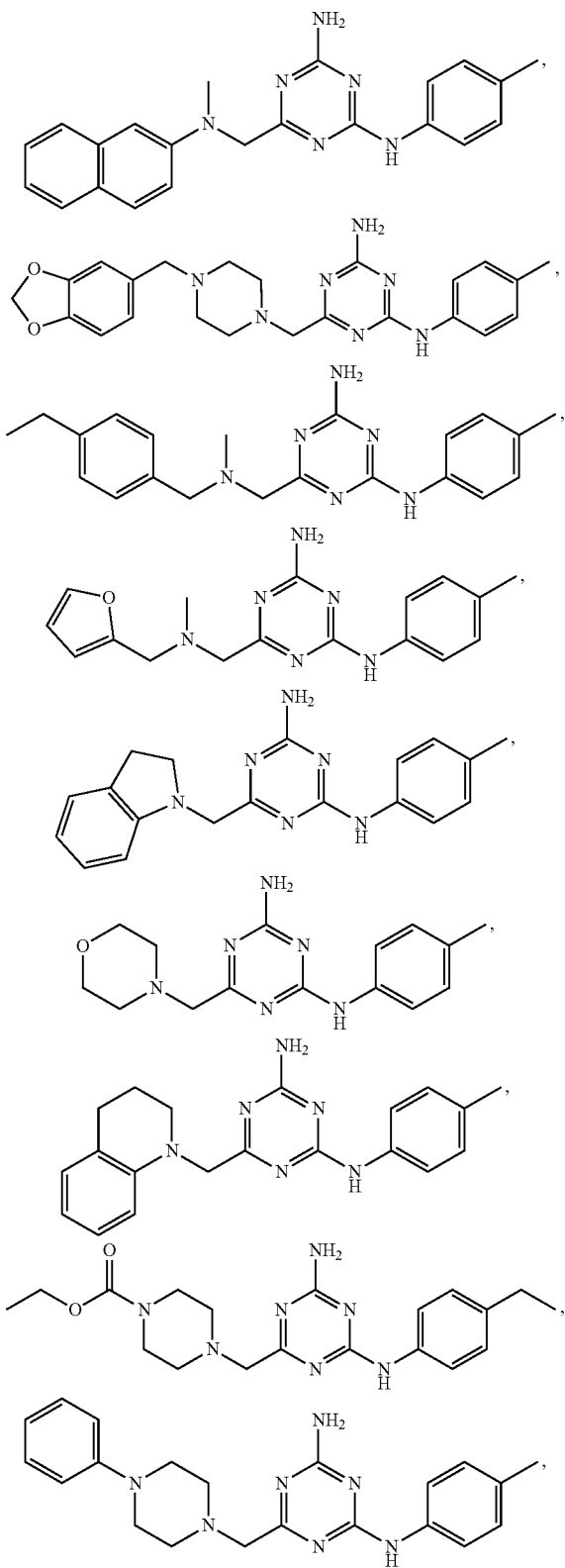

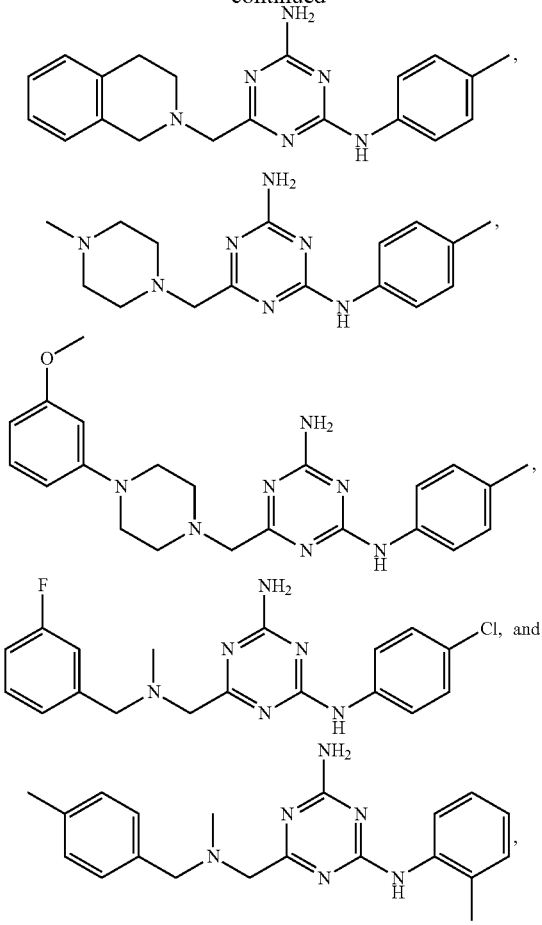

or a pharmaceutically acceptable salt or solvate thereof.

[29] Use of a compound of formula (I), or a pharmaceutically acceptable salt or solvate thereof, for the manufacture of a medicament for the treatment or prevention of Gaucher's disease, the compound of formula (I) having the structure:

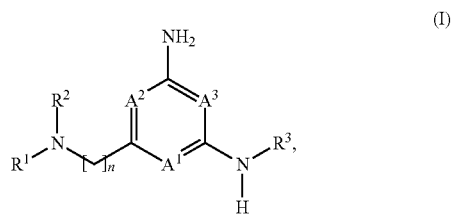

(I)

wherein
$A^1$, $A^2$, and $A^3$ are each independently selected from the group consisting of N, CH and $C(R^4)$, provided that at least one of $A^1$, $A^2$, or $A^3$ is N;
each $R^4$ is independent selected from the group consisting of halogen, $C_{1-4}$ alkyl, $C_{1-4}$ alkoxy, and CN;
n is 1 or 2:
$R^1$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{2-9}$ heterocyclyl, —$C_{1-4}$ alkyl-(5- to 10-membered)-$C_{2-9}$ heterocyclyl, and C(=O)Ra, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring; and $R^2$ is hydrogen or $C_{1-4}$ alkyl; or $R^1$ and $R^2$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;

Ra is selected from the group consisting of —$C_{1-4}$ alkyl, —$C_{3-10}$ cycloalkyl, alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{2-9}$ heterocyclyl, and —$C_{1-4}$ alkyl-(5- to 10-membered)-$C_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted $C_{6-10}$ aryl, optionally substituted (5- to 10-membered)-$C_{1-9}$ heteroaryl, and (5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring;

each Rb is independently hydrogen, —$C_{1-4}$ alkyl, —$C_{3-10}$ cycloalkyl, or (5- to 10-membered)-$C_{2-9}$ heterocyclyl, wherein said alkyl, cycloalkyl or heterocyclyl group is optionally substituted by 1, 2 or 3 flourine atoms;

$R^3$ is —$C_{6-10}$ aryl or -(5- to 10-membered)-$C_{1-9}$ heteroaryl, wherein said aryl or heteroaryl group is optionally substituted with 1, 2 or 3 groups each independently selected from the group consisting of halogen, hydroxy, CN, —ORb, —SRb, —N(Rb)$_2$, —$C_{1-4}$alkyl optionally substituted with 1, 2, or 3 groups each independently selected from the group consisting of halogen, CN, —ORb, and —N(Rb)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

[30] The use of [29], wherein the compound is as in any one of [1] to [20].

[31] The use of [29], wherein the compound is selected from the group consisting of

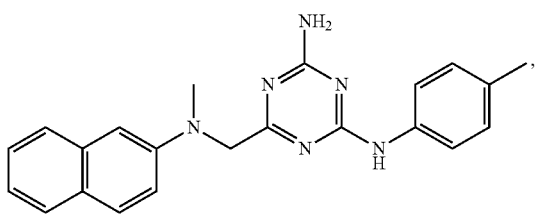

-continued

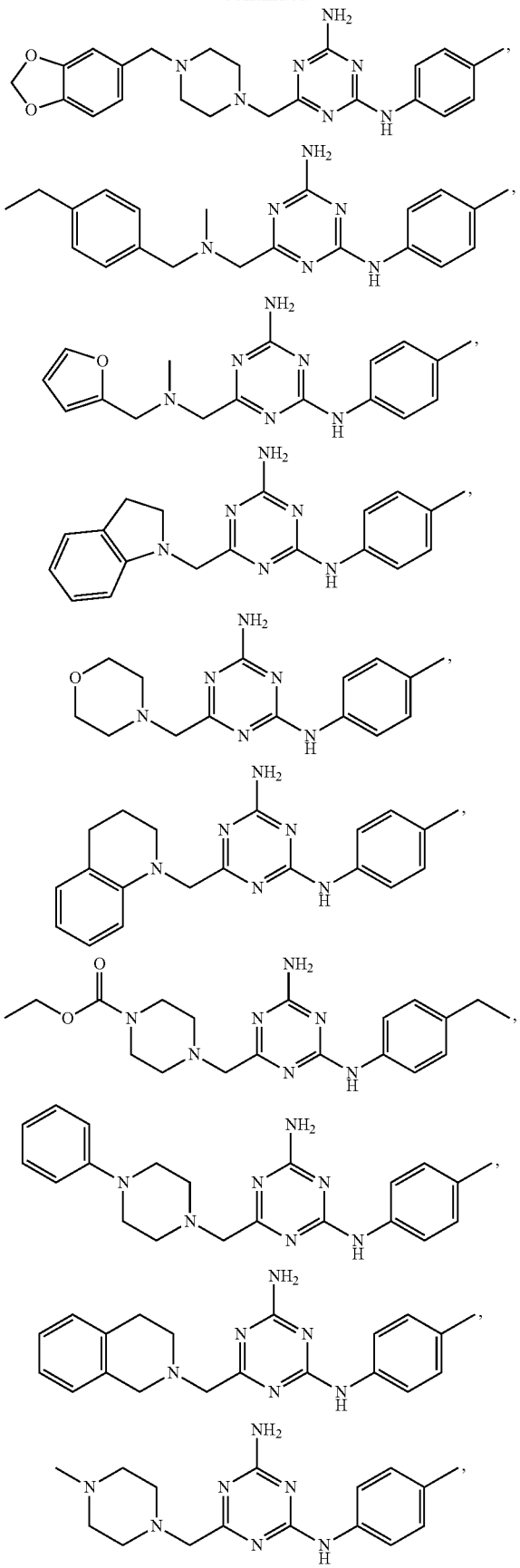

-continued

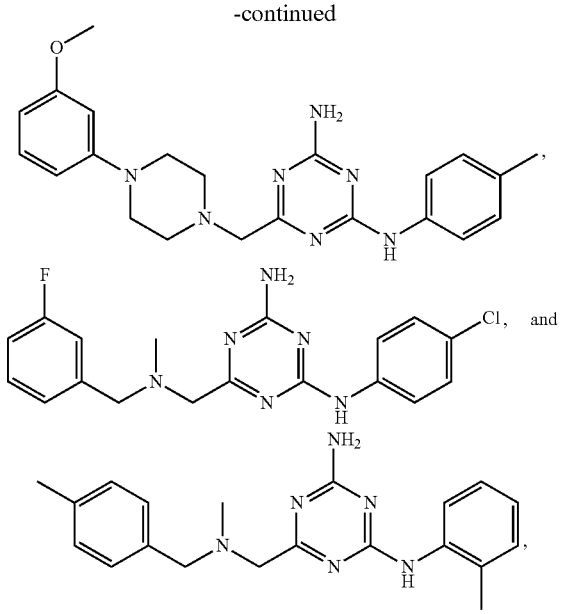

or a pharmaceutically acceptable salt or solvate thereof.

[32] A pharmaceutical composition, comprising an effective amount of a compound of formula (I):

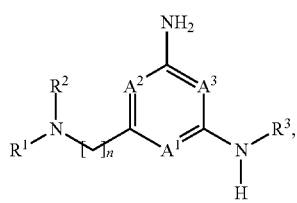

(I)

or a pharmaceutically acceptable Salt or solvate thereof, and at least one pharmaceutically acceptable excipient, for use in the treatment or prevention of Gaucher's disease, wherein
$A^1$, $A^2$, and $A^3$ are each independently selected from the group consisting of N, CH and C($R^4$), provided that at least one of $A^1$, $A^2$, or $A^3$ is N;
each $R^4$ is independent selected from the group consisting of halogen, $C_{1-4}$ alkyl, $C_{1-4}$ alkoxy, and CN;
n is 1 or 2;
$R^1$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_p$) heteroaryl, (5- to 10-membered)-$C_{2-9}$ heterocyclyl, —$C_{1-4}$ alkyl-(5- to 10-membered)-$C_{2-9}$ heterocyclyl, and C(=O)Ra, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring; and $R^2$ is hydrogen or $C_{1-4}$ alkyl; or $R^1$ and $R^2$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;

Ra is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, (5- to 10-membered)-$C_{1-9}$ heteroaryl, —$C_{1-4}$ alkyl-(5- to 10-membered)-$C_{1-9}$ heteroaryl, (5- to 10-membered)-$C_{1-9}$ heterocyclyl, and —$C_{1-4}$ alkyl-(5- to 10-membered)-$C_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted $C_{6-10}$ aryl, optionally substituted (5- to 10-membered)-$C_{1-9}$ heteroaryl, and (5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring:

each Rb is independently hydrogen, —$C_{1-4}$ alkyl, —$C_{3-10}$ cycloalkyl, or (5- to 10-membered)-$C_{2-9}$ heterocyclyl, wherein said alkyl, cycloalkyl or heterocyclyl group is optionally substituted by 1, 2 or 3 fluorine atoms;

$R^3$ is —$C_{6-10}$ aryl or -(5- to 10-membered)-$C_{1-9}$ heteroaryl, wherein said aryl or heteroaryl group is optionally substituted with 1, 2 or 3 substituents each independently selected from the group consisting of halogen, hydroxy, CN, —ORb, —SRb, —N(Rb)$_2$, —$C_{1-4}$alkyl optionally substituted with 1, 2, or 3 substituents each independently selected from the group consisting of halogen, CN, —ORb, and —N(Rb)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

All publications cited in this specification are incorporated herein by reference. While the disclosure has been described with reference to particular embodiments, it will be appreciated that modifications can be made without departing from the spirit of the disclosure. Such modifications are intended to fall within the scope of the appended claims.

The invention claimed is:

1. A method of treating a disease or disorder selected from the group consisting of Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, multiple myeloma, and a lysosomal storage disease, comprising administering to a patient in need thereof an effective amount of a compound of formula (I):

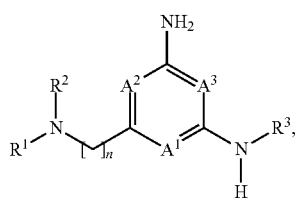

(I)

or a pharmaceutically acceptable salt or solvate thereof, wherein $A^1$, $A^2$, and $A^3$ are each independently selected from the group consisting of N, CH and $C(R^4)$, provided that at least one of $A^1$, $A^2$, or $A^3$ is N;

with the proviso that no more than two of $A^1$, $A^2$, or $A^3$ is N;

each $R^4$ is independent selected from the group consisting of halogen, —$C_{1-4}$ alkyl, —$C_{1-4}$ alkoxy, and —CN;

n is 1 or 2, wherein the alkylene chain can be optionally substituted with one or more —$C_{1-4}$ alkyl groups;

$R^1$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, —$C_{1-4}$ alkyl-(5- to 10-membered)-$C_{2-9}$ heterocyclyl, and —C(=O)Ra, wherein said —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl and —$C_{1-4}$ alkyl-(5- to 10-membered)-$C_{2-9}$ heterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, -(5- to 10-membered)-$C_{2-9}$ heterocyclyl, and optionally substituted —O-($C_{6-10}$ aryl), wherein the optional substituents in said optionally substituted —$C_{6-10}$ aryl and —O-($C_{6-10}$ aryl) are selected from 1, 2, or 3 substituents, which can be the same or different, selected from the group consisting of halogen, —OH, $C_{1-4}$ alkoxycarbonyl, hydroxycarbonyl, carbamoyl, —NO$_2$, —CN, —$C_{1-4}$ alkyl optionally substituted by one or more halogen atoms, —$C_{1-4}$ alkoxy optionally substituted by one or more halogen atoms and $C_{1-4}$ hydroxyalkyl groups; and wherein the optional substituents in said optionally substituted -(5- to 10-membered)-$C_{1-9}$ heteroaryl are selected from 1, 2, or 3 substituents, which can be the same or different, selected from the group consisting of halogen, $C_{1-4}$ alkoxycarbonyl, carbamoyl, —NO$_2$, —OH, —$C_{1-4}$ alkyl optionally substituted by one or more halogen atoms, and —$C_{1-4}$ alkoxy optionally substituted by one or more halogen atoms;

and wherein said —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl and —$C_{1-4}$ alkyl-(5- to 10-membered)-$C_{2-9}$ heterocyclyl is optionally fused to a further (second) ring; and $R^2$ is selected from the group consisting of hydrogen, —$C_{1-4}$ alkyl, and —$C_{3-6}$ cycloalkyl, wherein said —$C_{1-4}$ alkyl is optionally substituted with —O($C_{1-4}$) alkyl optionally substituted with —O($C_{1-4}$)NH$_2$, hydroxy, —CN, halogen, or —N(Rb)$_2$; or $R^1$ and $R^2$ together with the nitrogen atom to which they are attached form an optionally substituted 5- to 10-membered heterocyclic ring, wherein said 5- to 10-membered heterocyclic ring optionally contains 1, 2, or 3 additional heteroatoms selected from the group consisting of N, S, or O, and wherein said 5- to 10-membered heterocyclic ring is optionally fused to a phenyl ring;

Ra is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, and —$C_{1-4}$ alkyl-(5- to 10-membered)-$C_{2-9}$ heterocyclyl, wherein said —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl and —$C_{1-4}$ alkyl-(5- to 10-membered)-$C_{2-9}$ heterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl, wherein the optional substituents in said optionally substituted —$C_{6-10}$ aryl are selected from 1, 2, or 3 substituents, which can be the same or different, selected from the group consisting of halogen, —OH, $C_{1-4}$ alkoxycarbonyl, hydroxycarbonyl, carbamoyl, —NO$_2$, —CN, —$C_{1-4}$ alkyl optionally substituted by one or more halogen atoms, —$C_{1-4}$ alkoxy optionally substituted by one or more halogen atoms and $C_{1-4}$ hydroxyalkyl groups; and wherein the optional substituents in said optionally substituted -(5- to 10-membered)-$C_{1-9}$ heteroaryl are selected from 1, 2, or 3 substituents, which can be the same or different, selected from the group consisting of halogen, $C_{1-4}$ alkoxycarbonyl, carbamoyl, —NO$_2$, —OH, —$C_{1-4}$ alkyl optionally substituted by one or more halogen atoms, and —$C_{1-4}$ alkoxy optionally substituted by one or more halogen atoms;

and wherein said —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl and —$C_{1-4}$ alkyl-(5- to 10-membered)-$C_{2-9}$ heterocyclyl is optionally fused to a further (second) ring;

each Rb is independently hydrogen, —$C_{1-4}$ alkyl, —$C_{3-10}$ cycloalkyl, or -(5- to 10-membered)-$C_{2-9}$ heterocyclyl, wherein said —$C_{1-4}$ alkyl, —$C_{3-10}$ cycloalkyl or -(5- to 10-membered)-$C_{2-9}$ heterocyclyl group is optionally substituted by 1, 2 or 3 fluorine atoms; and $R^3$ is selected from the group consisting of —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl groups are optionally substituted with 1, 2 or 3 substituents each independently selected from the group consisting of halogen, hydroxy, —CN, —ORb, —SRb, —N(Rb)$_2$, —C$_{1-4}$alkyl optionally substituted with 1, 2, or 3 substituents each independently selected from the group consisting of halogen, —CN, —ORb, and —N(Rb)$_2$, optionally substituted —C$_{6-10}$ aryl, optionally substituted -(5- to 10-membered)-C$_{1-9}$ heteroaryl and -(5- to 10-membered)-C$_{2-9}$ heterocyclyl, wherein the optional substituents in said optionally substituted —C$_{6-10}$ aryl are selected from 1, 2, or 3 substituents, which can be the same or different, selected from the group consisting of halogen, —OH, C$_{1-4}$ alkoxycarbonyl, hydroxycarbonyl, carbamoyl, —NO$_2$, —CN, —C$_{1-4}$ alkyl optionally substituted by one or more halogen atoms, —C$_{1-4}$ alkoxy optionally substituted by one or more halogen atoms and C$_{1-4}$ hydroxyalkyl groups; and wherein the optional substituents in said optionally substituted -(5- to 10-membered)-C$_{1-9}$ heteroaryl are selected from 1, 2, or 3 substituents, which can be the same or different, selected from the group consisting of halogen, C$_{1-4}$ alkoxycarbonyl, carbamoyl, —NO$_2$, —OH, —C$_{1-4}$ alkyl optionally substituted by one or more halogen atoms, and —C$_{1-4}$ alkoxy optionally substituted by one or more halogen atoms, and wherein said —C$_{6-10}$ aryl, -(5- to 10-membered)-C$_{1-9}$ heteroaryl, —C$_{3-10}$ cycloalkyl, and -(5- to 10-membered)-C$_{2-9}$ heterocyclyl is optionally fused to a further (second) ring.

2. The method of claim 1, wherein the disease or disorder is a lysosomal storage disease.

3. The method of claim 2, wherein the lysosomal storage disease is Gaucher's disease.

4. The method of claim 1, wherein the disease or disorder is selected from the group consisting of Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, and multiple myeloma.

5. The method of claim 1, wherein in the compound administered is a compound of formula (I), or a pharmaceutically acceptable salt or solvate thereof, wherein each R$^4$ is independently selected from the group consisting of halogen, —C$_{1-4}$ alkyl, C$_{1-4}$ alkoxy, and —CN;

n is 1 or 2, wherein the alkylene chain can be optionally substituted with one or more —C$_{1-4}$ alkyl groups;

R$^1$ is selected from the group consisting of —C$_{1-4}$ alkyl substituted with 1, 2 or 3 substituents each independently selected from the group consisting of halogen, hydroxy, —CN, —ORb, —SRb, —N(Rb)$_2$, optionally substituted —C$_{6-10}$ aryl, optionally substituted -(5- to 10-membered)-C$_{1-9}$ heteroaryl, -(5- to 10-membered)-C$_{2-9}$ heterocyclyl, and optionally substituted —O-(C$_{6-10}$ aryl), —C$_{3-10}$ cycloalkyl, —C$_{1-4}$ alkyl-C$_{3-10}$ cycloalkyl, —C$_{6-10}$ aryl, —C$_{1-4}$ alkyl-C$_{6-10}$ aryl, -(5- to 10-membered)-C$_{1-9}$ heteroaryl, —C$_{1-4}$ alkyl-(5- to 10-membered)-C$_{1-9}$ heteroaryl, -(5- to 10-membered)-C$_{2-9}$ heterocyclyl, —C$_{1-4}$ alkyl-(5- to 10-membered)-C$_{2-9}$ heterocyclyl, and —C(=O)Ra, wherein said —C$_{3-11}$) cycloalkyl, —C$_{1-4}$ alkyl-C$_{3-10}$ cycloalkyl, —C$_{6-10}$ aryl, —C$_{1-4}$ alkyl-C$_{6-10}$ aryl, -(5- to 10-membered)-C$_{1-9}$ heteroaryl, —C$_{1-4}$ alkyl-(5- to 10-membered)-C$_{1-9}$ heteroaryl, -(5- to 10-membered)-C$_{2-9}$ heterocyclyl and —C$_{1-4}$ alkyl-(5- to 10-membered)-C$_{2-9}$ heterocyclyl groups are optionally substituted with 1, 2 or 3 substituents each independently selected from the group consisting of halogen, hydroxy, —CN, —ORb, —SRb, —N(Rb)$_2$, —C$_{1-4}$ alkyl optionally substituted with 1, 2, or 3 halogen atoms, optionally substituted —C$_{6-10}$ aryl, optionally substituted -(5- to 10-membered)-C$_{1-9}$ heteroaryl, -(5- to 10-membered)-C$_{2-9}$ heterocyclyl, and optionally substituted —O-(C$_{6-10}$ aryl), wherein the optional substituents in said optionally substituted —C$_{6-10}$ aryl and —O-(C$_{6-10}$ aryl) are selected from 1, 2, or 3 substituents, which can be the same or different, selected from the group consisting of halogen, —OH, C$_{1-4}$ alkoxycarbonyl, hydroxycarbonyl, carbamoyl, —NO$_2$, —CN, —C$_{1-4}$ alkyl optionally substituted by one or more halogen atoms, —C$_{1-4}$ alkoxy optionally substituted by one or more halogen atoms and C$_{1-4}$ hydroxyalkyl groups;

and wherein the optional substituents in said optionally substituted -(5- to 10-membered)-C$_{1-9}$ heteroaryl are selected from 1, 2, or 3 substituents, which can be the same or different, selected from the group consisting of halogen, C$_{1-4}$ alkoxycarbonyl, carbamoyl, —NO$_2$, —OH, —C$_{1-4}$ alkyl optionally substituted by one or more halogen atoms, and —C$_{1-4}$ alkoxy optionally substituted by one or more halogen atoms; and wherein said —C$_{3-10}$ cycloalkyl, —C$_{1-4}$ alkyl-C$_{3-10}$ cycloalkyl, —C$_{6-10}$ aryl, —C$_{1-4}$ alkyl-C$_{6-10}$ aryl, -(5- to 10-membered)-C$_{1-9}$ heteroaryl, —C$_{1-4}$ alkyl-(5- to 10-membered)-C$_{1-9}$ heteroaryl, -(5- to 10-membered)-C$_{2-9}$ heterocyclyl and —C$_{1-4}$ alkyl-(5- to 10-membered)-C$_{2-9}$ heterocyclyl is optionally fused to a further (second) ring; and R$^2$ is selected from the group consisting of hydrogen, —C$_{1-4}$ alkyl, and —C$_{3-6}$ cycloalkyl, wherein said —C$_{1-4}$ alkyl is optionally substituted with —O(C$_{1-4}$) alkyl optionally substituted with —O(C$_{1-4}$)NH$_2$, hydroxy, —CN, halogen, or —N(Rb)$_2$; or R$^1$ and R$^2$ together with the nitrogen atom to which they are attached form an optionally substituted 5- to 10-membered heterocyclic ring, wherein said 5- to 10-membered heterocyclic ring optionally contains 1, 2, or 3 additional heteroatoms selected from the group consisting of N, S, or O, and wherein said 5- to 10-membered heterocyclic ring is optionally fused to a phenyl ring;

Ra is selected from the group consisting of —C$_{1-4}$ alkyl, —C$_{3-10}$ cycloalkyl, —C$_{1-4}$ alkyl-C$_{3-10}$ cycloalkyl, —C$_{6-10}$ aryl, —C$_{1-4}$ alkyl-C$_{6-10}$ aryl, -(5- to 10-membered)-C$_{1-9}$ heteroaryl, —C$_{1-4}$ alkyl-(5- to 10-membered)-C$_{1-9}$ heteroaryl, -(5- to 10-membered)-C$_{2-9}$ heterocyclyl, and —C$_{1-4}$ alkyl-(5- to 10-membered)-C$_{2-9}$ heterocyclyl, wherein said —C$_{1-4}$ alkyl, —C$_{3-10}$ cycloalkyl, —C$_{1-4}$ alkyl-C$_{3-10}$ cycloalkyl, —C$_{6-10}$ aryl, —C$_{1-4}$ alkyl-C$_{6-10}$ aryl, -(5- to 10-membered)-C$_{1-9}$ heteroaryl, —C$_{1-4}$ alkyl-(5- to 10-membered)-C$_{1-9}$ heteroaryl, -(5- to 10-membered)-C$_{2-9}$ heterocyclyl and —C$_{1-4}$ alkyl-(5- to 10-membered)-C$_{2-9}$ heterocyclyl groups are optionally substituted with 1, 2 or 3 substituents each independently selected from the group consisting of halogen, hydroxy, —CN, —ORb, —SRb, —N(Rb)$_2$, —C$_{1-4}$ alkyl optionally substituted with 1, 2, or 3 halogen atoms, optionally substituted —C$_{6-10}$ aryl, optionally substituted -(5- to 10-membered)-C$_{1-9}$ heteroaryl, and -(5- to 10-membered)-C$_{2-9}$ heterocyclyl, wherein the optional substituents in said optionally substituted —C$_{6-10}$ aryl are selected from 1, 2, or 3 substituents, which can be the same or different, selected from the group consisting of halogen, —OH, $C_{1-4}$ alkoxycarbonyl, hydroxycarbonyl, aminocarbonyl, —$NO_2$, —CN, —$C_{1-4}$ alkyl optionally substituted by one or more halogen atoms, —$C_{1-4}$ alkoxy optionally substituted by one or more halogen atoms and $C_{1-4}$ hydroxyalkyl; and wherein the optional substituents in said optionally substituted -(5- to 10-membered)-$C_{1-9}$ heteroaryl are selected from 1, 2, or 3 substituents, which can be the same or different, selected from the group consisting of halogen, $C_{1-4}$ alkoxycarbonyl, carbamoyl, —$NO_2$, —OH, —$C_{1-4}$ alkyl optionally substituted by one or more halogen atoms, and —$C_{1-4}$ alkoxy optionally substituted by one or more halogen atoms;

and wherein said —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl and —$C_{1-4}$ alkyl-(5- to 10-membered)-$C_{2-9}$ heterocyclyl is optionally fused to a further (second) ring;

each Rb is independently hydrogen, —$C_{1-4}$ alkyl, —$C_{3-10}$ cycloalkyl, or -(5- to 10-membered)-$C_{2-9}$ heterocyclyl, wherein said —$C_{1-4}$ alkyl, —$C_{3-10}$ cycloalkyl or -(5- to 10-membered)-$C_{2-9}$ heterocyclyl group is optionally substituted by 1, 2 or 3 fluorine atoms; and $R^3$ is selected from the group consisting of —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl groups are optionally substituted with 1, 2 or 3 substituents each independently selected from the group consisting of halogen, hydroxy, —CN, —ORb, —SRb, —$N(Rb)_2$, —$C_{1-4}$alkyl optionally substituted with 1, 2, or 3 substituents each independently selected from the group consisting of halogen, —CN, —ORb, and —$N(Rb)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl, wherein the optional substituents in said optionally substituted —$C_{6-10}$ aryl are selected from 1, 2, or 3 substituents, which can be the same or different, selected from the group consisting of halogen, —OH, $C_{1-4}$ alkoxycarbonyl, hydroxycarbonyl, carbamoyl, —$NO_2$, —CN, —$C_{1-4}$ alkyl optionally substituted by one or more halogen atoms, —$C_{1-4}$ alkoxy optionally substituted by one or more halogen atoms and $C_{1-4}$ hydroxyalkyl groups; and wherein the optional substituents in said optionally substituted -(5- to 10-membered)-$C_{1-9}$ heteroaryl are selected from 1, 2, or 3 substituents, which can be the same or different, selected from the group consisting of halogen, $C_{1-4}$ alkoxycarbonyl, carbamoyl, —$NO_2$, —OH, —$C_{1-4}$ alkyl optionally substituted by one or more halogen atoms, and —$C_{1-4}$ alkoxy optionally substituted by one or more halogen atoms; and wherein said —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl is optionally fused to a further (second) ring;

provided that the compound is not:

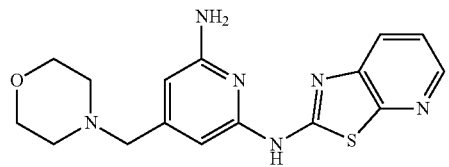

6. The method of claim 1, wherein the compound administered is a compound of formula (I), or a pharmaceutically acceptable salt or solvate thereof, wherein each $R^4$ is independently selected from the group consisting of halogen, —$C_{1-4}$ alkyl, —$C_{1-4}$ alkoxy, and —CN;

n is 1 or 2;

$R^1$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, —$C_{1-4}$ alkyl-(5- to 10-membered)-$C_{2-9}$ heterocyclyl, and —C(=O)Ra, wherein said —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl and —$C_{1-4}$ alkyl-(5- to 10-membered)-$C_{2-9}$ heterocyclyl groups are optionally substituted with 1, 2 or 3 substituents each independently selected from the group consisting of halogen, hydroxy, —CN, —ORb, —SRb, —$N(Rb)_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl, wherein the optional substituents in said optionally substituted —$C_{6-10}$ aryl are selected from 1, 2, or 3 substituents, which can be the same or different, selected from the group consisting of halogen, —OH, $C_{1-4}$ alkoxycarbonyl, hydroxycarbonyl, carbamoyl, —$NO_2$, —CN, —$C_{1-4}$ alkyl optionally substituted by one or more halogen atoms, —$C_{1-4}$ alkoxy optionally substituted by one or more halogen atoms and $C_{1-4}$ hydroxyalkyl groups;

and wherein the optional substituents in said optionally substituted -(5- to 10-membered)-$C_{1-9}$ heteroaryl are selected from 1, 2, or 3 substituents, which can be the same or different, selected from the group consisting of halogen, $C_{1-4}$ alkoxycarbonyl, carbamoyl, —$NO_2$, —OH, —$C_{1-4}$ alkyl optionally substituted by one or more halogen atoms, and —$C_{1-4}$ alkoxy optionally substituted by one or more halogen atoms;

and wherein said —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl and —$C_{1-4}$ alkyl-(5- to 10-membered)-$C_{2-9}$ heterocyclyl is optionally fused to a further (second) ring; and $R^2$ is hydrogen or —$C_{1-4}$ alkyl; or $R^1$ and $R^2$ together with the nitrogen atom to which they are attached form an optionally substituted 5- to 10-membered heterocyclic ring, wherein said 5- to 10-membered heterocyclic ring optionally contains 1, 2, or 3 additional heteroatoms selected from the group consisting of N, S, or O, and wherein said 5- to 10-membered heterocyclic ring is optionally fused to a phenyl ring;

Ra is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, and —$C_{1-4}$ alkyl-(5- to 10-membered)-$C_{2-9}$ heterocyclyl, wherein said —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl and —$C_{1-4}$ alkyl-(5- to 10-membered)-$C_{2-9}$ heterocyclyl groups are optionally substituted with 1, 2 or 3 substituents each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl, wherein the optional substituents in said optionally substituted —$C_{6-10}$ aryl are selected from 1, 2, or 3 substituents, which can be the same or different, selected from the group consisting of halogen, —OH, $C_{1-4}$ alkoxycarbonyl, hydroxycarbonyl, aminocarbonyl, —NO$_2$, —CN, —$C_{1-4}$ alkyl optionally substituted by one or more halogen atoms, —$C_{1-4}$ alkoxy optionally substituted by one or more halogen atoms and $C_{1-4}$ hydroxyalkyl; and wherein the optional substituents in said optionally substituted -(5- to 10-membered)-$C_{1-9}$ heteroaryl are selected from 1, 2, or 3 substituents, which can be the same or different, selected from the group consisting of halogen, $C_{1-4}$ alkoxycarbonyl, carbamoyl, —NO$_2$, —OH, —$C_{1-4}$ alkyl optionally substituted by one or more halogen atoms, and —$C_{1-4}$ alkoxy optionally substituted by one or more halogen atoms;

and wherein said —$C_{3-10}$ cycloalkyl, —$C_{1-4}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl and —$C_{1-4}$ alkyl-(5- to 10-membered)-$C_{2-9}$ heterocyclyl is optionally fused to a further (second) ring;

each Rb is independently hydrogen, —$C_{1-4}$ alkyl, —$C_{3-10}$ cycloalkyl, or -(5- to 10-membered)-$C_{2-9}$ heterocyclyl, wherein said —$C_{1-4}$ alkyl, —$C_{3-10}$ cycloalkyl or -(5- to 10-membered)-$C_{2-9}$ heterocyclyl group is optionally substituted by 1, 2 or 3 fluorine atoms;

$R^3$ is —$C_{6-10}$ aryl or -(5- to 10-membered)-$C_{1-9}$ heteroaryl, wherein said —$C_{6-10}$ aryl or -(5- to 10-membered)-$C_{1-9}$ heteroaryl group is optionally substituted with 1, 2 or 3 substituents each independently selected from the group consisting of halogen, hydroxy, —CN, —ORb, —SRb, —N(Rb)$_2$, —$C_{1-4}$alkyl optionally substituted with 1, 2, or 3 substituents each independently selected from the group consisting of halogen, —CN, —ORb, and —N(Rb)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl, wherein the optional substituents in said optionally substituted —$C_{6-10}$ aryl are selected from 1, 2, or 3 substituents, which can be the same or different, selected from the group consisting of halogen, —OH, $C_{1-4}$ alkoxycarbonyl, hydroxycarbonyl, carbamoyl, —NO$_2$, —CN, —$C_{1-4}$ alkyl optionally substituted by one or more halogen atoms, —$C_{1-4}$ alkoxy optionally substituted by one or more halogen atoms and $C_{1-4}$ hydroxyalkyl groups; and wherein the optional substituents in said optionally substituted -(5- to 10-membered)-$C_{1-9}$ heteroaryl are selected from 1, 2, or 3 substituents, which can be the same or different, selected from the group consisting of halogen, $C_{1-4}$ alkoxycarbonyl, carbamoyl, —NO$_2$, —OH, —$C_{1-4}$ alkyl optionally substituted by one or more halogen atoms, and —$C_{1-4}$ alkoxy optionally substituted by one or more halogen atoms; provided that the compound is not:

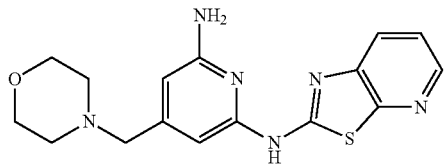

7. The method of claim 1, wherein the compound administered is a compound of formula (I), or a pharmaceutically acceptable salt or solvate thereof, wherein $A^1$ is N and $A^2$ and $A^3$ are each independently selected from the group consisting of CH and C($R^4$).

8. The method of claim 1, wherein the compound administered is a compound of formula (I), or a pharmaceutically acceptable salt or solvate thereof, wherein $A^2$ is N and $A^1$ and $A^3$ are each independently selected from the group consisting of CH and C($R^4$).

9. The method of claim 1, wherein the compound administered is a compound of formula (I), or a pharmaceutically acceptable salt or solvate thereof, wherein $A^3$ is N and $A^1$ and $A^2$ are each independently selected from the group consisting of CH and C($R^4$).

10. The method of claim 1, wherein the compound administered is a compound of formula (I), or a pharmaceutically acceptable salt or solvate thereof, wherein $A^1$ and $A^2$ are both N and $A^3$ is CH or C($R^4$).

11. The method of claim 1, wherein the compound administered is a compound of formula (I), or a pharmaceutically acceptable salt or solvate thereof, wherein $A^1$ and $A^3$ are both N and $A^2$ is CH or C($R^4$).

12. The method of claim 1, wherein the compound administered is a compound of formula (I), or a pharmaceutically acceptable salt or solvate thereof, wherein $A^2$ and $A^3$ are both N and $A^1$ is CH or C($R^4$).

13. The method of claim 1, wherein the compound administered is a compound of formula (I), or a pharmaceutically acceptable salt or solvate thereof, wherein n is 1.

14. The method of claim 1, wherein the compound administered is a compound of formula (I), or a pharmaceutically acceptable salt or solvate thereof, wherein n is 2.

15. The method of claim 1, wherein the compound administered is a compound of formula (I), or a pharmaceutically acceptable salt or solvate thereof, wherein $R^3$ is unsubstituted —$C_{6-10}$ aryl or —$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl).

16. The method of claim 1, wherein the compound administered is a compound of formula (I), or a pharmaceutically acceptable salt or solvate thereof, wherein $R^2$ is H.

17. The method of claim 1, wherein the compound administered is a compound of formula (I), or a pharmaceutically acceptable salt or solvate thereof, wherein $R^2$ is $—C_{1-4}$ alkyl.

18. The method of claim 1, wherein the compound administered is a compound of formula (I), or a pharmaceutically acceptable salt or solvate thereof, wherein $R^1$ is $—C_{6-10}$ aryl or $—C_{1-4}$ alkyl-$C_{6-10}$ aryl, wherein said $—C_{6-10}$ aryl or $—C_{1-4}$ alkyl-$C_{6-10}$ aryl is optionally substituted with 1, 2 or 3 groups each independently selected from the group consisting of halogen, hydroxy, —CN, —ORb, —SRb, —N(Rb)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl, wherein Rb is as defined in claim 1, and wherein the optional substituents in said optionally substituted —$C_{6-10}$ aryl and -(5- to 10-membered)-$C_{1-9}$ heteroaryl are as defined in claim 1.

19. The method of claim 18, wherein the compound administered is a compound of formula (I), or a pharmaceutically acceptable salt or solvate thereof, wherein $R^1$ is unsubstituted phenyl or unsubstituted benzyl.

20. The method of claim 1, wherein the compound administered is a compound of formula (I), or a pharmaceutically acceptable salt or solvate thereof, wherein Rb is hydrogen or —$C_{1-4}$ alkyl.

21. The method of claim 1, wherein the compound administered is a compound of formula (I), or a pharmaceutically acceptable salt or solvate thereof, wherein $R^1$ and $R^2$ together with the nitrogen atom to which they are attached form an optionally substituted 5 to 10-membered heterocyclic ring, wherein said 5- to 10-membered heterocyclic ring optionally contains 1, 2, or 3 additional heteroatoms selected from the group consisting of N, S, or O, and wherein said 5- to 10-membered heterocyclic ring is optionally fused to a phenyl ring.

22. The method of claim 21, wherein the compound administered is a compound of formula (I), or a pharmaceutically acceptable salt or solvate thereof, wherein R' and $R^2$ together with the nitrogen atom to which they are attached form a 5- or 6-membered ring optionally fused to a phenyl ring.

23. The method of claim 1, wherein the compound administered is selected from the group consisting of

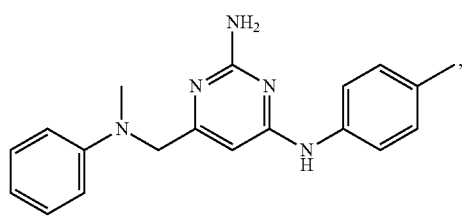

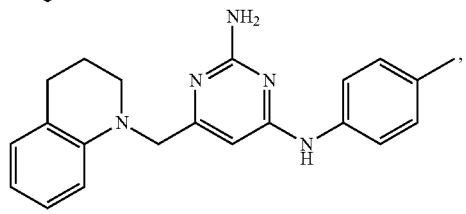

-continued

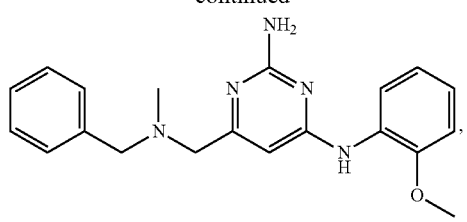

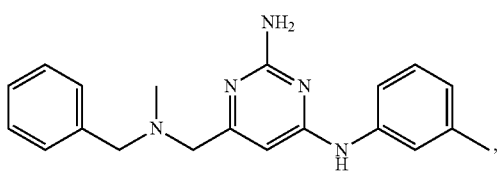

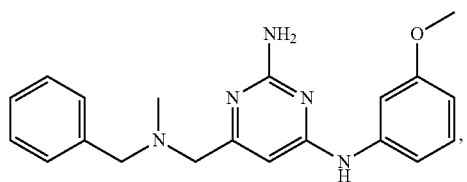

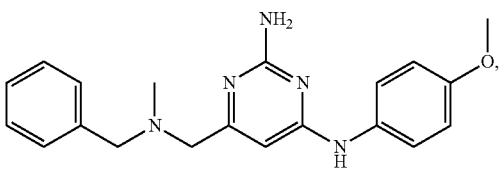

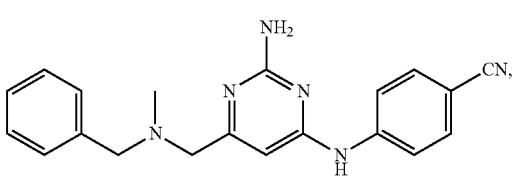

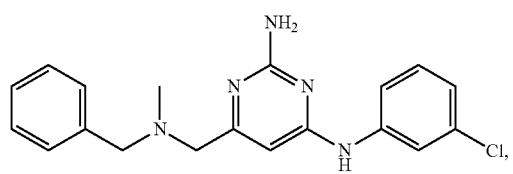

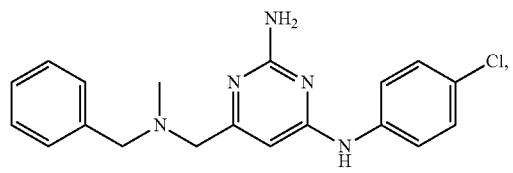

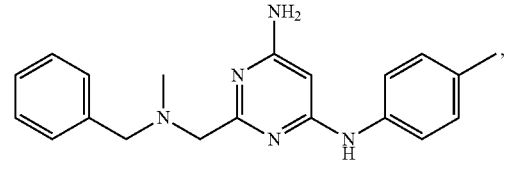

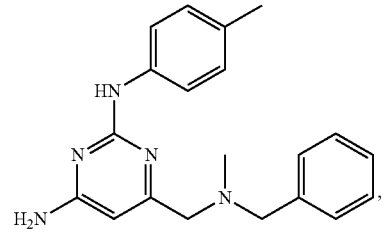

-continued
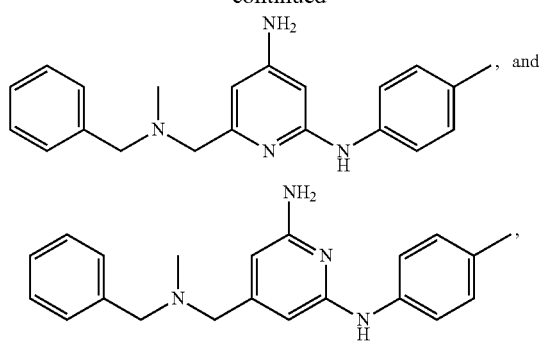
or a pharmaceutically acceptable salt or solvate thereof.
24. The method of claim 1, wherein the compound administered is selected from the group consisting of
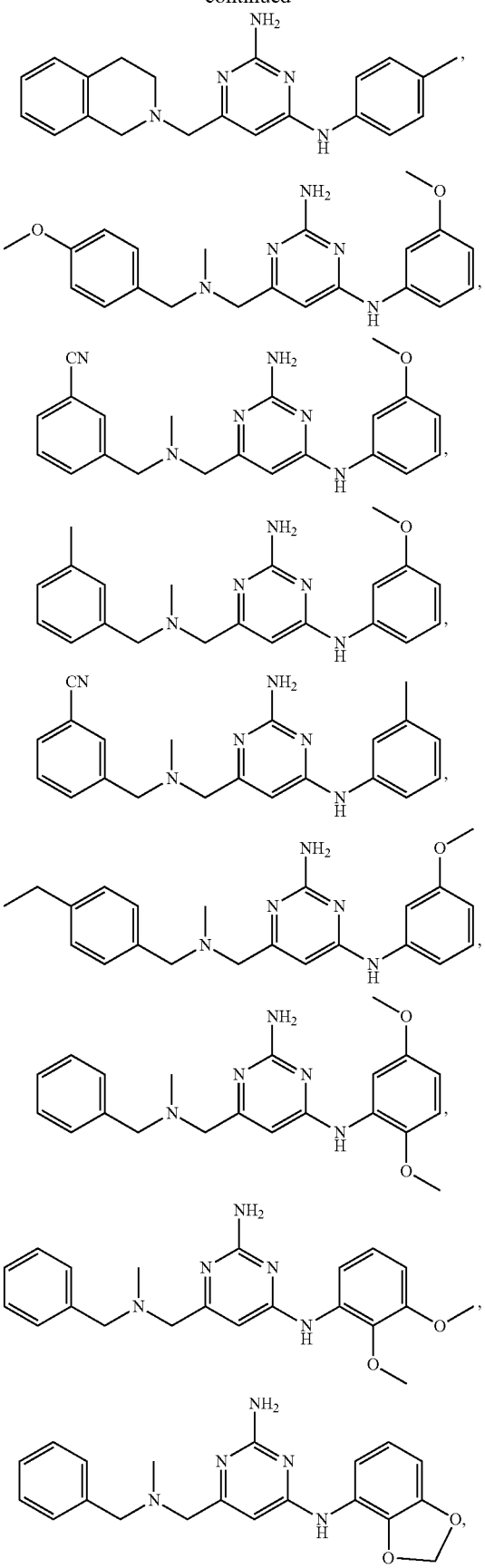

-continued
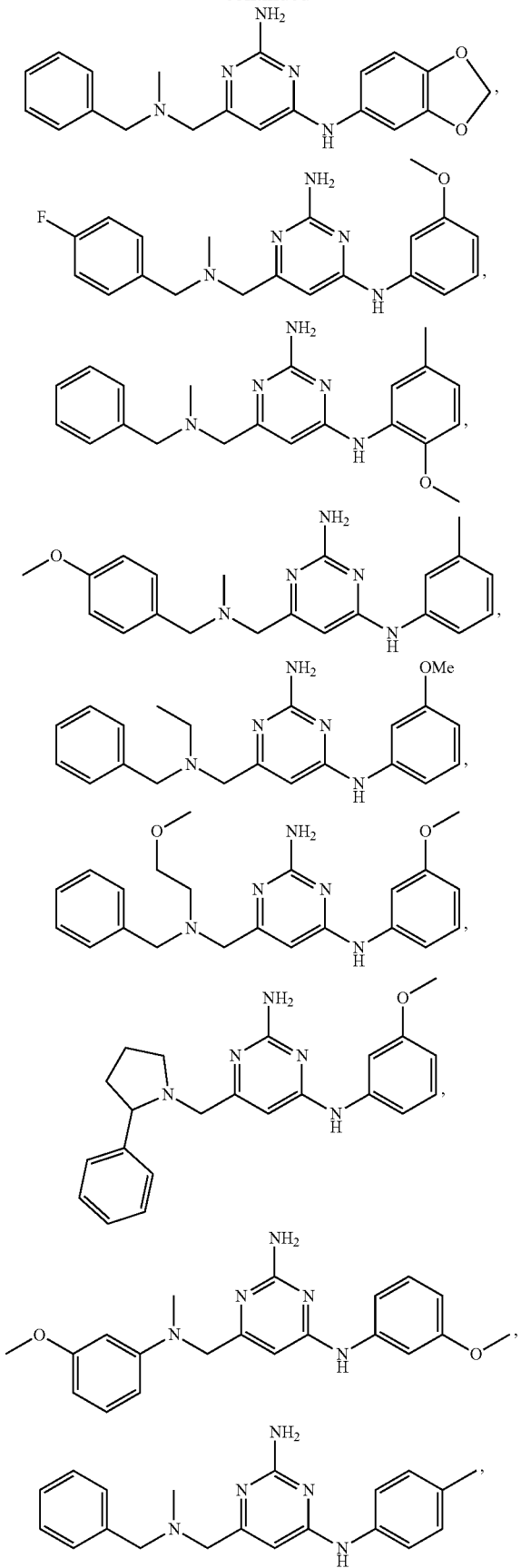
-continued
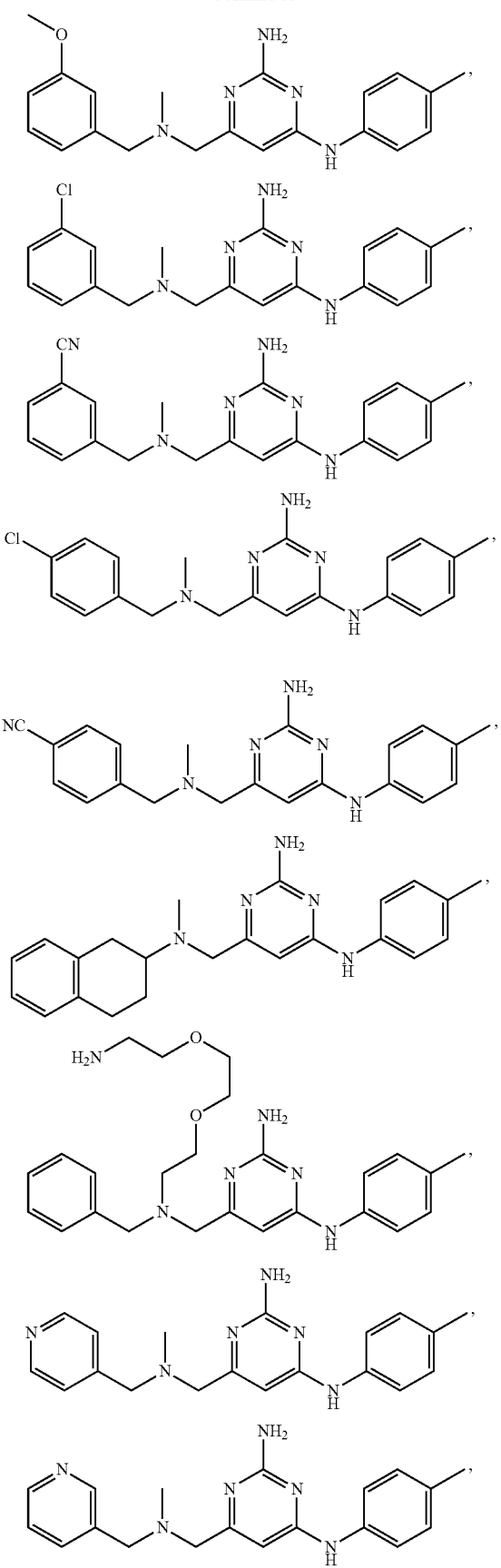

-continued

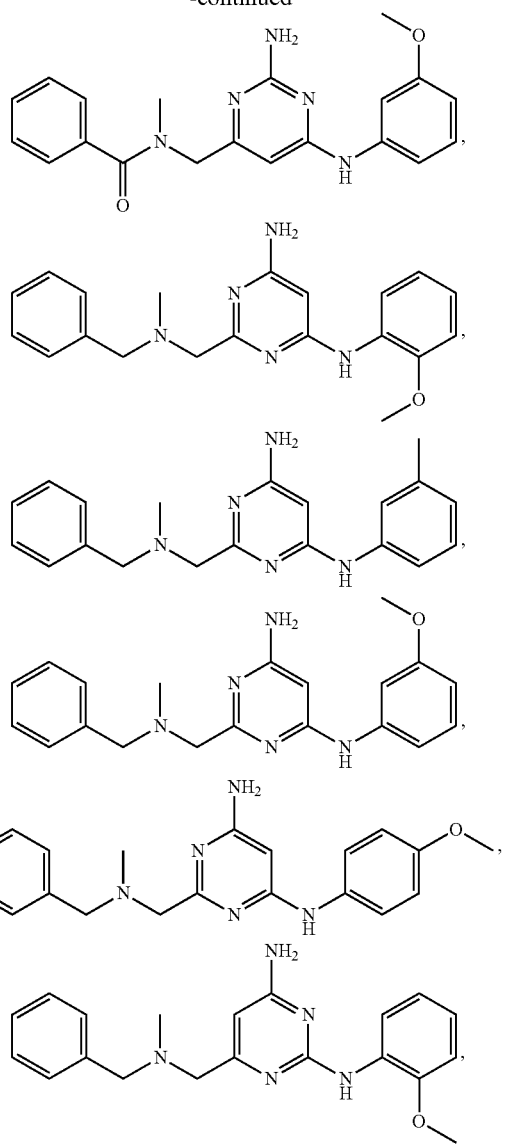

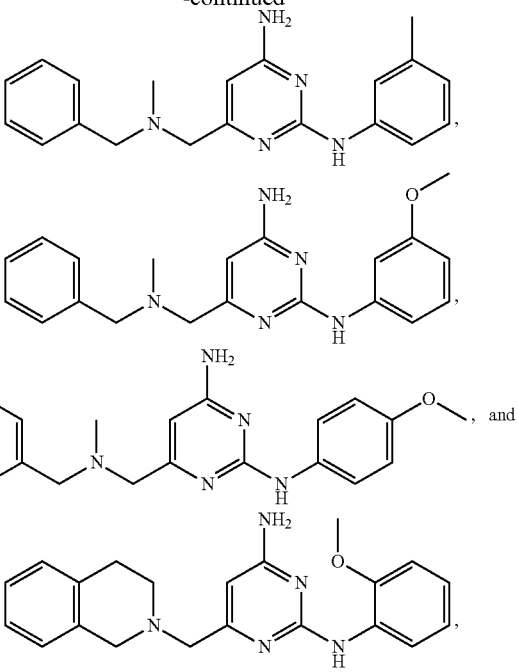

or a pharmaceutically acceptable salt or solvate thereof.

25. The method of claim 1, further comprising administering to the patient at least one other therapeutic agent.

26. The method of claim 25, wherein the therapeutic agent is an effective amount of an enzyme for enzyme replacement therapy.

27. The method of claim 26, wherein the enzyme is β-glucocerebrosidase.

28. The method of claim 25, wherein the therapeutic agent is an effective amount of a small molecule chaperone.

29. The method of claim 28, wherein the small molecule chaperone binds competitively to an enzyme.

30. The method of claim 28, wherein the small molecule chaperone is selected from the group consisting of imino-alditols, iminosugars, aminosugars, thiophenylglycosides, glycosidase, sulfatase, glycosyl transferase, phosphatase, and peptidase inhibitors.

* * * * *